United States Patent

Ishihara et al.

[11] Patent Number: 5,843,973
[45] Date of Patent: Dec. 1, 1998

[54] THIAZOLIDINONE COMPOUNDS AND COMPOSITION FOR ANGINA PECTORIS COMPRISING THE COMPOUNDS AS AN ACTIVE INGREDIENT

[75] Inventors: Sadao Ishihara, Saitama-ken; Fujio Saito, Urayasu; Yasuo Ohhata, Tokyo; Shigeki Miyake, Mitaka; Ryosuke Yorikane, Toda; Norio Fukuda, Tokyo, all of Japan

[73] Assignee: Sankyo Company, Limited, Tokyo, Japan

[21] Appl. No.: 872,770

[22] Filed: Jun. 10, 1997

Related U.S. Application Data

[63] Continuation of PCT/JP95/02545 Dec. 13, 1995 published as WO96/18620 Jun. 20, 1996.

[30] Foreign Application Priority Data

Dec. 15, 1994 [JP] Japan ................................. 6-311511

[51] Int. Cl.⁶ .................. A61K 31/42; A61K 31/425; C07D 263/24; C07D 277/14
[52] U.S. Cl. .................. 514/369; 514/326; 514/340; 514/342; 514/376; 546/209; 546/269.7; 546/271.4; 548/188; 548/230
[58] Field of Search ................. 546/209, 269.7, 546/271.4; 548/188, 230; 514/326, 340, 342, 369, 376

[56] References Cited

U.S. PATENT DOCUMENTS

| | | | |
|---|---|---|---|
| 4,923,886 | 5/1990 | Shiokawa et al. | 514/365 |
| 5,010,093 | 4/1991 | Shiokawa et al. | 514/374 |
| 5,298,516 | 3/1994 | Ishihara et al. | 514/369 |
| 5,356,918 | 10/1994 | Ishihara et al. | 514/376 |

FOREIGN PATENT DOCUMENTS

| | | |
|---|---|---|
| 0 300 400 A1 | 1/1989 | European Pat. Off. |
| 0 506 434 A1 | 9/1992 | European Pat. Off. |
| WO 96/26931 | 9/1996 | WIPO |

*Primary Examiner*—Richard L. Raymond
*Attorney, Agent, or Firm*—Frishauf, Holtz, Goodman, Langer & Chick, P.C.

[57] ABSTRACT

A thiazolidinone compound represented by general formula (I) or a pharmacoligically acceptable salt thereof,

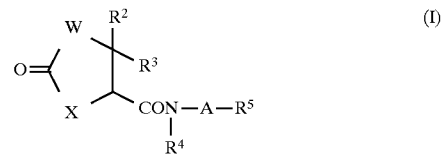

wherein W represents sulfur or oxygen and X represents —N($R^1$)—, or alternatively X represents sulfur or oxygen and W represents —N($R^1$)—, and $R^1$ represents hydrogen, alkyl or substituted alkyl; $R^2$ and $R^3$ are the same or different from each other, and each represents hydrogen, alkyl, substituted alkyl, aryl, or 5- or 6-membered heteroaryl; $R^4$ represents hydrogen, alkyl or substituted $C_1$–$C_4$ alkyl; $R^5$ represents substituted cycloalkyl which may contain nitrogen, provided the substituents include —B—$ONO_2$ (wherein B represents a single bond or alkylene) as the indispensable member and alkyl groups as optional members; and A represents a single bond or alkylene, has an excellent anti-anginal effect and thus is useful as an angina pectoris remedy or preventive.

74 Claims, No Drawings

THIAZOLIDINONE COMPOUNDS AND COMPOSITION FOR ANGINA PECTORIS COMPRISING THE COMPOUNDS AS AN ACTIVE INGREDIENT

This application is a continuation application of International Application No. PCT/JP95/02545 filed Dec. 13, 1995, published as WO96/18620 Jun. 20, 1996.

TECHNICAL FIELD

The present invention relates to thiazolidinone compounds or pharmacologically acceptable salts thereof, having an excellent collateral vessel dilating action and an anti-angina pectoris action, and a therapeutic agent or a preventing agent for angina pectoris comprising them as an active ingredient.

PRIOR ART

Conventionally, as a therapeutic agent for cardiovascular diseases, particularly for angina pectoris, nitroglycerin has been most frequently used clinically. However, nitroglycerin easily undergoes the first-pass effect, and has side effects such as headache, vertigo, tachycardia due to reduction in blood pressure, etc. For this reason, an angina pectoris therapeutic agent which clinically does not undergo the first-pass effect and gives less side effects has been desired.

As thiazolidinone derivatives having an anti-angina pectoris action, for example, the following compound A is known (Japanese Unexamined Patent Publication (KOKAI) No. Hei 5-213910).

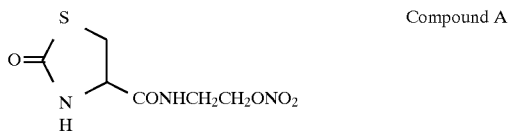

Compound A

DISCLOSURE OF THE INVENTION

The present inventors have prepared a series of nitrate derivatives and have investigated the pharmacological actions thereof for many years. As a result, the present inventors have found that thiazolidinone compounds having a specific substituent have an excellently prolonged collateral vessel dilating action and less side effects, and are useful as an angina pectoris therapeutic agent or a preventing agent to accomplish the present invention.

CONSTITUTION OF THE INVENTION

The thiazolidinone compound of the present invention has the general formula:

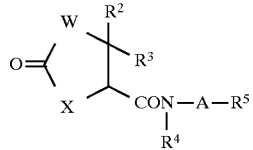

(I)

In the above formula W represents a sulfur atom or an oxygen atom, and X represents a group having the formula: —N($R^1$)—; or X represents a sulfur atom or an oxygen atom, and W represents a group having the formula: —N($R^1$)—;

$R^1$ represents a hydrogen atom, a $C_1$–$C_6$ alkyl group or a $C_{1–C4}$ alkyl group substituted with aryl;

$R^2$ and $R^3$ may be the same or different and each represents a hydrogen atom, a $C_1$–$C_6$ alkyl group, a $C_1$–$C_4$ alkyl group substituted with aryl, an aryl group or an optionally substituted 5- or 6-membered aromatic heterocyclic group containing 1 to 3 hetero atoms selected from the group consisting of nitrogen atoms, oxygen atoms and sulfur atoms (the substituent is $C_1$–$C_6$ alkyl, halogen, amino, or mono- or di-$C_1$–$C_6$ alkylamino);

$R^4$ represents a hydrogen atom, a $C_1$–$C_6$ alkyl group or a $C_{1–C4}$ alkyl group substituted with aryl;

$R^5$ represents a substituted $C_3$–$C_8$ cycloalkyl group optionally containing a nitrogen atom [said substituent is essentially a group having the formula: —B—$ONO_2$ (wherein B represents a single bond or a $C_1$–$C_6$ alkylene group) and optionally a $C_1$–$C_6$ alkyl group];

A represents a single bond or a $C_1$–$C_6$ alkylene group; and said aryl group represents a $C_6$–$C_{10}$ aryl group which may be optionally substituted (the substituent is $C_1$–$C_6$ alkyl, $C_1$–$C_6$ alkoxy, hydroxy, halogen, amino, mono- or di-$C_1$–$C_6$ alkylamino or nitro)].

The $C_1$–$C_6$ alkyl groups of $R^1$, $R^2$, $R^3$, $R^4$ and the like or the alkyl moieties in the $C_1$–$C_6$ alkoxy group, the $C_1$–$C_6$ alkylamino group, etc. contained in aryl and the like include, for example, a methyl, ethyl, propyl, isopropyl, butyl, s-butyl, t-butyl, isobutyl, pentyl and hexyl group and preferably a $C_1$–$C_4$ alkyl group, more preferably a $C_1$–$C_2$ alkyl group and particularly preferably a methyl group.

The aryl moieties of the $C_1$–$C_4$ alkyl groups substituted with aryls in $R^1$, $R^2$, $R^3$ and $R^4$ (the number of the substituents of aryl is preferably 1 or 2 and particularly preferably 1) are those as described below and the alkyl moieties are groups corresponding to the $C_1$–$C_6$ alkyl groups mentioned above. The $C_1$–$C_4$ alkyl groups substituted with an aryl group include, for example, a benzyl, phenethyl, 2-phenylpropyl, 3-phenylpropyl, 4-phenylbutyl, diphenylmethyl, 1-naphthylmethyl and 2-naphthylmethyl group, preferably a phenyl-($C_1$–$C_4$ alkyl) group, more preferably a benzyl or phenethyl group and particularly preferably a benzyl group.

$C_6$–$C_{10}$ aryl groups of $R^2$ and $R^3$ include, for example, a phenyl group and a naphthyl group and preferably a phenyl group.

The halogens, as the substituent in the $C_6$–$C_{10}$ aryl groups in $R^2$ and $R^3$ include, for example, a fluorine atom, a chlorine atom, a bromine atom and an iodine atom and preferably a fluorine atom or a chlorine atom.

Meanwhile, the substituent on the aryl group (the number of the substituents is preferably 1 to 3, more preferably 1 or 2 and particularly preferably 1) includes preferably a $C_1$–$C_4$ alkyl group, a $C_1$–$C_4$ alkoxy group, a hydroxy group, a halogen atom, an amino group, a mono- or di-$C_1$–$C_4$ alkylamino group or a nitro group, more preferably a $C_1$–$C_4$ alkyl group, a $C_1$–$C_4$ alkoxy group, a hydroxy group, a halogen atom or a nitro group, still more preferably a methyl group, a methoxy group, a hydroxy group, a fluorine atom or a chlorine atom and particularly preferably a methyl group or a methoxy group.

The 5- or 6-membered aromatic heterocyclic ring containing 1 to 3 hetero atoms selected from the group consisting of nitrogen atoms, oxygen atoms and sulfur atoms in $R^2$ and $R^3$ may be optionally condensed with a benzene ring and may include, for example, furyl, thienyl, pyrrolyl, oxazolyl, isoxazolyl, thiazolyl, isothiazolyl, imidazolyl, pyrazolyl, pyridyl, pyridazinyl, pyrimidinyl, indolyl, quinolyl and quinazolinyl, preferably furyl, thienyl, oxazolyl, isoxazolyl, thiazolyl, isothiazolyl or pyridyl, more preferably furyl, thienyl or pyridyl and particularly preferably thienyl.

The substituent on the 5- or 6-membered aromatic heterocyclic ring may include preferably a $C_1$–$C_4$ alkyl group, a halogen atom, an amino group or a mono- or di-$C_1$–$C_4$ alkylamino group, more preferably a $C_1$–$C_2$ alkyl group, a fluorine atom or a chlorine atom and particularly preferably a methyl group.

The cycloalkyl moiety of the substituted $C_3$–$C_8$ cycloalkyl group, which may optionally contain a nitrogen atom, in $R^5$ may include, for example, a cyclopropyl, cyclobutyl, cyclopentyl, cyclohexyl, cycloheptyl, cyclooctyl, aziridinyl, azetidinyl, pyrrolidinyl, piperidinyl, 2H-hexahydroazepinyl and octahydroazocinyl group, preferably a $C_3$–$C_6$ cycloalkyl group, a pyrrolidinyl group or a piperidinyl group, more preferably a cyclopropyl, cyclopentyl or cyclohexyl group, still more preferably a cyclopentyl group or a cyclohexyl group and particularly preferably a cyclohexyl group.

The substituted $C_3$–$C_8$ cycloalkyl group, which may optionally contain a nitrogen atom, may typically include, for example, a 1- or 2-nitroxymethylcyclopropyl group, a 1- or 2-(2-nitroxyethyl)cyclopropyl group, a 1- or 2-(3-nitroxypropyl)cyclopropyl group, a 1- or 2-(3-nitroxybutyl)cyclopropyl group, a 2- or 3-nitroxymethylcyclobutyl group, a 2- or 3-nitroxycyclopentyl group, a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyclohexyl group, a 3-, 4- or 5-nitroxymethylpyrrolidin-2-yl group, a 3-, 4- or 5-nitroxymethyl-1-methylpyrrolidin-2-yl group, a 3-, 4- or 5-(2-nitroxyethyl)pyrrolidin-2-yl group, a 3-, 4- or 5-(3-nitroxypropyl)pyrrolidin-2-yl group, a 3-, 4- or 5-(4-nitroxybutyl)pyrrolidin-2-yl group, a 3-, 4-, 5- or 6-nitroxypiperidin-2-yl group, a 3-, 4-, 5- or 6-nitroxymethylpiperidin-2-yl group, a 3-, 4-, 5- or 6-nitroxymethyl-1-methylpiperidin-2-yl group, a 5- or 6-nitroxymethylpiperidin-3-yl group, a 5- or 6-nitroxymethyl-1-methylpiperidin-3-yl group, a 3-, 4-, 5- or 6-(2-nitroxyethyl)piperidin-2-yl group, a 3-, 4-, 5- or 6-(3-nitroxypropyl)plperidin-2-yl, a 3-, 4-, 5- or 6-(4-nitroxybutyl)piperidin-2-yl group, preferably a 2-nitroxymethylcyclopropyl group, a 2- or 3-nitroxycyclopentyl group, a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyclohexyl group, a 3-, 4- or 5-nitroxymethylpyrrolidin-2-yl group, a 3-, 4- or 5-nitroxymethyl-1-methylpyrrolidin-2-yl group, a 3-, 4-, 5- or 6-nitroxymethylpiperidin-2-yl group, a 3-, 4-, 5- or 6-nitroxymethyl-1-methylpiperidin-2-yl group, a 5- or 6-nitroxymethylpiperidin-3-yl group, a 5- or 6-nitroxymethyl-1-methylpiperidin-3-yl group, a 3-, 4-, 5- or 6-(2-nitroxyethyl)piperidin-2-yl group, a 3-, 4-, 5- or 6-(3-nitroxypropyl)piperidin-2-yl and a 3-, 4-, 5- or 6-(4-nitroxybutyl)piperidin-2-yl group, more preferably a 2- or 3-nitroxymnethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyalohexyl group, a 3-, 4-, 5- or 6-nitroxymethylpiperidin-2-yl group or a 3-, 4-, 5- or 6-nitroxymethyl-1-methylpiperidin-2-yl group, still more preferably a 2- or 3-nitroxymethylcyclohexyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group or a 2-, 3- or 4-(4-nitroxybutyl)cyclohexyl group, still further more preferably a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl) cyclohexyl group, particularly preferably a 3- or 4-nitroxymethylcyclohexyl group, 4-(2-nitroxyethyl) cyclohexyl group, a 4-(3-nitroxypropyl)cyclohexyl group or 4-(4-nitroxybutyl)cyclohexyl group and most preferably 4-nitroxymethylcyclohexyl group.

The $C_1$–$C_6$ alkylene groups of A and B may include, for example, methylene, ethylene, propylene, trimethylene, tetramethylene, pentamethylene and hexamethylene, preferably a $C_1$–$C_4$ alkylene group; more preferably A is a methylene group or an ethylene group and B is a methylene group, an ethylene group, a trimethylene group or a tetramethylene group; and particularly preferably A is a methylene group and B is a methylene group or an ethylene group (particularly a methylene group).

In the compounds (I), those containing an acidic group such as a phenol moiety can form salts with bases. Such salts may include, for example, a salt with an alkali metal such as lithium, sodium and potassium, a salt with an alkaline earth metal such as barium and calcium, a salt with other metals such as magnesium and aluminum, a salt with an organic amine such as dicyclohexylamine and a salt with a basic amino acid such as lysine and arginine and preferably a salt with an alkali metal. Meanwhile, the compounds (I) containing a basic group such as amino or alkylamino moieties can form salts with an acid. Such salts may include, for example, a salt with an inorganic acid such as hydrochloric acid, hydrobromic acid, sulfuric acid, phosphoric acid and carbonic acid, a salt with a carboxylic acid such as acetic acid, fumaric acid, maleic acid, oxalic acid, malonic acid, succinic acid, citric acid, malic acid and benzoic acid, a salt with a sulfonic acid such as methanesulfonic acid, ethanesulfonic acid, benzenesulfonic acid and toluenesulfonic acid and a salt with an acidic amino acid such as glutamic acid and aspartic acid, and preferably a salt with hydrochloric acid or a carboxylic acid (particularly a salt with hydrochloric acid).

In the compound (I), the carbon atom to which $R^2$ and $R^3$ are bonded, the carbon atom to which the group having the formula: —CON($R^4$)—A—$R^5$ (wherein $R^4$, $R^5$ and A have the same meanings as defined above) is bonded and the carbon atom contained in $R^5$ may be asymmetric carbon atoms and isomers based on such carbon atoms are also included in the compounds of the present invention. Further, stereoisomers exist in the group having the formula: —A—$R^5$ (wherein $R^5$ and A have the same meanings as defined above) and each isomer or a mixture thereof is also included in the compound of the present invention (preferably a trans form) and moreover a hydrate of the compound (I) or the salt thereof is also included in the compound of the present invention.

The compound having the above-mentioned general formula (I) may include preferably:

(1) a compound in which W is a sulfur atom or an oxygen atom, and X is a group having the formula: —$NR^1$—; or X is a sulfur atom, and W is a group having the formula: —$NR^1$—;

(2) a compound in which W is a sulfur atom or an oxygen atom, and X is a group having the formula: —$NR^1$—;

(3) a compound in which W is a sulfur atom, and X is a group having the formula: —$NR^1$—;

(4) a compound in which $R^1$ is a hydrogen atom, a $C_1$–$C_4$ alkyl group, a benzyl group or a phenethyl group;

(5) a compound in which $R^1$ is a hydrogen atom, a methyl group or a benzyl group;

(6) a compound in which $R^1$ is a hydrogen atom;

(7) a compound in which $R^2$ and $R^3$ may be the same or different and each is a hydrogen atom, a $C_1$–$C_4$ alkyl group, a $C_1$–$C_4$ alkyl group substituted with phenyl (the phenyl group may be optionally substituted with $C_1$–$C_4$ alkyl, $C_1$–$C_4$ alkoxy, hydroxy, halogen or nitro), a naphthylmethyl group, a phenyl group (the phenyl group may be optionally substituted with $C_1$–$C_4$ alkyl, $C_1$–$C_4$ alkoxy, hydroxy, halogen or nitro), a naphthyl group or a furyl, thienyl, pyridyl, oxazolyl, thiazolyl, isoxazolyl or isothiazolyl group which may be optionally substituted with $C_1$–$C_2$ alkyl, fluoro or chloro;

(8) a compound in which $R^2$ and $R^3$ may be the same or different and each is a hydrogen atom, a methyl group, an ethyl group, a benzyl group which may be optionally substituted with methyl, methoxy, hydroxy, fluoro or chloro, a phenethyl group which may be optionally substituted with methyl, methoxy, hydroxy, fluoro or chloro, a phenyl group which may be optionally substituted with methyl, methoxy, hydroxy, fluoro or chloro, a furyl group, a thienyl group or a pyridyl group;

(9) a compound in which $R^2$ is a hydrogen atom, a methyl group, an ethyl group, a benzyl group which may be optionally substituted with methyl, methoxy or hydroxy or a phenyl group which may be optionally substituted with methyl or methoxy or a thienyl group, and $R^3$ is a hydrogen atom or $R^2$ and $R^3$ are a methyl group;

(10) a compound in which $R^2$ is a hydrogen atom, a methyl group, a benzyl group which may be optionally substituted with methyl or methoxy or a phenyl group, and $R^3$ is a hydrogen atom or $R^2$ and $R^3$ are a methyl group;

(11) a compound in which $R^2$ is a hydrogen atom, a methyl group or a benzyl group, and $R^3$ is a hydrogen atom;

(12) a compound in which $R^2$ is a hydrogen atom, and $R^3$ is a hydrogen atom;

(13) a compound in which $R^4$ is a hydrogen atom, a $C_1$–$C_4$ alkyl group, a benzyl group or a phenethyl group;

(14) a compound in which $R^4$ is a hydrogen atom, a methyl group or a benzyl group;

(15) a compound in which $R^4$ is a hydrogen atom;

(16) a compound in which $R^5$ is a substituted $C_3$–$C_6$ cycloalkyl group, pyrrolidinyl group or piperidinyl group [the substituent is essentially a group having the formula: —B—$ONO_2$ (wherein B represents a single bond, a methylene group, an ethylene group, a trimethylene group or a tetramethylene group) and optionally a methyl group];

(17) a compound in which $R^5$ is a substituted cyclopropyl group, cyclopentyl group or cyclohexyl group [the substituent is a group having the formula: —B—$ONO_2$ (wherein B represents a methylene group, an ethylene group, a trimethylene group or a tetramethylene group)];

(18) a compound in which $R^5$ is a substituted cyclopentyl group or cyclohexyl group [the substituent is a group having the formula: —B—$ONO_2$ (wherein B represents a methylene group, an ethylene group, a trimethylene group or a tetramethylene group)];

(19) a compound in which $R^5$ is a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyclohexyl group, a 3-, 4-, 5- or 6-nitroxymethylpiperidin-2-yl group or a 3-, 4-, 5- or 6-nitroxymethyl-1-methylpiperidin-2-yl group;

(20) a compound in which $R^5$ is a 2- or 3-nitroxymethylcyclopentyl group, a 2-, 3- or 4-nitroxycyclohexyl group, a 2-, 3- or 4-nitroxymethylcyclohexyl group, a 2-, 3- or 4-(2-nitroxyethyl)cyolohexyl group, a 2-, 3- or 4-(3-nitroxypropyl)cyclohexyl group or a 2-, 3- or 4-(4-nitroxybutyl)cyclohexyl group;

(21) a compound in which $R^5$ is a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl)cyclohexyl group;

(22) a compound in which $R^5$ is a 3- or 4-nitroxymethylcyclohexyl group, a 4-(2-nitroxyethyl)cyclohexyl group, a 4-(3-nitroxypropyl)cyclohexyl group or a 4-(4-nitroxybutyl)cyclohexyl group;

(23) a compound in which $R^5$ is a 4-nitroxymethylcyclohexyl group;

(24) a compound in which A is a single bond or a $C_1$–$C_2$ alkylene group;

(25) a compound in which A is a methylene group or an ethylene group; and

(26) a compound in which A is a methylene group.

Further, a combination of the compounds arbitrarily selected from the group consisting of (1)–(3), (4)–(6), (7)–(12), (13)–(15), (16)–(23) and (24)–(26) is also preferred, and includes, for example, those shown below.

(27) a compound in which W is a sulfur atom or an oxygen atom, and X is a group having the formula: —$NR^1$—; or X is a sulfur atom, and W is a group having the formula —$NR^1$—;

$R^1$ is a hydrogen atom, a $C_1$–$C_4$ alkyl group, a benzyl group or a phenethyl group;

$R^2$ and $R^3$ may be the same or different and each is a hydrogen atom, a $C_1$–$C_4$ alkyl group, a $C_1$–$C_4$ alkyl group substituted with phenyl (the phenyl may be optionally substituted with $C_1$–$C_4$ alkyl, $C_1$–$C_4$ alkoxy, hydroxy, halogen or nitro), a naphthylmethyl group, a phenyl group (the phenyl may be optionally substituted with $C_1$–$C_4$ alkyl, $C_1$–$C_4$ alkoxy, hydroxy, halogen or nitro), a naphthyl group, or a furyl, thienyl, pyridyl, oxazolyl, thiazolyl, isoxazolyl or isothiazolyl group which may be optionally substituted with $C_1$–$C_2$ alkyl, fluoro or chloro;

$R^4$ is a hydrogen atom, a $C_1$–$C_4$ alkyl group, a benzyl group or a phenethyl group;

$R^5$ is a substituted $C_3$–$C_6$ cycloalkyl group, pyrrolidinyl group or piperidinyl group [the substituent is essentially a group having the formula: —B—$ONO_2$ (wherein B represents a single bond, a methylene group, an ethylene group, a trimethylene group or a tetramethylene group) and optionally a methyl group]; and A is a single bond or a $C_1$–$C_2$ alkylene group;

(28) a compound in which W is a sulfur atom or an oxygen atom, and X is a group having the formula: —$NR^1$—;

$R^1$ is a hydrogen atom, a methyl group or a benzyl group;

$R^2$ and $R^3$ may be the same or different and each is a hydrogen atom, a methyl group, an ethyl group, a benzyl group which may be optionally substituted with methyl, methoxy, hydroxy, fluoro or chloro, a phenethyl group which may be optionally substituted with methyl, methoxy, hydroxy, fluoro or chloro, a phenyl group which may be optionally substituted with methyl, methoxy, hydroxy, fluoro or chloro, a furyl group, a thienyl group or a pyridyl group;

$R^4$ is a hydrogen atom, a methyl group or a benzyl group;

$R^5$ is a substituted $C_3$–$C_6$ cycloalkyl group, pyrrolidinyl group or piperidinyl group [the substituent is essentially a group having the formula: —B—$ONO_2$ (wherein B represents a single bond, a methylene group, an ethylene group, a trimethylene group or a tetramethylene group) and optionally a methyl group]; and A is a single bond or a $C_1$–$C_2$ alkylene group;

(29) a compound in which W is a sulfur atom, and X is a group having the formula: —$NR^1$—;

$R^1$ is a hydrogen atom, a methyl group or a benzyl group;

$R^2$ and $R^3$ may be the same or different and each is a hydrogen atom, a methyl group, an ethyl group, a benzyl group which may be optionally substituted with methyl, methoxy, hydroxy, fluoro or chloro, a phenethyl group which may be optionally substituted with methyl, methoxy, hydroxy, fluoro or chloro, a phenyl group which may be optionally substituted with methyl, methoxy, hydroxy, fluoro or chloro, a furyl group, a thienyl group or a pyridyl group;

$R^4$ is a hydrogen atom, a methyl group or a benzyl group;

$R^5$ is a substituted $C_3$–$C_6$ cycloalkyl group, pyrrolidinyl group or piperidinyl group [the substituent is essentially a group having the formula: —B—$ONO_2$ (wherein B represents a single bond, a methylene group, an ethylene group, a trimethylene group or a tetramethylene group) and optionally a methyl group]; and A is a single bond or a $C_1$–$C_2$ alkylene group;

(30) a compound in which W is a sulfur atom, and X is a group having the formula: —$NR^1$—;

$R^1$ is a hydrogen atom, a methyl group or a benzyl group;

$R^2$ is a hydrogen atom, a methyl group, an ethyl group, a benzyl group which may be optionally substituted with methyl, methoxy or hydroxyl or a phenyl group which may be optionally substituted with methyl or methoxy or a thienyl group, and $R^3$ is a hydrogen atom or $R^2$ and $R^3$ are a methyl group;

$R^4$ is a hydrogen atom, a methyl group or a benzyl group;

$R^5$ is a substituted cyclopropyl group, cyclopentyl group or cyclohexyl group [the substituent is a group having the formula: —B—$ONO_2$ (wherein B represents a methylene group, an ethylene group, a trimethylene group or a tetramethylene group)]; and A is a single bond or a $C_1$–$C_2$ alkylene group;

(31) a compound in which W is a sulfur atom, and X is a group having the formula: —$NR^1$—;

$R^1$ is a hydrogen atom, a methyl group or a benzyl group;

$R^2$ is a hydrogen atom, a methyl group, a benzyl group which may be optionally substituted with methyl or methoxy or a phenyl group, and $R^3$ is a hydrogen atom or $R^2$ and $R^3$ are a methyl group;

$R^4$ is a hydrogen atom, a methyl group or a benzyl group;

$R^5$ is a substituted cyclopentyl group or cyclohexyl group [the substituent is a group having the formula: —B—$ONO_2$ (wherein B represents a methylene group, an ethylene group, a trimethylene group or a tetramethylene group)]; and A is a single bond or a $C_1$–$C_2$ alkylene group;

(32) a compound in which W is a sulfur atom, and X is a group having the formula: —$NR^1$—;

$R^1$ is a hydrogen atom, a methyl group or a benzyl group;

$R^2$ is a hydrogen atom, a methyl group or a benzyl group;

$R^3$ is a hydrogen atom;

$R^4$ is a hydrogen atom, a methyl group or a benzyl group;

$R^5$ is a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyclohexyl group, a 3-, 4-, 5- or 6-nitroxymethylpiperidin-2-yl group or a 3-, 4-, 5- or 6-nitroxymethyl-1-methylpiperidin-2-yl group; and A is a single bond or a $C_1$–$C_2$ alkylene group;

(33) a compound in which W is a sulfur atom, and X is a group having the formula: —$NR^1$—;

$R^1$ is a hydrogen atom;

$R^2$ is a hydrogen atom, a methyl group or a benzyl group;

$R^3$ is a hydrogen atom;

$R^4$ is a hydrogen atom;

$R^5$ is a 2- or 3-nitroxymethylcyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group or a 2-, 3- or 4-(4-nitroxybutyl)cyclohexyl group; and A is a methylene group or an ethylene group;

(34) a compound in which W is a sulfur atom, and X is a group having the formula: —$NR^1$—;

$R^1$ is a hydrogen atom;

$R^2$ is a hydrogen atom, a methyl group or a benzyl group;

$R^3$ is a hydrogen atom;

$R^4$ is a hydrogen atom;

$R^5$ is a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl)cyclohexyl group; and A is a methylene group or an ethylene group;

(35) a compound in which W is a sulfur atom, and X is a group having the formula: —$NR^1$—;

$R^1$ is a hydrogen atom;

$R^2$ is a hydrogen atom;

$R^3$ is a hydrogen atom;

$R^4$ is a hydrogen atom;

$R^5$ is a 3- or 4-nitroxymethylcyclohexyl group, a 4-(2-nitroxyethyl)cyclohexyl group, a 4-(3-nitroxypropyl)cyclohexyl group or a 4-(4-nitroxybutyl)cyclohexyl group; and A is a methylene group; and

(36) a compound in which W is a sulfur atom, and X is a group having the formula: —$NR^1$—;

$R^1$ is a hydrogen atom;

$R^2$ is a hydrogen atom;

$R^3$ is a hydrogen atom;

$R^4$ is a hydrogen atom;

$R^5$ is a 4-nitroxymethylcyclohexyl group; and

A is a methylene group.

The preferred compounds having the general formula (I) can be specifically illustrated in Tables 1 and 2. The compounds shown in Table 1 and Table 2 have the structural formulae (I-1) and (I-2), respectively.

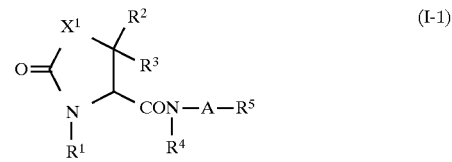

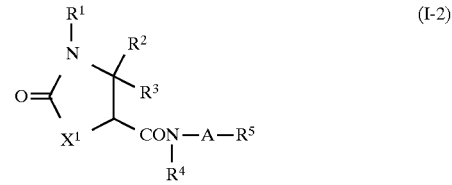

TABLE 1

| Compd. No. | $R^1$ | $R^2$ | $R^3$ | $R^4$ | $R^5$ | A | $X^1$ |
|---|---|---|---|---|---|---|---|
| 1-1 | H | H | H | H | 4-($ONO_2CH_2$)-$Hx^c$ | Single bond | S |
| 1-2 | Me | H | H | H | 4-($ONO_2CH_2$)-$Hx^c$ | Single bond | S |
| 1-3 | Et | H | H | H | 4-($ONO_2CH_2$)-$Hx^c$ | Single bond | S |
| 1-4 | Bz | H | H | H | 4-($ONO_2CH_2$)-$Hx^c$ | Single bond | S |
| 1-5 | H | Me | H | H | 4-($ONO_2CH_2$)-$Hx^c$ | Single bond | S |
| 1-6 | H | Et | H | H | 4-($ONO_2CH_2$)-$Hx^c$ | Single bond | S |
| 1-7 | H | Ph | H | H | 4-($ONO_2CH_2$)-$Hx^c$ | Single bond | S |
| 1-8 | H | 2-Then | H | H | 4-($ONO_2CH_2$)-$Hx^c$ | Single bond | S |
| 1-9 | H | 3-Then | H | H | 4-($ONO_2CH_2$)-$Hx^c$ | Single bond | S |
| 1-10 | H | 2-Fur | H | H | 4-($ONO_2CH_2$)-$Hx^c$ | Single bond | S |
| 1-11 | H | 3-Fur | H | H | 4-($ONO_2CH_2$)-$Hx^c$ | Single bond | S |
| 1-12 | H | 4-Me-Ph | H | H | 4-($ONO_2CH_2$)-$Hx^c$ | Single bond | S |
| 1-13 | H | 4-Cl-Ph | H | H | 4-($ONO_2CH_2$)-$Hx^c$ | Single bond | S |
| 1-14 | H | 4-MeO-Ph | H | H | 4-($ONO_2CH_2$)-$Hx^c$ | Single bond | S |
| 1-15 | H | 4-Thiz | H | H | 4-($ONO_2CH_2$)-$Hx^c$ | Single bond | S |
| 1-16 | H | 3-Pyr | H | H | 4-($ONO_2CH_2$)-$Hx^c$ | Single bond | S |
| 1-17 | H | Me | Me | H | 4-($ONO_2CH_2$)-$Hx^c$ | Single bond | S |
| 1-18 | Me | Me | Me | H | 4-($ONO_2CH_2$)-$Hx^c$ | Single bond | S |
| 1-19 | Me | Me | Me | Me | 4-($ONO_2CH_2$)-$Hx^c$ | Single bond | S |
| 1-20 | Et | Ph | H | H | 4-($ONO_2CH_2$)-$Hx^c$ | Single bond | S |
| 1-21 | Et | Et | H | Me | 4-($ONO_2CH_2$)-$Hx^c$ | Single bond | S |
| 1-22 | Bz | Me | H | Et | 4-($ONO_2CH_2$)-$Hx^c$ | Single bond | S |
| 1-23 | Bz | Ph | H | Et | 4-($ONO_2CH_2$)-$Hx^c$ | Single bond | S |
| 1-24 | Bu | H | H | H | 4-($ONO_2CH_2$)-$Hx^c$ | Single bond | S |
| 1-25 | H | 1-Np | H | H | 4-($ONO_2CH_2$)-$Hx^c$ | Single bond | S |
| 1-26 | H | H | H | Me | 4-($ONO_2CH_2$)-$Hx^c$ | Single bond | S |
| 1-27 | H | H | H | Bz | 4-($ONO_2CH_2$)-$Hx^c$ | Single bond | S |
| 1-28 | H | Bz | H | H | 4-($ONO_2CH_2$)-$Hx^c$ | Single bond | S |
| 1-29 | H | 4-Me-Bz | H | H | 4-($ONO_2CH_2$)-$Hx^c$ | Single bond | S |
| 1-30 | H | 4-OMe-Bz | H | H | 4-($ONO_2CH_2$)-$Hx^c$ | Single bond | S |
| 1-31 | H | 4-F-Bz | H | H | 4-($ONO_2CH_2$)-$Hx^c$ | Single bond | S |
| 1-32 | H | H | H | H | 4-($ONO_2CH_2$)-$Hx^c$ | $CH_2$ | S |
| 1-33 | Me | H | H | H | 4-($ONO_2CH_2$)-$Hx^c$ | $CH_2$ | S |
| 1-34 | Et | H | H | H | 4-($ONO_2CH_2$)-$Hx^c$ | $CH_2$ | S |
| 1-35 | Bz | H | H | H | 4-($ONO_2CH_2$)-$Hx^c$ | $CH_2$ | S |
| 1-36 | H | Me | H | H | 4-($ONO_2CH_2$)-$Hx^c$ | $CH_2$ | S |
| 1-37 | H | Et | H | H | 4-($ONO_2CH_2$)-$Hx^c$ | $CH_2$ | S |
| 1-38 | H | Ph | H | H | 4-($ONO_2CH_2$)-$Hx^c$ | $CH_2$ | S |
| 1-39 | H | 2-Then | H | H | 4-($ONO_2CH_2$)-$Hx^c$ | $CH_2$ | S |
| 1-40 | H | 3-Then | H | H | 4-($ONO_2CH_2$)-$Hx^c$ | $CH_2$ | S |
| 1-41 | H | 2-Fur | H | H | 4-($ONO_2CH_2$)-$Hx^c$ | $CH_2$ | S |
| 1-42 | H | 3-Fur | H | H | 4-($ONO_2CH_2$)-$Hx^c$ | $CH_2$ | S |
| 1-43 | H | 4-Me-Ph | H | H | 4-($ONO_2CH_2$)-$Hx^c$ | $CH_2$ | S |
| 1-44 | H | 4-Cl-Ph | H | H | 4-($ONO_2CH_2$)-$Hx^c$ | $CH_2$ | S |
| 1-45 | H | 4-MeO-Ph | H | H | 4-($ONO_2CH_2$)-$Hx^c$ | $CH_2$ | S |
| 1-46 | H | 4-Thiz | H | H | 4-($ONO_2CH_2$)-$Hx^c$ | $CH_2$ | S |
| 1-47 | H | 3-Pyr | H | H | 4-($ONO_2CH_2$)-$Hx^c$ | $CH_2$ | S |
| 1-48 | H | Me | Me | H | 4-($ONO_2CH_2$)-$Hx^c$ | $CH_2$ | S |
| 1-49 | Me | Me | Me | H | 4-($ONO_2CH_2$)-$Hx^c$ | $CH_2$ | S |
| 1-50 | Me | Me | Me | Me | 4-($ONO_2CH_2$)-$Hx^c$ | $CH_2$ | S |
| 1-51 | Et | Ph | H | H | 4-($ONO_2CH_2$)-$Hx^c$ | $CH_2$ | S |

TABLE 1-continued

| Compd. No. | R¹ | R² | R³ | R⁴ | R⁵ | A | X¹ |
|---|---|---|---|---|---|---|---|
| 1-52 | Et | Et | H | Me | 4-(ONO$_2$CH$_2$)-Hx$^c$ | CH$_2$ | S |
| 1-53 | Bz | Me | H | Et | 4-(ONO$_2$CH$_2$)-Hx$^c$ | CH$_2$ | S |
| 1-54 | Bz | Ph | H | Et | 4-(ONO$_2$CH$_2$)-Hx$^c$ | CH$_2$ | S |
| 1-55 | Bu | H | H | H | 4-(ONO$_2$CH$_2$)-Hx$^c$ | CH$_2$ | S |
| 1-56 | H | 1-Np | H | H | 4-(ONO$_2$CH$_2$)-Hx$^c$ | CH$_2$ | S |
| 1-57 | H | H | H | Me | 4-(ONO$_2$CH$_2$)-Hx$^c$ | CH$_2$ | S |
| 1-58 | H | H | H | Bz | 4-(ONO$_2$CH$_2$)-Hx$^c$ | CH$_2$ | S |
| 1-59 | H | Bz | H | H | 4-(ONO$_2$CH$_2$)-Hx$^c$ | CH$_2$ | S |
| 1-60 | H | 4-Me-Bz | H | H | 4-(ONO$_2$CH$_2$)-Hx$^c$ | CH$_2$ | S |
| 1-61 | H | 4-MeO-Bz | H | H | 4-(ONO$_2$CH$_2$)-Hx$^c$ | CH$_2$ | S |
| 1-62 | H | 4-F-Bz | H | H | 4-(ONO$_2$CH$_2$)-Hx$^c$ | CH$_2$ | S |
| 1-63 | H | 4-Cl-Bz | H | H | 4-(ONO$_2$CH$_2$)-Hx$^c$ | CH$_2$ | S |
| 1-64 | H | 4-OH-Bz | H | H | 4-(ONO$_2$CH$_2$)-Hx$^c$ | CH$_2$ | S |
| 1-65 | H | H | H | H | 4-(ONO$_2$CH$_2$)-Hx$^c$ | (CH$_2$)$_2$ | S |
| 1-66 | Me | H | H | H | 4-(ONO$_2$CH$_2$)-Hx$^c$ | (CH$_2$)$_2$ | S |
| 1-67 | Et | H | H | H | 4-(ONO$_2$CH$_2$)-Hx$^c$ | (CH$_2$)$_2$ | S |
| 1-68 | Bz | H | H | H | 4-(ONO$_2$CH$_2$)-Hx$^c$ | (CH$_2$)$_2$ | S |
| 1-69 | H | Me | H | H | 4-(ONO$_2$CH$_2$)-Hx$^c$ | (CH$_2$)$_2$ | S |
| 1-70 | H | Et | H | H | 4-(ONO$_2$CH$_2$)-Hx$^c$ | (CH$_2$)$_2$ | S |
| 1-71 | H | Ph | H | H | 4-(ONO$_2$CH$_2$)-Hx$^c$ | (CH$_2$)$_2$ | S |
| 1-72 | H | 2-Then | H | H | 4-(ONO$_2$CH$_2$)-Hx$^c$ | (CH$_2$)$_2$ | S |
| 1-73 | H | 3-Then | H | H | 4-(ONO$_2$CH$_2$)-Hx$^c$ | (CH$_2$)$_2$ | S |
| 1-74 | H | 2-Fur | H | H | 4-(ONO$_2$CH$_2$)-Hx$^c$ | (CH$_2$)$_2$ | S |
| 1-75 | H | 3-Fur | H | H | 4-(ONO$_2$CH$_2$)-Hx$^c$ | (CH$_2$)$_2$ | S |
| 1-76 | H | 4-Me-Ph | H | H | 4-(ONO$_2$CH$_2$)-Hx$^c$ | (CH$_2$)$_2$ | S |
| 1-77 | H | 4-Cl-Ph | H | H | 4-(ONO$_2$CH$_2$)-Hx$^c$ | (CH$_2$)$_2$ | S |
| 1-78 | H | 4-MeO-Ph | H | H | 4-(ONO$_2$CH$_2$)-Hx$^c$ | (CH$_2$)$_2$ | S |
| 1-79 | H | 4-Thiz | H | H | 4-(ONO$_2$CH$_2$)-Hx$^c$ | (CH$_2$)$_2$ | S |
| 1-80 | H | 3-Pyr | H | H | 4-(ONO$_2$CH$_2$)-Hx$^c$ | (CH$_2$)$_2$ | S |
| 1-81 | H | Me | Me | H | 4-(ONO$_2$CH$_2$)-Hx$^c$ | (CH$_2$)$_2$ | S |
| 1-82 | Me | Me | Me | H | 4-(ONO$_2$CH$_2$)-Hx$^c$ | (CH$_2$)$_2$ | S |
| 1-83 | Me | Me | Me | Me | 4-(ONO$_2$CH$_2$)-Hx$^c$ | (CH$_2$)$_2$ | S |
| 1-84 | Et | Ph | H | H | 4-(ONO$_2$CH$_2$)-Hx$^c$ | (CH$_2$)$_2$ | S |
| 1-85 | Et | Et | H | Me | 4-(ONO$_2$CH$_2$)-Hx$^c$ | (CH$_2$)$_2$ | S |
| 1-86 | Bz | Me | H | Et | 4-(ONO$_2$CH$_2$)-Hx$^c$ | (CH$_2$)$_2$ | S |
| 1-87 | Bz | Ph | H | Et | 4-(ONO$_2$CH$_2$)-Hx$^c$ | (CH$_2$)$_2$ | S |
| 1-88 | Bu | H | H | H | 4-(ONO$_2$CH$_2$)-Hx$^c$ | (CH$_2$)$_2$ | S |
| 1-89 | H | 1-Np | H | H | 4-(ONO$_2$CH$_2$)-Hx$^c$ | (CH$_2$)$_2$ | S |
| 1-90 | H | H | H | Me | 4-(ONO$_2$CH$_2$)-Hx$^c$ | (CH$_2$)$_2$ | S |
| 1-91 | H | H | H | Bz | 4-(ONO$_2$CH$_2$)-Hx$^c$ | (CH$_2$)$_2$ | S |
| 1-92 | H | Bz | H | H | 4-(ONO$_2$CH$_2$)-Hx$^c$ | (CH$_2$)$_2$ | S |
| 1-93 | H | 4-Me-Bz | H | H | 4-(ONO$_2$CH$_2$)-Hx$^c$ | (CH$_2$)$_2$ | S |
| 1-94 | H | 4-MeO-Bz | H | H | 4-(ONO$_2$CH$_2$)-Hx$^c$ | (CH$_2$)$_2$ | S |
| 1-95 | H | 4-F-Bz | H | H | 4-(ONO$_2$CH$_2$)-Hx$^c$ | (CH$_2$)$_2$ | S |
| 1-96 | H | H | H | H | 4-(ONO$_2$CH$_2$)-Hx$^c$ | (CH$_2$)$_3$ | S |
| 1-97 | H | Me | H | H | 4-(ONO$_2$CH$_2$)-Hx$^c$ | (CH$_2$)$_3$ | S |
| 1-98 | H | Bz | H | H | 4-(ONO$_2$CH$_2$)-Hx$^c$ | (CH$_2$)$_3$ | S |
| 1-99 | H | H | H | H | 4-(ONO$_2$CH$_2$)-Hx$^c$ | (CH$_2$)$_4$ | S |
| 1-100 | H | Me | H | H | 4-(ONO$_2$CH$_2$)-Hx$^c$ | (CH$_2$)$_4$ | S |
| 1-101 | H | H | H | H | 4-(ONO$_2$CH$_2$)-Hx$^c$ | (CH$_2$)$_5$ | S |
| 1-102 | H | Me | H | H | 4-(ONO$_2$CH$_2$)-Hx$^c$ | (CH$_2$)$_5$ | S |
| 1-103 | H | H | H | H | 4-(ONO$_2$CH$_2$)-Hx$^c$ | (CH$_2$)$_6$ | S |
| 1-104 | H | Me | H | H | 4-(ONO$_2$CH$_2$)-Hx$^c$ | (CH$_2$)$_6$ | S |
| 1-105 | H | H | H | H | 4-ONO$_2$-Hx$^c$ | single bond | S |
| 1-106 | Me | H | H | H | 4-ONO$_2$-Hx$^c$ | single bond | S |
| 1-107 | Et | H | H | H | 4-ONO$_2$-Hx$^c$ | single bond | S |
| 1-108 | Bz | H | H | H | 4-ONO$_2$-Hx$^c$ | single bond | S |
| 1-109 | H | Me | H | H | 4-ONO$_2$-Hx$^c$ | single bond | S |
| 1-110 | H | Et | H | H | 4-ONO$_2$-Hx$^c$ | single bond | S |
| 1-111 | H | Ph | H | H | 4-ONO$_2$-Hx$^c$ | single bond | S |
| 1-112 | H | Bz | H | H | 4-ONO$_2$-Hx$^c$ | single bond | S |
| 1-113 | H | 4-Me-Bz | H | H | 4-ONO$_2$-Hx$^c$ | single bond | S |
| 1-114 | H | 4-MeO-Bz | H | H | 4-ONO$_2$-Hx$^c$ | single bond | S |
| 1-115 | H | 4-F-Bz | H | H | 4-ONO$_2$-Hx$^c$ | single bond | S |
| 1-116 | H | 2-Then | H | H | 4-ONO$_2$-Hx$^c$ | single bond | S |
| 1-117 | H | 3-Then | H | H | 4-ONO$_2$-Hx$^c$ | single bond | S |
| 1-118 | H | 2-Fur | H | H | 4-ONO$_2$-Hx$^c$ | single bond | S |
| 1-119 | H | 3-Fur | H | H | 4-ONO$_2$-Hx$^c$ | single bond | S |
| 1-120 | H | 3-Pyr | H | H | 4-ONO$_2$-Hx$^c$ | single bond | S |
| 1-121 | H | H | H | Me | 4-ONO$_2$-Hx$^c$ | single bond | S |
| 1-122 | H | H | H | Et | 4-ONO$_2$-Hx$^c$ | single bond | S |
| 1-123 | H | H | H | Bz | 4-ONO$_2$-Hx$^c$ | single bond | S |
| 1-124 | H | H | H | H | 4-[ONO$_2$(CH$_2$)$_2$]-Hx$^c$ | single bond | S |
| 1-125 | H | Me | H | H | 4-[ONO$_2$(CH$_2$)$_2$]-Hx$^c$ | single bond | S |
| 1-126 | H | Et | H | H | 4-[ONO$_2$(CH$_2$)$_2$]-Hx$^c$ | single bond | S |
| 1-127 | H | Ph | H | H | 4-[ONO$_2$(CH$_2$)$_2$]-Hx$^c$ | single bond | S |

TABLE 1-continued

| Compd. No. | R¹ | R² | R³ | R⁴ | R⁵ | A | X¹ |
|---|---|---|---|---|---|---|---|
| 1-128 | H | Bz | H | H | 4-[ONO$_2$(CH$_2$)$_2$]-Hx$^c$ | single bond | S |
| 1-129 | H | 4-Me-Bz | H | H | 4-[ONO$_2$(CH$_2$)$_2$]-Hx$^c$ | single bond | S |
| 1-130 | H | 4-MeO-Bz | H | H | 4-[ONO$_2$(CH$_2$)$_2$]-Hx$^c$ | single bond | S |
| 1-131 | H | 4-F-Bz | H | H | 4-[ONO$_2$(CH$_2$)$_2$]-Hx$^c$ | single bond | S |
| 1-132 | H | 2-Then | H | H | 4-[ONO$_2$(CH$_2$)$_2$]-Hx$^c$ | single bond | S |
| 1-133 | H | 3-Then | H | H | 4-[ONO$_2$(CH$_2$)$_2$]-Hx$^c$ | single bond | S |
| 1-134 | H | 2-Fur | H | H | 4-[ONO$_2$(CH$_2$)$_2$]-Hx$^c$ | single bond | S |
| 1-135 | H | 3-Fur | H | H | 4-[ONO$_2$(CH$_2$)$_2$]-Hx$^c$ | single bond | S |
| 1-136 | H | 3-Pyr | H | H | 4-[ONO$_2$(CH$_2$)$_2$]-Hx$^c$ | single bond | S |
| 1-137 | H | 4-Thiz | H | H | 4-[ONO$_2$(CH$_2$)$_2$]-Hx$^c$ | single bond | S |
| 1-138 | H | H | H | H | 4-ONO$_2$-Hx$^c$ | CH$_2$ | S |
| 1-139 | Me | H | H | H | 4-ONO$_2$-Hx$^c$ | CH$_2$ | S |
| 1-140 | Et | H | H | H | 4-ONO$_2$-Hx$^c$ | CH$_2$ | S |
| 1-141 | Bz | H | H | H | 4-ONO$_2$-Hx$^c$ | CH$_2$ | S |
| 1-142 | H | Me | H | H | 4-ONO$_2$-Hx$^c$ | CH$_2$ | S |
| 1-143 | H | Et | H | H | 4-ONO$_2$-Hx$^c$ | CH$_2$ | S |
| 1-144 | H | Ph | H | H | 4-ONO$_2$-Hx$^c$ | CH$_2$ | S |
| 1-145 | H | 2-Then | H | H | 4-ONO$_2$-Hx$^c$ | CH$_2$ | S |
| 1-146 | H | 3-Then | H | H | 4-ONO$_2$-Hx$^c$ | CH$_2$ | S |
| 1-147 | H | 2-Fur | H | H | 4-ONO$_2$-Hx$^c$ | CH$_2$ | S |
| 1-148 | H | 3-Fur | H | H | 4-ONO$_2$-Hx$^c$ | CH$_2$ | S |
| 1-149 | H | 4-Me-Ph | H | H | 4-ONO$_2$-Hx$^c$ | CH$_2$ | S |
| 1-150 | H | 4-Cl-Ph | H | H | 4-ONO$_2$-Hx$^c$ | CH$_2$ | S |
| 1-151 | H | 4-MeO-Ph | H | H | 4-ONO$_2$-Hx$^c$ | CH$_2$ | S |
| 1-152 | H | 4-Thiz | H | H | 4-ONO$_2$-Hx$^c$ | CH$_2$ | S |
| 1-153 | H | 3-Pyr | H | H | 4-ONO$_2$-Hx$^c$ | CH$_2$ | S |
| 1-154 | H | Me | Me | H | 4-ONO$_2$-Hx$^c$ | CH$_2$ | S |
| 1-155 | Me | Me | Me | H | 4-ONO$_2$-Hx$^c$ | CH$_2$ | S |
| 1-156 | Me | Me | Me | Me | 4-ONO$_2$-Hx$^c$ | CH$_2$ | S |
| 1-157 | Et | Ph | H | H | 4-ONO$_2$-Hx$^c$ | CH$_2$ | S |
| 1-158 | Et | Et | H | Me | 4-ONO$_2$-Hx$^c$ | CH$_2$ | S |
| 1-159 | Bz | Me | H | Et | 4-ONO$_2$-Hx$^c$ | CH$_2$ | S |
| 1-160 | Bz | Ph | H | Et | 4-ONO$_2$-Hx$^c$ | CH$_2$ | S |
| 1-161 | Bu | H | H | H | 4-ONO$_2$-Hx$^c$ | CH$_2$ | S |
| 1-162 | H | 1-Np | H | H | 4-ONO$_2$-Hx$^c$ | CH$_2$ | S |
| 1-163 | H | H | H | Me | 4-ONO$_2$-Hx$^c$ | CH$_2$ | S |
| 1-164 | H | H | H | Bz | 4-ONO$_2$-Hx$^c$ | CH$_2$ | S |
| 1-165 | H | Bz | H | H | 4-ONO$_2$-Hx$^c$ | CH$_2$ | S |
| 1-166 | H | 4-Me-Bz | H | H | 4-ONO$_2$-Hx$^c$ | CH$_2$ | S |
| 1-167 | H | 4-MeO-Bz | H | H | 4-ONO$_2$-Hx$^c$ | CH$_2$ | S |
| 1-168 | H | 4-F-Bz | H | H | 4-ONO$_2$-Hx$^c$ | CH$_2$ | S |
| 1-169 | H | H | H | H | 4-[ONO$_2$(CH$_2$)$_2$]-Hx$^c$ | CH$_2$ | S |
| 1-170 | H | Me | H | H | 4-[ONO$_2$(CH$_2$)$_2$]-Hx$^c$ | CH$_2$ | S |
| 1-171 | H | Et | H | H | 4-[ONO$_2$(CH$_2$)$_2$]-Hx$^c$ | CH$_2$ | S |
| 1-172 | H | Ph | H | H | 4-[ONO$_2$(CH$_2$)$_2$]-Hx$^c$ | CH$_2$ | S |
| 1-173 | H | 2-Then | H | H | 4-[ONO$_2$(CH$_2$)$_2$]-Hx$^c$ | CH$_2$ | S |
| 1-174 | H | 3-Then | H | H | 4-[ONO$_2$(CH$_2$)$_2$]-Hx$^c$ | CH$_2$ | S |
| 1-175 | H | 2-Fur | H | H | 4-[ONO$_2$(CH$_2$)$_2$]-Hx$^c$ | CH$_2$ | S |
| 1-176 | H | 3-Fur | H | H | 4-[ONO$_2$(CH$_2$)$_2$]-Hx$^c$ | CH$_2$ | S |
| 1-177 | H | 3-Py | H | H | 4-[ONO$_2$(CH$_2$)$_2$]-Hx$^c$ | CH$_2$ | S |
| 1-178 | H | Bz | H | H | 4-[ONO$_2$(CH$_2$)$_2$]-Hx$^c$ | CH$_2$ | S |
| 1-179 | H | 4-Me-Bz | H | H | 4-[ONO$_2$(CH$_2$)$_2$]-Hx$^c$ | CH$_2$ | S |
| 1-180 | H | 4-MeO-Bz | H | H | 4-[ONO$_2$(CH$_2$)$_2$]-Hx$^c$ | CH$_2$ | S |
| 1-181 | H | 4-F-Bz | H | H | 4-[ONO$_2$(CH$_2$)$_2$]-Hx$^c$ | CH$_2$ | S |
| 1-182 | H | Me | Me | H | 4-[ONO$_2$(CH$_2$)$_2$]-Hx$^c$ | CH$_2$ | S |
| 1-183 | Me | Me | Me | H | 4-[ONO$_2$(CH$_2$)$_2$]-Hx$^c$ | CH$_2$ | S |
| 1-184 | Bz | Me | H | Et | 4-[ONO$_2$(CH$_2$)$_2$]-Hx$^c$ | CH$_2$ | S |
| 1-185 | Bu | H | H | H | 4-[ONO$_2$(CH$_2$)$_2$]-Hx$^c$ | CH$_2$ | S |
| 1-186 | H | 1-Np | H | H | 4-[ONO$_2$(CH$_2$)$_2$]-Hx$^c$ | CH$_2$ | S |
| 1-187 | H | H | H | Me | 4-[ONO$_2$(CH$_2$)$_2$]-Hx$^c$ | CH$_2$ | S |
| 1-188 | H | H | H | Bz | 4-[ONO$_2$(CH$_2$)$_2$]-Hx$^c$ | CH$_2$ | S |
| 1-189 | H | H | H | H | 4-[ONO$_2$(CH$_2$)$_2$]-Hx$^c$ | (CH$_2$)$_2$ | S |
| 1-190 | H | Me | H | H | 4-[ONO$_2$(CH$_2$)$_2$]-Hx$^c$ | (CH$_2$)$_2$ | S |
| 1-191 | H | Et | H | H | 4-[ONO$_2$(CH$_2$)$_2$]-Hx$^c$ | (CH$_2$)$_2$ | S |
| 1-192 | H | Ph | H | H | 4-[ONO$_2$(CH$_2$)$_2$]-Hx$^c$ | (CH$_2$)$_2$ | S |
| 1-193 | H | 2-Then | H | H | 4-[ONO$_2$(CH$_2$)$_2$]-Hx$^c$ | (CH$_2$)$_2$ | S |
| 1-194 | H | 3-Then | H | H | 4-[ONO$_2$(CH$_2$)$_2$]-Hx$^c$ | (CH$_2$)$_2$ | S |
| 1-195 | H | 2-Fur | H | H | 4-[ONO$_2$(CH$_2$)$_2$]-Hx$^c$ | (CH$_2$)$_2$ | S |
| 1-196 | H | 3-Fur | H | H | 4-[ONO$_2$(CH$_2$)$_2$]-Hx$^c$ | (CH$_2$)$_2$ | S |
| 1-197 | H | 3-Py | H | H | 4-[ONO$_2$(CH$_2$)$_2$]-Hx$^c$ | (CH$_2$)$_2$ | S |
| 1-198 | H | Bz | H | H | 4-[ONO$_2$(CH$_2$)$_2$]-Hx$^c$ | (CH$_2$)$_2$ | S |
| 1-199 | H | 4-Me-Bz | H | H | 4-[ONO$_2$(CH$_2$)$_2$]-Hx$^c$ | (CH$_2$)$_2$ | S |
| 1-200 | H | 4-MeO-Bz | H | H | 4-[ONO$_2$(CH$_2$)$_2$]-Hx$^c$ | (CH$_2$)$_2$ | S |
| 1-201 | H | 4-F-Bz | H | H | 4-[ONO$_2$(CH$_2$)$_2$]-Hx$^c$ | (CH$_2$)$_2$ | S |
| 1-202 | H | Me | Me | H | 4-[ONO$_2$(CH$_2$)$_2$]-Hx$^c$ | (CH$_2$)$_2$ | S |
| 1-203 | Bu | H | H | H | 4-[ONO$_2$(CH$_2$)$_2$]-Hx$^c$ | (CH$_2$)$_2$ | S |

TABLE 1-continued

| Compd. No. | R¹ | R² | R³ | R⁴ | R⁵ | A | X¹ |
|---|---|---|---|---|---|---|---|
| 1-204 | H | 1-Np | H | H | 4-[ONO$_2$(CH$_2$)$_2$]-Hx$^c$ | (CH$_2$)$_2$ | S |
| 1-205 | H | H | H | Me | 4-[ONO$_2$(CH$_2$)$_2$]-Hx$^c$ | (CH$_2$)$_2$ | S |
| 1-206 | H | H | H | Bz | 4-[ONO$_2$(CH$_2$)$_2$]-Hx$^c$ | (CH$_2$)$_2$ | S |
| 1-207 | H | H | H | H | 4-[ONO$_2$(CH$_2$)$_3$]-Hx$^c$ | (CH$_2$)$_2$ | S |
| 1-208 | H | Me | H | H | 4-[ONO$_2$(CH$_2$)$_3$]-Hx$^c$ | (CH$_2$)$_2$ | S |
| 1-209 | H | Bz | H | H | 4-[ONO$_2$(CH$_2$)$_3$]-Hx$^c$ | (CH$_2$)$_2$ | S |
| 1-210 | H | H | H | H | 4-[ONO$_2$(CH$_2$)$_4$]-Hx$^c$ | (CH$_2$)$_2$ | S |
| 1-211 | H | Me | H | H | 4-[ONO$_2$(CH$_2$)$_4$]-Hx$^c$ | (CH$_2$)$_2$ | S |
| 1-212 | H | Bz | H | H | 4-[ONO$_2$(CH$_2$)$_4$]-Hx$^c$ | (CH$_2$)$_2$ | S |
| 1-213 | H | H | H | H | 4-[ONO$_2$(CH$_2$)$_5$]-Hx$^c$ | (CH$_2$)$_2$ | S |
| 1-214 | H | Me | H | H | 4-[ONO$_2$(CH$_2$)$_5$]-Hx$^c$ | (CH$_2$)$_2$ | S |
| 1-215 | H | Bz | H | H | 4-[ONO$_2$(CH$_2$)$_5$]-Hx$^c$ | (CH$_2$)$_2$ | S |
| 1-216 | H | H | H | H | 4-[ONO$_2$(CH$_2$)$_6$]-Hx$^c$ | (CH$_2$)$_2$ | S |
| 1-217 | H | Me | H | H | 4-[ONO$_2$(CH$_2$)$_6$]-Hx$^c$ | (CH$_2$)$_2$ | S |
| 1-218 | H | Bz | H | H | 4-[ONO$_2$(CH$_2$)$_6$]-Hx$^c$ | (CH$_2$)$_2$ | S |
| 1-219 | H | H | H | H | 4-ONO$_2$-Hx$^c$ | (CH$_2$)$_2$ | S |
| 1-220 | Me | H | H | H | 4-ONO$_2$-Hx$^c$ | (CH$_2$)$_2$ | S |
| 1-221 | Bz | H | H | H | 4-ONO$_2$-Hx$^c$ | (CH$_2$)$_2$ | S |
| 1-222 | H | Me | H | H | 4-ONO$_2$-Hx$^c$ | (CH$_2$)$_2$ | S |
| 1-223 | H | Et | H | H | 4-ONO$_2$-Hx$^c$ | (CH$_2$)$_2$ | S |
| 1-224 | H | Ph | H | H | 4-ONO$_2$-Hx$^c$ | (CH$_2$)$_2$ | S |
| 1-225 | H | 2-Then | H | H | 4-ONO$_2$-Hx$^c$ | (CH$_2$)$_2$ | S |
| 1-226 | H | 3-Then | H | H | 4-ONO$_2$-Hx$^c$ | (CH$_2$)$_2$ | S |
| 1-227 | H | 2-Fur | H | H | 4-ONO$_2$-Hx$^c$ | (CH$_2$)$_2$ | S |
| 1-228 | H | 3-Fur | H | H | 4-ONO$_2$-Hx$^c$ | (CH$_2$)$_2$ | S |
| 1-229 | H | 4-Me-Ph | H | H | 4-ONO$_2$-Hx$^c$ | (CH$_2$)$_2$ | S |
| 1-230 | H | 4-Cl-Ph | H | H | 4-ONO$_2$-Hx$^c$ | (CH$_2$)$_2$ | S |
| 1-231 | H | 4-MeO-Ph | H | H | 4-ONO$_2$-Hx$^c$ | (CH$_2$)$_2$ | S |
| 1-232 | H | 4-Thiz | H | H | 4-ONO$_2$-Hx$^c$ | (CH$_2$)$_2$ | S |
| 1-233 | H | 3-Pyr | H | H | 4-ONO$_2$-Hx$^c$ | (CH$_2$)$_2$ | S |
| 1-234 | H | Me | Me | H | 4-ONO$_2$-Hx$^c$ | (CH$_2$)$_2$ | S |
| 1-235 | Bu | H | H | H | 4-ONO$_2$-Hx$^c$ | (CH$_2$)$_2$ | S |
| 1-236 | H | 1-Np | H | H | 4-ONO$_2$-Hx$^c$ | (CH$_2$)$_2$ | S |
| 1-237 | H | H | H | Me | 4-ONO$_2$-Hx$^c$ | (CH$_2$)$_2$ | S |
| 1-238 | H | H | H | Bz | 4-ONO$_2$-Hx$^c$ | (CH$_2$)$_2$ | S |
| 1-239 | H | Bz | H | H | 4-ONO$_2$-Hx$^c$ | (CH$_2$)$_2$ | S |
| 1-240 | H | 4-Me-Bz | H | H | 4-ONO$_2$-Hx$^c$ | (CH$_2$)$_2$ | S |
| 1-241 | H | 4-MeO-Bz | H | H | 4-ONO$_2$-Hx$^c$ | (CH$_2$)$_2$ | S |
| 1-242 | H | 4-F-Bz | H | H | 4-ONO$_2$-Hx$^c$ | (CH$_2$)$_2$ | S |
| 1-243 | H | H | H | H | 4-ONO$_2$-Hx$^c$ | (CH$_2$)$_3$ | S |
| 1-244 | H | Me | H | H | 4-ONO$_2$-Hx$^c$ | (CH$_2$)$_3$ | S |
| 1-245 | H | H | H | H | 4-ONO$_2$-Hx$^c$ | (CH$_2$)$_4$ | S |
| 1-246 | H | Me | H | H | 4-ONO$_2$-Hx$^c$ | (CH$_2$)$_4$ | S |
| 1-247 | H | H | H | H | 4-ONO$_2$-Hx$^c$ | (CH$_2$)$_5$ | S |
| 1-248 | H | Me | H | H | 4-ONO$_2$-Hx$^c$ | (CH$_2$)$_5$ | S |
| 1-249 | H | H | H | H | 4-ONO$_2$-Hx$^c$ | (CH$_2$)$_6$ | S |
| 1-250 | H | Me | H | H | 4-ONO$_2$-Hx$^c$ | (CH$_2$)$_6$ | S |
| 1-251 | H | H | H | H | 4-(ONO$_2$CH$_2$)-Hx$^c$ | single bond | O |
| 1-252 | Me | H | H | H | 4-(ONO$_2$CH$_2$)-Hx$^c$ | single bond | O |
| 1-253 | Et | H | H | H | 4-(ONO$_2$CH$_2$)-Hx$^c$ | single bond | O |
| 1-254 | Bz | H | H | H | 4-(ONO$_2$CH$_2$)-Hx$^c$ | single bond | O |
| 1-255 | H | Me | H | H | 4-(ONO$_2$CH$_2$)-Hx$^c$ | single bond | O |
| 1-256 | H | Et | H | H | 4-(ONO$_2$CH$_2$)-Hx$^c$ | single bond | O |
| 1-257 | H | Ph | H | H | 4-(ONO$_2$CH$_2$)-Hx$^c$ | single bond | O |
| 1-258 | H | 2-Then | H | H | 4-(ONO$_2$CH$_2$)-Hx$^c$ | single bond | O |
| 1-259 | H | 3-Then | H | H | 4-(ONO$_2$CH$_2$)-Hx$^c$ | single bond | O |
| 1-260 | H | 2-Fur | H | H | 4-(ONO$_2$CH$_2$)-Hx$^c$ | single bond | O |
| 1-261 | H | 3-Fur | H | H | 4-(ONO$_2$CH$_2$)-Hx$^c$ | single bond | O |
| 1-262 | H | 4-Me-Ph | H | H | 4-(ONO$_2$CH$_2$)-Hx$^c$ | single bond | O |
| 1-263 | H | 4-Cl-Ph | H | H | 4-(ONO$_2$CH$_2$)-Hx$^c$ | single bond | O |
| 1-264 | H | 4-MeO-Ph | H | H | 4-(ONO$_2$CH$_2$)-Hx$^c$ | single bond | O |
| 1-265 | H | 4-Thiz | H | H | 4-(ONO$_2$CH$_2$)-Hx$^c$ | single bond | O |
| 1-266 | H | 3-Pyr | H | H | 4-(ONO$_2$CH$_2$)-Hx$^c$ | single bond | O |
| 1-267 | H | Me | Me | H | 4-(ONO$_2$CH$_2$)-Hx$^c$ | single bond | O |
| 1-268 | Me | Me | Me | H | 4-(ONO$_2$CH$_2$)-Hx$^c$ | single bond | O |
| 1-269 | Me | Me | Me | Me | 4-(ONO$_2$CH$_2$)-Hx$^c$ | single bond | O |
| 1-270 | Et | Ph | H | H | 4-(ONO$_2$CH$_2$)-Hx$^c$ | single bond | O |
| 1-271 | Et | Et | H | Me | 4-(ONO$_2$CH$_2$)-Hx$^c$ | single bond | O |
| 1-272 | Bz | Me | H | Et | 4-(ONO$_2$CH$_2$)-Hx$^c$ | single bond | O |
| 1-273 | Bz | Ph | H | Et | 4-(ONO$_2$CH$_2$)-Hx$^c$ | single bond | O |
| 1-274 | Bu | H | H | H | 4-(ONO$_2$CH$_2$)-Hx$^c$ | single bond | O |
| 1-275 | H | 1-Np | H | H | 4-(ONO$_2$CH$_2$)-Hx$^c$ | single bond | O |
| 1-276 | H | H | H | Me | 4-(ONO$_2$CH$_2$)-Hx$^c$ | single bond | O |
| 1-277 | H | H | H | Bz | 4-(ONO$_2$CH$_2$)-Hx$^c$ | single bond | O |
| 1-278 | H | Bz | H | H | 4-(ONO$_2$CH$_2$)-Hx$^c$ | single bond | O |
| 1-279 | H | 4-Me-Bz | H | H | 4-(ONO$_2$CH$_2$)-Hx$^c$ | single bond | O |

TABLE 1-continued

| Compd. No. | R¹ | R² | R³ | R⁴ | R⁵ | A | X¹ |
|---|---|---|---|---|---|---|---|
| 1-280 | H | 4-OMe-Bz | H | H | 4-(ONO$_2$CH$_2$)-Hx$^c$ | single bond | O |
| 1-281 | H | 4-F-Bz | H | H | 4-(ONO$_2$CH$_2$)-Hx$^c$ | single bond | O |
| 1-282 | H | H | H | H | 4-(ONO$_2$CH$_2$)-Hx$^c$ | CH$_2$ | O |
| 1-283 | Me | H | H | H | 4-(ONO$_2$CH$_2$)-Hx$^c$ | CH$_2$ | O |
| 1-284 | Et | H | H | H | 4-(ONO$_2$CH$_2$)-Hx$^c$ | CH$_2$ | O |
| 1-285 | Bz | H | H | H | 4-(ONO$_2$CH$_2$)-Hx$^c$ | CH$_2$ | O |
| 1-286 | H | Me | H | H | 4-(ONO$_2$CH$_2$)-Hx$^c$ | CH$_2$ | O |
| 1-287 | H | Et | H | H | 4-(ONO$_2$CH$_2$)-Hx$^c$ | CH$_2$ | O |
| 1-288 | H | Ph | H | H | 4-(ONO$_2$CH$_2$)-Hx$^c$ | CH$_2$ | O |
| 1-289 | H | 2-Then | H | H | 4-(ONO$_2$CH$_2$)-Hx$^c$ | CH$_2$ | O |
| 1-290 | H | 3-Then | H | H | 4-(ONO$_2$CH$_2$)-Hx$^c$ | CH$_2$ | O |
| 1-291 | H | 2-Fur | H | H | 4-(ONO$_2$CH$_2$)-Hx$^c$ | CH$_2$ | O |
| 1-292 | H | 3-Fur | H | H | 4-(ONO$_2$CH$_2$)-Hx$^c$ | CH$_2$ | O |
| 1-293 | H | 4-Me-Ph | H | H | 4-(ONO$_2$CH$_2$)-Hx$^c$ | CH$_2$ | O |
| 1-294 | H | 4-Cl-Ph | H | H | 4-(ONO$_2$CH$_2$)-Hx$^c$ | CH$_2$ | O |
| 1-295 | H | 4-MeO-Ph | H | H | 4-(ONO$_2$CH$_2$)-Hx$^c$ | CH$_2$ | O |
| 1-296 | H | 4-Thiz | H | H | 4-(ONO$_2$CH$_2$)-Hx$^c$ | CH$_2$ | O |
| 1-297 | H | 3-Pyr | H | H | 4-(ONO$_2$CH$_2$)-Hx$^c$ | CH$_2$ | O |
| 1-298 | H | Me | Me | H | 4-(ONO$_2$CH$_2$)-Hx$^c$ | CH$_2$ | O |
| 1-299 | Me | Me | Me | H | 4-(ONO$_2$CH$_2$)-Hx$^c$ | CH$_2$ | O |
| 1-300 | Me | Me | Me | Me | 4-(ONO$_2$CH$_2$)-Hx$^c$ | CH$_2$ | O |
| 1-301 | Et | Ph | H | H | 4-(ONO$_2$CH$_2$)-Hx$^c$ | CH$_2$ | O |
| 1-302 | Et | Et | H | Me | 4-(ONO$_2$CH$_2$)-Hx$^c$ | CH$_2$ | O |
| 1-303 | Bz | Me | H | Et | 4-(ONO$_2$CH$_2$)-Hx$^c$ | CH$_2$ | O |
| 1-304 | Bz | Ph | H | Et | 4-(ONO$_2$CH$_2$)-Hx$^c$ | CH$_2$ | O |
| 1-305 | Bu | H | H | H | 4-(ONO$_2$CH$_2$)-Hx$^c$ | CH$_2$ | O |
| 1-306 | H | 1-Np | H | H | 4-(ONO$_2$CH$_2$)-Hx$^c$ | CH$_2$ | O |
| 1-307 | H | H | H | Me | 4-(ONO$_2$CH$_2$)-Hx$^c$ | CH$_2$ | O |
| 1-308 | H | H | H | Bz | 4-(ONO$_2$CH$_2$)-Hx$^c$ | CH$_2$ | O |
| 1-309 | H | Bz | H | H | 4-(ONO$_2$CH$_2$)-Hx$^c$ | CH$_2$ | O |
| 1-310 | H | 4-Me-Bz | H | H | 4-(ONO$_2$CH$_2$)-Hx$^c$ | CH$_2$ | O |
| 1-311 | H | 4-MeO-Bz | H | H | 4-(ONO$_2$CH$_2$)-Hx$^c$ | CH$_2$ | O |
| 1-312 | H | 4-F-Bz | H | H | 4-(ONO$_2$CH$_2$)-Hx$^c$ | CH$_2$ | O |
| 1-313 | H | 4-Cl-Bz | H | H | 4-(ONO$_2$CH$_2$)-Hx$^c$ | CH$_2$ | O |
| 1-314 | H | 4-OH-Bz | H | H | 4-(ONO$_2$CH$_2$)-Hx$^c$ | CH$_2$ | O |
| 1-315 | H | H | H | H | 4-(ONO$_2$CH$_2$)-Hx$^c$ | (CH$_2$)$_2$ | O |
| 1-316 | Me | H | H | H | 4-(ONO$_2$CH$_2$)-Hx$^c$ | (CH$_2$)$_2$ | O |
| 1-317 | Et | H | H | H | 4-(ONO$_2$CH$_2$)-Hx$^c$ | (CH$_2$)$_2$ | O |
| 1-318 | Bz | H | H | H | 4-(ONO$_2$CH$_2$)-Hx$^c$ | (CH$_2$)$_2$ | O |
| 1-319 | H | Me | H | H | 4-(ONO$_2$CH$_2$)-Hx$^c$ | (CH$_2$)$_2$ | O |
| 1-320 | H | Et | H | H | 4-(ONO$_2$CH$_2$)-Hx$^c$ | (CH$_2$)$_2$ | O |
| 1-321 | H | Ph | H | H | 4-(ONO$_2$CH$_2$)-Hx$^c$ | (CH$_2$)$_2$ | O |
| 1-322 | H | 2-Then | H | H | 4-(ONO$_2$CH$_2$)-Hx$^c$ | (CH$_2$)$_2$ | O |
| 1-323 | H | 3-Then | H | H | 4-(ONO$_2$CH$_2$)-Hx$^c$ | (CH$_2$)$_2$ | O |
| 1-324 | H | 2-Fur | H | H | 4-(ONO$_2$CH$_2$)-Hx$^c$ | (CH$_2$)$_2$ | O |
| 1-325 | H | 3-Fur | H | H | 4-(ONO$_2$CH$_2$)-Hx$^c$ | (CH$_2$)$_2$ | O |
| 1-326 | H | 4-Me-Ph | H | H | 4-(ONO$_2$CH$_2$)-Hx$^c$ | (CH$_2$)$_2$ | O |
| 1-327 | H | 4-Cl-Ph | H | H | 4-(ONO$_2$CH$_2$)-Hx$^c$ | (CH$_2$)$_2$ | O |
| 1-328 | H | 4-MeO-Ph | H | H | 4-(ONO$_2$CH$_2$)-Hx$^c$ | (CH$_2$)$_2$ | O |
| 1-329 | H | 4-Thiz | H | H | 4-(ONO$_2$CH$_2$)-Hx$^c$ | (CH$_2$)$_2$ | O |
| 1-330 | H | 3-Pyr | H | H | 4-(ONO$_2$CH$_2$)-Hx$^c$ | (CH$_2$)$_2$ | O |
| 1-331 | H | Me | Me | H | 4-(ONO$_2$CH$_2$)-Hx$^c$ | (CH$_2$)$_2$ | O |
| 1-332 | Me | Me | Me | H | 4-(ONO$_2$CH$_2$)-Hx$^c$ | (CH$_2$)$_2$ | O |
| 1-333 | Me | Me | Me | Me | 4-(ONO$_2$CH$_2$)-Hx$^c$ | (CH$_2$)$_2$ | O |
| 1-334 | Et | Ph | H | H | 4-(ONO$_2$CH$_2$)-Hx$^c$ | (CH$_2$)$_2$ | O |
| 1-335 | Et | Et | H | Me | 4-(ONO$_2$CH$_2$)-Hx$^c$ | (CH$_2$)$_2$ | O |
| 1-336 | Bz | Me | H | Et | 4-(ONO$_2$CH$_2$)-Hx$^c$ | (CH$_2$)$_2$ | O |
| 1-337 | Bz | Ph | H | Et | 4-(ONO$_2$CH$_2$)-Hx$^c$ | (CH$_2$)$_2$ | O |
| 1-338 | Bu | H | H | H | 4-(ONO$_2$CH$_2$)-Hx$^c$ | (CH$_2$)$_2$ | O |
| 1-339 | H | 1-Np | H | H | 4-(ONO$_2$CH$_2$)-Hx$^c$ | (CH$_2$)$_2$ | O |
| 1-340 | H | H | H | Me | 4-(ONO$_2$CH$_2$)-Hx$^c$ | (CH$_2$)$_2$ | O |
| 1-341 | H | H | H | Bz | 4-(ONO$_2$CH$_2$)-Hx$^c$ | (CH$_2$)$_2$ | O |
| 1-342 | H | Bz | H | H | 4-(ONO$_2$CH$_2$)-Hx$^c$ | (CH$_2$)$_2$ | O |
| 1-343 | H | 4-Me-Bz | H | H | 4-(ONO$_2$CH$_2$)-Hx$^c$ | (CH$_2$)$_2$ | O |
| 1-344 | H | 4-MeO-Bz | H | H | 4-(ONO$_2$CH$_2$)-Hx$^c$ | (CH$_2$)$_2$ | O |
| 1-345 | H | 4-F-Bz | H | H | 4-(ONO$_2$CH$_2$)-Hx$^c$ | (CH$_2$)$_2$ | O |
| 1-346 | H | H | H | H | 4-(ONO$_2$CH$_2$)-Hx$^c$ | (CH$_2$)$_3$ | O |
| 1-347 | H | Me | H | H | 4-(ONO$_2$CH$_2$)-Hx$^c$ | (CH$_2$)$_3$ | O |
| 1-348 | H | Bz | H | H | 4-(ONO$_2$CH$_2$)-Hx$^c$ | (CH$_2$)$_3$ | O |
| 1-349 | H | H | H | H | 4-(ONO$_2$CH$_2$)-Hx$^c$ | (CH$_2$)$_4$ | O |
| 1-350 | H | Me | H | H | 4-(ONO$_2$CH$_2$)-Hx$^c$ | (CH$_2$)$_4$ | O |
| 1-351 | H | H | H | H | 4-(ONO$_2$CH$_2$)-Hx$^c$ | (CH$_2$)$_5$ | O |
| 1-352 | H | Me | H | H | 4-(ONO$_2$CH$_2$)-Hx$^c$ | (CH$_2$)$_5$ | O |
| 1-353 | H | H | H | H | 4-(ONO$_2$CH$_2$)-Hx$^c$ | (CH$_2$)$_6$ | O |
| 1-354 | H | Me | H | H | 4-(ONO$_2$CH$_2$)-Hx$^c$ | (CH$_2$)$_6$ | O |
| 1-355 | H | H | H | H | 4-ONO$_2$-Hx$^c$ | single bond | O |

TABLE 1-continued

| Compd. No. | $R^1$ | $R^2$ | $R^3$ | $R^4$ | $R^5$ | A | $X^1$ |
|---|---|---|---|---|---|---|---|
| 1-356 | Me | H | H | H | 4-$ONO_2$-$Hx^c$ | single bond | O |
| 1-357 | Et | H | H | H | 4-$ONO_2$-$Hx^c$ | single bond | O |
| 1-358 | Bz | H | H | H | 4-$ONO_2$-$Hx^c$ | single bond | O |
| 1-359 | H | Me | H | H | 4-$ONO_2$-$Hx^c$ | single bond | O |
| 1-360 | H | Et | H | H | 4-$ONO_2$-$Hx^c$ | single bond | O |
| 1-361 | H | Ph | H | H | 4-$ONO_2$-$Hx^c$ | single bond | O |
| 1-362 | H | Bz | H | H | 4-$ONO_2$-$Hx^c$ | single bond | O |
| 1-363 | H | 4-Me-Bz | H | H | 4-$ONO_2$-$Hx^c$ | single bond | O |
| 1-364 | H | 4-MeO-Bz | H | H | 4-$ONO_2$-$Hx^c$ | single bond | O |
| 1-365 | H | 4-F-Bz | H | H | 4-$ONO_2$-$Hx^c$ | single bond | O |
| 1-366 | H | 2-Then | H | H | 4-$ONO_2$-$Hx^c$ | single bond | O |
| 1-367 | H | 3-Then | H | H | 4-$ONO_2$-$Hx^c$ | single bond | O |
| 1-368 | H | 2-Fur | H | H | 4-$ONO_2$-$Hx^c$ | single bond | O |
| 1-369 | H | 3-Fur | H | H | 4-$ONO_2$-$Hx^c$ | single bond | O |
| 1-370 | H | 3-Pyr | H | H | 4-$ONO_2$-$Hx^c$ | single bond | O |
| 1-371 | H | H | H | Me | 4-$ONO_2$-$Hx^c$ | single bond | O |
| 1-372 | H | H | H | Et | 4-$ONO_2$-$Hx^c$ | single bond | O |
| 1-373 | H | H | H | Bz | 4-$ONO_2$-$Hx^c$ | single bond | O |
| 1-374 | H | H | H | H | 4-[$ONO_2(CH_2)_2$]-$Hx^c$ | single bond | O |
| 1-375 | H | Me | H | H | 4-[$ONO_2(CH_2)_2$]-$Hx^c$ | single bond | O |
| 1-376 | H | Et | H | H | 4-[$ONO_2(CH_2)_2$]-$Hx^c$ | single bond | O |
| 1-377 | H | Ph | H | H | 4-[$ONO_2(CH_2)_2$]-$Hx^c$ | single bond | O |
| 1-378 | H | Bz | H | H | 4-[$ONO_2(CH_2)_2$]-$Hx^c$ | single bond | O |
| 1-379 | H | 4-Me-Bz | H | H | 4-[$ONO_2(CH_2)_2$]-$Hx^c$ | single bond | O |
| 1-380 | H | 4-MeO-Bz | H | H | 4-[$ONO_2(CH_2)_2$]-$Hx^c$ | single bond | O |
| 1-381 | H | 4-F-Bz | H | H | 4-[$ONO_2(CH_2)_2$]-$Hx^c$ | single bond | O |
| 1-382 | H | 2-Then | H | H | 4-($ONO_2(CH_2)_2$)-$Hx^c$ | single bond | O |
| 1-383 | H | 3-Then | H | H | 4-[$ONO_2(CH_2)_2$]-$Hx^c$ | single bond | O |
| 1-384 | H | 2-Fur | H | H | 4-[$ONO_2(CH_2)_2$]-$Hx^c$ | single bond | O |
| 1-385 | H | 3-Fur | H | H | 4-[$ONO_2(CH_2)_2$]-$Hx^c$ | single bond | O |
| 1-386 | H | 3-Pyr | H | H | 4-[$ONO_2(CH_2)_2$]-$Hx^c$ | single bond | O |
| 1-387 | H | 4-Thiz | H | H | 4-[$ONO_2(CH_2)_2$]-$Hx^c$ | single bond | O |
| 1-388 | H | H | H | H | 4-$ONO_2$-$Hx^c$ | $CH_2$ | O |
| 1-389 | Me | H | H | H | 4-$ONO_2$-$Hx^c$ | $CH_2$ | O |
| 1-390 | Et | H | H | H | 4-$ONO_2$-$Hx^c$ | $CH_2$ | O |
| 1-391 | Bz | H | H | H | 4-$ONO_2$-$Hx^c$ | $CH_2$ | O |
| 1-392 | H | Me | H | H | 4-$ONO_2$-$Hx^c$ | $CH_2$ | O |
| 1-393 | H | Et | H | H | 4-$ONO_2$-$Hx^c$ | $CH_2$ | O |
| 1-394 | H | Ph | H | H | 4-$ONO_2$-$Hx^c$ | $CH_2$ | O |
| 1-395 | H | 2-Then | H | H | 4-$ONO_2$-$Hx^c$ | $CH_2$ | O |
| 1-396 | H | 3-Then | H | H | 4-$ONO_2$-$Hx^c$ | $CH_2$ | O |
| 1-397 | H | 2-Fur | H | H | 4-$ONO_2$-$Hx^c$ | $CH_2$ | O |
| 1-398 | H | 3-Fur | H | H | 4-$ONO_2$-$Hx^c$ | $CH_2$ | O |
| 1-399 | H | 4-Me-Ph | H | H | 4-$ONO_2$-$Hx^c$ | $CH_2$ | O |
| 1-400 | H | 4-Cl-Ph | H | H | 4-$ONO_2$-$Hx^c$ | $CH_2$ | O |
| 1-401 | H | 4-MeO-Ph | H | H | 4-$ONO_2$-$Hx^c$ | $CH_2$ | O |
| 1-402 | H | 4-Thiz | H | H | 4-$ONO_2$-$Hx^c$ | $CH_2$ | O |
| 1-403 | H | 3-Pyr | H | H | 4-$ONO_2$-$Hx^c$ | $CH_2$ | O |
| 1-404 | H | Me | Me | H | 4-$ONO_2$-$Hx^c$ | $CH_2$ | O |
| 1-405 | Me | Me | Me | H | 4-$ONO_2$-$Hx^c$ | $CH_2$ | O |
| 1-406 | Me | Me | Me | Me | 4-$ONO_2$-$Hx^c$ | $CH_2$ | O |
| 1-407 | Et | Ph | H | H | 4-$ONO_2$-$Hx^c$ | $CH_2$ | O |
| 1-408 | Et | Et | H | Me | 4-$ONO_2$-$Hx^c$ | $CH_2$ | O |
| 1-409 | Bz | Me | H | Et | 4-$ONO_2$-$Hx^c$ | $CH_2$ | O |
| 1-410 | Bz | Ph | H | Et | 4-$ONO_2$-$Hx^c$ | $CH_2$ | O |
| 1-411 | Bz | H | H | H | 4-$ONO_2$-$Hx^c$ | $CH_2$ | O |
| 1-412 | H | 1-Np | H | H | 4-$ONO_2$-$Hx^c$ | $CH_2$ | O |
| 1-413 | H | H | H | Me | 4-$ONO_2$-$Hx^c$ | $CH_2$ | O |
| 1-414 | H | H | H | Bz | 4-$ONO_2$-$Hx^c$ | $CH_2$ | O |
| 1-415 | H | Bz | H | H | 4-$ONO_2$-$Hx^c$ | $CH_2$ | O |
| 1-416 | H | 4-Me-Bz | H | H | 4-$ONO_2$-$Hx^c$ | $CH_2$ | O |
| 1-417 | H | 4-MeO-Bz | H | H | 4-$ONO_2$-$Hx^c$ | $CH_2$ | O |
| 1-418 | H | 4-F-Bz | H | H | 4-$ONO_2$-$Hx^c$ | $CH_2$ | O |
| 1-419 | H | H | H | H | 4-[$ONO_2(CH_2)_2$]-$Hx^c$ | $CH_2$ | O |
| 1-420 | H | Me | H | H | 4-[$ONO_2(CH_2)_2$]-$Hx^c$ | $CH_2$ | O |
| 1-421 | H | Et | H | H | 4-[$ONO_2(CH_2)_2$]-$Hx^c$ | $CH_2$ | O |
| 1-422 | H | Ph | H | H | 4-[$ONO_2(CH_2)_2$]-$Hx^c$ | $CH_2$ | O |
| 1-423 | H | 2-Then | H | H | 4-[$ONO_2(CH_2)_2$]-$Hx^c$ | $CH_2$ | O |
| 1-424 | H | 3-Then | H | H | 4-[$ONO_2(CH_2)_2$]-$Hx^c$ | $CH_2$ | O |
| 1-425 | H | 2-Fur | H | H | 4-[$ONO_2(CH_2)_2$]-$Hx^c$ | $CH_2$ | O |
| 1-426 | H | 3-Fur | H | H | 4-[$ONO_2(CH_2)_2$]-$Hx^c$ | $CH_2$ | O |
| 1-427 | H | 3-Py | H | H | 4-[$ONO_2(CH_2)_2$]-$Hx^c$ | $CH_2$ | O |
| 1-428 | H | Bz | H | H | 4-[$ONO_2(CH_2)_2$]-$Hx^c$ | $CH_2$ | O |
| 1-429 | H | 4-Me-Bz | H | H | 4-[$ONO_2(CH_2)_2$]-$Hx^c$ | $CH_2$ | O |
| 1-430 | H | 4-MeO-Bz | H | H | 4-[$ONO_2(CH_2)_2$]-$Hx^c$ | $CH_2$ | O |
| 1-431 | H | 4-F-Bz | H | H | 4-[$ONO_2(CH_2)_2$]-$Hx^c$ | $CH_2$ | O |

TABLE 1-continued

| Compd. No. | R¹ | R² | R³ | R⁴ | R⁵ | A | X¹ |
|---|---|---|---|---|---|---|---|
| 1-432 | H | Me | Me | H | 4-[ONO₂(CH₂)₂]-Hx$^c$ | CH₂ | O |
| 1-433 | Me | Me | Me | H | 4-[ONO₂(CH₂)₂]-Hx$^c$ | CH₂ | O |
| 1-434 | Bz | Me | H | Et | 4-[ONO₂(CH₂)₂]-Hx$^c$ | CH₂ | O |
| 1-435 | Bu | H | H | H | 4-[ONO₂(CH₂)₂]-Hx$^c$ | CH₂ | O |
| 1-436 | H | 1-Np | H | H | 4-[ONO₂(CH₂)₂]-Hx$^c$ | CH₂ | O |
| 1-437 | H | H | H | Me | 4-[ONO₂(CH₂)₂]-Hx$^c$ | CH₂ | O |
| 1-438 | H | H | H | Bz | 4-[ONO₂(CH₂)₂]-Hx$^c$ | CH₂ | O |
| 1-439 | H | H | H | H | 4-[ONO₂(CH₂)₂]-Hx$^c$ | (CH₂)₂ | O |
| 1-440 | H | Me | H | H | 4-[ONO₂(CH₂)₂]-Hx$^c$ | (CH₂)₂ | O |
| 1-441 | H | Et | H | H | 4-[ONO₂(CH₂)₂]-Hx$^c$ | (CH₂)₂ | O |
| 1-442 | H | Ph | H | H | 4-[ONO₂(CH₂)₂]-Hx$^c$ | (CH₂)₂ | O |
| 1-443 | H | 2-Then | H | H | 4-[ONO₂(CH₂)₂]-Hx$^c$ | (CH₂)₂ | O |
| 1-444 | H | 3-Then | H | H | 4-[ONO₂(CH₂)₂]-Hx$^c$ | (CH₂)₂ | O |
| 1-445 | H | 2-Fur | H | H | 4-[ONO₂(CH₂)₂]-Hx$^c$ | (CH₂)₂ | O |
| 1-446 | H | 3-Fur | H | H | 4-[ONO₂(CH₂)₂]-Hx$^c$ | (CH₂)₂ | O |
| 1-447 | H | 3-Py | H | H | 4-[ONO₂(CH₂)₂]-Hx$^c$ | (CH₂)₂ | O |
| 1-448 | H | Bz | H | H | 4-[ONO₂(CH₂)₂]-Hx$^c$ | (CH₂)₂ | O |
| 1-449 | H | 4-Me-Bz | H | H | 4-[ONO₂(CH₂)₂]-Hx$^c$ | (CH₂)₂ | O |
| 1-450 | H | 4-MeO-Bz | H | H | 4-[ONO₂(CH₂)₂]-Hx$^c$ | (CH₂)₂ | O |
| 1-451 | H | 4-F-Bz | H | H | 4-[ONO₂(CH₂)₂]-Hx$^c$ | (CH₂)₂ | O |
| 1-452 | H | Me | Me | H | 4-[ONO₂(CH₂)₂]-Hx$^c$ | (CH₂)₂ | O |
| 1-453 | Bu | H | H | H | 4-[ONO₂(CH₂)₂]-Hx$^c$ | (CH₂)₂ | O |
| 1-454 | H | 1-Np | H | H | 4-[ONO₂(CH₂)₂]-Hx$^c$ | (CH₂)₂ | O |
| 1-455 | H | H | H | Me | 4-[ONO₂(CH₂)₂]-Hx$^c$ | (CH₂)₂ | O |
| 1-456 | H | H | H | Bz | 4-[ONO₂(CH₂)₂]-Hx$^c$ | (CH₂)₂ | O |
| 1-457 | H | H | H | H | 4-[ONO₂(CH₂)₃]-Hx$^c$ | (CH₂)₂ | O |
| 1-458 | H | Me | H | H | 4-[ONO₂(CH₂)₃]-Hx$^c$ | (CH₂)₂ | O |
| 1-459 | H | Bz | H | H | 4-[ONO₂(CH₂)₃]-Hx$^c$ | (CH₂)₂ | O |
| 1-460 | H | H | H | H | 4-[ONO₂(CH₂)₄]-Hx$^c$ | (CH₂)₂ | O |
| 1-461 | H | Me | H | H | 4-[ONO₂(CH₂)₄]-Hx$^c$ | (CH₂)₂ | O |
| 1-462 | H | Bz | H | H | 4-[ONO₂(CH₂)₄]-Hx$^c$ | (CH₂)₂ | O |
| 1-463 | H | H | H | H | 4-[ONO₂(CH₂)₅]-Hx$^c$ | (CH₂)₂ | O |
| 1-464 | H | Me | H | H | 4-[ONO₂(CH₂)₅]-Hx$^c$ | (CH₂)₂ | O |
| 1-465 | H | Bz | H | H | 4-[ONO₂(CH₂)₅]-Hx$^c$ | (CH₂)₂ | O |
| 1-466 | H | H | H | H | 4-[ONO₂(CH₂)₆]-Hx$^c$ | (CH₂)₂ | O |
| 1-467 | H | Me | H | H | 4-[ONO₂(CH₂)₆]-Hx$^c$ | (CH₂)₂ | O |
| 1-468 | H | Bz | H | H | 4-[ONO₂(CH₂)₆]-Hx$^c$ | (CH₂)₂ | O |
| 1-469 | H | H | H | H | 4-ONO₂-Hx$^c$ | (CH₂)₂ | O |
| 1-470 | Me | H | H | H | 4-ONO₂-Hx$^c$ | (CH₂)₂ | O |
| 1-471 | Bz | H | H | H | 4-ONO₂-Hx$^c$ | (CH₂)₂ | O |
| 1-472 | H | Me | H | H | 4-ONO₂-Hx$^c$ | (CH₂)₂ | O |
| 1-473 | H | Et | H | H | 4-ONO₂-Hx$^c$ | (CH₂)₂ | O |
| 1-474 | H | Ph | H | H | 4-ONO₂-Hx$^c$ | (CH₂)₂ | O |
| 1-475 | H | 2-Then | H | H | 4-ONO₂-Hx$^c$ | (CH₂)₂ | O |
| 1-476 | H | 3-Then | H | H | 4-ONO₂-Hx$^c$ | (CH₂)₂ | O |
| 1-477 | H | 2-Fur | H | H | 4-ONO₂-Hx$^c$ | (CH₂)₂ | O |
| 1-478 | H | 3-Fur | H | H | 4-ONO₂-Hx$^c$ | (CH₂)₂ | O |
| 1-479 | H | 4-Me-Ph | H | H | 4-ONO₂-Hx$^c$ | (CH₂)₂ | O |
| 1-480 | H | 4-Cl-Ph | H | H | 4-ONO₂-Hx$^c$ | (CH₂)₂ | O |
| 1-481 | H | 4-MeO-Ph | H | H | 4-ONO₂-Hx$^c$ | (CH₂)₂ | O |
| 1-482 | H | 4-Thiz | H | H | 4-ONO₂-Hx$^c$ | (CH₂)₂ | O |
| 1-483 | H | 3-Pyr | H | H | 4-ONO₂-Hx$^c$ | (CH₂)₂ | O |
| 1-484 | H | Me | Me | H | 4-ONO₂-Hx$^c$ | (CH₂)₂ | O |
| 1-485 | Bu | H | H | H | 4-ONO₂-Hx$^c$ | (CH₂)₂ | O |
| 1-486 | H | 1-Np | H | H | 4-ONO₂-Hx$^c$ | (CH₂)₂ | O |
| 1-487 | H | H | H | Me | 4-ONO₂-Hx$^c$ | (CH₂)₂ | O |
| 1-488 | H | H | H | Bz | 4-ONO₂-Hx$^c$ | (CH₂)₂ | O |
| 1-489 | H | Bz | H | H | 4-ONO₂-Hx$^c$ | (CH₂)₂ | O |
| 1-490 | H | 4-Me-Bz | H | H | 4-ONO₂-Hx$^c$ | (CH₂)₂ | O |
| 1-491 | H | 4-MeO-Bz | H | H | 4-ONO₂-Hx$^c$ | (CH₂)₂ | O |
| 1-492 | H | 4-F-Bz | H | H | 4-ONO₂-Hx$^c$ | (CH₂)₂ | O |
| 1-493 | H | H | H | H | 4-ONO₂-Hx$^c$ | (CH₂)₃ | O |
| 1-494 | H | Me | H | H | 4-ONO₂-Hx$^c$ | (CH₂)₃ | O |
| 1-495 | H | H | H | H | 4-ONO₂-Hx$^c$ | (CH₂)₄ | O |
| 1-496 | H | Me | H | H | 4-ONO₂-Hx$^c$ | (CH₂)₄ | O |
| 1-497 | H | H | H | H | 4-ONO₂-Hx$^c$ | (CH₂)₅ | O |
| 1-498 | H | Me | H | H | 4-ONO₂-Hx$^c$ | (CH₂)₅ | O |
| 1-499 | H | H | H | H | 4-ONO₂-Hx$^c$ | (CH₂)₆ | O |
| 1-500 | H | Me | H | H | 4-ONO₂-Hx$^c$ | (CH₂)₆ | O |
| 1-501 | H | H | H | H | 2-(ONO₂)-Pn$^c$ | single bond | S |
| 1-502 | H | Me | H | H | 2-(ONO₂)-Pn$^c$ | single bond | S |
| 1-503 | H | Bz | H | H | 2-(ONO₂)-Pn$^c$ | single bond | S |
| 1-504 | H | 4-Me-Bz | H | H | 2-(ONO₂)-Pn$^c$ | single bond | S |
| 1-505 | H | 4-MeO-Bz | H | H | 2-(ONO₂)-Pn$^c$ | single bond | S |
| 1-506 | H | 4-F-Bz | H | H | 2-(ONO₂)-Pn$^c$ | single bond | S |
| 1-507 | H | Ph | H | H | 2-(ONO₂)-Pn$^c$ | single bond | S |

TABLE 1-continued

| Compd. No. | R¹ | R² | R³ | R⁴ | R⁵ | A | X¹ |
|---|---|---|---|---|---|---|---|
| 1-508 | H | 2-Then | H | H | 2-($ONO_2$)-Pn$^c$ | single bond | S |
| 1-509 | H | 3-Then | H | H | 2-($ONO_2$)-Pn$^c$ | single bond | S |
| 1-510 | H | 2-Fur | H | H | 2-($ONO_2$)-Pn$^c$ | single bond | S |
| 1-511 | H | 3-Fur | H | H | 2-($ONO_2$)-Pn$^c$ | single bond | S |
| 1-512 | H | 3-Pyr | H | H | 2-($ONO_2$)-Pn$^c$ | single bond | S |
| 1-513 | H | H | H | H | 2-($ONO_2$)-Pn$^c$ | $CH_2$ | S |
| 1-514 | H | Me | H | H | 2-($ONO_2$)-Pn$^c$ | $CH_2$ | S |
| 1-515 | H | Bz | H | H | 2-($ONO_2$)-Pn$^c$ | $CH_2$ | S |
| 1-516 | H | 4-Me-Bz | H | H | 2-($ONO_2$)-Pn$^c$ | $CH_2$ | S |
| 1-517 | H | 4-MeO-Bz | H | H | 2-($ONO_2$)-Pn$^c$ | $CH_2$ | S |
| 1-518 | H | 4-F-Bz | H | H | 2-($ONO_2$)-Pn$^c$ | $CH_2$ | S |
| 1-519 | H | Ph | H | H | 2-($ONO_2$)-Pn$^c$ | $CH_2$ | S |
| 1-520 | H | 2-Then | H | H | 2-($ONO_2$)-Pn$^c$ | $CH_2$ | S |
| 1-521 | H | 3-Then | H | H | 2-($ONO_2$)-Pn$^c$ | $CH_2$ | S |
| 1-522 | H | 2-Fur | H | H | 2-($ONO_2$)-Pn$^c$ | $CH_2$ | S |
| 1-523 | H | 3-Fur | H | H | 2-($ONO_2$)-Pn$^c$ | $CH_2$ | S |
| 1-524 | H | 3-Pyr | H | H | 2-($ONO_2$)-Pn$^c$ | $CH_2$ | S |
| 1-525 | H | H | H | H | 2-($ONO_2CH_2$)-Pn$^c$ | single bond | S |
| 1-526 | H | Me | H | H | 2-($ONO_2CH_2$)-Pn$^c$ | single bond | S |
| 1-527 | H | Bz | H | H | 2-($ONO_2CH_2$)-Pn$^c$ | single bond | S |
| 1-528 | H | 4-Me-Bz | H | H | 2-($ONO_2CH_2$)-Pn$^c$ | single bond | S |
| 1-529 | H | 4-MeO-Bz | H | H | 2-($ONO_2CH_2$)-Pn$^c$ | single bond | S |
| 1-530 | H | 4-F-Bz | H | H | 2-($ONO_2CH_2$)-Pn$^c$ | single bond | S |
| 1-531 | H | Ph | H | H | 2-($ONO_2CH_2$)-Pn$^c$ | single bond | S |
| 1-532 | H | 2-Then | H | H | 2-($ONO_2CH_2$)-Pn$^c$ | single bond | S |
| 1-533 | H | 3-Then | H | H | 2-($ONO_2CH_2$)-Pn$^c$ | single bond | S |
| 1-534 | H | 2-Fur | H | H | 2-($ONO_2CH_2$)-Pn$^c$ | single bond | S |
| 1-535 | H | 3-Fur | H | H | 2-($ONO_2CH_2$)-Pn$^c$ | single bond | S |
| 1-536 | H | 3-Pyr | H | H | 2-($ONO_2CH_2$)-Pn$^c$ | single bond | S |
| 1-537 | H | H | H | H | 2-($ONO_2CH_2$)-Pn$^c$ | $CH_2$ | S |
| 1-538 | H | Me | H | H | 2-($ONO_2CH_2$)-Pn$^c$ | $CH_2$ | S |
| 1-539 | H | Bz | H | H | 2-($ONO_2CH_2$)-Pn$^c$ | $CH_2$ | S |
| 1-540 | H | 4-Me-Bz | H | H | 2-($ONO_2CH_2$)-Pn$^c$ | $CH_2$ | S |
| 1-541 | H | 4-MeO-Bz | H | H | 2-($ONO_2CH_2$)-Pn$^c$ | $CH_2$ | S |
| 1-542 | H | 4-F-Bz | H | H | 2-($ONO_2CH_2$)-Pn$^c$ | $CH_2$ | S |
| 1-543 | H | Ph | H | H | 2-($ONO_2CH_2$)-Pn$^c$ | $CH_2$ | S |
| 1-544 | H | 2-Then | H | H | 2-($ONO_2CH_2$)-Pn$^c$ | $CH_2$ | S |
| 1-545 | H | 3-Then | H | H | 2-($ONO_2CH_2$)-Pn$^c$ | $CH_2$ | S |
| 1-546 | H | 2-Fur | H | H | 2-($ONO_2CH_2$)-Pn$^c$ | $CH_2$ | S |
| 1-547 | H | 3-Fur | H | H | 2-($ONO_2CH_2$)-Pn$^c$ | $CH_2$ | S |
| 1-548 | H | 3-Pyr | H | H | 2-($ONO_2CH_2$)-Pn$^c$ | $CH_2$ | S |
| 1-549 | H | H | H | H | 3-($ONO_2$)-Pn$^c$ | single bond | S |
| 1-550 | H | Me | H | H | 3-($ONO_2$) Pn$^c$ | single bond | S |
| 1-551 | H | Bz | H | H | 3-($ONO_2$)-Pn$^c$ | single bond | S |
| 1-552 | H | 4-Me-Bz | H | H | 3-($ONO_2$)-Pn$^c$ | single bond | S |
| 1-553 | H | 4-MeO-Bz | H | H | 3-($ONO_2$)-Pn$^c$ | single bond | S |
| 1-554 | H | 4-F-Bz | H | H | 3-($ONO_2$)-Pn$^c$ | single bond | S |
| 1-555 | H | Ph | H | H | 3-($ONO_2$)-Pn$^c$ | single bond | S |
| 1-556 | H | 2-Then | H | H | 3-($ONO_2$)-Pn$^c$ | single bond | S |
| 1-557 | H | 3-Then | H | H | 3-($ONO_2$)-Pn$^c$ | single bond | S |
| 1-558 | H | 2-Fur | H | H | 3-($ONO_2$)-Pn$^c$ | single bond | S |
| 1-559 | H | 3-Fur | H | H | 3-($ONO_2$)-Pn$^c$ | single bond | S |
| 1-560 | H | 3-Pyr | H | H | 3-($ONO_2$)-Pn$^c$ | single bond | S |
| 1-561 | H | H | H | H | 3-($ONO_2$)-Pn$^c$ | $CH_2$ | S |
| 1-562 | H | Me | H | H | 3-($ONO_2$)-Pn$^c$ | $CH_2$ | S |
| 1-563 | H | Bz | H | H | 3-($ONO_2$)-Pn$^c$ | $CH_2$ | S |
| 1-564 | H | 4-Me-Bz | H | H | 3-($ONO_2$)-Pn$^c$ | $CH_2$ | S |
| 1-565 | H | 4-MeO-Bz | H | H | 3-($ONO_2$)-Pn$^c$ | $CH_2$ | S |
| 1-566 | H | 4-F-Bz | H | H | 3-($ONO_2$)-Pn$^c$ | $CH_2$ | S |
| 1-567 | H | Ph | H | H | 3-($ONO_2$)-Pn$^c$ | $CH_2$ | S |
| 1-568 | H | 2-Then | H | H | 3-($ONO_2$)-Pn$^c$ | $CH_2$ | S |
| 1-569 | H | 3-Then | H | H | 3-($ONO_2$)-Pn$^c$ | $CH_2$ | S |
| 1-570 | H | 2-Fur | H | H | 3-($ONO_2$)-Pn$^c$ | $CH_2$ | S |
| 1-571 | H | 3-Fur | H | H | 3-($ONO_2$)-Pn$^c$ | $CH_2$ | S |
| 1-572 | H | 3-Pyr | H | H | 3-($ONO_2$)-Pn$^c$ | $CH_2$ | S |
| 1-573 | H | H | H | H | 3-($ONO_2CH_2$)-Pn$^c$ | single bond | S |
| 1-574 | H | Me | H | H | 3-($ONO_2CH_2$)-Pn$^c$ | single bond | S |
| 1-575 | H | Bz | H | H | 3-($ONO_2CH_2$)-Pn$^c$ | single bond | S |
| 1-576 | H | 4-Me-Bz | H | H | 3-($ONO_2CH_2$)-Pn$^c$ | single bond | S |
| 1-577 | H | 4-MeO-Bz | H | H | 3-($ONO_2CH_2$)-Pn$^c$ | single bond | S |
| 1-578 | H | 4-F-Bz | H | H | 3-($ONO_2CH_2$)-Pn$^c$ | single bond | S |
| 1-579 | H | Ph | H | H | 3-($ONO_2CH_2$)-Pn$^c$ | single bond | S |
| 1-580 | H | 2-Then | H | H | 3-($ONO_2CH_2$)-Pn$^c$ | single bond | S |
| 1-581 | H | 3-Then | H | H | 3-($ONO_2CH_2$)-Pn$^c$ | single bond | S |
| 1-582 | H | 2-Fur | H | H | 3-($ONO_2CH_2$)-Pn$^c$ | single bond | S |
| 1-583 | H | 3-Fur | H | H | 3-($ONO_2CH_2$)-Pn$^c$ | single bond | S |

TABLE 1-continued

| Compd. No. | R$^1$ | R$^2$ | R$^3$ | R$^4$ | R$^5$ | A | X$^1$ |
|---|---|---|---|---|---|---|---|
| 1-584 | H | 3-Pyr | H | H | 3-(ONO$_2$CH$_2$)-Pn$^c$ | single bond | S |
| 1-585 | H | H | H | H | 3-(ONO$_2$CH$_2$)-Pn$^c$ | CH$_2$ | S |
| 1-586 | H | Me | H | H | 3-(ONO$_2$CH$_2$)-Pn$^c$ | CH$_2$ | S |
| 1-587 | H | Bz | H | H | 3-(ONO$_2$CH$_2$)-Pn$^c$ | CH$_2$ | S |
| 1-588 | H | 4-Me-Bz | H | H | 3-(ONO$_2$CH$_2$)-Pn$^c$ | CH$_2$ | S |
| 1-589 | H | 4-MeO-Bz | H | H | 3-(ONO$_2$CH$_2$)-Pn$^c$ | CH$_2$ | S |
| 1-590 | H | 4-F-Bz | H | H | 3-(ONO$_2$CH$_2$)-Pn$^c$ | CH$_2$ | S |
| 1-591 | H | Ph | H | H | 3-(ONO$_2$CH$_2$)-Pn$^c$ | CH$_2$ | S |
| 1-592 | H | 2-Then | H | H | 3-(ONO$_2$CH$_2$)-Pn$^c$ | CH$_2$ | S |
| 1-593 | H | 3-Then | H | H | 3-(ONO$_2$CH$_2$)-Pn$^c$ | CH$_2$ | S |
| 1-594 | H | 2-Fur | H | H | 3-(ONO$_2$CH$_2$)-Pn$^c$ | CH$_2$ | S |
| 1-595 | H | 3-Fur | H | H | 3-(ONO$_2$CH$_2$)-Pn$^c$ | CH$_2$ | S |
| 1-596 | H | 3-Pyr | H | H | 3-(ONO$_2$CH$_2$)-Pn$^c$ | CH$_2$ | S |
| 1-597 | H | H | H | H | 2-(ONO$_2$)-Hx$^c$ | single bond | S |
| 1-598 | H | Me | H | H | 2-(ONO$_2$)-Hx$^c$ | single bond | S |
| 1-599 | H | Bz | H | H | 2-(ONO$_2$)-Hx$^c$ | single bond | S |
| 1-600 | H | 4-Me-Bz | H | H | 2-(ONO$_2$)-Hx$^c$ | single bond | S |
| 1-601 | H | 4-MeO-Bz | H | H | 2-(ONO$_2$)-Hx$^c$ | single bond | S |
| 1-602 | H | 4-F-Bz | H | H | 2-(ONO$_2$)-Hx$^c$ | single bond | S |
| 1-603 | H | Ph | H | H | 2-(ONO$_2$)-Hx$^c$ | single bond | S |
| 1-604 | H | 2-Then | H | H | 2-(ONO$_2$)-Hx$^c$ | single bond | S |
| 1-605 | H | 3-Then | H | H | 2-(ONO$_2$)-Hx$^c$ | single bond | S |
| 1-606 | H | 2-Fur | H | H | 2-(ONO$_2$)-Hx$^c$ | single bond | S |
| 1-607 | H | 3-Fur | H | H | 2-(ONO$_2$)-Hx$^c$ | single bond | S |
| 1-608 | H | 3-Pyr | H | H | 2-(ONO$_2$)-Hx$^c$ | single bond | S |
| 1-609 | H | H | H | H | 2-(ONO$_2$)-Hx$^c$ | CH$_2$ | S |
| 1-610 | H | Me | H | H | 2-(ONO$_2$)-Hx$^c$ | CH$_2$ | S |
| 1-611 | H | Bz | H | H | 2-(ONO$_2$)-Hx$^c$ | CH$_2$ | S |
| 1-612 | H | 4-Me-Bz | H | H | 2-(ONO$_2$)-Hx$^c$ | CH$_2$ | S |
| 1-613 | H | 4-MeO-Bz | H | H | 2-(ONO$_2$)-Hx$^c$ | CH$_2$ | S |
| 1-614 | H | 4-F-Bz | H | H | 2-(ONO$_2$)-Hx$^c$ | CH$_2$ | S |
| 1-615 | H | Ph | H | H | 2-(ONO$_2$)-Hx$^c$ | CH$_2$ | S |
| 1-616 | H | 2-Then | H | H | 2-(ONO$_2$)-Hx$^c$ | CH$_2$ | S |
| 1-617 | H | 3-Then | H | H | 2-(ONO$_2$)-Hx$^c$ | CH$_2$ | S |
| 1-618 | H | 2-Fur | H | H | 2-(ONO$_2$)-Hx$^c$ | CH$_2$ | S |
| 1-619 | H | 3-Fur | H | H | 2-(ONO$_2$)-Hx$^c$ | CH$_2$ | S |
| 1-620 | H | 3-Pyr | H | H | 2-(ONO$_2$)-Hx$^c$ | CH$_2$ | S |
| 1-621 | H | H | H | H | 2-(ONO$_2$CH$_2$)-Hx$^c$ | single bond | S |
| 1-622 | H | Me | H | H | 2-(ONO$_2$CH$_2$)-Hx$^c$ | single bond | S |
| 1-623 | H | Bz | H | H | 2-(ONO$_2$CH$_2$)-Hx$^c$ | single bond | S |
| 1-624 | H | 4-Me-Bz | H | H | 2-(ONO$_2$CH$_2$)-Hx$^c$ | single bond | S |
| 1-625 | H | 4-MeO-Bz | H | H | 2-(ONO$_2$CH$_2$)-Hx$^c$ | single bond | S |
| 1-626 | H | 4-F-Bz | H | H | 2-(ONO$_2$CH$_2$)-Hx$^c$ | single bond | S |
| 1-627 | H | Ph | H | H | 2-(ONO$_2$CH$_2$)-Hx$^c$ | single bond | S |
| 1-628 | H | 2-Then | H | H | 2-(ONO$_2$CH$_2$)-Hx$^c$ | single bond | S |
| 1-629 | H | 3-Then | H | H | 2-(ONO$_2$CH$_2$)-Hx$^c$ | single bond | S |
| 1-630 | H | 2-Fur | H | H | 2-(ONO$_2$CH$_2$)-Hx$^c$ | single bond | S |
| 1-631 | H | 3-Fur | H | H | 2-(ONO$_2$CH$_2$)-Hx$^c$ | single bond | S |
| 1-632 | H | 3-Pyr | H | H | 2-(ONO$_2$CH$_2$)-Hx$^c$ | single bond | S |
| 1-633 | H | H | H | H | 2-(ONO$_2$CH$_2$)-Hx$^c$ | CH$_2$ | S |
| 1-634 | H | Me | H | H | 2-(ONO$_2$CH$_2$)-Hx$^c$ | CH$_2$ | S |
| 1-635 | H | Bz | H | H | 2-(ONO$_2$CH$_2$)-Hx$^c$ | CH$_2$ | S |
| 1-636 | H | 4-Me-Bz | H | H | 2-(ONO$_2$CH$_2$)-Hx$^c$ | CH$_2$ | S |
| 1-637 | H | 4-MeO-Bz | H | H | 2-(ONO$_2$CH$_2$)-Hx$^c$ | CH$_2$ | S |
| 1-638 | H | 4-F-Bz | H | H | 2-(ONO$_2$CH$_2$)-Hx$^c$ | CH$_2$ | S |
| 1-639 | H | Ph | H | H | 2-(ONO$_2$CH$_2$)-Hx$^c$ | CH$_2$ | S |
| 1-640 | H | 2-Then | H | H | 2-(ONO$_2$CH$_2$)-Hx$^c$ | CH$_2$ | S |
| 1-641 | H | 3-Then | H | H | 2-(ONO$_2$CH$_2$)-Hx$^c$ | CH$_2$ | S |
| 1-642 | H | 2-Fur | H | H | 2-(ONO$_2$CH$_2$)-Hx$^c$ | CH$_2$ | S |
| 1-643 | H | 3-Fur | H | H | 2-(ONO$_2$CH$_2$)-Hx$^c$ | CH$_2$ | S |
| 1-644 | H | 3-Pyr | H | H | 2-(ONO$_2$CH$_2$)-Hx$^c$ | CH$_2$ | S |
| 1-645 | H | H | H | H | 3-(ONO$_2$)-Hx$^c$ | single bond | S |
| 1-646 | H | Me | H | H | 3-(ONO$_2$)-Hx$^c$ | single bond | S |
| 1-647 | H | Bz | H | H | 3-(ONO$_2$)-Hx$^c$ | single bond | S |
| 1-648 | H | 4-Me-Bz | H | H | 3-(ONO$_2$)-Hx$^c$ | single bond | S |
| 1-649 | H | 4-MeO-Bz | H | H | 3-(ONO$_2$)-Hx$^c$ | single bond | S |
| 1-650 | H | 4-F-Bz | H | H | 3-(ONO$_2$)-Hx$^c$ | single bond | S |
| 1-651 | H | Ph | H | H | 3-(ONO$_2$)-Hx$^c$ | single bond | S |
| 1-652 | H | 2-Then | H | H | 3-(ONO$_2$)-Hx$^c$ | single bond | S |
| 1-653 | H | 3-Then | H | H | 3-(ONO$_2$)-Hx$^c$ | single bond | S |
| 1-654 | H | 2-Fur | H | H | 3-(ONO$_2$)-Hx$^c$ | single bond | S |
| 1-655 | H | 3-Fur | H | H | 3-(ONO$_2$)-Hx$^c$ | single bond | S |
| 1-656 | H | 3-Pyr | H | H | 3-(ONO$_2$)-Hx$^c$ | single bond | S |
| 1-657 | H | H | H | H | 3-(ONO$_2$)-Hx$^c$ | CH$_2$ | S |
| 1-658 | H | Me | H | H | 3-(ONO$_2$)-Hx$^c$ | CH$_2$ | S |
| 1-659 | H | Bz | H | H | 3-(ONO$_2$)-Hx$^c$ | CH$_2$ | S |

TABLE 1-continued

| Compd. No. | R¹ | R² | R³ | R⁴ | R⁵ | A | X¹ |
|---|---|---|---|---|---|---|---|
| 1-660 | H | 4-Me-Bz | H | H | 3-(ONO$_2$)-Hx$^c$ | CH$_2$ | S |
| 1-661 | H | 4-MeO-Bz | H | H | 3-(ONO$_2$)-Hx$^c$ | CH$_2$ | S |
| 1-662 | H | 4-F-Bz | H | H | 3-(ONO$_2$)-Hx$^c$ | CH$_2$ | S |
| 1-663 | H | Ph | H | H | 3-(ONO$_2$)-Hx$^c$ | CH$_2$ | S |
| 1-664 | H | 2-Then | H | H | 3-(ONO$_2$)-Hx$^c$ | CH$_2$ | S |
| 1-665 | H | 3-Then | H | H | 3-(ONO$_2$)-Hx$^c$ | CH$_2$ | S |
| 1-666 | H | 2-Fur | H | H | 3-(ONO$_2$)-Hx$^c$ | CH$_2$ | S |
| 1-667 | H | 3-Fur | H | H | 3-(ONO$_2$)-Hx$^c$ | CH$_2$ | S |
| 1-668 | H | 3-Pyr | H | H | 3-(ONO$_2$)-Hx$^c$ | CH$_2$ | S |
| 1-669 | H | H | H | H | 3-(ONO$_2$CH$_2$)-Hx$^c$ | single bond | S |
| 1-670 | H | Me | H | H | 3-(ONO$_2$CH$_2$)-Hx$^c$ | single bond | S |
| 1-671 | H | Bz | H | H | 3-(ONO$_2$CH$_2$)-Hx$^c$ | single bond | S |
| 1-672 | H | 4-Me-Bz | H | H | 3-(ONO$_2$CH$_2$)-Hx$^c$ | single bond | S |
| 1-673 | H | 4-MeO-Bz | H | H | 3-(ONO$_2$CH$_2$)-Hx$^c$ | single bond | S |
| 1-674 | H | 4-F-Bz | H | H | 3-(ONO$_2$CH$_2$)-Hx$^c$ | single bond | S |
| 1-675 | H | Ph | H | H | 3-(ONO$_2$CH$_2$)-Hx$^c$ | single bond | S |
| 1-676 | H | 2-Then | H | H | 3-(ONO$_2$CH$_2$)-Hx$^c$ | single bond | S |
| 1-677 | H | 3-Then | H | H | 3-(ONO$_2$CH$_2$)-Hx$^c$ | single bond | S |
| 1-678 | H | 2-Fur | H | H | 3-(ONO$_2$CH$_2$)-Hx$^c$ | single bond | S |
| 1-679 | H | 3-Fur | H | H | 3-(ONO$_2$CH$_2$)-Hx$^c$ | single bond | S |
| 1-680 | H | 3-Pyr | H | H | 3-(ONO$_2$CH$_2$)-Hx$^c$ | single bond | S |
| 1-681 | H | H | H | H | 3-(ONO$_2$CH$_2$)-Hx$^c$ | CH$_2$ | S |
| 1-682 | H | Me | H | H | 3-(ONO$_2$CH$_2$)-Hx$^c$ | CH$_2$ | S |
| 1-683 | H | Bz | H | H | 3-(ONO$_2$CH$_2$)-Hx$^c$ | CH$_2$ | S |
| 1-684 | H | 4-Me-Bz | H | H | 3-(ONO$_2$CH$_2$)-Hx$^c$ | CH$_2$ | S |
| 1-685 | H | 4-MeO-Bz | H | H | 3-(ONO$_2$CH$_2$)-Hx$^c$ | CH$_2$ | S |
| 1-686 | H | 4-F-Bz | H | H | 3-(ONO$_2$CH$_2$)-Hx$^c$ | CH$_2$ | S |
| 1-687 | H | Ph | H | H | 3-(ONO$_2$CH$_2$)-Hx$^c$ | CH$_2$ | S |
| 1-688 | H | 2-Then | H | H | 3-(ONO$_2$CH$_2$)-Hx$^c$ | CH$_2$ | S |
| 1-689 | H | 3-Then | H | H | 3-(ONO$_2$CH$_2$)-Hx$^c$ | CH$_2$ | S |
| 1-690 | H | 2-Fur | H | H | 3-(ONO$_2$CH$_2$)-Hx$^c$ | CH$_2$ | S |
| 1-691 | H | 3-Fur | H | H | 3-(ONO$_2$CH$_2$)-Hx$^c$ | CH$_2$ | S |
| 1-692 | H | 3-Pyr | H | H | 3-(ONO$_2$CH$_2$)-Hx$^c$ | CH$_2$ | S |
| 1-693 | H | H | H | H | 2-(ONO$_2$)-Pn$^c$ | single bond | O |
| 1-694 | H | Me | H | H | 2-(ONO$_2$)-Pn$^c$ | single bond | O |
| 1-695 | H | Bz | H | H | 2-(ONO$_2$)-Pn$^c$ | single bond | O |
| 1-696 | H | 4-Me-Bz | H | H | 2-(ONO$_2$)-Pn$^c$ | single bond | O |
| 1-697 | H | 4-MeO-Bz | H | H | 2-(ONO$_2$)-Pn$^c$ | single bond | O |
| 1-698 | H | 4-F-Bz | H | H | 2-(ONO$_2$)-Pn$^c$ | single bond | O |
| 1-699 | H | Ph | H | H | 2-(ONO$_2$)-Pn$^c$ | single bond | O |
| 1-700 | H | 2-Then | H | H | 2-(ONO$_2$)-Pn$^c$ | single bond | O |
| 1-701 | H | 3-Then | H | H | 2-(ONO$_2$)-Pn$^c$ | single bond | O |
| 1-702 | H | 2-Fur | H | H | 2-(ONO$_2$)-Pn$^c$ | single bond | O |
| 1-703 | H | 3-Fur | H | H | 2-(ONO$_2$)-Pn$^c$ | single bond | O |
| 1-704 | H | 3-Pyr | H | H | 2-(ONO$_2$)-Pn$^c$ | single bond | O |
| 1-705 | H | H | H | H | 2-(ONO$_2$)-Pn$^c$ | CH$_2$ | O |
| 1-706 | H | Me | H | H | 2-(ONO$_2$)-Pn$^c$ | CH$_2$ | O |
| 1-707 | H | Bz | H | H | 2-(ONO$_2$)-Pn$^c$ | CH$_2$ | O |
| 1-708 | H | 4-Me-Bz | H | H | 2-(ONO$_2$)-Pn$^c$ | CH$_2$ | O |
| 1-709 | H | 4-MeO-Bz | H | H | 2-(ONO$_2$)-Pn$^c$ | CH$_2$ | O |
| 1-710 | H | 4-F-Bz | H | H | 2-(ONO$_2$)-Pn$^c$ | CH$_2$ | O |
| 1-711 | H | Ph | H | H | 2-(ONO$_2$)-Pn$^c$ | CH$_2$ | O |
| 1-712 | H | 2-Then | H | H | 2-(ONO$_2$)-Pn$^c$ | CH$_2$ | O |
| 1-713 | H | 3-Then | H | H | 2-(ONO$_2$)-Pn$^c$ | CH$_2$ | O |
| 1-714 | H | 2-Fur | H | H | 2-(ONO$_2$)-Pn$^c$ | CH$_2$ | O |
| 1-715 | H | 3-Fur | H | H | 2-(ONO$_2$)-Pn$^c$ | CH$_2$ | O |
| 1-716 | H | 3-Pyr | H | H | 2-(ONO$_2$)-Pn$^c$ | CH$_2$ | O |
| 1-717 | H | H | H | H | 2-(ONO$_2$CH$_2$)-Pn$^c$ | single bond | O |
| 1-718 | H | Me | H | H | 2-(ONO$_2$CH$_2$)-Pn$^c$ | single bond | O |
| 1-719 | H | Bz | H | H | 2-(ONO$_2$CH$_2$)-Pn$^c$ | single bond | O |
| 1-720 | H | 4-Me-Bz | H | H | 2-(ONO$_2$CH$_2$)-Pn$^c$ | single bond | O |
| 1-721 | H | 4-MeO-Bz | H | H | 2-(ONO$_2$CH$_2$)-Pn$^c$ | single bond | O |
| 1-722 | H | 4-F-Bz | H | H | 2-(ONO$_2$CH$_2$)-Pn$^c$ | single bond | O |
| 1-723 | H | Ph | H | H | 2-(ONO$_2$CH$_2$)-Pn$^c$ | single bond | O |
| 1-724 | H | 2-Then | H | H | 2-(ONO$_2$CH$_2$)-Pn$^c$ | single bond | O |
| 1-725 | H | 3-Then | H | H | 2-(ONO$_2$CH$_2$)-Pn$^c$ | single bond | O |
| 1-726 | H | 2-Fur | H | H | 2-(ONO$_2$CH$_2$)-Pn$^c$ | single bond | O |
| 1-727 | H | 3-Fur | H | H | 2-(ONO$_2$CH$_2$)-Pn$^c$ | single bond | O |
| 1-728 | H | 3-Pyr | H | H | 2-(ONO$_2$CH$_2$)-Pn$^c$ | single bond | O |
| 1-729 | H | H | H | H | 2-(ONO$_2$CH$_2$)-Pn$^c$ | CH$_2$ | O |
| 1-730 | H | Me | H | H | 2-(ONO$_2$CH$_2$)-Pn$^c$ | CH$_2$ | O |
| 1-731 | H | Bz | H | H | 2-(ONO$_2$CH$_2$)-Pn$^c$ | CH$_2$ | O |
| 1-732 | H | 4-Me-Bz | H | H | 2-(ONO$_2$CH$_2$)-Pn$^c$ | CH$_2$ | O |
| 1-733 | H | 4-MeO-Bz | H | H | 2-(ONO$_2$CH$_2$)-Pn$^c$ | CH$_2$ | O |
| 1-734 | H | 4-F-Bz | H | H | 2-(ONO$_2$CH$_2$)-Pn$^c$ | CH$_2$ | O |
| 1-735 | H | Ph | H | H | 2-(ONO$_2$CH$_2$)-Pn$^c$ | CH$_2$ | O |

TABLE 1-continued

| Compd. No. | R¹ | R² | R³ | R⁴ | R⁵ | A | X¹ |
|---|---|---|---|---|---|---|---|
| 1-736 | H | 2-Then | H | H | 2-(ONO₂CH₂)-Pnᶜ | CH₂ | O |
| 1-737 | H | 3-Then | H | H | 2-(ONO₂CH₂)-Pnᶜ | CH₂ | O |
| 1-738 | H | 2-Fur | H | H | 2-(ONO₂CH₂)-Pnᶜ | CH₂ | O |
| 1-739 | H | 3-Fur | H | H | 2-(ONO₂CH₂)-Pnᶜ | CH₂ | O |
| 1-740 | H | 3-Pyr | H | H | 2-(ONO₂CH₂)-Pnᶜ | CH₂ | O |
| 1-741 | H | H | H | H | 3-(ONO₂)-Pnᶜ | single bond | O |
| 1-742 | H | Me | H | H | 3-(ONO₂)-Pnᶜ | single bond | O |
| 1-743 | H | Bz | H | H | 3-(ONO₂)-Pnᶜ | single bond | O |
| 1-744 | H | 4-Me-Bz | H | H | 3-(ONO₂)-Pnᶜ | single bond | O |
| 1-745 | H | 4-MeO-Bz | H | H | 3-(ONO₂)-Pnᶜ | single bond | O |
| 1-746 | H | 4-F-Bz | H | H | 3-(ONO₂)-Pnᶜ | single bond | O |
| 1-747 | H | Ph | H | H | 3-(ONO₂)-Pnᶜ | single bond | O |
| 1-748 | H | 2-Then | H | H | 3-(ONO₂)-Pnᶜ | single bond | O |
| 1-749 | H | 3-Then | H | H | 3-(ONO₂)-Pnᶜ | single bond | O |
| 1-750 | H | 2-Fur | H | H | 3-(ONO₂)-Pnᶜ | single bond | O |
| 1-751 | H | 3-Fur | H | H | 3-(ONO₂)-Pnᶜ | single bond | O |
| 1-752 | H | 3-Pyr | H | H | 3-(ONO₂)-Pnᶜ | single bond | O |
| 1-753 | H | H | H | H | 3-(ONO₂)-Pnᶜ | CH₂ | O |
| 1-754 | H | Me | H | H | 3-(ONO₂)-Pnᶜ | CH₂ | O |
| 1-755 | H | Bz | H | H | 3-(ONO₂)-Pnᶜ | CH₂ | O |
| 1-756 | H | 4-Me-Bz | H | H | 3-(ONO₂)-Pnᶜ | CH₂ | O |
| 1-757 | H | 4-MeO-Bz | H | H | 3-(ONO₂)-Pnᶜ | CH₂ | O |
| 1-758 | H | 4-F-Bz | H | H | 3-(ONO₂)-Pnᶜ | CH₂ | O |
| 1-759 | H | Ph | H | H | 3-(ONO₂)-Pnᶜ | CH₂ | O |
| 1-760 | H | 2-Then | H | H | 3-(ONO₂)-Pnᶜ | CH₂ | O |
| 1-761 | H | 3-Then | H | H | 3-(ONO₂)-Pnᶜ | CH₂ | O |
| 1-762 | H | 2-Fur | H | H | 3-(ONO₂)-Pnᶜ | CH₂ | O |
| 1-763 | H | 3-Fur | H | H | 3-(ONO₂)-Pnᶜ | CH₂ | O |
| 1-764 | H | 3-Pyr | H | H | 3-(ONO₂)-Pnᶜ | CH₂ | O |
| 1-765 | H | H | H | H | 3-(ONO₂CH₂)-Pnᶜ | single bond | O |
| 1-766 | H | Me | H | H | 3-(ONO₂CH₂)-Pnᶜ | single bond | O |
| 1-767 | H | Bz | H | H | 3-(ONO₂CH₂)-Pnᶜ | single bond | O |
| 1-768 | H | 4-Me-Bz | H | H | 3-(ONO₂CH₂)-Pnᶜ | single bond | O |
| 1-769 | H | 4-MeO-Bz | H | H | 3-(ONO₂CH₂)-Pnᶜ | single bond | O |
| 1-770 | H | 4-F-Bz | H | H | 3-(ONO₂CH₂)-Pnᶜ | single bond | O |
| 1-771 | H | Ph | H | H | 3-(ONO₂CH₂)-Pnᶜ | single bond | O |
| 1-772 | H | 2-Then | H | H | 3-(ONO₂CH₂)-Pnᶜ | single bond | O |
| 1-773 | H | 3-Then | H | H | 3-(ONO₂CH₂)-Pnᶜ | single bond | O |
| 1-774 | H | 2-Fur | H | H | 3-(ONO₂CH₂)-Pnᶜ | single bond | O |
| 1-775 | H | 3-Fur | H | H | 3-(ONO₂CH₂)-Pnᶜ | single bond | O |
| 1-776 | H | 3-Pyr | H | H | 3-(ONO₂CH₂)-Pnᶜ | single bond | O |
| 1-777 | H | H | H | H | 3-(ONO₂CH₂)-Pnᶜ | CH₂ | O |
| 1-778 | H | Me | H | H | 3-(ONO₂CH₂)-Pnᶜ | CH₂ | O |
| 1-779 | H | Bz | H | H | 3-(ONO₂CH₂)-Pnᶜ | CH₂ | O |
| 1-780 | H | 4-Me-Bz | H | H | 3-(ONO₂CH₂)-Pnᶜ | CH₂ | O |
| 1-781 | H | 4-MeO-Bz | H | H | 3-(ONO₂CH₂)-Pnᶜ | CH₂ | O |
| 1-782 | H | 4-F-Bz | H | H | 3-(ONO₂CH₂)-Pnᶜ | CH₂ | O |
| 1-783 | H | Ph | H | H | 3-(ONO₂CH₂)-Pnᶜ | CH₂ | O |
| 1-784 | H | 2-Then | H | H | 3-(ONO₂CH₂)-Pnᶜ | CH₂ | O |
| 1-785 | H | 3-Then | H | H | 3-(ONO₂CH₂)-Pnᶜ | CH₂ | O |
| 1-786 | H | 2-Fur | H | H | 3-(ONO₂CH₂)-Pnᶜ | CH₂ | |
| 1-787 | H | 3-Fur | H | H | 3-(ONO₂CH₂)-Pnᶜ | CH₂ | O |
| 1-788 | H | 3-Pyr | H | H | 3-(ONO₂CH₂)-Pnᶜ | CH₂ | O |
| 1-789 | H | H | H | H | 2-(ONO₂)-Hxᶜ | single bond | O |
| 1-790 | H | Me | H | H | 2-(ONO₂)-Hxᶜ | single bond | O |
| 1-791 | H | Bz | H | H | 2-(ONO₂)-Hxᶜ | single bond | O |
| 1-792 | H | 4-Me-Bz | H | H | 2-(ONO₂)-Hxᶜ | single bond | O |
| 1-793 | H | 4-MeO-Bz | H | H | 2-(ONO₂)-Hxᶜ | single bond | O |
| 1-794 | H | 4-F-Bz | H | H | 2-(ONO₂)-Hxᶜ | single bond | O |
| 1-795 | H | Ph | H | H | 2-(ONO₂)-Hxᶜ | single bond | O |
| 1-796 | H | 2-Then | H | H | 2-(ONO₂)-Hxᶜ | single bond | O |
| 1-797 | H | 3-Then | H | H | 2-(ONO₂)-Hxᶜ | single bond | O |
| 1-798 | H | 2-Fur | H | H | 2-(ONO₂)-Hxᶜ | single bond | O |
| 1-799 | H | 3-Fur | H | H | 2-(ONO₂)-Hxᶜ | single bond | O |
| 1-800 | H | 3-Pyr | H | H | 2-(ONO₂)-Hxᶜ | single bond | O |
| 1-801 | H | H | H | H | 2-(ONO₂)-Hxᶜ | CH₂ | O |
| 1-802 | H | Me | H | H | 2-(ONO₂)-Hxᶜ | CH₂ | O |
| 1-803 | H | Bz | H | H | 2-(ONO₂)-Hxᶜ | CH₂ | O |
| 1-804 | H | 4-Me-Bz | H | H | 2-(ONO₂)-Hxᶜ | CH₂ | O |
| 1-805 | H | 4-MeO-Bz | H | H | 2-(ONO₂)-Hxᶜ | CH₂ | O |
| 1-806 | H | 4-F-Bz | H | H | 2-(ONO₂)-Hxᶜ | CH₂ | O |
| 1-807 | H | Ph | H | H | 2-(ONO₂)-Hxᶜ | CH₂ | O |
| 1-808 | H | 2-Then | H | H | 2-(ONO₂)-Hxᶜ | CH₂ | O |
| 1-809 | H | 3-Then | H | H | 2-(ONO₂)-Hxᶜ | CH₂ | O |
| 1-810 | H | 2-Fur | H | H | 2-(ONO₂)-Hxᶜ | CH₂ | O |
| 1-811 | H | 3-Fur | H | H | 2-(ONO₂)-Hxᶜ | CH₂ | O |

TABLE 1-continued

| Compd. No. | R$^1$ | R$^2$ | R$^3$ | R$^4$ | R$^5$ | A | X$^1$ |
|---|---|---|---|---|---|---|---|
| 1-812 | H | 3-Pyr | H | H | 2-(ONO$_2$)-Hx$^c$ | CH$_2$ | O |
| 1-813 | H | H | H | H | 2-(ONO$_2$CH$_2$)-Hx$^c$ | single bond | O |
| 1-814 | H | Me | H | H | 2-(ONO$_2$CH$_2$)-Hx$^c$ | single bond | O |
| 1-815 | H | Bz | H | H | 2-(ONO$_2$CH$_2$)-Hx$^c$ | single bond | O |
| 1-816 | H | 4-Me-Bz | H | H | 2-(ONO$_2$CH$_2$)-Hx$^c$ | single bond | O |
| 1-817 | H | 4-MeO-Bz | H | H | 2-(ONO$_2$CH$_2$)-Hx$^c$ | single bond | O |
| 1-818 | H | 4-F-Bz | H | H | 2-(ONO$_2$CH$_2$)-Hx$^c$ | single bond | O |
| 1-819 | H | Ph | H | H | 2-(ONO$_2$CH$_2$)-Hx$^c$ | single bond | O |
| 1-820 | H | 2-Then | H | H | 2-(ONO$_2$CH$_2$)-Hx$^c$ | single bond | O |
| 1-821 | H | 3-Then | H | H | 2-(ONO$_2$CH$_2$)-Hx$^c$ | single bond | O |
| 1-822 | H | 2-Fur | H | H | 2-(ONO$_2$CH$_2$)-Hx$^c$ | single bond | O |
| 1-823 | H | 3-Fur | H | H | 2-(ONO$_2$CH$_2$)-Hx$^c$ | single bond | O |
| 1-824 | H | 3-Pyr | H | H | 2-(ONO$_2$CH$_2$)-Hx$^c$ | single bond | O |
| 1-825 | H | H | H | H | 2-(ONO$_2$CH$_2$)-Hx$^c$ | CH$_2$ | O |
| 1-826 | H | Me | H | H | 2-(ONO$_2$CH$_2$)-Hx$^c$ | CH$_2$ | O |
| 1-827 | H | Bz | H | H | 2-(ONO$_2$CH$_2$)-Hx$^c$ | CH$_2$ | O |
| 1-828 | H | 4-Me-Bz | H | H | 2-(ONO$_2$CH$_2$)-Hx$^c$ | CH$_2$ | O |
| 1-829 | H | 4-MeO-Bz | H | H | 2-(ONO$_2$CH$_2$)-Hx$^c$ | CH$_2$ | O |
| 1-830 | H | 4-F-Bz | H | H | 2-(ONO$_2$CH$_2$)-Hx$^c$ | CH$_2$ | O |
| 1-831 | H | Ph | H | H | 2-(ONO$_2$CH$_2$)-Hx$^c$ | CH$_2$ | O |
| 1-832 | H | 2-Then | H | H | 2-(ONO$_2$CH$_2$)-Hx$^c$ | CH$_2$ | O |
| 1-833 | H | 3-Then | H | H | 2-(ONO$_2$CH$_2$)-Hx$^c$ | CH$_2$ | O |
| 1-834 | H | 2-Fur | H | H | 2-(ONO$_2$CH$_2$)-Hx$^c$ | CH$_2$ | O |
| 1-835 | H | 3-Fur | H | H | 2-(ONO$_2$CH$_2$)-Hx$^c$ | CH$_2$ | O |
| 1-836 | H | 3-pyr | H | H | 2-(ONO$_2$CH$_2$)-Hx$^c$ | CH$_2$ | O |
| 1-837 | H | H | H | H | 3-(ONO$_2$)-Hx$^c$ | single bond | O |
| 1-838 | H | Me | H | H | 3-(ONO$_2$)-Hx$^c$ | single bond | O |
| 1-839 | H | Bz | H | H | 3-(ONO$_2$)-Hx$^c$ | single bond | O |
| 1-840 | H | 4-Me-Bz | H | H | 3-(ONO$_2$)-Hx$^c$ | single bond | O |
| 1-841 | H | 4-MeO-Bz | H | H | 3-(ONO$_2$)-Hx$^c$ | single bond | O |
| 1-842 | H | 4-F-Bz | H | H | 3-(ONO$_2$)-Hx$^c$ | single bond | O |
| 1-843 | H | Ph | H | H | 3-(ONO$_2$)-Hx$^c$ | single bond | O |
| 1-844 | H | 2-Then | H | H | 3-(ONO$_2$)-Hx$^c$ | sirigle bond | O |
| 1-845 | H | 3-Then | H | H | 3-(ONO$_2$)-Hx$^c$ | single bond | O |
| 1-846 | H | 2-Fur | H | H | 3-(ONO$_2$)-Hx$^c$ | single bond | O |
| 1-847 | H | 3-Fur | H | H | 3-(ONO$_2$)-Hx$^c$ | single bond | O |
| 1-848 | H | 3-Pyr | H | H | 3-(ONO$_2$)-Hx$^c$ | single bond | O |
| 1-849 | H | H | H | H | 3-(ONO$_2$)-Hx$^c$ | CH$_2$ | o |
| 1-850 | H | Me | H | H | 3-(ONO$_2$)-Hx$^c$ | CH$_2$ | O |
| 1-851 | H | Bz | H | H | 3-(ONO$_2$)-Hx$^c$ | CH$_2$ | O |
| 1-852 | H | 4-Me-Bz | H | H | 3-(ONO$_2$)-Hx$^c$ | CH$_2$ | O |
| 1-853 | H | 4-MeO-Bz | H | H | 3-(ONO$_2$)-Hx$^c$ | CH$_2$ | O |
| 1-854 | H | 4-F-Bz | H | H | 3-(ONO$_2$)-Hx$^c$ | CH$_2$ | O |
| 1-855 | H | Ph | H | H | 3-(ONO$_2$)-Hx$^c$ | CH$_2$ | O |
| 1-856 | H | 2-Then | H | H | 3-(ONO$_2$)-Hx$^c$ | CH$_2$ | O |
| 1-857 | H | 3-Then | H | H | 3-(ONO$_2$)-Hx$^c$ | CH$_2$ | O |
| 1-858 | H | 2-Fur | H | H | 3-(ONO$_2$)-Hx$^c$ | CH$_2$ | O |
| 1-859 | H | 3-Fur | H | H | 3-(ONO$_2$)-Hx$^c$ | CH$_2$ | O |
| 1-860 | H | 3-Pyr | H | H | 3-(ONO$_2$)-Hx$^c$ | CH$_2$ | O |
| 1-861 | H | H | H | H | 3-(ONO$_2$CH$_2$)-Hx$^c$ | single bond | O |
| 1-862 | H | Me | H | H | 3-(ONO$_2$CH$_2$)-Hx$^c$ | single bond | O |
| 1-863 | H | Bz | H | H | 3-(ONO$_2$CH$_2$)-Hx$^c$ | single bond | O |
| 1-864 | H | 4-Me-Bz | H | H | 3-(ONO$_2$CH$_2$)-Hx$^c$ | single bond | O |
| 1-865 | H | 4-MeO-Bz | H | H | 3-(ONO$_2$CH$_2$)-Hx$^c$ | single bond | O |
| 1-866 | H | 4-F-Bz | H | H | 3-(ONO$_2$CH$_2$)-Hx$^c$ | single bond | O |
| 1-867 | H | Ph | H | H | 3-(ONO$_2$CH$_2$)-Hx$^c$ | single bond | O |
| 1-868 | H | 2-Then | H | H | 3-(ONO$_2$CH$_2$)-Hx$^c$ | single bond | O |
| 1-869 | H | 3-Then | H | H | 3-(ONO$_2$CH$_2$)-Hx$^c$ | single bond | O |
| 1-870 | H | 2-Fur | H | H | 3-(ONO$_2$CH$_2$)-Hx$^c$ | single bond | O |
| 1-871 | H | 3-Fur | H | H | 3-(ONO$_2$CH$_2$)-Hx$^c$ | single bond | O |
| 1-872 | H | 3-Pyr | H | H | 3-(ONO$_2$CH$_2$)-Hx$^c$ | single bond | O |
| 1-873 | H | H | H | H | 3-(ONO$_2$CH$_2$)-Hx$^c$ | CH$_2$ | O |
| 1-874 | H | Me | H | H | 3-(ONO$_2$CH$_2$)-Hx$^c$ | CH$_2$ | O |
| 1-875 | H | Bz | H | H | 3-(ONO$_2$CH$_2$)-Hx$^c$ | CH$_2$ | O |
| 1-876 | H | 4-Me-Bz | H | H | 3-(ONO$_2$CH$_2$)-Hx$^c$ | CH$_2$ | O |
| 1-877 | H | 4-MeO-Bz | H | H | 3-(ONO$_2$CH$_2$)-Hx$^c$ | CH$_2$ | O |
| 1-878 | H | 4-F-Bz | H | H | 3-(ONO$_2$CH$_2$)-Hx$^c$ | CH$_2$ | O |
| 1-879 | H | Ph | H | H | 3-(ONO$_2$CH$_2$)-Hx$^c$ | CH$_2$ | O |
| 1-880 | H | 2-Then | H | H | 3-(ONO$_2$CH$_2$)-Hx$^c$ | CH$_2$ | O |
| 1-881 | H | 3-Then | H | H | 3-(ONO$_2$CH$_2$)-Hx$^c$ | CH$_2$ | O |
| 1-882 | H | 2-Fur | H | H | 3-(ONO$_2$CH$_2$)-Hx$^c$ | CH$_2$ | O |
| 1-883 | H | 3-Fur | H | H | 3-(ONO$_2$CH$_2$)-Hx$^c$ | CH$_2$ | O |
| 1-884 | H | 3-Pyr | H | H | 3-(ONO$_2$CH$_2$)-Hx$^c$ | CH$_2$ | O |
| 1-885 | H | H | H | H | 2-[ONO$_2$(CH$_2$)$_3$]-Hx$^c$ | single bond | S |
| 1-886 | H | Me | H | H | 2-[ONO$_2$(CH$_2$)$_3$]-Hx$^c$ | single bond | S |
| 1-887 | H | Bz | H | H | 2-[ONO$_2$(CH$_2$)$_3$]-Hx$^c$ | single bond | S |

TABLE 1-continued

| Compd. No. | R¹ | R² | R³ | R⁴ | R⁵ | A | X¹ |
|---|---|---|---|---|---|---|---|
| 1-888 | H | H | H | H | 2-[ONO$_2$(CH$_2$)$_3$]-Hx$^c$ | CH$_2$ | S |
| 1-889 | H | Me | H | H | 2-[ONO$_2$(CH$_2$)$_3$]-Hx$^c$ | CH$_2$ | S |
| 1-890 | H | Bz | H | H | 2-[ONO$_2$(CH$_2$)$_3$]-Hx$^c$ | CH$_2$ | S |
| 1-891 | H | H | H | H | 3-[ONO$_2$(CH$_2$)$_3$]-Hx$^c$ | single bond | S |
| 1-892 | H | Me | H | H | 3-[ONO$_2$(CH$_2$)$_3$]-Hx$^c$ | single bond | S |
| 1-893 | H | Bz | H | H | 3-[ONO$_2$(CH$_2$)$_3$]-Hx$^c$ | single bond | S |
| 1-894 | H | H | H | H | 3-[ONO$_2$(CH$_2$)$_3$]-Hx$^c$ | CH$_2$ | S |
| 1-895 | H | Me | H | H | 3-[ONO$_2$(CH$_2$)$_3$]-Hx$^c$ | CH$_2$ | S |
| 1-896 | H | Bz | H | H | 3-[ONO$_2$(CH$_2$)$_3$]-Hx$^c$ | CH$_2$ | S |
| 1-897 | H | H | H | H | 4-[ONO$_2$(CH$_2$)$_3$]-Hx$^c$ | single bond | S |
| 1-898 | H | Me | H | H | 4-[ONO$_2$(CH$_2$)$_3$]-Hx$^c$ | single bond | S |
| 1-899 | H | Bz | H | H | 4-[ONO$_2$(CH$_2$)$_3$]-Hx$^c$ | single bond | S |
| 1-900 | H | H | H | H | 4-[ONO$_2$(CH$_2$)$_3$]-Hx$^c$ | CH$_2$ | S |
| 1-901 | H | Me | H | H | 4-[ONO$_2$(CH$_2$)$_3$]-Hx$^c$ | CH$_2$ | S |
| 1-902 | H | Bz | H | H | 4-[ONO$_2$(CH$_2$)$_3$]-Hx$^c$ | CH$_2$ | S |
| 1-903 | H | H | H | H | 2-[ONO$_2$(CH$_2$)$_3$]-Pn$^c$ | single bond | S |
| 1-904 | H | Me | H | H | 2-[ONO$_2$(CH$_2$)$_3$]-Pn$^c$ | single bond | S |
| 1-905 | H | Bz | H | H | 2-[ONO$_2$(CH$_2$)$_3$]-Pn$^c$ | single bond | S |
| 1-906 | H | H | H | H | 2-[ONO$_2$(CH$_2$)$_3$]-Pn$^c$ | CH$_2$ | S |
| 1-907 | H | Me | H | H | 2-[ONO$_2$(CH$_2$)$_3$]-Pn$^c$ | CH$_2$ | S |
| 1-908 | H | Bz | H | H | 2-[ONO$_2$(CH$_2$)$_3$]-Pn$^c$ | CH$_2$ | S |
| 1-909 | H | H | H | H | 3-[ONO$_2$(CH$_2$)$_3$]-Pn$^c$ | single bond | S |
| 1-910 | H | Me | H | H | 3-[ONO$_2$(CH$_2$)$_3$]-Pn$^c$ | single bond | S |
| 1-911 | H | Bz | H | H | 3-[ONO$_2$(CH$_2$)$_3$]-Pn$^c$ | single bond | S |
| 1-912 | H | H | H | H | 3-[ONO$_2$(CH$_2$)$_3$]-Pn$^c$ | CH$_2$ | S |
| 1-913 | H | Me | H | H | 3-[ONO$_2$(CH$_2$)$_3$]-Pn$^c$ | CH$_2$ | S |
| 1-914 | H | Bz | H | H | 3-[ONO$_2$(CH$_2$)$_3$]-Pn$^c$ | CH$_2$ | S |
| 1-915 | H | H | H | H | 2-(ONO$_2$CH$_2$]-Bu$^c$ | single bond | S |
| 1-916 | H | Me | H | H | 2-(ONO$_2$CH$_2$]-Bu$^c$ | single bond | S |
| 1-917 | H | Bz | H | H | 2-(ONO$_2$CH$_2$]-Bu$^c$ | single bond | S |
| 1-918 | H | H | H | H | 2-(ONO$_2$CH$_2$]-Bu$^c$ | CH$_2$ | S |
| 1-919 | H | Me | H | H | 2-(ONO$_2$CH$_2$]-Bu$^c$ | CH$_2$ | S |
| 1-920 | H | Bz | H | H | 2-(ONO$_2$CH$_2$]-Bu$^c$ | CH$_2$ | S |
| 1-921 | H | H | H | H | 3-(ONO$_2$CH$_2$]-Bu$^c$ | single bond | S |
| 1-922 | H | Me | H | H | 3-(ONO$_2$CH$_2$]-Bu$^c$ | single bond | S |
| 1-923 | H | Bz | H | H | 3-(ONO$_2$CH$_2$]-Bu$^c$ | single bond | S |
| 1-924 | H | H | H | H | 3-(ONO$_2$CH$_2$]-Bu$^c$ | CH$_2$ | S |
| 1-925 | H | Me | H | H | 3-(ONO$_2$CH$_2$]-Bu$^c$ | CH$_2$ | S |
| 1-926 | H | Bz | H | H | 3-(ONO$_2$CH$_2$]-Bu$^c$ | CH$_2$ | S |
| 1-927 | H | H | H | H | 2-(ONO$_2$CH$_2$]-Pr$^c$ | single bond | S |
| 1-928 | H | Me | H | H | 2-(ONO$_2$CH$_2$]-Pr$^c$ | single bond | S |
| 1-929 | H | Bz | H | H | 2-(ONO$_2$CH$_2$]-Pr$^c$ | single bond | S |
| 1-930 | H | H | H | H | 2-(ONO$_2$CH$_2$]-Pr$^c$ | CH$_2$ | S |
| 1-931 | H | Me | H | H | 2-(ONO$_2$CH$_2$]-Pr$^c$ | CH$_2$ | S |
| 1-932 | H | Bz | H | H | 2-(ONO$_2$CH$_2$]-Pr$^c$ | CH$_2$ | S |
| 1-933 | H | H | H | H | 2-(ONO$_2$CH$_2$)-Pn$^c$ | (CH$_2$)$_2$ | S |
| 1-934 | H | Me | H | H | 2-(ONO$_2$CH$_2$)-Pn$^c$ | (CH$_2$)$_2$ | S |
| 1-935 | H | Bz | H | H | 2-(ONO$_2$CH$_2$)-Pn$^c$ | (CH$_2$)$_2$ | S |
| 1-936 | H | 4-Me-Bz | H | H | 2-(ONO$_2$CH$_2$)-Pn$^c$ | (CH$_2$)$_2$ | S |
| 1-937 | H | 4-MeO-Bz | H | H | 2-(ONO$_2$CH$_2$)-Pn$^c$ | (CH$_2$)$_2$ | S |
| 1-938 | H | Ph | H | H | 2-(ONO$_2$CH$_2$)-Pn$^c$ | (CH$_2$)$_2$ | S |
| 1-939 | H | 2-Then | H | H | 2-(ONO$_2$CH$_2$)-Pn$^c$ | (CH$_2$)$_2$ | S |
| 1-940 | H | 2-Fur | H | H | 2-(ONO$_2$CH$_2$)-Pn$^c$ | (CH$_2$)$_2$ | S |
| 1-941 | H | 3-Pyr | H | H | 2-(ONO$_2$CH$_2$)-Pn$^c$ | (CH$_2$)$_2$ | S |
| 1-942 | H | H | H | H | 3-(ONO$_2$CH$_2$)-Pn$^c$ | (CH$_2$)$_2$ | S |
| 1-943 | H | Me | H | H | 3-(ONO$_2$CH$_2$)-Pn$^c$ | (CH$_2$)$_2$ | S |
| 1-944 | H | Bz | H | H | 3-(ONO$_2$CH$_2$)-Pn$^c$ | (CH$_2$)$_2$ | S |
| 1-945 | H | 4-Me-Bz | H | H | 3-(ONO$_2$CH$_2$)-Pn$^c$ | (CH$_2$)$_2$ | S |
| 1-946 | H | 4-MeO-Bz | H | H | 3-(ONO$_2$CH$_2$)-Pn$^c$ | (CH$_2$)$_2$ | S |
| 1-947 | H | Ph | H | H | 3-(ONO$_2$CH$_2$)-Pn$^c$ | (CH$_2$)$_2$ | S |
| 1-948 | H | 2-Then | H | H | 3-(ONO$_2$CH$_2$)-Pn$^c$ | (CH$_2$)$_2$ | S |
| 1-949 | H | 2-Fur | H | H | 3-(ONO$_2$CH$_2$)-Pn$^c$ | (CH$_2$)$_2$ | S |
| 1-950 | H | 3-Pyr | H | H | 3-(ONO$_2$CH$_2$)-Pn$^c$ | (CH$_2$)$_2$ | S |
| 1-951 | H | H | H | H | 2-[ONO$_2$(CH$_2$)$_2$]-Pn$^c$ | (CH$_2$)$_2$ | S |
| 1-952 | H | Me | H | H | 2-[ONO$_2$(CH$_2$)$_2$]-Pn$^c$ | (CH$_2$)$_2$ | S |
| 1-953 | H | Bz | H | H | 2-[ONO$_2$(CH$_2$)$_2$]-Pn$^c$ | (CH$_2$)$_2$ | S |
| 1-954 | H | H | H | H | 3-[ONO$_2$(CH$_2$)$_2$]-Pn$^c$ | (CH$_2$)$_2$ | S |
| 1-955 | H | Me | H | H | 3-[ONO$_2$(CH$_2$)$_2$]-Pn$^c$ | (CH$_2$)$_2$ | S |
| 1-956 | H | Bz | H | H | 3-[ONO$_2$(CH$_2$)$_2$]-Pn$^c$ | (CH$_2$)$_2$ | S |
| 1-957 | H | H | H | H | 2-[ONO$_2$(CH$_2$)$_3$]-Pn$^c$ | (CH$_2$)$_2$ | S |
| 1-958 | H | Me | H | H | 2-[ONO$_2$(CH$_2$)$_3$]-Pn$^c$ | (CH$_2$)$_2$ | S |
| 1-959 | H | Bz | H | H | 2-[ONO$_2$(CH$_2$)$_3$]-Pn$^c$ | (CH$_2$)$_2$ | S |
| 1-960 | H | H | H | H | 3-[ONO$_2$(CH$_2$)$_3$]-Pn$^c$ | (CH$_2$)$_2$ | S |
| 1-961 | H | Me | H | H | 3-[ONO$_2$(CH$_2$)$_3$]-Pn$^c$ | (CH$_2$)$_2$ | S |
| 1-962 | H | Bz | H | H | 3-[ONO$_2$(CH$_2$)$_3$]-Pn$^c$ | (CH$_2$)$_2$ | S |
| 1-963 | H | H | H | H | 2-[ONO$_2$(CH$_2$)$_4$]-Pn$^c$ | (CH$_2$)$_2$ | S |

TABLE 1-continued

| Compd. No. | R¹ | R² | R³ | R⁴ | R⁵ | A | X¹ |
|---|---|---|---|---|---|---|---|
| 1-964 | H | Me | H | H | 2-[ONO$_2$(CH$_2$)$_4$]-Pn$^c$ | (CH$_2$)$_2$ | S |
| 1-965 | H | Bz | H | H | 2-[ONO$_2$(CH$_2$)$_4$]-Pn$^c$ | (CH$_2$)$_2$ | S |
| 1-966 | H | H | H | H | 3-[ONO$_2$(CH$_2$)$_4$]-Pn$^c$ | (CH$_2$)$_2$ | S |
| 1-967 | H | Me | H | H | 3-[ONO$_2$(CH$_2$)$_4$]-Pn$^c$ | (CH$_2$)$_2$ | S |
| 1-968 | H | Bz | H | H | 3-[ONO$_2$(CH$_2$)$_4$]-Pn$^c$ | (CH$_2$)$_2$ | S |
| 1-969 | H | H | H | H | 2-(ONO$_2$CH$_2$)-Pn$^c$ | (CH$_2$)$_3$ | S |
| 1-970 | H | Me | H | H | 2-(ONO$_2$CH$_2$)-Pn$^c$ | (CH$_2$)$_3$ | S |
| 1-971 | H | Bz | H | H | 2-(ONO$_2$CH$_2$)-Pn$^c$ | (CH$_2$)$_3$ | S |
| 1-972 | H | H | H | H | 3-(ONO$_2$CH$_2$)-Pn$^c$ | (CH$_2$)$_3$ | S |
| 1-973 | H | Me | H | H | 3-(ONO$_2$CH$_2$)-Pn$^c$ | (CH$_2$)$_3$ | S |
| 1-974 | H | Bz | H | H | 3-(ONO$_2$CH$_2$)-Pn$^c$ | (CH$_2$)$_3$ | S |
| 1-975 | H | H | H | H | 2-[ONO$_2$(CH$_2$)$_2$]-Pn$^c$ | (CH$_2$)$_3$ | S |
| 1-976 | H | H | H | H | 3-[ONO$_2$(CH$_2$)$_2$]-Pn$^c$ | (CH$_2$)$_3$ | S |
| 1-977 | H | H | H | H | 2-[ONO$_2$(CH$_2$)$_3$]-Pn$^c$ | (CH$_2$)$_3$ | S |
| 1-978 | H | H | H | H | 3-[ONO$_2$(CH$_2$)$_3$]-Pn$^c$ | (CH$_2$)$_3$ | S |
| 1-979 | H | H | H | H | 2-[ONO$_2$(CH$_2$)$_4$]-Pn$^c$ | (CH$_2$)$_3$ | S |
| 1-980 | H | H | H | H | 3-[ONO$_2$(CH$_2$)$_4$]-Pn$^c$ | (CH$_2$)$_3$ | S |
| 1-981 | H | H | H | H | 2-(ONO$_2$CH$_2$)-Pn$^c$ | (CH$_2$)$_2$ | O |
| 1-982 | H | Me | H | H | 2-(ONO$_2$CH$_2$)-Pn$^c$ | (CH$_2$)$_2$ | O |
| 1-983 | H | Bz | H | H | 2-(ONO$_2$CH$_2$)-Pn$^c$ | (CH$_2$)$_2$ | O |
| 1-984 | H | 4-Me-Bz | H | H | 2-(ONO$_2$CH$_2$)-Pn$^c$ | (CH$_2$)$_2$ | O |
| 1-985 | H | 4-MeO-Bz | H | H | 2-(ONO$_2$CH$_2$)-Pn$^c$ | (CH$_2$)$_2$ | O |
| 1-986 | H | Ph | H | H | 2-(ONO$_2$CH$_2$)-Pn$^c$ | (CH$_2$)$_2$ | O |
| 1-987 | H | 2-Then | H | H | 2-(ONO$_2$CH$_2$)-Pn$^c$ | (CH$_2$)$_2$ | O |
| 1-988 | H | 2-Fur | H | H | 2-(ONO$_2$CH$_2$)-Pn$^c$ | (CH$_2$)$_2$ | O |
| 1-989 | H | 3-Pyr | H | H | 2-(ONO$_2$CH$_2$)-Pn$^c$ | (CH$_2$)$_2$ | O |
| 1-990 | H | H | H | H | 3-(ONO$_2$CH$_2$)-Pn$^c$ | (CH$_2$)$_2$ | O |
| 1-991 | H | Me | H | H | 3-(ONO$_2$CH$_2$)-Pn$^c$ | (CH$_2$)$_2$ | O |
| 1-992 | H | Bz | H | H | 3-(ONO$_2$CH$_2$)-Pn$^c$ | (CH$_2$)$_2$ | O |
| 1-993 | H | 4-Me-Bz | H | H | 3-(ONO$_2$CH$_2$)-Pn$^c$ | (CH$_2$)$_2$ | O |
| 1-994 | H | 4-MeO-Bz | H | H | 3-(ONO$_2$CH$_2$)-Pn$^c$ | (CH$_2$)$_2$ | O |
| 1-995 | H | Ph | H | H | 3-(ONO$_2$CH$_2$)-Pn$^c$ | (CH$_2$)$_2$ | O |
| 1-996 | H | 2-Then | H | H | 3-(ONO$_2$CH$_2$)-Pn$^c$ | (CH$_2$)$_2$ | O |
| 1-997 | H | 2-Fur | H | H | 3-(ONO$_2$CH$_2$)-Pn$^c$ | (CH$_2$)$_2$ | O |
| 1-998 | H | 3-pyr | H | H | 3-(ONO$_2$CH$_2$)-Pn$^c$ | (CH$_2$)$_2$ | O |
| 1-999 | H | H | H | H | 2-[ONO$_2$(CH$_2$)$_2$]-Pn$^c$ | (CH$_2$)$_2$ | O |
| 1-1000 | H | Me | H | H | 2-[ONO$_2$(CH$_2$)$_2$]-Pn$^c$ | (CH$_2$)$_2$ | O |
| 1-1001 | H | Bz | H | H | 2-[ONO$_2$(CH$_2$)$_2$]-Pn$^c$ | (CH$_2$)$_2$ | O |
| 1-1002 | H | H | H | H | 3-[ONO$_2$(CH$_2$)$_2$]-Pn$^c$ | (CH$_2$)$_2$ | O |
| 1-1003 | H | Me | H | H | 3-[ONO$_2$(CH$_2$)$_2$]-Pn$^c$ | (CH$_2$)$_2$ | O |
| 1-1004 | H | Bz | H | H | 3-[ONO$_2$(CH$_2$)$_2$]-Pn$^c$ | (CH$_2$)$_2$ | O |
| 1-1005 | H | H | H | H | 2-[ONO$_2$(CH$_2$)$_3$]-Pn$^c$ | (CH$_2$)$_2$ | O |
| 1-1006 | H | Me | H | H | 2-[ONO$_2$(CH$_2$)$_3$]-Pn$^c$ | (CH$_2$)$_2$ | O |
| 1-1007 | H | Bz | H | H | 2-[ONO$_2$(CH$_2$)$_3$]-Pn$^c$ | (CH$_2$)$_2$ | O |
| 1-1008 | H | H | H | H | 3-[ONO$_2$(CH$_2$)$_3$]-Pn$^c$ | (CH$_2$)$_2$ | O |
| 1-1009 | H | Me | H | H | 3-[ONO$_2$(CH$_2$)$_3$]-Pn$^c$ | (CH$_2$)$_2$ | O |
| 1-1010 | H | Bz | H | H | 3-[ONO$_2$(CH$_2$)$_3$]-Pn$^c$ | (CH$_2$)$_2$ | O |
| 1-1011 | H | H | H | H | 2-[ONO$_2$(CH$_2$)$_4$]-Pn$^c$ | (C:H2)$_2$ | O |
| 1-1012 | H | Me | H | H | 2-[ONO$_2$(CH$_2$)$_4$]-Pn$^c$ | (CH$_2$)$_2$ | O |
| 1-1013 | H | Bz | H | H | 2-[ONO$_2$(CH$_2$)$_4$]-Pn$^c$ | (CH$_2$)$_2$ | O |
| 1-1014 | H | H | H | H | 3-[ONO$_2$(CH$_2$)$_4$]-Pn$^c$ | (CH$_2$)$_2$ | O |
| 1-1015 | H | Me | H | H | 3-[ONO$_2$(CH$_2$)$_4$]-Pn$^c$ | (CH$_2$)$_2$ | O |
| 1-1016 | H | Bz | H | H | 3-[ONO$_2$(CH$_2$)$_4$]-Pn$^c$ | (CH$_2$)$_2$ | O |
| 1-1017 | H | H | H | H | 2-(ONO$_2$CH$_2$)-Pn$^c$ | (CH$_2$)$_3$ | O |
| 1-1018 | H | Me | H | H | 2-(ONO$_2$CH$_2$)-Pn$^c$ | (CH$_2$)$_3$ | O |
| 1-1019 | H | Bz | H | H | 2-(ONO$_2$CH$_2$)-Pn$^c$ | (CH$_2$)$_3$ | O |
| 1-1020 | H | H | H | H | 3-(ONO$_2$CH$_2$)-Pn$^c$ | (CH$_2$)$_3$ | O |
| 1-1021 | H | Me | H | H | 3-(ONO$_2$CH$_2$)-Pn$^c$ | (CH$_2$)$_3$ | O |
| 1-1022 | H | Bz | H | H | 3-(ONO$_2$CH$_2$)-Pn$^c$ | (CH$_2$)$_3$ | O |
| 1-1023 | H | H | H | H | 2-[ONO$_2$(CH$_2$)$_2$]-Pn$^c$ | (CH$_2$)$_3$ | O |
| 1-1024 | H | H | H | H | 3-[ONO$_2$(CH$_2$)$_2$]-Pn$^c$ | (CH$_2$)$_3$ | O |
| 1-1025 | H | H | H | H | 2-[ONO$_2$(CH$_2$)$_3$]-Pn$^c$ | (CH$_2$)$_3$ | O |
| 1-1026 | H | H | H | H | 3-[ONO$_2$(CH$_2$)$_3$]-Pn$^c$ | (CH$_2$)$_3$ | O |
| 1-1027 | H | H | H | H | 2-[ONO$_2$(CH$_2$)$_4$]-Pn$^c$ | (CH$_2$)$_3$ | O |
| 1-1028 | H | H | H | H | 3-[ONO$_2$(CH$_2$)$_4$]-Pn$^c$ | (CH$_2$)$_3$ | O |
| 1-1030 | H | H | H | H | 5-ONO$_2$-2-Pip | single bond | S |
| 1-1031 | H | H | H | H | 6-ONO$_2$-3-Pip | single bond | S |
| 1-1032 | H | H | H | H | 5-(ONO$_2$CH$_2$)-2-Pip | single bond | S |
| 1-1033 | H | H | H | H | 5-[ONO$_2$(CH$_2$)$_2$]-2-Pip | single bond | S |
| 1-1034 | H | H | H | H | 5-[ONO$_2$(CH$_2$)$_3$]-2-Pip | single bond | S |
| 1-1035 | H | H | H | H | 5-[ONO$_2$(CH$_2$)$_4$]-2-Pip | single bond | S |
| 1-1036 | H | H | H | H | 6-(ONO$_2$CH$_2$)-3-Pip | single bond | S |
| 1-1037 | H | H | H | H | 6-[ONO$_2$(CH$_2$)$_2$]-3-Pip | single bond | S |
| 1-1038 | H | H | H | H | 6-[ONO$_2$(CH$_2$)$_3$]-3-Pip | single bond | S |
| 1-1039 | H | H | H | H | 6-[ONO$_2$(CH$_2$)$_4$]-3-Pip | single bond | S |
| 1-1040 | H | H | H | H | 5-(ONO$_2$CH$_2$)-2-Pip | CH$_2$ | S |

TABLE 1-continued

| Compd. No. | R¹ | R² | R³ | R⁴ | R⁵ | A | X¹ |
|---|---|---|---|---|---|---|---|
| 1-1041 | H | Me | H | H | 5-(ONO$_2$CH$_2$)-2-Pip | CH$_2$ | S |
| 1-1042 | H | Ph | H | H | 5-(ONO$_2$CH$_2$)-2-Pip | CH$_2$ | S |
| 1-1043 | H | Bz | H | H | 5-(ONO$_2$CH$_2$)-2-Pip | CH$_2$ | S |
| 1-1044 | H | 4-Me-Bz | H | H | 5-(ONO$_2$CH$_2$)-2-Pip | CH$_2$ | S |
| 1-1045 | H | 4-MeO-Bz | H | H | 5-(ONO$_2$CH$_2$)-2-Pip | CH$_2$ | S |
| 1-1046 | H | H | H | H | 1-Me-5-(ONO$_2$CH$_2$)-2-Pip | CH$_2$ | S |
| 1-1047 | H | H | H | H | 5-[ONO$_2$(CH$_2$)$_2$]-2-Pip | CH$_2$ | S |
| 1-1048 | H | Me | H | H | 5-[ONO$_2$(CH$_2$)$_2$]-2-Pip | CH$_2$ | S |
| 1-1049 | H | Bz | H | H | 5-[ONO$_2$(CH$_2$)$_2$]-2-Pip | CH$_2$ | S |
| 1-1050 | H | H | H | H | 5-[ONO$_2$(CH$_2$)$_3$]-2-Pip | CH$_2$ | S |
| 1-1051 | H | Me | H | H | 5-[ONO$_2$(CH$_2$)$_3$]-2-Pip | CH$_2$ | S |
| 1-1052 | H | Bz | H | H | 5-[ONO$_2$(CH$_2$)$_3$]-2-Pip | CH$_2$ | S |
| 1-1053 | H | H | H | H | 5-[ONO$_2$(CH$_2$)$_4$]-2-Pip | CH$_2$ | S |
| 1-1054 | H | Me | H | H | 5-[ONO$_2$(CH$_2$)$_4$]-2-Pip | CH$_2$ | S |
| 1-1055 | H | Bz | H | H | 5-[ONO$_2$(CH$_2$)$_4$]-2-Pip | CH$_2$ | S |
| 1-1056 | H | H | H | H | 6-(ONO$_2$CH$_2$)-3-Pip | CH$_2$ | S |
| 1-1057 | H | Me | H | H | 6-(ONO$_2$CH$_2$)-3-Pip | CH$_2$ | S |
| 1-1058 | H | Ph | H | H | 6-(ONO$_2$CH$_2$)-3-Pip | CH$_2$ | S |
| 1-1059 | H | Bz | H | H | 6-(ONO$_2$CH$_2$)-3-Pip | CH$_2$ | S |
| 1-1060 | H | 4-Me-Bz | H | H | 6-(ONO$_2$CH$_2$)-3-Pip | CH$_2$ | S |
| 1-1061 | H | 4-MeO-Bz | H | H | 6-(ONO$_2$CH$_2$)-3-Pip | CH$_2$ | S |
| 1-1062 | H | H | H | H | 1-Me-6-(ONO$_2$CH$_2$)-3-Pip | CH$_2$ | S |
| 1-1063 | H | H | H | H | 6-[ONO$_2$(CH$_2$)$_2$]-3-Pip | CH$_2$ | S |
| 1-1064 | H | Me | H | H | 6-[ONO$_2$(CH$_2$)$_2$]-3-Pip | CH$_2$ | S |
| 1-1065 | H | Bz | H | H | 6-[ONO$_2$(CH$_2$)$_2$]-3-Pip | CH$_2$ | S |
| 1-1066 | H | H | H | H | 6-[ONO$_2$(CH$_2$)$_3$]-3-Pip | CH$_2$ | S |
| 1-1067 | H | Me | H | H | 6-[ONO$_2$(CH$_2$)$_3$]-3-Pip | CH$_2$ | S |
| 1-1068 | H | Bz | H | H | 6-[ONO$_2$(CH$_2$)$_3$]-3-Pip | CH$_2$ | S |
| 1-1069 | H | H | H | H | 6-[ONO$_2$(CH$_2$)$_4$]-3-Pip | CH$_2$ | S |
| 1-1070 | H | Me | H | H | 6-[ONO$_2$(CH$_2$)$_4$]-3-Pip | CH$_2$ | S |
| 1-1071 | H | Bz | H | H | 6-[ONO$_2$(CH$_2$)$_4$]-3-Pip | CH$_2$ | S |
| 1-1072 | H | H | H | H | 5-(ONO$_2$CH$_2$)-2-Pip | (CH$_2$)$_2$ | S |
| 1-1073 | H | Me | H | H | 5-(ONO$_2$CH$_2$)-2-Pip | (CH$_2$)$_2$ | S |
| 1-1074 | H | Bz | H | H | 5-(ONO$_2$CH$_2$)-2-Pip | (CH$_2$) 2 | S |
| 1-1075 | H | H | H | H | 1-Me-5-(ONO$_2$CH$_2$)-2-Pip | (CH$_2$)$_2$ | S |
| 1-1076 | H | H | H | H | 5-[ONO$_2$(CH$_2$)$_2$]-2-Pip | (CH$_2$)$_2$ | S |
| 1-1077 | H | H | H | H | 5-[ONO$_2$(CH$_2$)$_3$]-2-Pip | (CH$_2$)$_2$ | S |
| 1-1078 | H | H | H | H | 5-[ONO$_2$(CH$_2$)$_4$]-2-Pip | (CH$_2$)$_2$ | S |
| 1-1079 | H | H | H | H | 6-(ONO$_2$CH$_2$)-3-Pip | (CH$_2$)$_2$ | S |
| 1-1080 | H | Me | H | H | 6-(ONO$_2$CH$_2$)-3-Pip | (CH$_2$)$_2$ | S |
| 1-1081 | H | Bz | H | H | 6-(ONO$_2$CH$_2$)-3-Pip | (CH$_2$)$_2$ | S |
| 1-1082 | H | H | H | H | 1-Me-6-(ONO$_2$CH$_2$)-3-Pip | (CH$_2$)$_2$ | S |
| 1-1083 | H | H | H | H | 6-[ONO$_2$(CH$_2$)$_2$]-3-Pip | (CH$_2$)$_2$ | S |
| 1-1084 | H | H | H | H | 6-[ONO$_2$(CH$_2$)$_3$]-3-Pip | (CH$_2$)$_2$ | S |
| 1-1085 | H | H | H | H | 6-[ONO$_2$(CH$_2$)$_4$]-3-Pip | (CH$_2$)$_2$ | S |
| 1-1086 | H | H | H | H | 5-[ONO$_2$(CH$_2$)$_2$]-2-Pip | (CH$_2$)$_3$ | S |
| 1-1087 | H | H | H | H | 6-(ONO$_2$CH$_2$)-2-Pip | (CH$_2$)$_3$ | S |
| 1-1088 | H | H | H | H | 5-ONO$_2$-2-Pip | single bond | O |
| 1-1089 | H | H | H | H | 6-ONO$_2$-3-Pip | single bond | O |
| 1-1090 | H | H | H | H | 5-(ONO$_2$CH$_2$)-2-Pip | single bond | O |
| 1-1091 | H | H | H | H | 5-[ONO$_2$(CH$_2$)$_2$]-2-Pip | single bond | O |
| 1-1092 | H | H | H | H | 5-[ONO$_2$(CH$_2$)$_3$]-2-Pip | single bond | O |
| 1-1093 | H | H | H | H | 5-[ONO$_2$(CH$_2$)$_4$]-2-Pip | single bond | O |
| 1-1094 | H | H | H | H | 6-(ONO$_2$CH$_2$)-3-Pip | single bond | O |
| 1-1095 | H | H | H | H | G-[ONO$_2$(CH$_2$)$_2$]-3-Pip | single bond | O |
| 1-1096 | H | H | H | H | 6-[ONO$_2$(CH$_2$)$_3$]-3-Pip | single bond | O |
| 1-1097 | H | H | H | H | 6-[ONO$_2$(CH$_2$)$_4$]-3-Pip | single bond | O |
| 1-1098 | H | H | H | H | 5-(ONO$_2$CH$_2$)-2-Pip | CH$_2$ | O |
| 1-1099 | H | Me | H | H | 5-(ONO$_2$CH$_2$)-2-Pip | CH$_2$ | O |
| 1-1100 | H | Ph | H | H | 5-(ONO$_2$CH$_2$)-2-Pip | CH$_2$ | O |
| 1-1101 | H | Bz | H | H | 5-(ONO$_2$CH$_2$)-2-Pip | CH$_2$ | O |
| 1-1102 | H | 4-Me-Bz | H | H | 5-(ONO$_2$CH$_2$)-2-Pip | CH$_2$ | O |
| 1-1103 | H | 4-MeO-Bz | H | H | 5-(ONO$_2$CH$_2$)-2-Pip | CH$_2$ | O |
| 1-1104 | H | H | H | H | 1-Me-5-(ONO$_2$CH$_2$)-2-Pip | CH$_2$ | O |
| 1-1105 | H | H | H | H | 5-[ONO$_2$(CH$_2$)$_2$]-2-Pip | CH$_2$ | O |
| 1-1106 | H | Me | H | H | 5-[ONO$_2$(CH$_2$)$_2$]-2-Pip | CH$_2$ | O |
| 1-1107 | H | Bz | H | H | 5-[ONO$_2$(CH$_2$)21-2-Pip | CH$_2$ | O |
| 1-1108 | H | H | H | H | 5-[ONO$_2$(CH$_2$)$_3$]-2-Pip | CH$_2$ | O |
| 1-1109 | H | Me | H | H | 5-[ONO$_2$(CH$_2$)$_3$]-2-Pip | CH$_2$ | O |
| 1-1110 | H | Bz | H | H | 5-[ONO$_2$(CH$_2$)$_3$]-2-Pip | CH$_2$ | O |
| 1-1111 | H | H | H | H | 5-[ONO$_2$(CH$_2$)$_4$]-2-Pip | CH$_2$ | O |
| 1-1112 | H | Me | H | H | 5-[ONO$_2$(CH$_2$)$_4$]-2-Pip | CH$_2$ | O |
| 1-1113 | H | Bz | H | H | 5-[ONO$_2$(CH$_2$)$_4$]-2-Pip | CH$_2$ | O |
| 1-1114 | H | H | H | H | 6-(ONO$_2$CH$_2$)-3-Pip | CH$_2$ | O |
| 1-1115 | H | Me | H | H | 6-(ONO$_2$CH$_2$)-3-Pip | CH$_2$ | O |
| 1-1116 | H | Ph | H | H | 6-(ONO$_2$CH$_2$)-3-Pip | CH$_2$ | O |

TABLE 1-continued

| Compd. No. | R¹ | R² | R³ | R⁴ | R⁵ | A | X¹ |
|---|---|---|---|---|---|---|---|
| 1-1117 | H | Bz | H | H | 6-(ONO$_2$CH$_2$)-3-Pip | CH$_2$ | O |
| 1-1118 | H | 4-Me-Bz | H | H | 6-(ONO$_2$CH$_2$)-3-Pip | CH$_2$ | O |
| 1-1119 | H | 4-MeO-Bz | H | H | 6-(ONO$_2$CH$_2$)-3-Pip | CH$_2$ | O |
| 1-1120 | H | H | H | H | 1-Me-6-(ONO$_2$CH$_2$)-3-Pip | CH$_2$ | O |
| 1-1121 | H | H | H | H | 6-[ONO$_2$(CH$_2$)$_2$]-3-Pip | CH$_2$ | O |
| 1-1122 | H | Me | H | H | 6-[ONO$_2$(CH$_2$)$_2$]-3-Pip | CH$_2$ | O |
| 1-1123 | H | Bz | H | H | 6-[ONO$_2$(CH$_2$)$_2$]-3-Pip | CH$_2$ | O |
| 1-1124 | H | H | H | H | 6-[ONO$_2$(CH$_2$)$_3$]-3-Pip | CH$_2$ | O |
| 1-1125 | H | Me | H | H | 6-[ONO$_2$(CH$_2$)$_3$]-3-Pip | CH$_2$ | O |
| 1-1126 | H | Bz | H | H | 6-[ONO$_2$(CH$_2$)$_3$]-3-Pip | CH$_2$ | O |
| 1-1127 | H | H | H | H | 6-[ONO$_2$(CH$_2$)$_4$]-3-Pip | CH$_2$ | O |
| 1-1128 | H | Me | H | H | 6-[ONO$_2$(CH$_2$)$_4$]-3-Pip | CH$_2$ | O |
| 1-1129 | H | Bz | H | H | 6-[ONO$_2$(CH$_2$)$_4$]-3-Pip | CH$_2$ | O |
| 1-1130 | H | H | H | H | 5-(ONO$_2$CH$_2$)-2-Pip | (CH$_2$)$_2$ | O |
| 1-1131 | H | Me | H | H | 5-(ONO$_2$CH$_2$)-2-Pip | (CH$_2$)$_2$ | O |
| 1-1132 | H | Bz | H | H | 5-(ONO$_2$CH$_2$)-2-Pip | (CH$_2$)$_2$ | O |
| 1-1133 | H | H | H | H | 1-Me-5-(ONO$_2$CH$_2$)-2-Pip | (CH$_2$)$_2$ | O |
| 1-1134 | H | H | H | H | 5-[ONO$_2$(CH$_2$)$_2$]-2-Pip | (CH$_2$)$_2$ | O |
| 1-1135 | H | H | H | H | 5-[ONO$_2$(CH$_2$)$_3$]-2-Pip | (CH$_2$)$_2$ | O |
| 1-1136 | H | H | H | H | 5-[ONO$_2$(CH$_2$)$_4$]-2-Pip | (CH$_2$)$_2$ | O |
| 1-1137 | H | H | H | H | 6-(ONO$_2$CH$_2$)-3-Pip | (CH$_2$)$_2$ | O |
| 1-1138 | H | Me | H | H | 6-(ONO$_2$CH$_2$)-3-Pip | (CH$_2$)$_2$ | O |
| 1-1139 | H | Bz | H | H | 6-(ONO$_2$CH$_2$)-3-Pip | (CH$_2$)$_2$ | O |
| 1-1140 | H | H | H | H | 1-Me-6-(ONO$_2$CH$_2$)-3-Pip | (CH$_2$)$_2$ | O |
| 1-1141 | H | H | H | H | 6-[ONO$_2$(CH$_2$)$_2$]-3-Pip | (CH$_2$)$_2$ | O |
| 1-1142 | H | H | H | H | 6-[ONO$_2$(CH$_2$)$_3$]-3-Pip | (CH$_2$)$_2$ | O |
| 1-1143 | H | H | H | H | 6-[ONO$_2$(CH$_2$)$_4$]-3-Pip | (CH$_2$)$_2$ | O |
| 1-1144 | H | H | H | H | 5-(ONO$_2$CH$_2$)-2-Pip | (CH$_2$)$_3$ | O |
| 1-1145 | H | H | H | H | 6-(ONO$_2$CH$_2$)-2-Pip | (CH$_2$)$_3$ | O |
| 1-1146 | H | H | H | H | 5-(ONO$_2$)-2-Pyrr | single bond | S |
| 1-1147 | H | H | H | H | 4-(ONO$_2$)-2-Pyrr | single bond | S |
| 1-1148 | H | H | H | H | 5-(ONO$_2$CH$_2$)-2-Pyrr | single bond | S |
| 1-1149 | H | H | H | H | 4-(ONO$_2$CH$_2$)-2-Pyrr | single bond | S |
| 1-1150 | H | H | H | H | 5-(ONO$_2$)-2-Pyrr | CH$_2$ | S |
| 1-1151 | H | H | H | H | 4-(ONO$_2$)-2-Pyrr | CH$_2$ | S |
| 1-1152 | H | H | H | H | 5-(ONO$_2$CH$_2$)-2-Pyrr | CH$_2$ | S |
| 1-1153 | H | Me | H | H | 5-(ONO$_2$CH$_2$)-2-Pyrr | CH$_2$ | S |
| 1-1154 | H | Bz | H | H | 5-(ONO$_2$CH$_2$)-2-Pyrr | CH$_2$ | S |
| 1-1155 | H | H | H | H | 1-Me-5-(ONO$_2$CH$_2$)-2-Pyrr | CH$_2$ | S |
| 1-1156 | H | H | H | H | 4-(ONO$_2$CH$_2$)-2-Pyrr | CH$_2$ | S |
| 1-1157 | H | Me | H | H | 4-(ONO$_2$CH$_2$)-2-Pyrr | CH$_2$ | S |
| 1-1158 | H | Bz | H | H | 4-(ONO$_2$CH$_2$)-2-Pyrr | CH$_2$ | S |
| 1-1159 | H | H | H | H | 5-[ONO$_2$(CH$_2$)$_2$]-2-Pyrr | CH$_2$ | S |
| 1-1160 | H | H | H | H | 4-[ONO$_2$(CH$_2$)$_2$]-2-Pyrr | CH$_2$ | S |
| 1-1161 | H | H | H | H | 5-[ONO$_2$(CH$_2$)$_3$]-2-Pyrr | CH$_2$ | S |
| 1-1162 | H | H | H | H | 4-[ONO$_2$(CH$_2$)$_3$]-2-Pyrr | CH$_2$ | S |
| 1-1163 | H | H | H | H | 5-[ONO$_2$(CH$_2$)$_4$]-2-Pyrr | CH$_2$ | S |
| 1-1164 | H | H | H | H | 4-[ONO$_2$(CH$_2$)$_4$]-2-Pyrr | CH$_2$ | S |
| 1-1165 | H | H | H | H | 5-(ONO$_2$CH$_2$)-2-Pyrr | (CH$_2$)$_2$ | S |
| 1-1166 | H | H | H | H | 4-(ONO$_2$CH$_2$)-2-Pyrr | (CH$_2$)$_2$ | S |
| 1-1167 | H | H | H | H | 5-(ONO$_2$)-2-Pyrr | single bond | O |
| 1-1168 | H | H | H | H | 4-(ONO$_2$)-2-Pyrr | single bond | O |
| 1-1169 | H | H | H | H | 5-(ONO$_2$CH$_2$)-2-Pyrr | single bond | O |
| 1-1170 | H | H | H | H | 4-(ONO$_2$CH$_2$)-2-Prrr | single bond | O |
| 1-1171 | H | H | H | H | 5-(ONO$_2$)-2-Pyrr | CH$_2$ | O |
| 1-1172 | H | H | H | H | 4-(ONO$_2$)-2-Pyrr | CH$_2$ | O |
| 1-1173 | H | H | H | H | 5-(ONO$_2$CH$_2$)-2-Pyrr | CH$_2$ | O |
| 1-1174 | H | Me | H | H | 5-(ONO$_2$-2)-2-Prrr | CH$_2$ | O |
| 1-1175 | H | Bz | H | H | 5-(ONO$_2$-2)-2-Prrr | CH$_2$ | O |
| 1-1176 | H | H | H | H | 1-Me-5-(ONO$_2$CH$_2$)-2-Pyrr | CH$_2$ | O |
| 1-1177 | H | H | H | H | 4-(ONO$_2$CH$_2$)-2-Prrr | CH$_2$ | O |
| 1-1178 | H | Me | H | H | 4-(ONO$_2$CH$_2$)-2-Prrr | CH$_2$ | O |
| 1-1179 | H | Bz | H | H | 4-(ONO$_2$CH$_2$)-2-Pyrr | CH$_2$ | O |
| 1-1180 | H | H | H | H | 5-[ONO$_2$(CH$_2$)$_2$]-2-Pyrr | CH$_2$ | O |
| 1-1181 | H | H | H | H | 4-[ONO$_2$(CH$_2$)$_2$]-2-Pyrr | CH$_2$ | O |
| 1-1182 | H | H | H | H | 5-[ONO$_2$(CH$_2$)$_3$]-2-Pyrr | CH$_2$ | O |
| 1-1183 | H | H | H | H | 4-[ONO$_2$(CH$_2$)$_3$]-2-Pyrr | CH$_2$ | O |
| 1-1184 | H | H | H | H | 5-[ONO$_2$(CH$_2$)$_4$]-2-Pyrr | CH$_2$ | O |
| 1-1185 | H | H | H | H | 4-[ONO$_2$(CH$_2$)$_4$]-2-Pyrr | CH$_2$ | O |
| 1-1186 | H | H | H | H | 5-(ONO$_2$CH$_2$)-2-Pyrr | (CH$_2$)$_2$ | O |
| 1-1187 | H | H | H | H | 4-(ONO$_2$CH$_2$)-2-Pyrr | (CH$_2$)$_2$ | O |
| 1-1188 | H | H | H | H | 4-(ONO$_2$CH$_2$)-2-Aze | CH$_2$ | S |
| 1-1189 | H | H | H | H | 2-(ONO$_2$CH$_2$)-2-Azi | CH$_2$ | S |
| 1-1190 | H | H | H | H | 4-(ONO$_2$CH$_2$)-2-Aze | CH$_2$ | O |
| 1-1191 | H | H | H | H | 2-(ONO$_2$CH$_2$)-2-Azi | CH$_2$ | O |
| 1-1192 | H | H | H | H | 4-(ONO$_2$CH$_2$)-Hx$^c$ | CH(Me) | S |

TABLE 1-continued

| Compd. No. | R¹ | R² | R³ | R⁴ | R⁵ | A | X¹ |
|---|---|---|---|---|---|---|---|
| 1-1193 | H | Me | H | H | 4-(ONO$_2$CH$_2$)-Hx$^c$ | CH(Me) | S |
| 1-1194 | H | Bz | H | H | 4-(ONO$_2$CH$_2$)-Hx$^c$ | CH(Me) | S |
| 1-1195 | H | 4-Me-Bz | H | H | 4-(ONO$_2$CH$_2$)-Hx$^c$ | CH(Me) | S |
| 1-1196 | H | 4-MeO-Bz | H | H | 4-(ONO$_2$CH$_2$)-Hx$^c$ | CH(Me) | S |
| 1-1197 | H | H | H | H | 4-[ONO$_2$(CH$_2$)$_2$]-Hx$^c$ | CH(Me) | S |
| 1-1198 | H | Me | H | H | 4-[ONO$_2$(CH$_2$)$_2$]-Hx$^c$ | CH(Me) | S |
| 1-1199 | H | Bz | H | H | 4-[ONO$_2$(CH$_2$)$_2$]-Hx$^c$ | CH(Me) | S |
| 1-1200 | H | H | H | H | 4-[ONO$_2$CH(Me)]-Hx$^c$ | single bond | S |
| 1-1201 | H | H | H | H | 4-[ONO$_2$CH(Me)]-Hx$^c$ | CH$_2$ | S |
| 1-1202 | H | Me | H | H | 4-[ONO$_2$CH(Me)]-Hx$^c$ | CH$_2$ | S |
| 1-1203 | H | Bz | H | H | 4-[ONO$_2$CH(Me)]-Hx$^c$ | CH$_2$ | S |
| 1-1204 | H | 4-Me-Bz | H | H | 4-[ONO$_2$CH(Me)]-Hx$^c$ | CH$_2$ | S |
| 1-1205 | H | 4-MeO-Bz | H | H | 4-[ONO$_2$CH(Me)]-Hx$^c$ | CH$_2$ | S |
| 1-1206 | H | H | H | H | 4-[ONO$_2$CH(Me)]-Hx$^c$ | (CH$_2$)$_2$ | S |
| 1-1207 | H | Me | H | H | 4-[ONO$_2$CH(Me)]-Hx$^c$ | (CH$_2$)$_2$ | S |
| 1-1208 | H | Bz | H | H | 4-[ONO$_2$CH(Me)]-Hx$^c$ | (CH$_2$)$_2$ | S |
| 1-1209 | H | H | H | H | 4-[ONO$_2$CH$_2$CH(Me)]-Hx$^c$ | single bond | S |
| 1-1210 | H | H | H | H | 4-[ONO$_2$CH$_2$CH(Me)]-Hx$^c$ | CH$_2$ | S |
| 1-1211 | H | Me | H | H | 4-[ONO$_2$CH$_2$CH(Me)]-Hx$^c$ | CH$_2$ | S |
| 1-1212 | H | Bz | H | H | 4-[ONO$_2$CH$_2$CH(Me)]-Hx$^c$ | CH$_2$ | S |
| 1-1213 | H | 4-Me-Bz | H | H | 4-[ONO$_2$CH$_2$CH(Me)]-Hx$^c$ | CH$_2$ | S |
| 1-1214 | H | 4-MeO-Bz | H | H | 4-[ONO$_2$CH$_2$CH(Me)]-Hx$^c$ | CH$_2$ | S |
| 1-1215 | H | H | H | H | 4-[ONO$_2$CH$_2$CH(Me)]-Hx$^c$ | (CH$_2$)$_2$ | S |
| 1-1216 | H | Me | H | H | 4-[ONO$_2$CH$_2$CH(Me)]-Hx$^c$ | (CH$_2$)$_2$ | S |
| 1-1217 | H | Bz | H | H | 4-[ONO$_2$CH$_2$CH(Me)]-Hx$^c$ | (CH$_2$)$_2$ | S |
| 1-1218 | H | 4-Me-Bz | H | H | 4-ONO$_2$(CH$_2$)$_3$-Hx$^c$ | CH$_2$ | S |
| 1-1219 | H | 4-MeO-Bz | H | H | 4-ONO$_2$(CH$_2$)$_3$-Hx$^c$ | CH$_2$ | S |
| 1-1220 | H | H | H | H | 4-ONO$_2$(CH$_2$)$_3$-Hx$^c$ | CH(Me) | S |
| 1-1221 | H | Me | H | H | 4-ONO$_2$(CH$_2$)$_3$-Hx$^c$ | CH(Me) | S |
| 1-1222 | H | Bz | H | H | 4-ONO$_2$(CH$_2$)$_3$-Hx$^c$ | CH(Me) | S |
| 1-1223 | H | H | H | H | 4-ONO$_2$(CH$_2$)$_4$-Hx$^c$ | single bond | S |
| 1-1224 | H | H | H | H | 4-ONO$_2$(CH$_2$)$_4$-Hx$^c$ | CH$_2$ | S |
| 1-1225 | H | Me | H | H | 4-ONO$_2$(CH$_2$)$_4$-Hx$^c$ | CH$_2$ | S |
| 1-1226 | H | Bz | H | H | 4-ONO$_2$(CH$_2$)$_4$-Hx$^c$ | CH$_2$ | S |
| 1-1227 | H | 4-Me-Bz | H | H | 4-ONO$_2$(CH$_2$)$_4$-Hx$^c$ | CH$_2$ | S |
| 1-1228 | H | 4-MeO-Bz | H | H | 4-ONO$_2$(CH$_2$)$_4$-Hx$^c$ | CH$_2$ | S |
| 1-1229 | H | H | H | H | 4-ONO$_2$(CH$_2$)$_4$-Hx$^c$ | CH(Me) | S |
| 1-1230 | H | Me | H | H | 4-ONO$_2$(CH$_2$)$_4$-Hx$^c$ | CH(Me) | S |
| 1-1231 | H | Bz | H | H | 4-ONO$_2$(CH$_2$)$_4$-Hx$^c$ | CH(Me) | S |
| 1-1232 | H | H | H | H | 3-(ONO$_2$CH$_2$)-Hx$^c$ | CH(Me) | S |
| 1-1233 | H | Me | H | H | 3-(ONO$_2$CH$_2$)-Hx$^c$ | CH(Me) | S |
| 1-1234 | H | Bz | H | H | 3-(ONO$_2$CH$_2$)-Hx$^c$ | CH(Me) | S |
| 1-1235 | H | H | H | H | 3-[ONO$_2$(CH$_2$)$_2$]-Hx$^c$ | CH(Me) | S |
| 1-1236 | H | H | H | H | 3-[ONO$_2$CH(Me)]-Hx$^c$ | CH$_2$ | S |
| 1-1237 | H | Me | H | H | 3-[ONO$_2$CH(Me)]-Hx$^c$ | CH$_2$ | S |
| 1-1238 | H | Bz | H | H | 3-[ONO$_2$CH(Me)]-Hx$^c$ | CH$_2$ | S |
| 1-1239 | H | H | H | H | 3-[ONO$_2$CH(Me)]-Hx$^c$ | (CH$_2$)$_2$ | S |
| 1-1240 | H | H | H | H | 3-[ONO$_2$CH$_2$CH(Me)]-Hx$^c$ | CH$_2$ | S |
| 1-1241 | H | Me | H | H | 3-[ONO$_2$CH$_2$CH(Me)]-Hx$^c$ | CH$_2$ | S |
| 1-1242 | H | Bz | H | H | 3-[ONO$_2$CH$_2$CH(Me)]-Hx$^c$ | CH$_2$ | S |
| 1-1243 | H | H | H | H | 3-[ONO$_2$CH$_2$CH(Me)]-Hx$^c$ | (CH$_2$)$_2$ | S |
| 1-1244 | H | Me | H | H | 3-[ONO$_2$CH$_2$CH(Me)]-Hx$^c$ | (CH$_2$)$_2$ | S |
| 1-1245 | H | Bz | H | H | 3-[ONO$_2$CH$_2$CH(Me)]-Hx$^c$ | (CH$_2$)$_2$ | S |
| 1-1246 | H | H | H | H | 3-ONO$_2$(CH$_2$)$_3$-Hx$^c$ | CH(Me) | S |
| 1-1247 | H | H | H | H | 3-ONO$_2$(CH$_2$)$_4$-Hx$^c$ | CH$_2$ | S |
| 1-1248 | H | Me | H | H | 3-ONO$_2$(CH$_2$)$_4$-Hx$^c$ | CH$_2$ | S |
| 1-1249 | H | Bz | H | H | 3-ONO$_2$(CH$_2$)$_4$-Hx$^c$ | CH$_2$ | S |
| 1-1250 | H | H | H | H | 3-ONO$_2$(CH$_2$)$_4$-Hx$^c$ | CH(Me) | S |
| 1-1251 | H | H | H | H | 2-(ONO$_2$CH$_2$)-Hx$^c$ | CH(Me) | S |
| 1-1252 | H | Me | H | H | 2-(ONO$_2$CH$_2$)-Hx$^c$ | CH(Me) | S |
| 1-12253 | H | Bz | H | H | 2-(ONO$_2$CH$_2$)-Hx$^c$ | CH(Me) | S |
| 1-1254 | H | H | H | H | 2-[ONO$_2$(CH$_2$)$_2$]-Hx$^c$ | CH(Me) | S |
| 1-1255 | H | H | H | H | 2-[ONO$_2$CH(Me)]-Hx$^c$ | CH$_2$ | S |
| 1-1256 | H | Me | H | H | 2-[ONO$_2$CH(Me)]-Hx$^c$ | CH$_2$ | S |
| 1-1257 | H | Bz | H | H | 2-[ONO$_2$CH(Me)]-Hx$^c$ | CH$_2$ | S |
| 1-1258 | H | H | H | H | 2-[ONO$_2$CH(Me)]-Hx$^c$ | (CH$_2$)$_2$ | S |
| 1-1259 | H | H | H | H | 2-[ONO$_2$CH$_2$CH(Me)]-Hex$^c$ | CH$_2$ | S |
| 1-1260 | H | Me | H | H | 2-[ONO$_2$CH$_2$CH(Me)]-Hex$^c$ | CH$_2$ | S |
| 1-1261 | H | Bz | H | H | 2-[ONO$_2$CH$_2$CH(Me)]-Hex$^c$ | CH$_2$ | S |
| 1-1262 | H | H | H | H | 2-[ONO$_2$CH$_2$CH(Me)]-Hex$^c$ | (CH$_2$)$_2$ | S |
| 1-1263 | H | Me | H | H | 2-[ONO$_2$CH$_2$CH(Me)]-Hex$^c$ | (CH$_2$)$_2$ | S |
| 1-1264 | H | Bz | H | H | 2-[ONO$_2$CH$_2$CH(Me)]-Hex$^c$ | (CH$_2$)$_2$ | S |
| 1-1265 | H | H | H | H | 2-ONO$_2$(CH$_2$)$_3$-Hx$^c$ | CH(Me) | S |
| 1-1266 | H | H | H | H | 2-ONO$_2$(CH$_2$)$_4$-Hx$^c$ | CH$_2$ | S |
| 1-1267 | H | Me | H | H | 2-ONO$_2$(CH$_2$)$_4$-Hx$^c$ | CH$_2$ | S |
| 1-1268 | H | Bz | H | H | 2-ONO$_2$(CH$_2$)$_4$-Hx$^c$ | CH$_2$ | S |

TABLE 1-continued

| Compd. No. | R$^1$ | R$^2$ | R$^3$ | R$^4$ | R$^5$ | A | X$^1$ |
|---|---|---|---|---|---|---|---|
| 1-1269 | H | H | H | H | 2-ONO$_2$(CH$_2$)$_4$-Hx$^c$ | CH(Me) | S |
| 1-1270 | H | H | H | H | 3-(ONO$_2$CH$_2$)-Pn$^c$ | CH(Me) | S |
| 1-1271 | H | H | H | H | 3-[ONO$_2$CH(Me)]-Pn$^c$ | CH$_2$ | S |
| 1-1272 | H | H | H | H | 3-[ONO$_2$CH(Me)]-Pn$^c$ | (CH$_2$)$_2$ | S |
| 1-1273 | H | H | H | H | 3-[ONO$_2$CH$_2$CH(Me)]-Pn$^c$ | CH$_2$ | S |
| 1-1274 | H | H | H | H | 3-[ONO$_2$CH$_2$CH(Me)]-Pn$^c$ | (CH$_2$)$_2$ | S |
| 1-1275 | H | H | H | H | 3-ONO$_2$(CH$_2$)$_3$-Pn$^c$ | CH(Me) | S |
| 1-1276 | H | H | H | H | 3-ONO$_2$(CH$_2$)$_4$-Pn$^c$ | CH$_2$ | S |
| 1-1277 | H | Me | H | H | 3-ONO$_2$(CH$_2$)$_4$-Pn$^c$ | CH$_2$ | S |
| 1-1278 | H | Bz | H | H | 3-ONO$_2$(CH$_2$)$_4$-Pn$^c$ | CH$_2$ | S |
| 1-1279 | H | H | H | H | 2-(ONO$_2$CH$_2$)-Pn$^c$ | CH(Me) | S |
| 1-1280 | H | H | H | H | 2-[ONO$_2$CH(Me)]-Pn$^c$ | CH$_2$ | S |
| 1-1281 | H | H | H | H | 2-[ONO$_2$CH(Me)]-Pn$^c$ | (CH$_2$)$_2$ | S |
| 1-1282 | H | H | H | H | 2-[ONO$_2$CH$_2$CH(Me)]-Pn$^c$ | CH$_2$ | S |
| 1-1283 | H | H | H | H | 2-[ONO$_2$CH$_2$CH(Me)]-Pn$^c$ | (CH$_2$)$_2$ | S |
| 1-1284 | H | H | H | H | 2-ONO$_2$(CH$_2$)$_3$-Pn$^c$ | CH(Me) | S |
| 1-1285 | H | H | H | H | 2-ONO$_2$(CH$_2$)$_4$-Pn$^c$ | CH$_2$ | S |
| 1-1286 | H | Me | H | H | 2-ONO$_2$(CH$_2$)$_4$-Pn$^c$ | CH$_2$ | S |
| 1-1287 | H | Bz | H | H | 2-ONO$_2$(CH$_2$)$_4$-Pn$^c$ | CH$_2$ | S |
| 1-1288 | H | H | H | H | 4-(ONO$_2$CH$_2$)-Hx$^c$ | CH(Me) | O |
| 1-1289 | H | Me | H | H | 4-(ONO$_2$CH$_2$)-Hx$^c$ | CH(Me) | O |
| 1-1290 | H | Bz | H | H | 4-(ONO$_2$CH$_2$)-Hx$^c$ | CH(Me) | O |
| 1-1291 | H | 4-Me-Bz | H | H | 4-(ONO$_2$CH$_2$)-Hx$^c$ | CH(Me) | O |
| 1-1292 | H | 4-MeO-Bz | H | H | 4-(ONO$_2$CH$_2$)-Hx$^c$ | CH(Me) | O |
| 1-1293 | H | H | H | H | 4-[ONO$_2$(CH$_2$)$_2$]-Hx$^c$ | CH(Me) | O |
| 1-1294 | H | Me | H | H | 4-[ONO$_2$(CH$_2$)$_2$]-Hx$^c$ | CH(Me) | O |
| 1-1295 | H | Bz | H | H | 4-[ONO$_2$(CH$_2$)$_2$]-Hx$^c$ | CH(Me) | O |
| 1-1296 | H | H | H | H | 4-[ONO$_2$CH(Me)]-Hx$^c$ | single bond | O |
| 1-1297 | H | H | H | H | 4-[ONO$_2$CH(Me)]-Hx$^c$ | CH$_2$ | O |
| 1-1298 | H | Me | H | H | 4-[ONO$_2$CH(Me)]-Hx$^c$ | CH$_2$ | O |
| 1-1299 | H | Bz | H | H | 4-[ONO$_2$CH(Me)]-Hx$^c$ | CH$_2$ | O |
| 1-1300 | H | 4-Me-Bz | H | H | 4-[ONO$_2$CH(Me)]-Hx$^c$ | CH$_2$ | O |
| 1-1301 | H | 4-MeO-Bz | H | H | 4-[ONO$_2$CH(Me)]-Hx$^c$ | CH$_2$ | O |
| 1-1302 | H | H | H | H | 4-[ONO$_2$CH(Me)]-Hx$^c$ | (CH$_2$)$_2$ | O |
| 1-1303 | H | Me | H | H | 4-[ONO$_2$CH(Me)]-Hx$^c$ | (CH$_2$)$_2$ | O |
| 1-1304 | H | Bz | H | H | 4-[ONO$_2$CH(Me)]-Hx$^c$ | (CH$_2$)$_2$ | O |
| 1-1305 | H | H | H | H | 4-[ONO$_2$CH$_2$CH(Me)]-Hx$^c$ | single bond | O |
| 1-1306 | H | H | H | H | 4-[ONO$_2$CH$_2$CH(Me)]-Hx$^c$ | CH$_2$ | O |
| 1-1307 | H | Me | H | H | 4-[ONO$_2$CH$_2$CH(Me)]-Hx$^c$ | CH$_2$ | O |
| 1-1308 | H | Bz | H | H | 4-[ONO$_2$CH$_2$CH(Me)]-Hx$^c$ | CH$_2$ | O |
| 1-1309 | H | 4-Me-Bz | H | H | 4-[ONO$_2$CH$_2$CH(Me)]-Hx$^c$ | CH$_2$ | O |
| 1-1310 | H | 4-MeO-Bz | H | H | 4-[ONO$_2$CH$_2$CH(Me)]-Hx$^c$ | CH$_2$ | O |
| 1-1311 | H | H | H | H | 4-[ONO$_2$CH$_2$CH(Me)]-Hx$^c$ | (CH$_2$)$_2$ | O |
| 1-1312 | H | Me | H | H | 4-[ONO$_2$CH$_2$CH(Me)]-Hx$^c$ | (CH$_2$)$_2$ | O |
| 1-1313 | H | Bz | H | H | 4-[ONO$_2$CH$_2$CH(Me)]-Hx$^c$ | (CH$_2$)$_2$ | O |
| 1-1314 | H | 4-Me-Bz | H | H | 4-ONO$_2$(CH$_2$)$_3$-Hx$^c$ | CH$_2$ | O |
| 1-1315 | H | 4-MeO-Bz | H | H | 4-ONO$_2$(CH$_2$)$_3$-Hx$^c$ | CH$_2$ | O |
| 1-1316 | H | H | H | H | 4-ONO$_2$(CH$_2$)$_3$-Hx$^c$ | CH(Me) | O |
| 1-1317 | H | Me | H | H | 4-ONO$_2$(CH$_2$)$_3$-Hx$^c$ | CH(Me) | O |
| 1-1318 | H | Bz | H | H | 4-ONO$_2$(CH$_2$)$_3$-Hx$^c$ | CH(Me) | O |
| 1-1319 | H | H | H | H | 4-ONO$_2$(CH$_2$)$_4$-Hx$^c$ | single bond | O |
| 1-1320 | H | H | H | H | 4-ONO$_2$(CH$_2$)$_4$-Hx$^c$ | CH$_2$ | O |
| 1-1321 | H | Me | H | H | 4-ONO$_2$(CH$_2$)$_4$-Hx$^c$ | CH$_2$ | O |
| 1-1322 | H | Bz | H | H | 4-ONO$_2$(CH$_2$)$_4$-Hx$^c$ | CH$_2$ | O |
| 1-1323 | H | 4-Me-Bz | H | H | 4-ONO$_2$(CH$_2$)$_4$-Hx$^c$ | CH$_2$ | O |
| 1-1324 | H | 4-MeO-Bz | H | H | 4-ONO$_2$(CH$_2$)$_4$-Hx$^c$ | CH$_2$ | O |
| 1-1325 | H | H | H | H | 4-ONO$_2$(CH$_2$)$_4$-Hx$^c$ | CH(Me) | O |
| 1-1326 | H | Me | H | H | 4-ONO$_2$(CH$_2$)$_4$-Hx$^c$ | CH(Me) | O |
| 1-1327 | H | Bz | H | H | 4-ONO$_2$(CH$_2$)$_4$-Hx$^c$ | CH(Me) | O |
| 1-1328 | H | H | H | H | 3-(ONO$_2$CH$_2$)-Hx$^c$ | CH(Me) | O |
| 1-1329 | H | Me | H | H | 3-(ONO$_2$CH$_2$)-Hx$^c$ | CH(Me) | O |
| 1-1330 | H | Bz | H | H | 3-(ONO$_2$CH$_2$)-Hx$^c$ | CH(Me) | O |
| 1-1331 | H | H | H | H | 3-[ONO$_2$(CH$_2$)$_2$]-Hx$^c$ | CH(Me) | O |
| 1-1332 | H | H | H | H | 3-[ONO$_2$CH(Me)]-Hx$^c$ | CH$_2$ | O |
| 1-1333 | H | Me | H | H | 3-[ONO$_2$CH(Me)]-Hx$^c$ | CH$_2$ | O |
| 1-1334 | H | Bz | H | H | 3-[ONO$_2$CH(Me)]-Hx$^c$ | CH$_2$ | O |
| 1-1335 | H | H | H | H | 3-[ONO$_2$CH(Me)]-Hx$^c$ | (CH$_2$)$_2$ | O |
| 1-1336 | H | H | H | H | 3-[ONO$_2$CH$_2$CH(Me)]-Hx$^c$ | CH$_2$ | O |
| 1-1337 | H | Me | H | H | 3-[ONO$_2$CH$_2$CH(Me)]-Hx$^c$ | CH$_2$ | O |
| 1-1338 | H | Bz | H | H | 3-[ONO$_2$CH$_2$CH(Me)]-Hx$^c$ | CH$_2$ | O |
| 1-1339 | H | H | H | H | 3-[ONO$_2$CH$_2$CH(Me)]-Hx$^c$ | (CH$_2$)$_2$ | O |
| 1-1340 | H | Me | H | H | 3-[ONO$_2$CH$_2$CH(Me)]-Hx$^c$ | (CH$_2$)$_2$ | O |
| 1-1341 | H | Bz | H | H | 3-[ONO$_2$CH$_2$CH(Me)]-Hx$^c$ | (CH$_2$)$_2$ | O |
| 1-1342 | H | H | H | H | 2-ONO$_2$(CH$_2$)$_3$-Hx$^c$ | CH(Me) | O |
| 1-1343 | H | H | H | H | 2-ONO$_2$(CH$_2$)$_4$-Hx$^c$ | CH$_2$ | O |
| 1-1344 | H | Me | H | H | 2-ONO$_2$(CH$_2$)$_4$-Hx$^c$ | CH$_2$ | O |

TABLE 1-continued

| Compd. No. | $R^1$ | $R^2$ | $R^3$ | $R^4$ | $R^5$ | A | $X^1$ |
|---|---|---|---|---|---|---|---|
| 1-1345 | H | Bz | H | H | 2-$ONO_2(CH_2)_4$-Hx$^c$ | $CH_2$ | O |
| 1-1346 | H | H | H | H | 2-$ONO_2(CH_2)_4$-Hx$^c$ | CH(Me) | O |
| 1-1347 | H | H | H | H | 2-$(ONO_2CH_2)$-Hx$^c$ | CH(Me) | O |
| 1-1348 | H | Me | H | H | 2-$(ONO_2CH_2)$-Hx$^c$ | CH(Me) | O |
| 1-1349 | H | Bz | H | H | 2-$(ONO_2CH_2)$-Hx$^c$ | CH(Me) | O |
| 1-1350 | H | H | H | H | 2-$[ONO_2(CH_2)_2]$-Hx$^c$ | CH(Me) | O |
| 1-1351 | H | H | H | H | 2-$[ONO_2CH(Me)]$-Hx$^c$ | $CH_2$ | O |
| 1-1352 | H | Me | H | H | 2-$[ONO_2CH(Me)]$-Hx$^c$ | $CH_2$ | O |
| 1-1353 | H | Bz | H | H | 2-$[ONO_2CH(Me)]$-Hx$^c$ | $CH_2$ | O |
| 1-1354 | H | H | H | H | 2-$[ONO_2CH(Me)]$-Hx$^c$ | $(CH_2)_2$ | O |
| 1-1355 | H | H | H | H | 2-$[ONO_2CH_2CH(Me)]$-Hx$^c$ | $CH_2$ | O |
| 1-1356 | H | Me | H | H | 2-$[ONO_2CH_2CH(Me)]$-Hx$^c$ | $CH_2$ | O |
| 1-1357 | H | Bz | H | H | 2-$[ONO_2CH_2CH(Me)]$-Hx$^c$ | $CH_2$ | O |
| 1-1358 | H | H | H | H | 2-$[ONO_2CH_2CH(Me)]$-Hx$^c$ | $(CH_2)_2$ | O |
| 1-1359 | H | Me | H | H | 2-$[ONO_2CH_2CH(Me)]$-Hx$^c$ | $(CH_2)_2$ | O |
| 1-1360 | H | Bz | H | H | 2-$[ONO_2CH_2CH(Me)]$-Hx$^c$ | $(CH_2)_2$ | O |
| 1-1361 | H | H | H | H | 2-$ONO_2(CH_2)_3$-Hx$^c$ | CH(Me) | O |
| 1-1362 | H | H | H | H | 2-$ONO_2(CH_2)_4$-Hx$^c$ | $CH_2$ | O |
| 1-1363 | H | Me | H | H | 2-$ONO_2(CH_2)_4$-Hx$^c$ | $CH_2$ | O |
| 1-1364 | H | Bz | H | H | 2-$ONO_2(CH_2)_4$-Hx$^c$ | $CH_2$ | O |
| 1-1365 | H | H | H | H | 2-$ONO_2(CH_2)_4$-Hx$^c$ | CH(Me) | O |
| 1-1366 | H | H | H | H | 3-$(ONO_2CH_2)$-Pn$^c$ | C)-(Me) | O |
| 1-1367 | H | H | H | H | 3-$[ONO_2CH(Me)]$-Pn$^c$ | $CH_2$ | O |
| 1-1368 | H | H | H | H | 3-$[ONO_2CH(Me)]$-Pn$^c$ | $(CH_2)_2$ | O |
| 1-1369 | H | H | H | H | 3-$[ONO_2CH_2CH(Me)]$-Pn$^c$ | $CH_2$ | O |
| 1-1370 | H | H | H | H | 3-$[ONO_2CH_2CH(Me)]$-Pn$^c$ | $(CH_2)_2$ | O |
| 1-1371 | H | H | H | H | 3-$ONO_2(CH_2)_3$-Pn$^c$ | CH(Me) | |
| 1-1372 | H | H | H | H | 3-$ONO_2(CH_2)_4$-Pn$^c$ | $CH_2$ | O |
| 1-1373 | H | Me | H | H | 3-$ONO_2(CH_2)_4$-Pn$^c$ | $CH_2$ | O |
| 1-1374 | H | Bz | H | H | 3-$ONO_2(CH_2)_4$-Pn$^c$ | $CH_2$ | O |
| 1-1375 | H | H | H | H | 2-$(ONO_2CH_2)$-Pn$^c$ | CH(Me) | O |
| 1-1376 | H | H | H | H | 2-$[ONO_2CH(Me)]$-Pn$^c$ | $CH_2$ | O |
| 1-1377 | H | H | H | H | 2-$[ONO_2CH(Me)]$-Pn$^c$ | $(CH_2)_2$ | O |
| 1-1378 | H | H | H | H | 2-$[ONO_2CH_2CH(Me)]$-Pn$^c$ | $CH_2$ | O |
| 1-1379 | H | H | H | H | 2-$[ONO_2CH_2CH(Me)]$-Pn$^c$ | $(CH_2)_2$ | O |
| 1-1380 | H | H | H | H | 2-$ONO_2(CH_2)_3$-Pn$^c$ | CH(Me) | O |
| 1-1381 | H | H | H | H | 2-$ONO_2(CH_2)_4$-Pn$^c$ | $CH_2$ | O |
| 1-1382 | H | Me | H | H | 2-$ONO_2(CH_2)_4$-Pn$^c$ | $CH_2$ | O |
| 1-1383 | H | Bz | H | H | 2-$ONO_2(CH_2)_4$-Pn$^c$ | $CH_2$ | O |
| 1-1384 | H | H | H | H | 3-$[ONO_2(CH_2)_2]$-Pn$^c$ | $CH_2$ | S |
| 1-1385 | H | Me | H | H | 3-$[ONO_2(CH_2)_2]$-Pn$^c$ | $CH_2$ | S |
| 1-1386 | H | Bz | H | H | 3-$[ONO_2(CH_2)_2]$-Pn$^c$ | $CH_2$ | S |
| 1-1387 | H | H | H | H | 2-$[ONO_2(CH_2)_2]$-Pn$^c$ | $CH_2$ | S |
| 1-1388 | H | Me | H | H | 2-$[ONO_2(CH_2)_2]$-Pn$^c$ | $CH_2$ | S |
| 1-1389 | H | Bz | H | H | 2-$[ONO_2(CH_2)_2]$-Pn$^c$ | $CH_2$ | S |
| 1-1390 | H | H | H | H | 3-$[ONO_2(CH_2)_2]$-Pn$^c$ | $CH_2$ | O |
| 1-1391 | H | Me | H | H | 3-$[ONO_2(CH_2)_2]$-Pn$^c$ | $CH_2$ | O |
| 1-1392 | H | Bz | H | H | 3-$[ONO_2(CH_2)_2]$-Pn$^c$ | $CH_2$ | O |
| 1-1393 | H | H | H | H | 2-$[ONO_2(CH_2)_2]$-Pn$^c$ | $CH_2$ | O |
| 1-1394 | H | Me | H | H | 2-$[ONO_2(CH_2)_2]$-Pn$^c$ | $CH_2$ | O |
| 1-1395 | H | Bz | H | H | 2-$[ONO_2(CH_2)_2]$-Pn$^c$ | $CH_2$ | O |
| 1-1396 | H | H | H | H | 5-$ONO_2$-2-Pip | $CH_2$ | S |
| 1-1397 | H | Me | H | H | 5-$ONO_2$-2-Pip | $CH_2$ | S |
| 1-1398 | H | Bz | H | H | 5-$ONO_2$-2-Pip | $CH_2$ | S |
| 1-1399 | H | H | H | H | 6-$ONO_2$-3-Pip | $CH_2$ | S |
| 1-1400 | H | Me | H | H | 6-$ONO_2$-3-Pip | $CH_2$ | S |
| 1-1401 | H | Bz | H | H | 6-$ONO_2$-3-Pip | $CH_2$ | S |
| 1-1402 | H | H | H | H | 5-$ONO_2$-2-Pip | $CH_2$ | O |
| 1-1403 | H | Me | H | H | 5-$ONO_2$-2-Pip | $CH_2$ | O |
| 1-1404 | H | Bz | H | H | 5-$ONO_2$-2-Pip | $CH_2$ | O |
| 1-1405 | H | H | H | H | 6-$ONO_2$-3-Pip | $CH_2$ | O |
| 1-1406 | H | Me | H | H | 6-$ONO_2$-3-Pip | $CH_2$ | O |
| 1-1407 | H | Bz | H | H | 6-$ONO_2$-3-Pip | $CH_2$ | O |

TABLE 2

| Compd. No. | $R^1$ | $R^2$ | $R^3$ | $R^4$ | $R^5$ | A | $X^1$ |
|---|---|---|---|---|---|---|---|
| 2-1 | H | H | H | H | 4-$(ONO_2CH_2)$-Hx$^c$ | single bond | S |
| 2-2 | Me | H | H | H | 4-$(ONO_2CH_2)$-Hx$^c$ | single bond | S |
| 2-3 | Et | H | H | H | 4-$(ONO_2CH_2)$-Hx$^c$ | single bond | S |
| 2-4 | Bz | H | H | H | 4-$(ONO_2CH_2)$-Hx$^c$ | single bond | S |

TABLE 2-continued

| Compd. No. | R¹ | R² | R³ | R⁴ | R⁵ | A | X¹ |
|---|---|---|---|---|---|---|---|
| 2-5 | H | Me | H | H | 4-(ONO$_2$CH$_2$)-Hx$^c$ | single bond | S |
| 2-6 | H | Et | H | H | 4-(ONO$_2$CH$_2$)-Hx$^c$ | single bond | S |
| 2-7 | H | Ph | H | H | 4-(ONO$_2$CH$_2$)-Hx$^c$ | single bond | S |
| 2-8 | H | 2-Then | H | H | 4-(ONO$_2$CH$_2$)-Hx$^c$ | single bond | S |
| 2-9 | H | 3-Then | H | H | 4-(ONO$_2$CH$_2$)-Hx$^c$ | single bond | S |
| 2-10 | H | 2-Fur | H | H | 4-(ONO$_2$CH$_2$)-Hx$^c$ | single bond | S |
| 2-11 | H | 3-Fur | H | H | 4-(ONO$_2$CH$_2$)-Hx$^c$ | single bond | S |
| 2-12 | H | 4-Me-Ph | H | H | 4-(ONO$_2$CH$_2$)-Hx$^c$ | single bond | S |
| 2-13 | H | 4-Cl-Ph | H | H | 4-(ONO$_2$CH$_2$)-Hx$^c$ | single bond | S |
| 2-14 | H | 4-MeO-Ph | H | H | 4-(ONO$_2$CH$_2$)-Hx$^c$ | single bond | S |
| 2-15 | H | 4-Thiz | H | H | 4-(ONO$_2$CH$_2$)-Hx$^c$ | single bond | S |
| 2-16 | H | 3-Pyr | H | H | 4-(ONO$_2$CH$_2$)-Hx$^c$ | single bond | S |
| 2-17 | H | Me | Me | H | 4-(ONO$_2$CH$_2$)-Hx$^c$ | single bond | S |
| 2-18 | Me | Me | Me | H | 4-(ONO$_2$CH$_2$)-Hx$^c$ | single bond | S |
| 2-19 | Me | Me | Me | Me | 4-(ONO$_2$CH$_2$)-Hx$^c$ | single bond | S |
| 2-20 | Et | Ph | H | H | 4-(ONO$_2$CH$_2$)-Hx$^c$ | single bond | S |
| 2-21 | Et | Et | H | Me | 4-(ONO$_2$CH$_2$)-Hx$^c$ | single bond | S |
| 2-22 | Bz | Me | H | Et | 4-(ONO$_2$CH$_2$)-Hx$^c$ | single bond | S |
| 2-23 | Bz | Ph | H | Et | 4-(ONO$_2$CH$_2$)-Hx$^c$ | single bond | S |
| 2-24 | Bu | H | H | H | 4-(ONO$_2$CH$_2$)-Hx$^c$ | single bond | S |
| 2-25 | H | 1-Np | H | H | 4-(ONO$_2$CH$_2$)-Hx$^c$ | single bond | S |
| 2-26 | H | H | H | Me | 4-(ONO$_2$CH$_2$)-Hx$^c$ | single bond | S |
| 2-27 | H | H | H | Bz | 4-(ONO$_2$CH$_2$)-Hx$^c$ | single bond | S |
| 2-28 | H | Bz | H | H | 4-(ONO$_2$CH$_2$)-Hx$^c$ | single bond | S |
| 2-29 | H | 4-Me-Bz | H | H | 4-(ONO$_2$CH$_2$)-Hx$^c$ | single bond | S |
| 2-30 | H | 4-OMe-Bz | H | H | 4-(ONO$_2$CH$_2$)-Hx$^c$ | single bond | S |
| 2-31 | H | 4-F-Bz | H | H | 4-(ONO$_2$CH$_2$)-Hx$^c$ | single bond | S |
| 2-32 | H | H | H | H | 4-(ONO$_2$CH$_2$)-Hx$^c$ | CH$_2$ | S |
| 2-33 | Me | H | H | H | 4-(ONO$_2$CH$_2$)-Hx$^c$ | CH$_2$ | S |
| 2-34 | Et | H | H | H | 4-(ONO$_2$CH$_2$)-Hx$^c$ | CH$_2$ | S |
| 2-35 | Bz | H | H | H | 4-(ONO$_2$CH$_2$)-Hx$^c$ | CH$_2$ | S |
| 2-36 | H | Me | H | H | 4-(ONO$_2$CH$_2$)-Hx$^c$ | CH$_2$ | S |
| 2-37 | H | Et | H | H | 4-(ONO$_2$CH$_2$)-Hx$^c$ | CH$_2$ | S |
| 2-38 | H | Ph | H | H | 4-(ONO$_2$CH$_2$)-Hx$^c$ | CH$_2$ | S |
| 2-39 | H | 2-Then | H | H | 4-(ONO$_2$CH$_2$)-Hx$^c$ | CH$_2$ | S |
| 2-40 | H | 3-Then | H | H | 4-(ONO$_2$CH$_2$)-Hx$^c$ | CH$_2$ | S |
| 2-41 | H | 2-Fur | H | H | 4-(ONO$_2$CH$_2$)-Hx$^c$ | CH$_2$ | S |
| 2-42 | H | 3-Fur | H | H | 4-(ONO$_2$CH$_2$)-Hx$^c$ | CH$_2$ | S |
| 2-43 | H | 4-Me-Ph | H | H | 4-(ONO$_2$CH$_2$)-Hx$^c$ | CH$_2$ | S |
| 2-44 | H | 4-Cl-Ph | H | H | 4-(ONO$_2$CH$_2$)-Hx$^c$ | CH$_2$ | S |
| 2-45 | H | 4-MeO-Ph | H | H | 4-(ONO$_2$CH$_2$)-Hx$^c$ | CH$_2$ | S |
| 2-46 | H | 4-Thiz | H | H | 4-(ONO$_2$CH$_2$)-Hx$^c$ | CH$_2$ | S |
| 2-47 | H | 3-Pyr | H | H | 4-(ONO$_2$CH$_2$)-Hx$^c$ | CH$_2$ | S |
| 2-48 | H | Me | Me | H | 4-(ONO$_2$CH$_2$)-Hx$^c$ | CH$_2$ | S |
| 2-49 | Me | Me | Me | H | 4-(ONO$_2$CH$_2$)-Hx$^c$ | CH$_2$ | S |
| 2-50 | Me | Me | Me | Me | 4-(ONO$_2$CH$_2$)-Hx$^c$ | CH$_2$ | S |
| 2-51 | Et | Ph | H | H | 4-(ONO$_2$CH$_2$)-Hx$^c$ | CH$_2$ | S |
| 2-52 | Et | Et | H | Me | 4-(ONO$_2$CH$_2$)-Hx$^c$ | CH$_2$ | S |
| 2-53 | Bz | Me | H | Et | 4-(ONO$_2$CH$_2$)-Hx$^c$ | CH$_2$ | S |
| 2-54 | Bz | Ph | H | Et | 4-(ONO$_2$CH$_2$)-Hx$^c$ | CH$_2$ | S |
| 2-55 | Bu | H | H | H | 4-(ONO$_2$CH$_2$)-Hx$^c$ | CH$_2$ | S |
| 2-56 | H | 1-Np | H | H | 4-(ONO$_2$CH$_2$)-Hx$^c$ | CH$_2$ | S |
| 2-57 | H | H | H | Me | 4-(ONO$_2$CH$_2$)-Hx$^c$ | CH$_2$ | S |
| 2-58 | H | H | H | Bz | 4-(ONO$_2$CH$_2$)-Hx$^c$ | CH$_2$ | S |
| 2-59 | H | Bz | H | H | 4-(ONO$_2$CH$_2$)-Hx$^c$ | CH$_2$ | S |
| 2-60 | H | 4-Me-Bz | H | H | 4-(ONO$_2$CH$_2$)-Hx$^c$ | CH$_2$ | S |
| 2-61 | H | 4-MeO-Bz | H | H | 4-(ONO$_2$CH$_2$)-Hx$^c$ | CH$_2$ | S |
| 2-62 | H | 4-F-Bz | H | H | 4-(ONO$_2$CH$_2$)-Hx$^c$ | CH$_2$ | S |
| 2-63 | H | 4-Cl-Bz | H | H | 4-(ONO$_2$CH$_2$)-Hx$^c$ | CH$_2$ | S |
| 2-64 | H | 4-OH-Bz | H | H | 4-(ONO$_2$CH$_2$)-Hx$^c$ | CH$_2$ | S |
| 2-65 | H | H | H | H | 4-(ONO$_2$CH$_2$)-Hx$^c$ | (CH$_2$)$_2$ | S |
| 2-66 | Me | H | H | H | 4-(ONO$_2$CH$_2$)-Hx$^c$ | (CH$_2$)$_2$ | S |
| 2-67 | Et | H | H | H | 4-(ONO$_2$CH$_2$)-Hx$^c$ | (CH$_2$)$_2$ | S |
| 2-68 | Bz | H | H | H | 4-(ONO$_2$CH$_2$)-Hx$^c$ | (CH$_2$)$_2$ | S |
| 2-69 | H | Me | H | H | 4-(ONO$_2$CH$_2$)-Hx$^c$ | (CH$_2$)$_2$ | S |
| 2-70 | H | Et | H | H | 4-(ONO$_2$CH$_2$)-Hx$^c$ | (CH$_2$)$_2$ | S |
| 2-71 | H | Ph | H | H | 4-(ONO$_2$CH$_2$)-Hx$^c$ | (CH$_2$)$_2$ | S |
| 2-72 | H | 2-Then | H | H | 4-(ONO$_2$CH$_2$)-Hx$^c$ | (CH$_2$)$_2$ | S |
| 2-73 | H | 3-Then | H | H | 4-(ONO$_2$CH$_2$)-Hx$^c$ | (CH$_2$)$_2$ | S |
| 2-74 | H | 2-Fur | H | H | 4-(ONO$_2$CH$_2$)-Hx$^c$ | (CH$_2$)$_2$ | S |
| 2-75 | H | 3-Fur | H | H | 4-(ONO$_2$CH$_2$)-Hx$^c$ | (CH$_2$)$_2$ | S |
| 2-76 | H | 4-Me-Ph | H | H | 4-(ONO$_2$CH$_2$)-Hx$^c$ | (CH$_2$)$_2$ | S |
| 2-77 | H | 4-Cl-Ph | H | H | 4-(ONO$_2$CH$_2$)-Hx$^c$ | (CH$_2$)$_2$ | S |
| 2-78 | H | 4-MeO-Ph | H | H | 4-(ONO$_2$CH$_2$)-Hx$^c$ | (CH$_2$)$_2$ | S |
| 2-79 | H | 4-Thiz | H | H | 4-(ONO$_2$CH$_2$)-Hx$^c$ | (CH$_2$)$_2$ | S |
| 2-80 | H | 3-Pyr | H | H | 4-(ONO$_2$CH$_2$)-Hx$^c$ | (CH$_2$)$_2$ | S |

TABLE 2-continued

| Compd. No. | R¹ | R² | R³ | R⁴ | R⁵ | A | X¹ |
|---|---|---|---|---|---|---|---|
| 2-81 | H | Me | Me | H | 4-(ONO₂CH₂)-Hx^c | (CH₂)₂ | S |
| 2-82 | Me | Me | Me | H | 4-(ONO₂CH₂)-Hx^c | (CH₂)₂ | S |
| 2-83 | Me | Me | Me | Me | 4-(ONO₂CH₂)-Hx^c | (CH₂)₂ | S |
| 2-84 | Et | Ph | H | H | 4-(ONO₂CH₂)-Hx^c | (CH₂)₂ | S |
| 2-85 | Et | Et | H | Me | 4-(ONO₂CH₂)-Hx^c | (CH₂)₂ | S |
| 2-86 | Bz | Me | H | Et | 4-(ONO₂CH₂)-Hx^c | (CH₂)₂ | S |
| 2-87 | Bz | Ph | H | Et | 4-(ONO₂CH₂)-Hx^c | (CH₂)₂ | S |
| 2-88 | Bu | H | H | H | 4-(ONO₂CH₂)-Hx^c | (CH₂)₂ | S |
| 2-89 | H | 1-Np | H | H | 4-(ONO₂CH₂)-Hx^c | (CH₂)₂ | S |
| 2-90 | H | H | H | Me | 4-(ONO₂CH₂)-Hx^c | (CH₂)₂ | S |
| 2-91 | H | H | H | Bz | 4-(ONO₂CH₂)-Hx^c | (CH₂)₂ | S |
| 2-92 | H | Bz | H | H | 4-(ONO₂CH₂)-Hx^c | (CH₂)₂ | S |
| 2-93 | H | 4-Me-Bz | H | H | 4-(ONO₂CH₂)-Hx^c | (CH₂)₂ | S |
| 2-94 | H | 4-MeO-Bz | H | H | 4-(ONO₂CH₂)-Hx^c | (CH₂)₂ | S |
| 2-95 | H | 4-F-Bz | H | H | 4-(ONO₂CH₂)-Hx^c | (CH₂)₂ | S |
| 2-96 | H | H | H | H | 4-(ONO₂CH₂)-Hx^c | (CH₂)3 | S |
| 2-97 | H | Me | H | H | 4(ONO₂CH₂)-Hx^c | (CH₂)3 | S |
| 2-98 | H | Bz | H | H | 4-(ONO₂CH₂)-Hx^c | (CH₂)3 | S |
| 2-99 | H | H | H | H | 4-(ONO₂CH₂)-Hx^c | (CH₂)4 | S |
| 2-100 | H | Me | H | H | 4-(ONO₂CH₂)-Hx^c | (CH₂)4 | S |
| 2-101 | H | H | H | H | 4-(ONO₂CH₂)-Hx^c | (CH₂)5 | S |
| 2-102 | H | Me | H | H | 4-(ONO₂CH₂)-Hx^c | (CH₂)5 | S |
| 2-103 | H | H | H | H | 4-(ONO₂CH₂)-Hx^c | (CH₂)6 | S |
| 2-104 | H | Me | H | H | 4-(ONO₂CH₂)-Hx^c | (CH₂)6 | S |
| 2-105 | H | H | H | H | 4-ONO₂-Hx^c | single bond | S |
| 2-106 | Me | H | H | H | 4-ONO₂-Hx^c | single bond | S |
| 2-107 | Et | H | H | H | 4-ONO₂-Hx^c | single bond | S |
| 2-108 | Bz | H | H | H | 4-ONO₂-Hx^c | single bond | S |
| 2-109 | H | Me | H | H | 4-ONO₂-Hx^c | single bond | S |
| 2-110 | H | Et | H | H | 4-ONO₂-Hx^c | single bond | S |
| 2-111 | H | Ph | H | H | 4-ONO₂-Hx^c | single bond | S |
| 2-112 | H | Bz | H | H | 4-ONO₂-Hx^c | single bond | S |
| 2-113 | H | 4-Me-Bz | H | H | 4-ONO₂-Hx^c | single bond | S |
| 2-114 | H | 4-MeO-Bz | H | H | 4-ONO₂-Hx^c | single bond | S |
| 2-115 | H | 4-F-Bz | H | H | 4-ONO₂-Hx^c | single bond | S |
| 2-116 | H | 2-Then | H | H | 4-ONO₂-Hx^c | single bond | S |
| 2-117 | H | 3-Then | H | H | 4-ONO₂-Hx^c | single bond | S |
| 2-118 | H | 2-Fur | H | H | 4-ONO₂-Hx^c | single bond | S |
| 2-119 | H | 3-Fur | H | H | 4-ONO₂-Hx^c | single bond | S |
| 2-120 | H | 3-Pyr | H | H | 4-ONO₂-Hx^c | single bond | S |
| 2-121 | H | H | H | Me | 4-ONO₂-Hx^c | single bond | S |
| 2-122 | H | H | H | Et | 4-ONO₂-Hx^c | single bond | S |
| 2-123 | H | H | H | Bz | 4-ONO₂-Hx^c | single bond | S |
| 2-124 | H | H | H | H | 4-[ONO₂(CH₂)₂]-Hx^c | single bond | S |
| 2-125 | H | Me | H | H | 4-[ONO₂(CH₂)₂]-Hx^c | single bond | S |
| 2-126 | H | Et | H | H | 4-[ONO₂(CH₂)₂]-Hx^c | single bond | S |
| 2-127 | H | Ph | H | H | 4-[ONO₂(CH₂)₂]-Hx^c | single bond | S |
| 2-128 | H | Bz | H | H | 4-[ONO₂(CH₂)₂]-Hx^c | single bond | S |
| 2-129 | H | 4-Me-Bz | H | H | 4-[ONO₂(CH₂)₂]-Hx^c | single bond | S |
| 2-130 | H | 4-MeO-Bz | H | H | 4-[ONO₂(CH₂)₂]-Hx^c | single bond | S |
| 2-131 | H | 4-F-Bz | H | H | 4-[ONO₂(CH₂)₂]-Hx^c | single bond | S |
| 2-132 | H | 2-Then | H | H | 4-[ONO₂(CH₂)₂]-Hx^c | single bond | S |
| 2-133 | H | 3-Then | H | H | 4-[ONO₂(CH₂)₂]-Hx^c | single bond | S |
| 2-134 | H | 2-Fur | H | H | 4-[ONO₂(CH₂)₂]-Hx^c | single bond | S |
| 2-135 | H | 3-Fur | H | H | 4-[ONO₂(CH₂)₂]-Hx^c | single bond | S |
| 2-136 | H | 3-Pyr | H | H | 4-[ONO₂(CH₂)₂]-Hx^c | single bond | S |
| 2-137 | H | 4-Thiz | H | H | 4-[ONO₂(CH₂)₂]-Hx^c | single bond | S |
| 2-138 | H | H | H | H | 4-ONO₂-Hx^c | CH₂ | S |
| 2-139 | Me | H | H | H | 4-ONO₂-Hx^c | CH₂ | S |
| 2-140 | Et | H | H | H | 4-ONO₂-Hx^c | CH₂ | S |
| 2-141 | Bz | H | H | H | 4-ONO₂-Hx^c | CH₂ | S |
| 2-142 | H | Me | H | H | 4-ONO₂-Hx^c | CH₂ | S |
| 2-143 | H | Et | H | H | 4-ONO₂-Hx^c | CH₂ | S |
| 2-144 | H | Ph | H | H | 4-ONO₂-Hx^c | CH₂ | S |
| 2-145 | H | 2-Then | H | H | 4-ONO₂-Hx^c | CH₂ | S |
| 2-146 | H | 3-Then | H | H | 4-ONO₂-Hx^c | CH₂ | S |
| 2-147 | H | 2-Fur | H | H | 4-ONO₂-Hx^c | CH₂ | S |
| 2-148 | H | 3-Fur | H | H | 4-ONO₂-Hx^c | CH₂ | S |
| 2-149 | H | 4-Me-Ph | H | H | 4-ONO₂-Hx^c | CH₂ | S |
| 2-150 | H | 4-Cl-Ph | H | H | 4-ONO₂-Hx^c | CH₂ | 8 |
| 2-151 | H | 4-MeO-Ph | H | H | 4-ONO₂-Hx^c | CH₂ | S |
| 2-152 | H | 4-Thiz | H | H | 4-ONO₂-Hx^c | CH₂ | S |
| 2-153 | H | 3-Pyr | H | H | 4-ONO₂-Hx^c | CH₂ | S |
| 2-154 | H | Me | Me | H | 4-ONO₂-Hx^c | CH₂ | S |
| 2-155 | Me | Me | Me | H | 4-ONO₂-Hx^c | CH₂ | S |
| 2-156 | Me | Me | Me | Me | 4-ONO₂-Hx^c | CH₂ | S |

TABLE 2-continued

| Compd. No. | R$^1$ | R$^2$ | R$^3$ | R$^4$ | R$^5$ | A | X$^1$ |
|---|---|---|---|---|---|---|---|
| 2-157 | Et | Ph | H | H | 4-ONO$_2$-Hx$^c$ | CH$_2$ | S |
| 2-158 | Et | Et | H | Me | 4-ONO$_2$-Hx$^c$ | CH$_2$ | S |
| 2-159 | Bz | Me | H | Et | 4-ONO$_2$-Hx$^c$ | CH$_2$ | S |
| 2-160 | Bz | Ph | H | Et | 4-ONO$_2$-Hx$^c$ | CH$_2$ | S |
| 2-161 | Bu | H | H | H | 4-ONO$_2$-Hx$^c$ | CH$_2$ | S |
| 2-162 | H | 1-Np | H | H | 4-ONO$_2$-Hx$^c$ | CH$_2$ | S |
| 2-163 | H | H | H | Me | 4-ONO$_2$-Hx$^c$ | CH$_2$ | S |
| 2-164 | H | H | H | Bz | 4-ONO$_2$-Hx$^c$ | CH$_2$ | S |
| 2-165 | H | Bz | H | H | 4-ONO$_2$-Hx$^c$ | CH$_2$ | S |
| 2-166 | H | 4-Me-Bz | H | H | 4-ONO$_2$-Hx$^c$ | CH$_2$ | S |
| 2-167 | H | 4-MeO-Bz | H | H | 4-ONO$_2$-Hx$^c$ | CH$_2$ | S |
| 2-168 | H | 4-F-Bz | H | H | 4-ONO$_2$-Hx$^c$ | CH$_2$ | S |
| 2-169 | H | H | H | H | 4-[ONO$_2$(CH$_2$)$_2$]-Hx$^c$ | CH$_2$ | S |
| 2-170 | H | Me | H | H | 4-[ONO$_2$(CH$_2$)$_2$]-Hx$^c$ | CH$_2$ | S |
| 2-171 | H | Et | H | H | 4-[ONO$_2$(CH$_2$)$_2$]-Hx$^c$ | CH$_2$ | S |
| 2-172 | H | Ph | H | H | 4-[ONO$_2$(CH$_2$)$_2$]-Hx$^c$ | CH$_2$ | S |
| 2-173 | H | 2-Then | H | H | 4-[ONO$_2$(CH$_2$)$_2$]-Hx$^c$ | CH$_2$ | S |
| 2-174 | H | 3-Then | H | H | 4-[ONO$_2$(CH$_2$)$_2$]-Hx$^c$ | CH$_2$ | S |
| 2-175 | H | 2-Fur | H | H | 4-[ONO$_2$(CH$_2$)$_2$]-Hx$^c$ | CH$_2$ | S |
| 2-176 | H | 3-Fur | H | H | 4-[ONO$_2$(CH$_2$)$_2$]-Hx$^c$ | CH$_2$ | S |
| 2-177 | H | 3-Py | H | H | 4-[ONO$_2$(CH$_2$)$_2$]-Hx$^c$ | CH$_2$ | S |
| 2-178 | H | Bz | H | H | 4-[ONO$_2$(CH$_2$)$_2$]-Hx$^c$ | CH$_2$ | S |
| 2-179 | H | 4-Me-Bz | H | H | 4-[ONO$_2$(CH$_2$)$_2$]-Hx$^c$ | CH$_2$ | S |
| 2-180 | H | 4-MeO-Bz | H | H | 4-[ONO$_2$(CH$_2$)$_2$]-Hx$^c$ | CH$_2$ | S |
| 2-181 | H | 4-F-Bz | H | H | 4-[ONO$_2$(CH$_2$)$_2$]-Hx$^c$ | CH$_2$ | S |
| 2-182 | H | Me | Me | H | 4-[ONO$_2$(CH$_2$)$_2$]-Hx$^c$ | CH$_2$ | S |
| 2-183 | Me | Me | Me | H | 4-[ONO$_2$(CH$_2$)$_2$]-Hx$^c$ | CH$_2$ | S |
| 2-184 | Bz | Me | H | Et | 4-[ONO$_2$(CH$_2$)$_2$]-Hx$^c$ | CH$_2$ | S |
| 2-185 | Bu | H | H | H | 4-[ONO$_2$(CH$_2$)$_2$]-Hx$^c$ | CH$_2$ | S |
| 2-186 | H | 1-Np | H | H | 4-[ONO$_2$(CH$_2$)$_2$]-Hx$^c$ | CH$_2$ | S |
| 2-187 | H | H | H | Me | 4-[ONO$_2$(CH$_2$)$_2$]-Hx$^c$ | CH$_2$ | S |
| 2-188 | H | H | H | Bz | 4-[ONO$_2$(CH$_2$)$_2$]-Hx$^c$ | CH$_2$ | S |
| 2-189 | H | H | H | H | 4-[ONO$_2$(CH$_2$)$_2$]-Hx$^c$ | (CH$_2$)$_2$ | S |
| 2-190 | H | Me | H | H | 4-[ONO$_2$(CH$_2$)$_2$]-Hx$^c$ | (CH$_2$)$_2$ | S |
| 2-191 | H | Et | H | H | 4-[ONO$_2$(CH$_2$)$_2$]-Hx$^c$ | (CH$_2$)$_2$ | S |
| 2-192 | H | Ph | H | H | 4-[ONO$_2$(CH$_2$)$_2$]-Hx$^c$ | (CH$_2$)$_2$ | S |
| 2-193 | H | 2-Then | H | H | 4-[ONO$_2$(CH$_2$)$_2$]-Hx$^c$ | (CH$_2$)$_2$ | S |
| 2-194 | H | 3-Then | H | H | 4-[ONO$_2$(CH$_2$)$_2$]-Hx$^c$ | (CH$_2$)$_2$ | S |
| 2-195 | H | 2-Fur | H | H | 4-[ONO$_2$(CH$_2$)$_2$]-Hx$^c$ | (CH$_2$)$_2$ | S |
| 2-196 | H | 3-Fur | H | H | 4-[ONO$_2$(CH$_2$)$_2$]-Hx$^c$ | (CH$_2$)$_2$ | S |
| 2-197 | H | 3-Py | H | H | 4-[ONO$_2$(CH$_2$)$_2$]-Hx$^c$ | (CH$_2$)$_2$ | S |
| 2-198 | H | Bz | H | H | 4-[ONO$_2$(CH$_2$)$_2$]-Hx$^c$ | (CH$_2$)$_2$ | S |
| 2-199 | H | 4-Me-Bz | H | H | 4-[ONO$_2$(CH$_2$)$_2$]-Hx$^c$ | (CH$_2$)$_2$ | S |
| 2-200 | H | 4-MeO-Bz | H | H | 4-[ONO$_2$(CH$_2$)$_2$]-Hx$^c$ | (CH$_2$)$_2$ | S |
| 2-201 | H | 4-F-Bz | H | H | 4-[ONO$_2$(CH$_2$)$_2$]-Hx$^c$ | (CH$_2$)$_2$ | S |
| 2-202 | H | Me | Me | H | 4-[ONO$_2$(CH$_2$)$_2$]-Hx$^c$ | (CH$_2$)$_2$ | S |
| 2-203 | Bu | H | H | H | 4-[ONO$_2$(CH$_2$)$_2$]-Hx$^c$ | (CH$_2$)$_2$ | S |
| 2-204 | H | 1-Np | H | H | 4-[ONO$_2$(CH$_2$)$_2$]-Hx$^c$ | (CH$_2$)$_2$ | S |
| 2-205 | H | H | H | Me | 4-[ONO$_2$(CH$_2$)$_2$]-Hx$^c$ | (CH$_2$)$_2$ | S |
| 2-206 | H | H | H | Bz | 4-[ONO$_2$(CH$_2$)$_2$]-Hx$^c$ | (CH$_2$)$_2$ | S |
| 2-207 | H | H | H | H | 4-[ONO$_2$(CH$_2$)$_3$]-Hx$^c$ | (CH$_2$)$_2$ | S |
| 2-208 | H | Me | H | H | 4-[ONO$_2$(CH$_2$)$_3$]-Hx$^c$ | (CH$_2$)$_2$ | S |
| 2-209 | H | Bz | H | H | 4-[ONO$_2$(CH$_2$)$_3$]-Hx$^c$ | (CH$_2$)$_2$ | S |
| 2-210 | H | H | H | H | 4-[ONO$_2$(CH$_2$)$_4$]-Hx$^c$ | (CH$_2$)$_2$ | S |
| 2-211 | H | Me | H | H | 4-[ONO$_2$(CH$_2$)$_4$]-Hx$^c$ | (CH$_2$)$_2$ | S |
| 2-212 | H | Bz | H | H | 4-[ONO$_2$(CH$_2$)$_4$]-Hx$^c$ | (CH$_2$)$_2$ | S |
| 2-213 | H | H | H | H | 4-[ONO$_2$(CH$_2$)$_5$]-Hx$^c$ | (CH$_2$)$_2$ | S |
| 2-214 | H | Me | H | H | 4-[ONO$_2$(CH$_2$)$_5$]-Hx$^c$ | (CH$_2$)$_2$ | S |
| 2-215 | H | Bz | H | H | 4-[ONO$_2$(CH$_2$)$_5$]-Hx$^c$ | (CH$_2$)$_2$ | S |
| 2-216 | H | H | H | H | 4-[ONO$_2$(CH$_2$)$_6$]-Hx$^c$ | (CH$_2$)$_2$ | S |
| 2-217 | H | Me | H | H | 4-[ONO$_2$(CH$_2$)$_6$]-Hx$^c$ | (CH$_2$)$_2$ | S |
| 2-218 | H | Bz | H | H | 4-[ONO$_2$(CH$_2$)$_6$]-Hx$^c$ | (CH$_2$)$_2$ | S |
| 2-219 | H | H | H | H | 4-ONO$_2$-Hx$^c$ | (CH$_2$)$_2$ | S |
| 2-220 | Me | H | H | H | 4-ONO$_2$-Hx$^c$ | (CH$_2$)$_2$ | S |
| 2-221 | Bz | H | H | H | 4-ONO$_2$-Hx$^c$ | (CH$_2$)$_2$ | S |
| 2-222 | H | Me | H | H | 4-ONO$_2$-Hx$^c$ | (CH$_2$)$_2$ | S |
| 2-223 | H | Et | H | H | 4-ONO$_2$-Hx$^c$ | (CH$_2$)$_2$ | S |
| 2-224 | H | Ph | H | H | 4-ONO$_2$-Hx$^c$ | (CH$_2$)$_2$ | S |
| 2-225 | H | 2-Then | H | H | 4-ONO$_2$-Hx$^c$ | (CH$_2$)$_2$ | S |
| 2-226 | H | 3-Then | H | H | 4-ONO$_2$-Hx$^c$ | (CH$_2$)$_2$ | S |
| 2-227 | H | 2-Fur | H | H | 4-ONO$_2$-Hx$^c$ | (CH$_2$)$_2$ | S |
| 2-228 | H | 3-Fur | H | H | 4-ONO$_2$-Hx$^c$ | (CH$_2$)$_2$ | S |
| 2-229 | H | 4-Me-Ph | H | H | 4-ONO$_2$-Hx$^c$ | (CH$_2$)$_2$ | S |
| 2-230 | H | 4-Cl-Ph | H | H | 4-ONO$_2$-Hx$^c$ | (CH$_2$)$_2$ | S |
| 2-231 | H | 4-MeO-Ph | H | H | 4-ONO$_2$-Hx$^c$ | (CH$_2$)$_2$ | S |
| 2-232 | H | 4-Thiz | H | H | 4-ONO$_2$-Hx$^c$ | (CH$_2$)$_2$ | S |

TABLE 2-continued

| Compd. No. | R¹ | R² | R³ | R⁴ | R⁵ | A | X¹ |
|---|---|---|---|---|---|---|---|
| 2-233 | H | 3-Pyr | H | H | 4-ONO$_2$-Hx$^c$ | (CH$_2$)$_2$ | S |
| 2-234 | H | Me | Me | H | 4-ONO$_2$-Hx$^c$ | (CH$_2$)$_2$ | S |
| 2-235 | Bu | H | H | H | 4-ONO$_2$-Hx$^c$ | (CH$_2$)$_2$ | S |
| 2-236 | H | 1-Np | H | H | 4-ONO$_2$-Hx$^c$ | (CH$_2$)$_2$ | S |
| 2-237 | H | H | H | Me | 4-ONO$_2$-Hx$^c$ | (CH$_2$)$_2$ | S |
| 2-238 | H | H | H | Bz | 4-ONO$_2$-Hx$^c$ | (CH$_2$)$_2$ | S |
| 2-239 | H | Bz | H | H | 4-ONO$_2$-Hx$^c$ | (CH$_2$)$_2$ | S |
| 2-240 | H | 4-Me-Bz | H | H | 4-ONO$_2$-Hx$^c$ | (CH$_2$)$_2$ | S |
| 2-241 | H | 4-MeO-Bz | H | H | 4-ONO$_2$-Hx$^c$ | (CH$_2$)$_2$ | S |
| 2-242 | H | 4-F-Bz | H | H | 4-ONO$_2$-Hx$^c$ | (CH$_2$)$_2$ | S |
| 2-243 | H | H | H | H | 4-ONO$_2$-Hx$^c$ | (CH$_2$)$_3$ | S |
| 2-244 | H | Me | H | H | 4-ONO$_2$-Hx$^c$ | (CH$_2$)$_3$ | S |
| 2-245 | H | H | H | H | 4-ONO$_2$-Hx$^c$ | (CH$_2$)$_4$ | S |
| 2-246 | H | Me | H | H | 4-ONO$_2$-Hx$^c$ | (CH$_2$)$_4$ | S |
| 2-247 | H | H | H | H | 4-ONO$_2$-Hx$^c$ | (CH$_2$)$_5$ | S |
| 2-248 | H | Me | H | H | 4-ONO$_2$-Hx$^c$ | (CH$_2$)$_5$ | S |
| 2-249 | H | H | H | H | 4-ONO$_2$-Hx$^c$ | (CH$_2$)$_6$ | S |
| 2-250 | H | Me | H | H | 4-ONO$_2$-Hx$^c$ | (CH$_2$)$_6$ | S |
| 2-251 | H | H | H | H | 4-(ONO$_2$CH$_2$)-Hx$^c$ | single bond | O |
| 2-252 | Me | H | H | H | 4-(ONO$_2$CH$_2$)-Hx$^c$ | single bond | O |
| 2-253 | Et | H | H | H | 4-(ONO$_2$CH$_2$)-Hx$^c$ | single bond | O |
| 2-254 | Bz | H | H | H | 4-(ONO$_2$CH$_2$)-Hx$^c$ | single bond | O |
| 2-255 | H | Me | H | H | 4-(ONO$_2$CH$_2$)-Hx$^c$ | single bond | O |
| 2-256 | H | Et | H | H | 4-(ONO$_2$CH$_2$)-Hx$^c$ | single bond | O |
| 2-257 | H | Ph | H | H | 4-(ONO$_2$CH$_2$)-Hx$^c$ | single bond | O |
| 2-258 | H | 2-Then | H | H | 4-(ONO$_2$CH$_2$)-Hx$^c$ | single bond | O |
| 2-259 | H | 3-Then | H | H | 4-(ONO$_2$CH$_2$)-Hx$^c$ | single bond | O |
| 2-260 | H | 2-Fur | H | H | 4-(ONO$_2$CH$_2$)-Hx$^c$ | single bond | O |
| 2-261 | H | 3-Fur | H | H | 4-(ONO$_2$CH$_2$)-Hx$^c$ | single bond | O |
| 2-262 | H | 4-Me-Ph | H | H | 4-(ONO$_2$CH$_2$)-Hx$^c$ | single bond | O |
| 2-263 | H | 4-Cl-Ph | H | H | 4-(ONO$_2$CH$_2$)-Hx$^c$ | single bond | O |
| 2-264 | H | 4-MeO-Ph | H | H | 4-(ONO$_2$CH$_2$)-Hx$^c$ | single bond | O |
| 2-265 | H | 4-Thiz | H | H | 4-(ONO$_2$CH$_2$)-Hx$^c$ | single bond | O |
| 2-266 | H | 3-Pyr | H | H | 4-(ONO$_2$CH$_2$)-Hx$^c$ | single bond | O |
| 2-267 | H | Me | Me | H | 4-(ONO$_2$CH$_2$)-Hx$^c$ | single bond | O |
| 2-268 | Me | Me | Me | H | 4-(ONO$_2$CH$_2$)-Hx$^c$ | single bond | O |
| 2-269 | Me | Me | Me | Me | 4-(ONO$_2$CH$_2$)-Hx$^c$ | single bond | O |
| 2-270 | Et | Ph | H | H | 4-(ONO$_2$CH$_2$)-Hx$^c$ | single bond | O |
| 2-271 | Et | Et | H | Me | 4-(ONO$_2$CH$_2$)-Hx$^c$ | single bond | Q |
| 2-272 | Bz | Me | H | Et | 4-(ONO$_2$CH$_2$)-Hx$^c$ | single bond | O |
| 2-273 | Bz | Ph | H | Et | 4-(ONO$_2$CH$_2$)-Hx$^c$ | single bond | O |
| 2-274 | Bu | H | H | H | 4-(ONO$_2$CH$_2$)-Hx$^c$ | single bond | O |
| 2-275 | H | 1-Np | H | H | 4-(ONO$_2$CH$_2$)-Hx$^c$ | single bond | O |
| 2-276 | H | H | H | Me | 4-(ONO$_2$CH$_2$)-Hx$^c$ | single bond | O |
| 2-277 | H | H | H | Bz | 4-(ONO$_2$CH$_2$)-Hx$^c$ | single bond | O |
| 2-278 | H | Bz | H | H | 4-(ONO$_2$CH$_2$)-Hx$^c$ | single bond | O |
| 2-279 | H | 4-Me-Bz | H | H | 4-(ONO$_2$CH$_2$)-Hx$^c$ | single bond | O |
| 2-280 | H | 4-OMe-Bz | H | H | 4-(ONO$_2$CH$_2$)-Hx$^c$ | single bond | O |
| 2-281 | H | 4-F-Bz | H | H | 4-(ONO$_2$CH$_2$)-Hx$^c$ | single bond | O |
| 2-282 | H | H | H | H | 4-(ONO$_2$CH$_2$)-Hx$^c$ | CH$_2$ | O |
| 2-283 | Me | H | H | H | 4-(ONO$_2$CH$_2$)-Hx$^c$ | CH$_2$ | O |
| 2-284 | Et | H | H | H | 4-(ONO$_2$CH$_2$)-Hx$^c$ | CH$_2$ | O |
| 2-285 | Bz | H | H | H | 4-(ONO$_2$CH$_2$)-Hx$^c$ | CH$_2$ | O |
| 2-286 | H | Me | H | H | 4-(ONO$_2$CH$_2$)-Hx$^c$ | CH$_2$ | O |
| 2-287 | H | Et | H | H | 4-(ONO$_2$CH$_2$)-Hx$^c$ | CH$_2$ | O |
| 2-288 | H | Ph | H | H | 4-(ONO$_2$CH$_2$)-Hx$^c$ | CH$_2$ | O |
| 2-289 | H | 2-Then | H | H | 4-(ONO$_2$CH$_2$)-Hx$^c$ | CH$_2$ | O |
| 2-290 | H | 3-Then | H | H | 4-(ONO$_2$CH$_2$)-Hx$^c$ | CH$_2$ | O |
| 2-291 | H | 2-Fur | H | H | 4-(ONO$_2$CH$_2$)-Hx$^c$ | CH$_2$ | O |
| 2-292 | H | 3-Fur | H | H | 4-(ONO$_2$CH$_2$)-Hx$^c$ | CH$_2$ | O |
| 2-293 | H | 4-Me-Ph | H | H | 4-(ONO$_2$CH$_2$)-Hx$^c$ | CH$_2$ | O |
| 2-294 | H | 4-Cl-Ph | H | H | 4-(ONO$_2$CH$_2$)-Hx$^c$ | CH$_2$ | O |
| 2-295 | H | 4-MeO-Ph | H | H | 4-(ONO$_2$CH$_2$)-Hx$^c$ | CH$_2$ | O |
| 2-296 | H | 4-Thiz | H | H | 4-(ONO$_2$CH$_2$)-Hx$^c$ | CH$_2$ | O |
| 2-297 | H | 3-Pyr | H | H | 4-(ONO$_2$CH$_2$)-Hx$^c$ | CH$_2$ | O |
| 2-298 | H | Me | Me | H | 4-(ONO$_2$CH$_2$)-Hx$^c$ | CH$_2$ | O |
| 2-299 | Me | Me | Me | H | 4-(ONO$_2$CH$_2$)-Hx$^c$ | CH$_2$ | O |
| 2-300 | Me | Me | Me | Me | 4-(ONO$_2$CH$_2$)-Hx$^c$ | CH$_2$ | O |
| 2-301 | Et | Ph | H | H | 4-(ONO$_2$CH$_2$)-Hx$^c$ | CH$_2$ | O |
| 2-302 | Et | Et | H | Me | 4-(ONO$_2$CH$_2$)-Hx$^c$ | CH$_2$ | O |
| 2-303 | Bz | Me | H | Et | 4-(ONO$_2$CH$_2$)-Hx$^c$ | CH$_2$ | O |
| 2-304 | Bz | Ph | H | Et | 4-(ONO$_2$CH$_2$)-Hx$^c$ | CH$_2$ | O |
| 2-305 | Bu | H | H | H | 4-(ONO$_2$CH$_2$)-Hx$^c$ | CH$_2$ | O |
| 2-306 | H | 1-Np | H | H | 4-(ONO$_2$CH$_2$)-Hx$^c$ | CH$_2$ | O |
| 2-307 | H | H | H | Me | 4-(ONO$_2$CH$_2$)-Hx$^c$ | CH$_2$ | O |
| 2-308 | H | H | H | Bz | 4-(ONO$_2$CH$_2$)-Hx$^c$ | CH$_2$ | O |

TABLE 2-continued

| Compd. No. | R¹ | R² | R³ | R⁴ | R⁵ | A | X¹ |
|---|---|---|---|---|---|---|---|
| 2-309 | H | Bz | H | H | 4-(ONO$_2$CH$_2$)-Hx$^c$ | CH$_2$ | O |
| 2-310 | H | 4-Me-Bz | H | H | 4-(ONO$_2$CH$_2$)-Hx$^c$ | CH$_2$ | O |
| 2-311 | H | 4-MeO-Bz | H | H | 4-(ONO$_2$CH$_2$)-Hx$^c$ | CH$_2$ | O |
| 2-312 | H | 4-F-Bz | H | H | 4-(ONO$_2$CH$_2$)-Hx$^c$ | CH$_2$ | O |
| 2-313 | H | 4-Cl-Bz | H | H | 4-(ONO$_2$CH$_2$)-Hx$^c$ | CH$_2$ | O |
| 2-314 | H | 4-OH-Bz | H | H | 4-(ONO$_2$CH$_2$)-Hx$^c$ | CH$_2$ | O |
| 2-315 | H | H | H | H | 4-(ONO$_2$CH$_2$)-Hx$^c$ | (CH$_2$)$_2$ | O |
| 2-316 | Me | H | H | H | 4-(ONO$_2$CH$_2$)-Hx$^c$ | (CH$_2$)$_2$ | O |
| 2-317 | Et | H | H | H | 4-(ONO$_2$CH$_2$)-Hx$^c$ | (CH$_2$)$_2$ | O |
| 2-318 | Bz | H | H | H | 4-(ONO$_2$CH$_2$)-Hx$^c$ | (CH$_2$)$_2$ | O |
| 2-319 | H | Me | H | H | 4-(ONO$_2$CH$_2$)-Hx$^c$ | (CH$_2$)$_2$ | O |
| 2-320 | H | Et | H | H | 4-(ONO$_2$CH$_2$)-Hx$^c$ | (CH$_2$)$_2$ | O |
| 2-321 | H | Ph | H | H | 4-(ONO$_2$CH$_2$)-Hx$^c$ | (CH$_2$)$_2$ | O |
| 2-322 | H | 2-Then | H | H | 4-(ONO$_2$CH$_2$)-Hx$^c$ | (CH$_2$)$_2$ | O |
| 2-323 | H | 3-Then | H | H | 4-(ONO$_2$CH$_2$)-Hx$^c$ | (CH$_2$)$_2$ | O |
| 2-324 | H | 2-Fur | H | H | 4-(ONO$_2$CH$_2$)-Hx$^c$ | (CH$_2$)$_2$ | |
| 2-325 | H | 3-Fur | H | H | 4-(ONO$_2$CH$_2$)-Hx$^c$ | (CH$_2$)$_2$ | O |
| 2-326 | H | 4-Me-Ph | H | H | 4-(ONO$_2$CH$_2$)-Hx$^c$ | (CH$_2$)$_2$ | O |
| 2-327 | H | 4-Cl-Ph | H | H | 4-(ONO$_2$CH$_2$)-Hx$^c$ | (CH$_2$)$_2$ | O |
| 2-328 | H | 4-MeO-Ph | H | H | 4-(ONO$_2$CH$_2$)-Hx$^c$ | (CH$_2$)$_2$ | O |
| 2-329 | H | 4-Thiz | H | H | 4-(ONO$_2$CH$_2$)-Hx$^c$ | (CH$_2$)$_2$ | O |
| 2-330 | H | 3-Pyr | H | H | 4-(ONO$_2$CH$_2$)-Hx$^c$ | (CH$_2$)$_2$ | O |
| 2-331 | H | Me | Me | H | 4-(ONO$_2$CH$_2$)-Hx$^c$ | (CH$_2$)$_2$ | O |
| 2-332 | Me | Me | Me | H | 4-(ONO$_2$CH$_2$)-Hx$^c$ | (CH$_2$)$_2$ | O |
| 2-333 | Me | Me | Me | Me | 4-(ONO$_2$CH$_2$)-Hx$^c$ | (CH$_2$)$_2$ | O |
| 2-334 | Et | Ph | H | H | 4-(ONO$_2$CH$_2$)-Hx$^c$ | (CH$_2$)$_2$ | O |
| 2-335 | Et | Et | H | Me | 4-(ONO$_2$CH$_2$)-Hx$^c$ | (CH$_2$)$_2$ | O |
| 2-336 | Bz | Me | H | Et | 4-(ONO$_2$CH$_2$)-Hx$^c$ | (CH$_2$)$_2$ | O |
| 2-337 | Bz | Ph | H | Et | 4-(ONO$_2$CH$_2$)-Hx$^c$ | (CH$_2$)$_2$ | O |
| 2-338 | Bu | H | H | H | 4-(ONO$_2$CH$_2$)-Hx$^c$ | (CH$_2$)$_2$ | O |
| 2-339 | H | 1-Np | H | H | 4-(ONO$_2$CH$_2$)-Hx$^c$ | (CH$_2$)$_2$ | O |
| 2-340 | H | H | H | Me | 4-(ONO$_2$CH$_2$)-Hx$^c$ | (CH$_2$)$_2$ | O |
| 2-341 | H | H | H | Bz | 4-(ONO$_2$CH$_2$)-Hx$^c$ | (CH$_2$)$_2$ | O |
| 2-342 | H | Bz | H | H | 4-(ONO$_2$CH$_2$)-Hx$^c$ | (CH$_2$)$_2$ | O |
| 2-343 | H | 4-Me-Bz | H | H | 4-(ONO$_2$CH$_2$)-Hx$^c$ | (CH$_2$)$_2$ | O |
| 2-344 | H | 4-MeO-Bz | H | H | 4-(ONO$_2$CH$_2$)-Hx$^c$ | (CH$_2$)$_2$ | O |
| 2-345 | H | 4-F-Bz | H | H | 4-(ONO$_2$CH$_2$)-Hx$^c$ | (CH$_2$)$_2$ | O |
| 2-346 | H | H | H | H | 4-(ONO$_2$CH$_2$)-Hx$^c$ | (CH$_2$)$_3$ | O |
| 2-347 | H | Me | H | H | 4-(ONO$_2$CH$_2$)-Hx$^c$ | (CH$_2$)$_3$ | O |
| 2-348 | H | Bz | H | H | 4-(ONO$_2$CH$_2$)-Hx$^c$ | (CH$_2$)$_3$ | O |
| 2-349 | H | H | H | H | 4-(ONO$_2$CH$_2$)-Hx$^c$ | (CH$_2$)$_4$ | O |
| 2-350 | H | Me | H | H | 4-(ONO$_2$CH$_2$)-Hx$^c$ | (CH$_2$)$_4$ | O |
| 2-351 | H | H | H | H | 4-(ONO$_2$CH$_2$)-Hx$^c$ | (CH$_2$)$_5$ | O |
| 2-352 | H | Me | H | H | 4-(ONO$_2$CH$_2$)-Hx$^c$ | (CH$_2$)$_5$ | O |
| 2-353 | H | H | H | H | 4-(ONO$_2$CH$_2$)-Hx$^c$ | (CH$_2$)$_6$ | O |
| 2-354 | H | Me | H | H | 4-(ONO$_2$CH$_2$)-Hx$^c$ | (CH$_2$)$_6$ | O |
| 2-355 | H | H | H | H | 4-ONO$_2$-Hx$^c$ | single bond | O |
| 2-356 | Me | H | H | H | 4-ONO$_2$-Hx$^c$ | single bond | O |
| 2-357 | Et | H | H | H | 4-ONO$_2$-Hx$^c$ | single bond | O |
| 2-358 | Bz | H | H | H | 4-ONO$_2$-Hx$^c$ | single bond | O |
| 2-359 | H | Me | H | H | 4-ONO$_2$-Hx$^c$ | single bond | O |
| 2-360 | H | Et | H | H | 4-ONO$_2$-Hx$^c$ | single bond | O |
| 2-361 | H | Ph | H | H | 4-ONO$_2$-Hx$^c$ | single bond | O |
| 2-362 | H | Bz | H | H | 4-ONO$_2$-Hx$^c$ | single bond | O |
| 2-363 | H | 4-Me-Bz | H | H | 4-ONO$_2$-Hx$^c$ | single bond | O |
| 2-364 | H | 4-MeO-Bz | H | H | 4-ONO$_2$-Hx$^c$ | single bond | O |
| 2-365 | H | 4-F-Bz | H | H | 4-ONO$_2$-Hx$^c$ | single bond | O |
| 2-366 | H | 2-Then | H | H | 4-ONO$_2$-Hx$^c$ | single bond | O |
| 2-367 | H | 3-Then | H | H | 4-ONO$_2$-Hx$^c$ | single bond | O |
| 2-368 | H | 2-Fur | H | H | 4-ONO$_2$-Hx$^c$ | single bond | O |
| 2-369 | H | 3-Fur | H | H | 4-ONO$_2$-Hx$^c$ | single bond | O |
| 2-370 | H | 3-Pyr | H | H | 4-ONO$_2$-Hx$^c$ | single bond | O |
| 2-371 | H | H | H | Me | 4-ONO$_2$-Hx$^c$ | single bond | O |
| 2-372 | H | H | H | Et | 4-ONO$_2$-Hx$^c$ | single bond | O |
| 2-373 | H | H | H | Bz | 4-ONO$_2$-Hx$^c$ | single bond | O |
| 2-374 | H | H | H | H | 4-[ONO$_2$(CH$_2$)$_2$]-Hx$^c$ | single bond | O |
| 2-375 | H | Me | H | H | 4-[ONO$_2$(CH$_2$)$_2$]-Hx$^c$ | single bond | O |
| 2-376 | H | Et | H | H | 4-[ONO$_2$(CH$_2$)$_2$]-Hx$^c$ | single bond | O |
| 2-377 | H | Ph | H | H | 4-[ONO$_2$(CH$_2$)$_2$]-Hx$^c$ | single bond | O |
| 2-378 | H | Bz | H | H | 4-[ONO$_2$(CH$_2$)$_2$]-Hx$^c$ | single bond | O |
| 2-379 | H | 4-Me-Bz | H | H | 4-[ONO$_2$(CH$_2$)$_2$]-Hx$^c$ | single bond | O |
| 2-380 | H | 4-MeO-Bz | H | H | 4-[ONO$_2$(CH$_2$)$_2$]-Hx$^c$ | single bond | O |
| 2-381 | H | 4-F-Bz | H | H | 4-[ONO$_2$(CH$_2$)$_2$]-Hx$^c$ | single bond | O |
| 2-382 | H | 2-Then | H | H | 4-[ONO$_2$(CH$_2$)$_2$]-Hx$^c$ | single bond | O |
| 2-383 | H | 3-Then | H | H | 4-[ONO$_2$(CH$_2$)$_2$]-Hx$^c$ | single bond | O |
| 2-384 | H | 2-Fur | H | H | 4-[ONO$_2$(CH$_2$)$_2$]-Hx$^c$ | single bond | O |

TABLE 2-continued

| Compd. No. | $R^1$ | $R^2$ | $R^3$ | $R^4$ | $R^5$ | A | $X^1$ |
|---|---|---|---|---|---|---|---|
| 2-385 | H | 3-Fur | H | H | 4-[ONO$_2$(CH$_2$)$_2$]-Hx$^c$ | single bond | O |
| 2-386 | H | 3-Pyr | H | H | 4-[ONO$_2$(CH$_2$)$_2$]-Hx$^c$ | single bond | O |
| 2-387 | H | 4-Thiz | H | H | 4-[ONO$_2$(CH$_2$)$_2$]-Hx$^c$ | single bond | O |
| 2-388 | H | H | H | H | 4-ONO$_2$-Hx$^c$ | CH$_2$ | O |
| 2-389 | Me | H | H | H | 4-ONO$_2$-Hx$^c$ | CH$_2$ | O |
| 2-390 | Et | H | H | H | 4-ONO$_2$-Hx$^c$ | CH$_2$ | O |
| 2-391 | Bz | H | H | H | 4-ONO$_2$-Hx$^c$ | CH$_2$ | O |
| 2-392 | H | Me | H | H | 4-ONO$_2$-Hx$^c$ | CH$_2$ | O |
| 2-393 | H | Et | H | H | 4-ONO$_2$-Hx$^c$ | CH$_2$ | O |
| 2-394 | H | Ph | H | H | 4-ONO$_2$-Hx$^c$ | CH$_2$ | O |
| 2-395 | H | 2-Then | H | H | 4-ONO$_2$-Hx$^c$ | CH$_2$ | O |
| 2-396 | H | 3-Then | H | H | 4-ONO$_2$-Hx$^c$ | CH$_2$ | O |
| 2-397 | H | 2-Fur | H | H | 4-ONO$_2$-Hx$^c$ | CH$_2$ | O |
| 2-398 | H | 3-Fur | H | H | 4-ONO$_2$-Hx$^c$ | CH$_2$ | O |
| 2-399 | H | 4-Me-Ph | H | H | 4-ONO$_2$-Hx$^c$ | CH$_2$ | O |
| 2-400 | H | 4-Cl-Ph | H | H | 4-ONO$_2$-Hx$^c$ | CH$_2$ | O |
| 2-401 | H | 4-MeO-Ph | H | H | 4-ONO$_2$-Hx$^c$ | CH$_2$ | O |
| 2-402 | H | 4-Thiz | H | H | 4-ONO$_2$-Hx$^c$ | CH$_2$ | O |
| 2-403 | H | 3-Pyr | H | H | 4-ONO$_2$-Hx$^c$ | CH$_2$ | O |
| 2-404 | H | Me | Me | H | 4-ONO$_2$-Hx$^c$ | CH$_2$ | O |
| 2-405 | Me | Me | Me | H | 4-ONO$_2$-Hx$^c$ | CH$_2$ | O |
| 2-406 | Me | Me | Me | Me | 4-ONO$_2$-Hx$^c$ | CH$_2$ | O |
| 2-407 | Et | Ph | H | H | 4-ONO$_2$-Hx$^c$ | CH$_2$ | O |
| 2-408 | Et | Et | H | Me | 4-ONO$_2$-Hx$^c$ | CH$_2$ | O |
| 2-409 | Bz | Me | H | Et | 4-ONO$_2$-Hx$^c$ | CH$_2$ | O |
| 2-410 | Bz | Ph | H | Et | 4-ONO$_2$-Hx$^c$ | CH$_2$ | O |
| 2-411 | Bu | H | H | H | 4-ONO$_2$-Hx$^c$ | CH$_2$ | O |
| 2-412 | H | 1-Np | H | H | 4-ONO$_2$-Hx$^c$ | CH$_2$ | O |
| 2-413 | H | H | H | Me | 4-ONO$_2$-Hx$^c$ | CH$_2$ | O |
| 2-414 | H | H | H | Bz | 4-ONO$_2$-Hx$^c$ | CH$_2$ | O |
| 2-415 | H | Bz | H | H | 4-ONO$_2$-Hx$^c$ | CH$_2$ | O |
| 2-416 | H | 4-Me-Bz | H | H | 4-ONO$_2$-Hx$^c$ | CH$_2$ | O |
| 2-417 | H | 4-MeO-Bz | H | H | 4-ONO$_2$-Hx$^c$ | CH$_2$ | O |
| 2-418 | H | 4-F-Bz | H | H | 4-ONO$_2$-Hx$^c$ | CH$_2$ | O |
| 2-419 | H | H | H | H | 4-[ONO$_2$(CH$_2$)$_2$]-Hx$^c$ | CH$_2$ | O |
| 2-420 | H | Me | H | H | 4-[ONO$_2$(CH$_2$)$_2$]-Hx$^c$ | CH$_2$ | O |
| 2-421 | H | Et | H | H | 4-[ONO$_2$(CH$_2$)$_2$]-Hx$^c$ | CH$_2$ | O |
| 2-422 | H | Ph | H | H | 4-[ONO$_2$(CH$_2$)$_2$]-Hx$^c$ | CH$_2$ | O |
| 2-423 | H | 2-Then | H | H | 4-[ONO$_2$(CH$_2$)$_2$]-Hx$^c$ | CH$_2$ | O |
| 2-424 | H | 3-Then | H | H | 4-[ONO$_2$(CH$_2$)$_2$]-Hx$^c$ | CH$_2$ | O |
| 2-425 | H | 2-Fur | H | H | 4-[ONO$_2$(CH$_2$)$_2$]-Hx$^c$ | CH$_2$ | O |
| 2-426 | H | 3-Fur | H | H | 4-[ONO$_2$(CH$_2$)$_2$]-Hx$^c$ | CH$_2$ | O |
| 2-427 | H | 3-Py | H | H | 4-[ONO$_2$(CH$_2$)$_2$]-Hx$^c$ | CH$_2$ | O |
| 2-428 | H | Bz | H | H | 4-[ONO$_2$(CH$_2$)$_2$]-Hx$^c$ | CH$_2$ | O |
| 2-429 | H | 4-Me-Bz | H | H | 4-[ONO$_2$(CH$_2$)$_2$]-Hx$^c$ | CH$_2$ | O |
| 2-430 | H | 4-MeO-Bz | H | H | 4-[ONO$_2$(CH$_2$)$_2$]-Hx$^c$ | CH$_2$ | O |
| 2-431 | H | 4-F-Bz | H | H | 4-[ONO$_2$(CH$_2$)$_2$]-Hx$^c$ | CH$_2$ | O |
| 2-432 | H | Me | Me | H | 4-[ONO$_2$(CH$_2$)$_2$]-Hx$^c$ | CH$_2$ | O |
| 2-433 | Me | Me | Me | H | 4-[ONO$_2$(CH$_2$)$_2$]-Hx$^c$ | CH$_2$ | O |
| 2-434 | Bz | Me | H | Et | 4-[ONO$_2$(CH$_2$)$_2$]-Hx$^c$ | CH$_2$ | O |
| 2-435 | Bu | H | H | H | 4-[ONO$_2$(CH$_2$)$_2$]-Hx$^c$ | CH$_2$ | O |
| 2-436 | H | 1-Np | H | H | 4-[ONO$_2$(CH$_2$)$_2$]-Hx$^c$ | CH$_2$ | O |
| 2-437 | H | H | H | Me | 4-[ONO$_2$(CH$_2$)$_2$]-Hx$^c$ | CH$_2$ | O |
| 2-438 | H | H | H | Bz | 4-[ONO$_2$(CH$_2$)$_2$]-Hx$^c$ | CH$_2$ | O |
| 2-439 | H | H | H | H | 4-[ONO$_2$(CH$_2$)$_2$]-Hx$^c$ | (CH$_2$)$_2$ | O |
| 2-440 | H | Me | H | H | 4-[ONO$_2$(CH$_2$)$_2$]-Hx$^c$ | (CH$_2$)$_2$ | O |
| 2-441 | H | Et | H | H | 4-[ONO$_2$(CH$_2$)$_2$]-Hx$^c$ | (CH$_2$)$_2$ | O |
| 2-442 | H | Ph | H | H | 4-[ONO$_2$(CH$_2$)$_2$]-Hx$^c$ | (CH$_2$)$_2$ | O |
| 2-443 | H | 2-Then | H | H | 4-[ONO$_2$(CH$_2$)$_2$]-Hx$^c$ | (CH$_2$)$_2$ | O |
| 2-444 | H | 3-Then | H | H | 4-[ONO$_2$(CH$_2$)$_2$]-Hx$^c$ | (CH$_2$)$_2$ | O |
| 2-445 | H | 2-Fur | H | H | 4-[ONO$_2$(CH$_2$)$_2$]-Hx$^c$ | (CH$_2$)$_2$ | O |
| 2-446 | H | 3-Fur | H | H | 4-[ONO$_2$(CH$_2$)$_2$]-Hx$^c$ | (CH$_2$)2 | O |
| 2-447 | H | 3-Py | H | H | 4-[ONO$_2$(CH$_2$)$_2$]-Hx$^c$ | (CH$_2$)$_2$ | O |
| 2-448 | H | Bz | H | H | 4-[ONO$_2$(CH$_2$)$_2$]-Hx$^c$ | (CH$_2$)$_2$ | O |
| 2-449 | H | 4-Me-Bz | H | H | 4-[ONO$_2$(CH$_2$)$_2$]-Hx$^c$ | (CH$_2$)$_2$ | O |
| 2-450 | H | 4-MeO-Bz | H | H | 4-[ONO$_2$(CH$_2$)$_2$]-Hx$^c$ | (CH$_2$)$_2$ | O |
| 2-451 | H | 4-F-Bz | H | H | 4-[ONO$_2$(CH$_2$)$_2$]-Hx$^c$ | (CH$_2$)$_2$ | O |
| 2-452 | H | Me | Me | H | 4-[ONO$_2$(CH$_2$)$_2$]-Hx$^c$ | (CH$_2$)$_2$ | O |
| 2-453 | Bu | H | H | H | 4-[ONO$_2$(CH$_2$)$_2$]-Hx$^c$ | (CH$_2$)$_2$ | O |
| 2-454 | H | 1-Np | H | H | 4-[ONO$_2$(CH$_2$)$_2$]-Hx$^c$ | (CH$_2$)$_2$ | O |
| 2-455 | H | H | H | Me | 4-[ONO$_2$(CH$_2$)$_2$]-Hx$^c$ | (CH$_2$)$_2$ | O |
| 2-456 | H | H | H | Bz | 4-[ONO$_2$(CH$_2$)$_2$]-Hx$^c$ | (CH$_2$)$_2$ | O |
| 2-457 | H | H | H | H | 4-[ONO$_2$(CH$_2$)$_3$]-Hx$^c$ | (CH$_2$)$_2$ | O |
| 2-458 | H | Me | H | H | 4-[ONO$_2$(CH$_2$)$_3$]-Hx$^c$ | (CH$_2$)$_2$ | O |
| 2-459 | H | Bz | H | H | 4-[ONO$_2$(CH$_2$)$_3$]-Hx$^c$ | (CH$_2$)$_2$ | O |
| 2-460 | H | H | H | H | 4-[ONO$_2$(CH$_2$)$_4$]-Hx$^c$ | (CH$_2$)$_2$ | O |

TABLE 2-continued

| Compd. No. | $R^1$ | $R^2$ | $R^3$ | $R^4$ | $R^5$ | A | $X^1$ |
|---|---|---|---|---|---|---|---|
| 2-461 | H | Me | H | H | 4-[ONO$_2$(CH$_2$)$_4$]-Hx$^c$ | (CH$_2$)$_2$ | O |
| 2-462 | H | Bz | H | H | 4-[ONO$_2$(CH$_2$)$_4$]-Hx$^c$ | (CH$_2$)$_2$ | O |
| 2-463 | H | H | H | H | 4-[ONO$_2$(CH$_2$)$_5$]-Hx$^c$ | (CH$_2$)$_2$ | O |
| 2-464 | H | Me | H | H | 4-[ONO$_2$(CH$_2$)$_5$]-Hx$^c$ | (CH$_2$)$_2$ | O |
| 2-465 | H | Bz | H | H | 4-[ONO$_2$(CH$_2$)$_5$]-Hx$^c$ | (CH$_2$)$_2$ | O |
| 2-466 | H | H | H | H | 4-[ONO$_2$(CH$_2$)$_6$]-Hx$^c$ | (CH$_2$)$_2$ | O |
| 2-467 | H | Me | H | H | 4-[ONO$_2$(CH$_2$)$_6$]-Hx$^c$ | (CH$_2$)$_2$ | O |
| 2-468 | H | Bz | H | H | 4-[ONO$_2$(CH$_2$)$_6$]-Hx$^c$ | (CH$_2$)$_2$ | O |
| 2-469 | H | H | H | H | 4-ONO$_2$-Hx$^c$ | (CH$_2$)$_2$ | O |
| 2-470 | Me | H | H | H | 4-ONO$_2$-Hx$^c$ | (CH$_2$)$_2$ | O |
| 2-471 | Bz | H | H | H | 4-ONO$_2$-Hx$^c$ | (CH$_2$)$_2$ | O |
| 2-472 | H | Me | H | H | 4-ONO$_2$-Hx$^c$ | (CH$_2$)$_2$ | O |
| 2-473 | H | Et | H | H | 4-ONO$_2$-Hx$^c$ | (CH$_2$)$_2$ | O |
| 2-474 | H | Ph | H | H | 4-ONO$_2$-Hx$^c$ | (CH$_2$)$_2$ | O |
| 2-475 | H | 2-Then | H | H | 4-ONO$_2$-Hx$^c$ | (CH$_2$)$_2$ | O |
| 2-476 | H | 3-Then | H | H | 4-ONO$_2$-Hx$^c$ | (CH$_2$)$_2$ | O |
| 2-477 | H | 2-Fur | H | H | 4-ONO$_2$-Hx$^c$ | (CH$_2$)$_2$ | O |
| 2-478 | H | 3-Fur | H | H | 4-ONO$_2$-Hx$^c$ | (CH$_2$)$_2$ | O |
| 2-479 | H | 4-Me-Ph | H | H | 4-ONO$_2$-Hx$^c$ | (CH$_2$)$_2$ | O |
| 2-480 | H | 4-Cl-Ph | H | H | 4-ONO$_2$-Hx$^c$ | (CH$_2$)$_2$ | O |
| 2-481 | H | 4-MeO-Ph | H | H | 4-ONO$_2$-Hx$^c$ | (CH$_2$)$_2$ | O |
| 2-482 | H | 4-Thiz | H | H | 4-ONO$_2$-Hx$^c$ | (CH$_2$)$_2$ | O |
| 2-483 | H | 3-Pyr | H | H | 4-ONO$_2$-Hx$^c$ | (CH$_2$)$_2$ | O |
| 2-484 | H | Me | Me | H | 4-ONO$_2$-Hx$^c$ | (CH$_2$)$_2$ | O |
| 2-485 | Bu | H | H | H | 4-ONO$_2$-Hx$^c$ | (CH$_2$)$_2$ | O |
| 2-486 | H | 1-Np | H | H | 4-ONO$_2$-Hx$^c$ | (CH$_2$)$_2$ | O |
| 2-487 | H | H | H | Me | 4-ONO$_2$-Hx$^c$ | (CH$_2$)$_2$ | O |
| 2-488 | H | H | H | Bz | 4-ONO$_2$-Hx$^c$ | (CH$_2$)$_2$ | O |
| 2-489 | H | Bz | H | H | 4-ONO$_2$-Hx$^c$ | (CH$_2$)$_2$ | O |
| 2-490 | H | 4-Me-Bz | H | H | 4-ONO$_2$-Hx$^c$ | (CH$_2$)$_2$ | O |
| 2-491 | H | 4-MeO-Bz | H | H | 4-ONO$_2$-Hx$^c$ | (CH$_2$)$_2$ | O |
| 2-492 | H | 4-F-Bz | H | H | 4-ONO$_2$-Hx$^c$ | (CH$_2$)$_2$ | O |
| 2-493 | H | H | H | H | 4-ONO$_2$-Hx$^c$ | (CH$_2$)$_3$ | O |
| 2-494 | H | Me | H | H | 4-ONO$_2$-Hx$^c$ | (CH$_2$)$_3$ | O |
| 2-495 | H | H | H | H | 4-ONO$_2$-Hx$^c$ | (CH$_2$)$_4$ | O |
| 2-496 | H | Me | H | H | 4-ONO$_2$-Hx$^c$ | (CH$_2$)$_4$ | O |
| 2-497 | H | H | H | H | 4-ONO$_2$-Hx$^c$ | (CH$_2$)$_5$ | O |
| 2-498 | H | Me | H | H | 4-ONO$_2$-Hx$^c$ | (CH$_2$)$_5$ | O |
| 2-499 | H | H | H | H | 4-ONO$_2$-Hx$^c$ | (CH$_2$)$_6$ | O |
| 2-500 | H | Me | H | H | 4-ONO$_2$-Hx$^c$ | (CH$_2$)$_6$ | O |
| 2-501 | H | H | H | H | 2-(ONO$_2$)-Pn$^c$ | single bond | S |
| 2-502 | H | Me | H | H | 2-(ONO$_2$)-Pn$^c$ | single bond | S |
| 2-503 | H | Bz | H | H | 2-(ONO$_2$)-Pn$^c$ | single bond | S |
| 2-504 | H | 4-Me-Bz | H | H | 2-(ONO$_2$)-Pn$^c$ | single bond | S |
| 2-505 | H | 4-MeO-Bz | H | H | 2-(ONO$_2$)-Pn$^c$ | single bond | S |
| 2-506 | H | 4-F-Bz | H | H | 2-(ONO$_2$)-Pn$^c$ | single bond | S |
| 2-507 | H | Ph | H | H | 2-(ONO$_2$)-Pn$^c$ | single bond | S |
| 2-508 | H | 2-Then | H | H | 2-(ONO$_2$)-Pn$^c$ | single bond | S |
| 2-509 | H | 3-Then | H | H | 2-(ONO$_2$)-Pn$^c$ | single bond | S |
| 2-510 | H | 2-Fur | H | H | 2-(ONO$_2$)-Pn$^c$ | single bond | S |
| 2-511 | H | 3-Fur | H | H | 2-(ONO$_2$)-Pn$^c$ | single bond | S |
| 2-512 | H | 3-Pyr | H | H | 2-(ONO$_2$)-Pn$^c$ | sin̩gle bond | S |
| 2-513 | H | H | H | H | 2-(ONO$_2$)-Pn$^c$ | CH$_2$ | S |
| 2-514 | H | Me | H | H | 2-(ONO$_2$)-Pn$^c$ | CH$_2$ | S |
| 2-515 | H | Bz | H | H | 2-(ONO$_2$)-Pn$^c$ | CH$_2$ | S |
| 2-516 | H | 4-Me-Bz | H | H | 2-(ONO$_2$)-Pn$^c$ | CH$_2$ | S |
| 2-517 | H | 4-MeO-Bz | H | H | 2-(ONO$_2$)-Pn$^c$ | CH$_2$ | S |
| 2-518 | H | 4-F-Bz | H | H | 2-(ONO$_2$)-Pn$^c$ | CH$_2$ | S |
| 2-519 | H | Ph | H | H | 2-(ONO$_2$)-Pn$^c$ | CH$_2$ | S |
| 2-520 | H | 2-Then | H | H | 2-(ONO$_2$)-Pn$^c$ | CH$_2$ | S |
| 2-521 | H | 3-Then | H | H | 2-(ONO$_2$)-Pn$^c$ | CH$_2$ | S |
| 2-522 | H | 2-Fur | H | H | 2-(ONO$_2$)-Pn$^c$ | CH$_2$ | S |
| 2-523 | H | 3-Fur | H | H | 2-(ONO$_2$)-Pn$^c$ | CH$_2$ | S |
| 2-524 | H | 3-Pyr | H | H | 2-(ONO$_2$)-Pn$^c$ | CH$_2$ | S |
| 2-525 | H | H | H | H | 2-(ONO$_2$CH$_2$)-Pn$^c$ | single bond | S |
| 2-526 | H | Me | H | H | 2-(ONO$_2$CH$_2$)-Pn$^c$ | single bond | S |
| 2-527 | H | Bz | H | H | 2-(ONO$_2$CH$_2$)-Pn$^c$ | single bond | S |
| 2-528 | H | 4-Me-Bz | H | H | 2-(ONO$_2$CH$_2$)-Pn$^c$ | single bond | S |
| 2-529 | H | 4-MeO-Bz | H | H | 2-(ONO$_2$CH$_2$)-Pn$^c$ | single bond | S |
| 2-530 | H | 4-F-Bz | H | H | 2-(ONO$_2$CH$_2$)-Pn$^c$ | single bond | S |
| 2-531 | H | Ph | H | H | 2-(ONO$_2$CH$_2$)-Pn$^c$ | single bond | S |
| 2-532 | H | 2-Then | H | H | 2-(ONO$_2$CH$_2$)-Pn$^c$ | single bond | S |
| 2-533 | H | 3-Then | H | H | 2-(ONO$_2$CH$_2$)-Pn$^c$ | single bond | S |
| 2-534 | H | 2-Fur | H | H | 2-(ONO$_2$CH$_2$)-Pn$^c$ | si-gle bond | S |
| 2-535 | H | 3-Fur | H | H | 2-(ONO$_2$CH$_2$)-Pn$^c$ | single bond | S |
| 2-536 | H | 3-Pyr | H | H | 2-(ONO$_2$CH$_2$)-Pn$^c$ | single bond | S |

TABLE 2-continued

| Compd. No. | R¹ | R² | R³ | R⁴ | R⁵ | A | X¹ |
|---|---|---|---|---|---|---|---|
| 2-537 | H | H | H | H | 2-(ONO$_2$CH$_2$)-Pn$^c$ | CH$_2$ | S |
| 2-538 | H | Me | H | H | 2-(ONO$_2$CH$_2$)-Pn$^c$ | CH$_2$ | S |
| 2-539 | H | Bz | H | H | 2-(ONO$_2$CH$_2$)-Pn$^c$ | CH$_2$ | S |
| 2-540 | H | 4-Me-Bz | H | H | 2-(ONO$_2$CH$_2$)-Pn$^c$ | CH$_2$ | S |
| 2-541 | H | 4-MeO-Bz | H | H | 2-(ONO$_2$CH$_2$)-Pn$^c$ | CH$_2$ | S |
| 2-542 | H | 4-F-Bz | H | H | 2-(ONO$_2$CH$_2$)-Pn$^c$ | CH$_2$ | S |
| 2-543 | H | Ph | H | H | 2-(ONO$_2$CH$_2$)-Pn$^c$ | CH$_2$ | S |
| 2-544 | H | 2-Then | H | H | 2-(ONO$_2$CH$_2$)-Pn$^c$ | CH$_2$ | S |
| 2-545 | H | 3-Then | H | H | 2-(ONO$_2$CH$_2$)-Pn$^c$ | CH$_2$ | S |
| 2-546 | H | 2-Fur | H | H | 2-(ONO$_2$CH$_2$)-Pn$^c$ | CH$_2$ | S |
| 2-547 | H | 3-Fur | H | H | 2-(ONO$_2$CH$_2$)-Pn$^c$ | CH$_2$ | S |
| 2-548 | H | 3-Pyr | H | H | 2-(ONO$_2$CH$_2$)-Pn$^c$ | CH$_2$ | S |
| 2-549 | H | H | H | H | 3-(ONO$_2$)-Pn$^c$ | single bond | S |
| 2-550 | H | Me | H | H | 3-(ONO$_2$)-Pn$^c$ | single bond | S |
| 2-551 | H | Bz | H | H | 3-(ONO$_2$)-Pn$^c$ | single bond | S |
| 2-552 | H | 4-Me-Bz | H | H | 3-(ONO$_2$)-Pn$^c$ | single bond | S |
| 2-553 | H | 4-MeO-Bz | H | H | 3-(ONO$_2$)-Pn$^c$ | single bond | S |
| 2-554 | H | 4-F-Bz | H | H | 3-(ONO$_2$)-Pn$^c$ | single bond | S |
| 2-555 | H | Ph | H | H | 3-(ONO$_2$)-Pn$^c$ | single bond | S |
| 2-556 | H | 2-Then | H | H | 3-(ONO$_2$)-Pn$^c$ | single bond | S |
| 2-557 | H | 3-Then | H | H | 3-(ONO$_2$)-Pn$^c$ | single bond | S |
| 2-558 | H | 2-Fur | H | H | 3-(ONO$_2$)-Pn$^c$ | single bond | S |
| 2-559 | H | 3-Fur | H | H | 3-(ONO$_2$)-Pn$^c$ | single bond | S |
| 2-560 | H | 3-Pyr | H | H | 3-(ONO$_2$)-Pn$^c$ | single bond | S |
| 2-561 | H | H | H | H | 3-(ONO$_2$)-Pn$^c$ | CH$_2$ | S |
| 2-562 | H | Me | H | H | 3-(ONO$_2$)-Pn$^c$ | CH$_2$ | S |
| 2-563 | H | Bz | H | H | 3-(ONO$_2$)-Pn$^c$ | CH$_2$ | S |
| 2-564 | H | 4-Me-Bz | H | H | 3-(ONO$_2$)-Pn$^c$ | CH$_2$ | S |
| 2-565 | H | 4-MeO-Bz | H | H | 3-(ONO$_2$)-Pn$^c$ | CH$_2$ | S |
| 2-566 | H | 4-F-Bz | H | H | 3-(ONO$_2$)-Pn$^c$ | CH$_2$ | S |
| 2-567 | H | Ph | H | H | 3-(ONO$_2$)-Pn$^c$ | CH$_2$ | S |
| 2-568 | H | 2-Then | H | H | 3-(ONO$_2$)-Pn$^c$ | CH$_2$ | S |
| 2-569 | H | 3-Then | H | H | 3-(ONO$_2$)-Pn$^c$ | CH$_2$ | S |
| 2-570 | H | 2-Fur | H | H | 3-(ONO$_2$)-Pn$^c$ | CH$_2$ | S |
| 2-571 | H | 3-Fur | H | H | 3-(ONO$_2$)-Pn$^c$ | CH$_2$ | S |
| 2-572 | H | 3-Pyr | H | H | 3-(ONO$_2$)-Pn$^c$ | CH$_2$ | S |
| 2-573 | H | H | H | H | 3-(ONO$_2$CH$_2$)-Pn$^c$ | single bond | S |
| 2-574 | H | Me | H | H | 3-(ONO$_2$CH$_2$)-Pn$^c$ | single bond | S |
| 2-575 | H | Bz | H | H | 3-(ONO$_2$CH$_2$)-Pn$^c$ | single bond | S |
| 2-576 | H | 4-Me-Bz | H | H | 3-(ONO$_2$CH$_2$)-Pn$^c$ | single bond | S |
| 2-577 | H | 4-MeO-Bz | H | H | 3-(ONO$_2$CH$_2$)-Pn$^c$ | single bond | S |
| 2-578 | H | 4-F-Bz | H | H | 3-(ONO$_2$CH$_2$)-Pn$^c$ | single bond | 6 |
| 2-579 | H | Ph | H | H | 3-(ONO$_2$CH$_2$)-Pn$^c$ | single bond | S |
| 2-580 | H | 2-Then | H | H | 3-(ONO$_2$CH$_2$)-Pn$^c$ | single bond | S |
| 2-581 | H | 3-Then | H | H | 3-(ONO$_2$CH$_2$)-Pn$^c$ | single bond | S |
| 2-582 | H | 2-Fur | H | H | 3-(ONO$_2$CH$_2$)-Pn$^c$ | single bond | S |
| 2-583 | H | 3-Fur | H | H | 3-(ONO$_2$CH$_2$)-Pn$^c$ | single bond | S |
| 2-584 | H | 3-Pyr | H | W | 3-(ONO$_2$CH$_2$)-Pn$^c$ | single bond | S |
| 2-585 | H | H | H | H | 3-(ONO$_2$CH$_2$)-Pn$^c$ | CH$_2$ | S |
| 2-586 | H | Me | H | H | 3-(ONO$_2$CH$_2$)-Pn$^c$ | CH$_2$ | S |
| 2-587 | H | Bz | H | H | 3-(ONO$_2$CH$_2$)-Pn$^c$ | CH$_2$ | S |
| 2-588 | H | 4-Me-Bz | H | H | 3-(ONO$_2$CH$_2$)-Pn$^c$ | CH$_2$ | S |
| 2-589 | H | 4-MeO-Bz | H | H | 3-(ONO$_2$CH$_2$)-Pn$^c$ | CH$_2$ | S |
| 2-590 | H | 4-F-Bz | H | H | 3-(ONO$_2$CH$_2$)-Pn$^c$ | CH$_2$ | S |
| 2-591 | H | Ph | H | H | 3-(ONO$_2$CH$_2$)-Pn$^c$ | CH$_2$ | S |
| 2-592 | H | 2-Then | H | H | 3-(ONO$_2$CH$_2$)-Pn$^c$ | CH$_2$ | S |
| 2-593 | H | 3-Then | H | H | 3-(ONO$_2$CH$_2$)-Pn$^c$ | CH$_2$ | S |
| 2-594 | H | 2-Fur | H | H | 3-(ONO$_2$CH$_2$)-Pn$^c$ | CH$_2$ | S |
| 2-595 | H | 3-Fur | H | H | 3-(ONO$_2$CH$_2$)-Pn$^c$ | CH$_2$ | S |
| 2-596 | H | 3-Pyr | H | H | 3-(ONO$_2$CH$_2$)-Pn$^c$ | CH$_2$ | S |
| 2-597 | H | H | H | H | 2-(ONO$_2$)-Hx$^c$ | single bond | S |
| 2-598 | H | Me | H | H | 2-(ONO$_2$)-Hx$^c$ | single bond | S |
| 2-599 | H | Bz | H | H | 2-(ONO$_2$)-Hx$^c$ | single bond | S |
| 2-600 | H | 4-Me-Bz | H | H | 2-(ONO$_2$)-Hx$^c$ | single bond | S |
| 2-601 | H | 4-MeO-Bz | H | H | 2-(ONO$_2$)-Hx$^c$ | single bond | S |
| 2-602 | H | 4-F-Bz | H | H | 2-(ONO$_2$)-Hx$^c$ | single bond | S |
| 2-603 | H | Ph | H | H | 2-(ONO$_2$)-Hx$^c$ | single bond | S |
| 2-604 | H | 2-Then | H | H | 2-(ONO$_2$)-Hx$^c$ | single bond | S |
| 2-605 | H | 3-Then | H | H | 2-(ONO$_2$)-Hx$^c$ | single bond | S |
| 2-606 | H | 2-Fur | H | H | 2-(ONO$_2$)-Hx$^c$ | single bond | S |
| 2-607 | H | 3-Fur | H | H | 2-(ONO$_2$)-Hx$^c$ | single bond | S |
| 2-608 | H | 3-Pyr | H | H | 2-(ONO$_2$)-Hx$^c$ | single bond | S |
| 2-609 | H | H | H | H | 2-(ONO$_2$)-Hx$^c$ | CH$_2$ | S |
| 2-610 | H | Me | H | H | 2-(ONO$_2$)-Hx$^c$ | CH$_2$ | S |
| 2-611 | H | Bz | H | H | 2-(ONO$_2$)-Hx$^c$ | CH$_2$ | S |
| 2-612 | H | 4-Me-Bz | H | H | 2-(ONO$_2$)-Hx$^c$ | CH$_2$ | S |

TABLE 2-continued

| Compd. No. | R¹ | R² | R³ | R⁴ | R⁵ | A | X¹ |
|---|---|---|---|---|---|---|---|
| 2-613 | H | 4-MeO-Bz | H | H | 2-(ONO$_2$)-Hx$^c$ | CH$_2$ | S |
| 2-614 | H | 4-F-Bz | H | H | 2-(ONO$_2$)-Hx$^c$ | CH$_2$ | S |
| 2-615 | H | Ph | H | H | 2-(ONO$_2$)-Hx$^c$ | CH$_2$ | S |
| 2-616 | H | 2-Then | H | H | 2-(ONO$_2$)-Hx$^c$ | CH$_2$ | S |
| 2-617 | H | 3-Then | H | H | 2-(ONO$_2$)-Hx$^c$ | CH$_2$ | S |
| 2-618 | H | 2-Fur | H | H | 2-(ONO$_2$)-Hx$^c$ | CH$_2$ | S |
| 2-619 | H | 3-Fur | H | H | 2-(ONO$_2$)-Hx$^c$ | CH$_2$ | S |
| 2-620 | H | 3-Pyr | H | H | 2-(ONO$_2$)-Hx$^c$ | CH$_2$ | S |
| 2-621 | H | H | H | H | 2-(ONO$_2$CH$_2$)-Hx$^c$ | single bond | S |
| 2-622 | H | Me | H | H | 2-(ONO$_2$CH$_2$)-Hx$^c$ | single bond | S |
| 2-623 | H | Bz | H | H | 2-(ONO$_2$CH$_2$)-Hx$^c$ | single bond | S |
| 2-624 | H | 4-Me-Bz | H | H | 2-(ONO$_2$CH$_2$)-Hx$^c$ | single bond | S |
| 2-625 | H | 4-MeO-Bz | H | H | 2-(ONO$_2$CH$_2$)-Hx$^c$ | single bond | S |
| 2-626 | H | 4-F-Bz | H | H | 2-(ONO$_2$CH$_2$)-Hx$^c$ | single bond | S |
| 2-627 | H | Ph | H | H | 2-(ONO$_2$CH$_2$)-Hx$^c$ | single bond | S |
| 2-628 | H | 2-Then | H | H | 2-(ONO$_2$CH$_2$)-Hx$^c$ | single bond | S |
| 2-629 | H | 3-Then | H | H | 2-(ONO$_2$CH$_2$)-Hx$^c$ | single bond | S |
| 2-630 | H | 2-Fur | H | H | 2-(ONO$_2$CH$_2$)-Hx$^c$ | single bond | S |
| 2-631 | H | 3-Fur | H | H | 2-(ONO$_2$CH$_2$)-Hx$^c$ | single bond | S |
| 2-632 | H | 3-Pyr | H | H | 2-(ONO$_2$CH$_2$)-Hx$^c$ | single bond | S |
| 2-633 | H | H | H | H | 2-(ONO$_2$CH$_2$)-Hx$^c$ | CH$_2$ | S |
| 2-634 | H | Me | H | H | 2-(ONO$_2$CH$_2$)-Hx$^c$ | CH$_2$ | S |
| 2-635 | H | Bz | H | H | 2-(ONO$_2$CH$_2$)-Hx$^c$ | CH$_2$ | S |
| 2-636 | H | 4-Me-Bz | H | H | 2-(ONO$_2$CH$_2$)-Hx$^c$ | CH$_2$ | S |
| 2-637 | H | 4-MeO-Bz | H | H | 2-(ONO$_2$CH$_2$)-Hx$^c$ | CH$_2$ | S |
| 2-638 | H | 4-F-Bz | H | H | 2-(ONO$_2$CH$_2$)-Hx$^c$ | CH$_2$ | S |
| 2-639 | H | Ph | H | H | 2-(ONO$_2$CH$_2$)-Hx$^c$ | CH$_2$ | S |
| 2-640 | H | 2-Then | H | H | 2-(ONO$_2$CH$_2$)-Hx$^c$ | CH$_2$ | S |
| 2-641 | H | 3-Then | H | H | 2-(ONO$_2$CH$_2$)-Hx$^c$ | CH$_2$ | S |
| 2-642 | H | 2-Fur | H | H | 2-(ONO$_2$CH$_2$)-Hx$^c$ | CH$_2$ | S |
| 2-643 | H | 3-Fur | H | H | 2-(ONO$_2$CH$_2$)-Hx$^c$ | CH$_2$ | S |
| 2-644 | H | 3-Pyr | H | H | 2-(ONO$_2$CH$_2$)-Hx$^c$ | CH$_2$ | S |
| 2-645 | H | H | H | H | 3-(ONO$_2$CH$_2$)-Hx$^c$ | single bond | S |
| 2-646 | H | Me | H | H | 3-(ONO$_2$CH$_2$)-Hx$^c$ | single bond | S |
| 2-647 | H | Bz | H | H | 3-(ONO$_2$CH$_2$)-Hx$^c$ | single bond | S |
| 2-648 | H | 4-Me-Bz | H | H | 3-(ONO$_2$CH$_2$)-Hx$^c$ | single bond | S |
| 2-649 | H | 4-MeO-Bz | H | H | 3-(ONO$_2$CH$_2$)-Hx$^c$ | single bond | S |
| 2-650 | H | 4-F-Bz | H | H | 3-(ONO$_2$CH$_2$)-Hx$^c$ | single bond | S |
| 2-651 | H | Ph | H | H | 3-(ONO$_2$CH$_2$)-Hx$^c$ | single bond | S |
| 2-652 | H | 2-Then | H | H | 3-(ONO$_2$CH$_2$)-Hx$^c$ | single bond | S |
| 2-653 | H | 3-Then | H | H | 3-(ONO$_2$CH$_2$)-Hx$^c$ | single bond | S |
| 2-654 | H | 2-Fur | H | H | 3-(ONO$_2$CH$_2$)-Hx$^c$ | single bond | S |
| 2-655 | H | 3-Fur | H | H | 3-(ONO$_2$CH$_2$)-Hx$^c$ | single bond | S |
| 2-656 | H | 3-Pyr | H | H | 3-(ONO$_2$CH$_2$)-Hx$^c$ | single bond | S |
| 2-657 | H | H | H | H | 3-(ONO$_2$CH$_2$)-Hx$^c$ | CH$_2$ | S |
| 2-658 | H | Me | H | H | 3-(ONO$_2$CH$_2$)-Hx$^c$ | CH$_2$ | S |
| 2-659 | H | Bz | H | H | 3-(ONO$_2$CH$_2$)-Hx$^c$ | CH$_2$ | S |
| 2-660 | H | 4-Me-Bz | H | H | 3-(ONO$_2$CH$_2$)-Hx$^c$ | CH$_2$ | S |
| 2-661 | H | 4-MeO-Bz | H | H | 3-(ONO$_2$)-Hx$^c$ | CH$_2$ | S |
| 2-662 | H | 4-F-Bz | H | H | 3-(ONO$_2$)-Hx$^c$ | CH$_2$ | S |
| 2-663 | H | Ph | H | H | 3-(ONO$_2$)-Hx$^c$ | CH$_2$ | S |
| 2-664 | H | 2-Then | H | H | 3-(ONO$_2$)-Hx$^c$ | CH$_2$ | S |
| 2-665 | H | 3-Then | H | H | 3-(ONO$_2$)-Hx$^c$ | CH$_2$ | S |
| 2-666 | H | 2-Fur | H | H | 3-(ONO$_2$)-Hx$^c$ | CH$_2$ | S |
| 2-667 | H | 3-Fur | H | H | 3-(ONO$_2$)-Hx$^c$ | CH$_2$ | S |
| 2-668 | H | 3-Pyr | H | H | 3-(ONO$_2$)-Hx$^c$ | CH$_2$ | S |
| 2-669 | H | H | H | H | 3-(ONO$_2$CH$_2$)-Hx$^c$ | single bond | S |
| 2-670 | H | Me | H | H | 3-(ONO$_2$CH$_2$)-Hx$^c$ | single bond | S |
| 2-671 | H | Bz | H | H | 3-(ONO$_2$CH$_2$)-Hx$^c$ | single bond | S |
| 2-672 | H | 4-Me-Bz | H | H | 3-(ONO$_2$CH$_2$)-Hx$^c$ | single bond | S |
| 2-673 | H | 4-MeO-Bz | H | H | 3-(ONO$_2$CH$_2$)-Hx$^c$ | single bond | S |
| 2-674 | H | 4-F-Bz | H | H | 3-(ONO$_2$CH$_2$)-Hx$^c$ | single bond | S |
| 2-675 | H | Ph | H | H | 3-(ONO$_2$CH$_2$)-Hx$^c$ | single bond | S |
| 2-676 | H | 2-Then | H | H | 3-(ONO$_2$CH$_2$)-Hx$^c$ | single bond | S |
| 2-677 | H | 3-Then | H | H | 3-(ONO$_2$CH$_2$)-Hx$^c$ | single borid | S |
| 2-678 | H | 2-Fur | H | H | 3-(ONO$_2$CH$_2$)-Hx$^c$ | single bond | S |
| 2-679 | H | 3-Fur | H | H | 3-(ONO$_2$CH$_2$)-Hx$^c$ | single bond | S |
| 2-680 | H | 3-Pyr | H | H | 3-(ONO$_2$CH$_2$)-Hx$^c$ | single bond | S |
| 2-681 | H | H | H | H | 3-(ONO$_2$CH$_2$)-Hx$^c$ | CH$_2$ | S |
| 2-682 | H | Me | H | H | 3-(ONO$_2$CH$_2$)-Hx$^c$ | CH$_2$ | S |
| 2-683 | H | Bz | H | H | 3-(ONO$_2$CH$_2$)-Hx$^c$ | CH$_2$ | S |
| 2-684 | H | 4-Me-Bz | H | H | 3-(ONO$_2$CH$_2$)-Hx$^c$ | CH$_2$ | S |
| 2-685 | H | 4-MeO-Bz | H | H | 3-(ONO$_2$CH$_2$)-Hx$^c$ | CH$_2$ | S |
| 2-686 | H | 4-F-Bz | H | H | 3-(ONO$_2$CH$_2$)-Hx$^c$ | CH$_2$ | S |
| 2-687 | H | Ph | H | H | 3-(ONO$_2$CH$_2$)-Hx$^c$ | CH$_2$ | S |
| 2-688 | H | 2-Then | H | H | 3-(ONO$_2$CH$_2$)-Hx$^c$ | CH$_2$ | S |

TABLE 2-continued

| Compd. No. | R¹ | R² | R³ | R⁴ | R⁵ | A | X¹ |
|---|---|---|---|---|---|---|---|
| 2-689 | H | 3-Then | H | H | 3-(ONO$_2$CH$_2$)-Hx$^c$ | CH$_2$ | S |
| 2-690 | H | 2-Fur | H | H | 3-(ONO$_2$CH$_2$)-Hx$^c$ | CH$_2$ | S |
| 2-691 | H | 3-Fur | H | H | 3-(ONO$_2$CH$_2$)-Hx$^c$ | CH$_2$ | S |
| 2-692 | H | 3-Pyr | H | H | 3-(ONO$_2$CH$_2$)-Hx$^c$ | CH$_2$ | S |
| 2-693 | H | H | H | H | 2-(ONO$_2$)-Pn$^c$ | single bond | O |
| 2-694 | H | Me | H | H | 2-(ONO$_2$)-Pn$^c$ | single bond | O |
| 2-695 | H | Bz | H | H | 2-(ONO$_2$)-Pn$^c$ | single bond | O |
| 2-696 | H | 4-Me-Bz | H | H | 2-(ONO$_2$)-Pn$^c$ | single bond | O |
| 2-697 | H | 4-MeO-Bz | H | H | 2-(ONO$_2$)-Pn$^c$ | single bond | O |
| 2-698 | H | 4-F-Bz | H | H | 2-(ONO$_2$)-Pn$^c$ | single bond | O |
| 2-699 | H | Ph | H | H | 2-(ONO$_2$)-Pn$^c$ | single bond | O |
| 2-700 | H | 2-Then | H | H | 2-(ONO$_2$)-Pn$^c$ | single bond | O |
| 2-701 | H | 3-Then | H | H | 2-(ONO$_2$)-Pn$^c$ | single bond | O |
| 2-702 | H | --Fur | H | H | 2-(ONO$_2$)-Pn$^c$ | single bond | O |
| 2-703 | H | 3-Fur | H | H | 2-(ONO$_2$)-Pn$^c$ | single bond | O |
| 2-704 | H | 3-Pyr | H | H | 2-(ONO$_2$)-Pn$^c$ | single bond | O |
| 2-705 | H | H | H | H | 2-(ONO$_2$)-Pn$^c$ | CH$_2$ | O |
| 2-706 | H | Me | H | H | 2-(ONO$_2$)-Pn$^c$ | CH$_2$ | O |
| 2-707 | H | Bz | H | H | 2-(ONO$_2$)-Pn$^c$ | CH$_2$ | O |
| 2-708 | H | 4-Me-Bz | H | H | 2-(ONO$_2$)-Pn$^c$ | CH$_2$ | O |
| 2-709 | H | 4-MeO-Bz | H | H | 2-(ONO$_2$)-Pn$^c$ | CH$_2$ | O |
| 2-710 | H | 4-F-Bz | H | H | 2-(ONO$_2$)-Pn$^c$ | CH$_2$ | O |
| 2-711 | H | Ph | H | H | 2-(ONO$_2$)-Pn$^c$ | CH$_2$ | O |
| 2-712 | H | 2-Then | H | H | 2-(ONO$_2$)-Pn$^c$ | CH$_2$ | O |
| 2-713 | H | 3-Then | H | H | 2-(ONO$_2$)-Pn$^c$ | CH$_2$ | O |
| 2-714 | H | 2-Fur | H | H | 2-(ONO$_2$)-Pn$^c$ | CH$_2$ | O |
| 2-715 | H | 3-Fur | H | H | 2-(ONO$_2$)-Pn$^c$ | CH$_2$ | O |
| 2-716 | H | 3-Pyr | H | H | 2-(ONO$_2$)-Pn$^c$ | CH$_2$ | O |
| 2-717 | H | H | H | H | 2-(ONO$_2$CH$_2$)-Pn$^c$ | single bond | O |
| 2-718 | H | Me | H | H | 2-(ONO$_2$CH$_2$)-Pn$^c$ | single bond | O |
| 2-719 | H | Bz | H | H | 2-(ONO$_2$CH$_2$)-Pn$^c$ | single bond | O |
| 2-720 | H | 4-Me-Bz | H | H | 2-(ONO$_2$CH$_2$)-Pn$^c$ | single bond | O |
| 2-721 | H | 4-MeO-Bz | H | H | 2-(ONO$_2$CH$_2$)-Pn$^c$ | single bond | O |
| 2-722 | H | 4-F-Bz | H | H | 2-(ONO$_2$CH$_2$)-Pn$^c$ | single bbnd | O |
| 2-723 | H | Ph | H | H | 2-(ONO$_2$CH$_2$)-Pn$^c$ | single bond | O |
| 2-724 | H | 2-Then | H | H | 2-(ONO$_2$CH$_2$)-Pn$^c$ | single bond | O |
| 2-725 | H | 3-Then | H | H | 2-(ONO$_2$CH$_2$)-Pn$^c$ | single bond | O |
| 2-726 | H | 2-Fur | H | H | 2-(ONO$_2$CH$_2$)-Pn$^c$ | single bond | O |
| 2-727 | H | 3-Fur | H | H | 2-(ONO$_2$CH$_2$)-Pn$^c$ | single bond | O |
| 2-728 | H | 3-Pyr | H | H | 2-(ONO$_2$CH$_2$)-Pn$^c$ | single bond | O |
| 2-729 | H | H | H | H | 2-(ONO$_2$CH$_2$)-Pn$^c$ | CH$_2$ | O |
| 2-730 | H | Me | H | H | 2-(ONO$_2$CH$_2$)-Pn$^c$ | CH$_2$ | O |
| 2-731 | H | Bz | H | H | 2-(ONO$_2$CH$_2$)-Pn$^c$ | CH$_2$ | O |
| 2-732 | H | 4-Me-Bz | H | H | 2-(ONO$_2$CH$_2$)-Pn$^c$ | CH$_2$ | O |
| 2-733 | H | 4-MeO-Bz | H | H | 2-(ONO$_2$CH$_2$)-Pn$^c$ | CH$_2$ | O |
| 2-734 | H | 4-F-Bz | H | H | 2-(ONO$_2$CH$_2$)-Pn$^c$ | CH$_2$ | O |
| 2-735 | H | Ph | H | H | 2-(ONO$_2$CH$_2$)-Pn$^c$ | CH$_2$ | O |
| 2-736 | H | 2-Then | H | H | 2-(ONO$_2$CH$_2$)-Pn$^c$ | CH$_2$ | O |
| 2-737 | H | 3-Then | H | H | 2-(ONO$_2$CH$_2$)-Pn$^c$ | CH$_2$ | O |
| 2-738 | H | 2-Fur | H | H | 2-(ONO$_2$CH$_2$)-Pn$^c$ | CH$_2$ | O |
| 2-739 | H | 3-Fur | H | H | 2-(ONO$_2$CH$_2$)-Pn$^c$ | CH$_2$ | O |
| 2-740 | H | 3-Pyr | H | H | 2-(ONO$_2$CH$_2$)-Pn$^c$ | CH$_2$ | O |
| 2-741 | H | H | H | H | 3-(ONO$_2$)-Pn$^c$ | single bond | O |
| 2-742 | H | Me | H | H | 3-(ONO$_2$)-Pn$^c$ | single bond | O |
| 2-743 | H | Bz | H | H | 3-(ONO$_2$)-Pn$^c$ | single bond | O |
| 2-744 | H | 4-Me-Bz | H | H | 3-(ONO$_2$)-Pn$^c$ | single bond | O |
| 2-745 | H | 4-MeO-Bz | H | H | 3-(ONO$_2$)-Pn$^c$ | single bond | O |
| 2-746 | H | 4-F-Bz | H | H | 3-(ONO$_2$)-Pn$^c$ | single bond | O |
| 2-747 | H | Ph | H | H | 3-(ONO$_2$)-Pn$^c$ | single bond | O |
| 2-748 | H | 2-Then | H | H | 3-(ONO$_2$)-Pn$^c$ | single bond | O |
| 2-749 | H | 3-Then | H | H | 3-(ONO$_2$)-Pn$^c$ | single bond | O |
| 2-750 | H | 2-Fur | H | H | 3-(ONO$_2$)-Pn$^c$ | single bond | O |
| 2-751 | H | 3-Fur | H | H | 3-(ONO$_2$)-Pn$^c$ | single bond | O |
| 2-752 | H | 3-pyr | H | H | 3-(ONO$_2$)-Pn$^c$ | single bond | O |
| 2-753 | H | H | H | H | 3-(ONO$_2$)-Pn$^c$ | CH$_2$ | O |
| 2-754 | H | Me | H | H | 3-(ONO$_2$)-Pn$^c$ | CH$_2$ | O |
| 2-755 | H | Bz | H | H | 3-(ONO$_2$)-Pn$^c$ | CH$_2$ | O |
| 2-756 | H | 4-Me-Bz | H | H | 3-(ONO$_2$)-Pn$^c$ | CH$_2$ | O |
| 2-757 | H | 4-MeO-Bz | H | H | 3-(ONO$_2$)-Pn$^c$ | CH$_2$ | O |
| 2-758 | H | 4-F-Bz | H | H | 3-(ONO$_2$)-Pn$^c$ | CH$_2$ | O |
| 2-759 | H | Ph | H | H | 3-(ONO$_2$)-Pn$^c$ | CH$_2$ | O |
| 2-760 | H | 2-Then | H | H | 3-(ONO$_2$)-Pn$^c$ | CH$_2$ | O |
| 2-761 | H | 3-Then | H | H | 3-(ONO$_2$)-Pn$^c$ | CH$_2$ | O |
| 2-762 | H | 2-Fur | H | H | 3-(ONO$_2$)-Pn$^c$ | CH$_2$ | O |
| 2-763 | H | 3-Fur | H | H | 3-(ONO$_2$)-Pn$^c$ | CH$_2$ | O |
| 2-764 | H | 3-Pyr | H | H | 3-(ONO$_2$)-Pn$^c$ | CH$_2$ | O |

TABLE 2-continued

| Compd. No. | R¹ | R² | R³ | R⁴ | R⁵ | A | X¹ |
|---|---|---|---|---|---|---|---|
| 2-765 | H | H | H | H | 3-(ONO₂CH₂)-Pnᶜ | single bond | O |
| 2-766 | H | Me | H | H | 3-(ONO₂CH₂)-Pnᶜ | single bond | O |
| 2-767 | H | Bz | H | H | 3-(ONO₂CH₂)-Pnᶜ | single bond | O |
| 2-768 | H | 4-Me-Bz | H | H | 3-(ONO₂CH₂)-Pnᶜ | single bond | O |
| 2-769 | H | 4-MeO-Bz | H | H | 3-(ONO₂CH₂)-Pnᶜ | single bond | O |
| 2-770 | H | 4-F-Bz | H | H | 3-(ONO₂CH₂)-Pnᶜ | single bond | O |
| 2-771 | H | Ph | H | H | 3-(ONO₂CH₂)-Pnᶜ | single bond | O |
| 2-772 | H | 2-Then | H | H | 3-(ONO₂CH₂)-Pnᶜ | single bond | O |
| 2-773 | H | 3-Then | H | H | 3-(ONO₂CH₂)-Pnᶜ | single bond | O |
| 2-774 | H | 2-Fur | H | H | 3-(ONO₂CH₂)-Pnᶜ | single bond | O |
| 2-775 | H | 3-Fur | H | H | 3-(ONO₂CH₂)-Pnᶜ | single bond | O |
| 2-776 | H | 3-Pyr | H | H | 3-(ONO₂CH₂)-Pnᶜ | single bond | O |
| 2-777 | H | H | H | H | 3-(ONO₂CH₂)-Pnᶜ | CH₂ | O |
| 2-778 | H | Me | H | H | 3-(ONO₂CH₂)-Pnᶜ | CH₂ | O |
| 2-779 | H | Bz | H | H | 3-(ONO₂CH₂)-Pnᶜ | CH₂ | O |
| 2-780 | H | 4-Me-Bz | H | H | 3-(ONO₂CH₂)-Pnᶜ | CH₂ | O |
| 2-781 | H | 4-MeO-Bz | H | H | 3-(ONO₂CH₂)-Pnᶜ | CH₂ | O |
| 2-782 | H | 4-F-Bz | H | H | 3-(ONO₂CH₂)-Pnᶜ | CH₂ | O |
| 2-783 | H | Ph | H | H | 3-(ONO₂CH₂)-Pnᶜ | CH₂ | O |
| 2-784 | H | 2-Then | H | H | 3-(ONO₂CH₂)-Pnᶜ | CH₂ | O |
| 2-785 | H | 3-Then | H | H | 3-(ONO₂CH₂)-Pnᶜ | CH₂ | O |
| 2-786 | H | 2-Fur | H | H | 3-(ONO₂CH₂)-Pnᶜ | CH₂ | O |
| 2-787 | H | 3-Fur | H | H | 3-(ONO₂CH₂)-Pnᶜ | CH₂ | O |
| 2-788 | H | 3-Pyr | H | H | 3-(ONO₂CH₂)-Pnᶜ | CH₂ | O |
| 2-789 | H | H | H | H | 2-(ONO₂)-Hxᶜ | single bond | O |
| 2-790 | H | Me | H | H | 2-(ONO₂)-Hxᶜ | single bond | O |
| 2-791 | H | Bz | H | H | 2-(ONO₂)-Hxᶜ | single bond | O |
| 2-792 | H | 4-Me-Bz | H | H | 2-(ONO₂)-Hxᶜ | single bond | O |
| 2-793 | H | 4-MeO-Bz | H | H | 2-(ONO₂)-Hxᶜ | single bond | O |
| 2-794 | H | 4-F-Bz | H | H | 2-(ONO₂)-Hxᶜ | single bond | O |
| 2-795 | H | Ph | H | H | 2-(ONO₂)-Hxᶜ | single bond | O |
| 2-796 | H | 2-Then | H | H | 2-(ONO₂)-Hxᶜ | single bond | O |
| 2-797 | H | 3-Then | H | H | 2-(ONO₂)-Hxᶜ | single bond | O |
| 2-798 | H | 2-Fur | H | H | 2-(ONO₂)-Hxᶜ | single bond | O |
| 2-799 | H | 3-Fur | H | H | 2-(ONO₂)-Hxᶜ | single bond | O |
| 2-800 | H | 3-Pyr | H | H | 2-(ONO₂)-Hxᶜ | single bond | O |
| 2-801 | H | H | H | H | 2-(ONO₂)-Hxᶜ | CH₂ | O |
| 2-802 | H | Me | H | H | 2-(ONO₂)-Hxᶜ | CH₂ | O |
| 2-803 | H | Bz | H | H | 2-(ONO₂)-Hxᶜ | CH₂ | O |
| 2-804 | H | 4-Me-Bz | H | H | 2-(ONO₂)-Hxᶜ | CH₂ | O |
| 2-805 | H | 4-MeO-Bz | H | H | 2-(ONO₂)-Hxᶜ | CH₂ | O |
| 2-806 | H | 4-F-Bz | H | H | 2-(ONO₂)-Hxᶜ | CH₂ | O |
| 2-807 | H | Ph | H | H | 2-(ONO₂)-Hxᶜ | CH₂ | O |
| 2-808 | H | 2-Then | H | H | 2-(ONO₂)-Hxᶜ | CH₂ | O |
| 2-809 | H | 3-Then | H | H | 2-(ONO₂)-Hxᶜ | CH₂ | O |
| 2-810 | H | 2-Fur | H | H | 2-(ONO₂)-Hxᶜ | CH₂ | O |
| 2-811 | H | 3-Fur | H | H | 2-(ONO₂)-Hxᶜ | CH₂ | O |
| 2-812 | H | 3-Pyr | H | H | 2-(ONO₂)-Hxᶜ | CH₂ | O |
| 2-813 | H | H | H | H | 2-(ONO₂CH₂)-Hxᶜ | single bond | O |
| 2-814 | H | Me | H | H | 2-(ONO₂CH₂)-Hxᶜ | single bond | O |
| 2-815 | H | Bz | H | H | 2-(ONO₂CH₂)-Hxᶜ | single bond | O |
| 2-816 | H | 4-Me-Bz | H | H | 2-(ONO₂CH₂)-Hxᶜ | single bond | O |
| 2-817 | H | 4-MeO-Bz | H | H | 2-(ONO₂CH₂)-Hxᶜ | single bond | O |
| 2-818 | H | 4-F-Bz | H | H | 2-(ONO₂CH₂)-Hxᶜ | single bond | O |
| 2-819 | H | Ph | H | H | 2-(ONO₂CH₂)-Hxᶜ | single bond | O |
| 2-820 | H | 2-Then | H | H | 2-(ONO₂CH₂)-Hxᶜ | single bond | O |
| 2-821 | H | 3-Then | H | H | 2-(ONO₂CH₂)-Hxᶜ | single bond | O |
| 2-822 | H | 2-Fur | H | H | 2-(ONO₂CH₂)-Hxᶜ | single bond | O |
| 2-823 | H | 3-Fur | H | H | 2-(ONO₂CH₂)-Hxᶜ | single bond | O |
| 2-824 | H | 3-Pyr | H | H | 2-(ONO₂CH₂)-Hxᶜ | single bond | O |
| 2-825 | H | H | H | H | 2-(ONO₂CH₂)-Hxᶜ | CH₂ | O |
| 2-826 | H | Me | H | H | 2-(ONO₂CH₂)-Hxᶜ | CH₂ | O |
| 2-827 | H | Bz | H | H | 2-(ONO₂CH₂)-Hxᶜ | CH₂ | O |
| 2-828 | H | 4-Me-Bz | H | H | 2-(ONO₂CH₂)-Hxᶜ | CH₂ | O |
| 2-829 | H | 4-MeO-Bz | H | H | 2-(ONO₂CH₂)-Hxᶜ | CH₂ | O |
| 2-830 | H | 4-F-Bz | H | H | 2-(ONO₂CH₂)-Hxᶜ | CH₂ | O |
| 2-831 | H | Ph | H | H | 2-(ONO₂CH₂)-Hxᶜ | CH₂ | O |
| 2-832 | H | 2-Then | H | H | 2-(ONO₂CH₂)-Hxᶜ | CH₂ | O |
| 2-833 | H | 3-Then | H | H | 2-(ONO₂CH₂)-Hxᶜ | CH₂ | O |
| 2-834 | H | 2-Fur | H | H | 2-(ONO₂CH₂)-Hxᶜ | CH₂ | O |
| 2-835 | H | 3-Fur | H | H | 2-(ONO₂CH₂)-Hxᶜ | CH₂ | O |
| 2-836 | H | 3-Pyr | H | H | 2-(ONO₂CH₂)-Hxᶜ | CH₂ | O |
| 2-837 | H | H | H | H | 3-(ONO₂)-Hxᶜ | single bond | O |
| 2-838 | H | Me | H | H | 3-(ONO₂)-Hxᶜ | single bond | O |
| 2-839 | H | Bz | H | H | 3-(ONO₂)-Hxᶜ | single bond | O |
| 2-840 | H | 4-Me-Bz | H | H | 3-(ONO₂)-Hxᶜ | single bond | O |

TABLE 2-continued

| Compd. No. | R¹ | R² | R³ | R⁴ | R⁵ | A | X¹ |
|---|---|---|---|---|---|---|---|
| 2-841 | H | 4-MeO-Bz | H | H | 3-(ONO$_2$)-Hx$^c$ | single bond | O |
| 2-842 | H | 4-F-Bz | H | H | 3-(ONO$_2$)-Hx$^c$ | single bond | O |
| 2-843 | H | Ph | H | H | 3-(ONO$_2$)-Hx$^c$ | single bond | O |
| 2-844 | H | 2-Then | H | H | 3-(ONO$_2$)-Hx$^c$ | single bond | O |
| 2-845 | H | 3-Then | H | H | 3-(ONO$_2$)-Hx$^c$ | single bond | O |
| 2-846 | H | 2-Fur | H | H | 3-(ONO$_2$)-Hx$^c$ | single bond | O |
| 2-847 | H | 3-Fur | H | H | 3-(ONO$_2$)-Hx$^c$ | single bond | O |
| 2-848 | H | 3-Pyr | H | H | 3-(ONO$_2$)-Hx$^c$ | single bond | O |
| 2-849 | H | H | H | H | 3-(ONO$_2$)-Hx$^c$ | CH$_2$ | O |
| 2-850 | H | Me | H | H | 3-(ONO$_2$)-Hx$^c$ | CH$_2$ | O |
| 2-851 | H | Bz | H | H | 3-(ONO$_2$)-Hx$^c$ | CH$_2$ | O |
| 2-852 | H | 4-Me-Bz | H | H | 3-(ONO$_2$)-Hx$^c$ | CH$_2$ | O |
| 2-853 | H | 4-MeO-Bz | H | H | 3-(ONO$_2$)-Hx$^c$ | CH$_2$ | O |
| 2-854 | H | 4-F-Bz | H | H | 3-(ONO$_2$)-Hx$^c$ | CH$_2$ | O |
| 2-855 | H | Ph | H | H | 3-(ONO$_2$)-Hx$^c$ | CH$_2$ | O |
| 2-856 | H | 2-Then | H | H | 3-(ONO$_2$)-Hx$^c$ | CH$_2$ | O |
| 2-857 | H | 3-Then | H | H | 3-(ONO$_2$)-Hx$^c$ | CH$_2$ | O |
| 2-858 | H | 2-Fur | H | H | 3-(ONO$_2$)-Hx$^c$ | CH$_2$ | O |
| 2-859 | H | 3-Fur | H | H | 3-(ONO$_2$)-Hx$^c$ | CH$_2$ | O |
| 2-860 | H | 3-Pyr | H | H | 3-(ONO$_2$)-Hx$^c$ | CH$_2$ | O |
| 2-861 | H | H | H | H | 3-(ONO$_2$CH$_2$)-Hx$^c$ | single bond | O |
| 2-862 | H | Me | H | H | 3-(ONO$_2$CH$_2$)-Hx$^c$ | single bond | O |
| 2-863 | H | Bz | H | H | 3-(ONO$_2$CH$_2$)-Hx$^c$ | single bond | O |
| 2-864 | H | 4-Me-Bz | H | H | 3-(ONO$_2$CH$_2$)-Hx$^c$ | single bond | O |
| 2-865 | H | 4-MeO-Bz | H | H | 3-(ONO$_2$CH$_2$)-Hx$^c$ | single bond | O |
| 2-866 | H | 4-F-Bz | H | H | 3-(ONO$_2$CH$_2$)-Hx$^c$ | single bond | O |
| 2-867 | H | Ph | H | H | 3-(ONO$_2$CH$_2$)-Hx$^c$ | single bond | O |
| 2-868 | H | 2-Then | H | H | 3-(ONO$_2$CH$_2$)-Hx$^c$ | single bond | O |
| 2-869 | W | 3-Then | H | H | 3-(ONO$_2$CH$_2$)-Hx$^c$ | single bond | O |
| 2-870 | H | 2-Fur | H | H | 3-(ONO$_2$CH$_2$)-Hx$^c$ | single bond | O |
| 2-871 | H | 3-Fur | H | H | 3-(ONO$_2$CH$_2$)-Hx$^c$ | single bond | O |
| 2-872 | H | 3-Pyr | H | H | 3-(ONO$_2$CH$_2$)-Hx$^c$ | single bond | O |
| 2-873 | H | H | H | H | 3-(ONO$_2$CH$_2$)-Hx$^c$ | CH$_2$ | O |
| 2-874 | H | Me | H | H | 3-(ONO$_2$CH$_2$)-Hx$^c$ | CH$_2$ | O |
| 2-875 | H | Bz | H | H | 3-(ONO$_2$CH$_2$)-Hx$^c$ | CH$_2$ | O |
| 2-876 | H | 4-Me-Bz | H | H | 3-(ONO$_2$CH$_2$)-Hx$^c$ | CH$_2$ | O |
| 2-877 | H | 4-MeO-Bz | H | H | 3-(ONO$_2$CH$_2$)-Hx$^c$ | CH$_2$ | O |
| 2-878 | H | 4-F-Bz | H | H | 3-(ONO$_2$CH$_2$)-Hx$^c$ | CH$_2$ | O |
| 2-879 | H | Ph | H | H | 3-(ONO$_2$CH$_2$)-Hx$^c$ | CH$_2$ | O |
| 2-880 | H | 2-Then | H | H | 3-(ONO$_2$CH$_2$)-Hx$^c$ | CH$_2$ | O |
| 2-881 | H | 3-Then | H | H | 3-(ONO$_2$CH$_2$)-Hx$^c$ | CH$_2$ | O |
| 2-882 | H | 2-Fur | H | H | 3-(ONO$_2$CH$_2$)-Hx$^c$ | CH$_2$ | O |
| 2-883 | H | 3-Fur | H | H | 3-(ONO$_2$CH$_2$)-Hx$^c$ | CH$_2$ | O |
| 2-884 | H | 3-Pyr | H | H | 3-(ONO$_2$CH$_2$)-Hx$^c$ | CH$_2$ | O |
| 2-885 | H | H | H | H | 2-[ONO$_2$(CH$_2$)$_3$]-Hx$^c$ | single bond | S |
| 2-886 | H | Me | H | H | 2-[ONO$_2$(CH$_2$)$_3$]-Hx$^c$ | single bond | S |
| 2-887 | H | Bz | H | H | 2-[ONO$_2$(CH$_2$)$_3$]-Hx$^c$ | single bond | S |
| 2-888 | H | H | H | H | 2-[ONO$_2$(CH$_2$)$_3$]-Hx$^c$ | CH$_2$ | S |
| 2-889 | H | Me | H | H | 2-[ONO$_2$(CH$_2$)$_3$]-Hx$^c$ | CH$_2$ | S |
| 2-890 | H | Bz | H | H | 2-[ONO$_2$(CH$_2$)$_3$]-Hx$^c$ | CH$_2$ | S |
| 2-891 | H | H | H | H | 3-[ONO$_2$(CH$_2$)$_3$]-Hx$^c$ | single bond | S |
| 2-892 | H | Me | H | H | 3-[ONO$_2$(CH$_2$)$_3$]-Hx$^c$ | single bond | S |
| 2-893 | H | Bz | H | H | 3-[ONO$_2$(CH$_2$)$_3$]-Hx$^c$ | single bond | S |
| 2-894 | H | H | H | H | 3-[ONO$_2$(CH$_2$)$_3$]-Hx$^c$ | CH$_2$ | S |
| 2-895 | H | Me | H | H | 3-[ONO$_2$(CH$_2$)$_3$]-Hx$^c$ | CH$_2$ | S |
| 2-896 | H | Bz | H | H | 3-[ONO$_2$(CH$_2$)$_3$]-Hx$^c$ | CH$_2$ | S |
| 2-897 | H | H | H | H | 4-[ONO$_2$(CH$_2$)$_3$]-Hx$^c$ | single bond | S |
| 2-898 | H | Me | H | H | 4-[ONO$_2$(CH$_2$)$_3$]-Hx$^c$ | single bond | S |
| 2-899 | H | Bz | H | H | 4-[ONO$_2$(CH$_2$)$_3$]-Hx$^c$ | single bond | S |
| 2-900 | H | H | H | H | 4-[ONO$_2$(CH$_2$)$_3$]-Hx$^c$ | CH$_2$ | S |
| 2-901 | H | Me | H | H | 4-[ONO$_2$(CH$_2$)$_3$]-Hx$^c$ | CH$_2$ | S |
| 2-902 | H | Bz | H | H | 4-[ONO$_2$(CH$_2$)$_3$]-Hx$^c$ | CH$_2$ | S |
| 2-903 | H | H | H | H | 2-[ONO$_2$(CH$_2$)$_3$]-Pn$^c$ | single bond | S |
| 2-904 | H | Me | H | H | 2-[ONO$_2$(CH$_2$)$_3$]-Pn$^c$ | single bond | S |
| 2-905 | H | Bz | H | H | 2-[ONO$_2$(CH$_2$)$_3$]-Pn$^c$ | single bond | S |
| 2-906 | H | H | H | H | 2-[ONO$_2$(CH$_2$)$_3$]-Pn$^c$ | CH$_2$ | S |
| 2-907 | H | Me | H | H | 2-[ONO$_2$(CH$_2$)$_3$]-Pn$^c$ | CH$_2$ | S |
| 2-908 | H | Bz | H | H | 2-[ONO$_2$(CH$_2$)$_3$]-Pn$^c$ | CH$_2$ | S |
| 2-909 | H | H | H | H | 3-[ONO$_2$(CH$_2$)$_3$]-Pn$^c$ | single bond | S |
| 2-910 | H | Me | H | H | 3-[ONO$_2$(CH$_2$)$_3$]-Pn$^c$ | single bond | S |
| 2-911 | H | Bz | H | H | 3-[ONO$_2$(CH$_2$)$_3$]-Pn$^c$ | single bond | S |
| 2-912 | H | H | H | H | 3-[ONO$_2$(CH$_2$)$_3$]-Pn$^c$ | CH$_2$ | S |
| 2-913 | H | Me | H | H | 3-[ONO$_2$(CH$_2$)$_3$]-Pn$^c$ | CH$_2$ | S |
| 2-914 | H | Bz | H | H | 3-[ONO$_2$(CH$_2$)$_3$]-Pn$^c$ | CH$_2$ | S |
| 2-915 | H | H | H | H | 2-(ONO$_2$CH$_2$]-Bu$^c$ | single bond | S |
| 2-916 | H | Me | H | H | 2-(ONO$_2$CH$_2$]-Bu$^c$ | single bond | S |

TABLE 2-continued

| Compd. No. | R$^1$ | R$^2$ | R$^3$ | R$^4$ | R$^5$ | A | X$^1$ |
|---|---|---|---|---|---|---|---|
| 2-917 | H | Bz | H | H | 2-(ONO$_2$CH$_2$]-Bu$^c$ | single bond | S |
| 2-918 | H | H | H | H | 2-(ONO$_2$CH$_2$]-Bu$^c$ | CH$_2$ | S |
| 2-919 | H | Me | H | H | 2-(ONO$_2$CH$_2$]-Bu$^c$ | CH$_2$ | S |
| 2-920 | H | Bz | H | H | 2-(ONO$_2$CH$_2$]-Bu$^c$ | CH$_2$ | S |
| 2-921 | H | H | H | H | 3-(ONO$_2$CH$_2$]-Bu$^c$ | single bond | S |
| 2-922 | H | Me | H | H | 3-(ONO$_2$CH$_2$]-Bu$^c$ | single bond | S |
| 2-923 | H | Bz | H | H | 3-(ONO$_2$CH$_2$]-Bu$^c$ | single bond | S |
| 2-924 | H | H | H | H | 3-(ONO$_2$CH$_2$]-Bu$^c$ | CH$_2$ | S |
| 2-925 | H | Me | H | H | 3-(ONO$_2$CH$_2$]-Bu$^c$ | CH$_2$ | S |
| 2-926 | H | Bz | H | H | 3-(ONO$_2$CH$_2$]-Bu$^c$ | CH$_2$ | S |
| 2-927 | H | H | H | H | 2-(ONO$_2$CH$_2$]-Pr$^c$ | single bond | S |
| 2-928 | H | Me | H | H | 2-(ONO$_2$CH$_2$]-Pr$^c$ | single bond | S |
| 2-929 | H | Bz | H | H | 2-(ONO$_2$CH$_2$]-Pr$^c$ | single bond | S |
| 2-930 | H | H | H | H | 2-(ONO$_2$CH$_2$]-Pr$^c$ | CH$_2$ | S |
| 2-931 | H | Me | H | H | 2-(ONO$_2$CH$_2$]-Pr$^c$ | CH$_2$ | S |
| 2-932 | H | Bz | H | H | 2-(ONO$_2$CH$_2$]-Pr$^c$ | CH$_2$ | S |
| 2-933 | H | H | H | H | 2-(ONO$_2$CH$_2$)-Pn$^c$ | (CH$_2$)$_2$ | S |
| 2-934 | H | Me | H | H | 2-(ONO$_2$CH$_2$)-Pn$^c$ | (CH$_2$)$_2$ | S |
| 2-935 | H | Bz | H | H | 2-(ONO$_2$CH$_2$)-Pn$^c$ | (CH$_2$)$_2$ | S |
| 2-936 | H | 4-Me-Bz | H | H | 2-(ONO$_2$CH$_2$)-Pn$^c$ | (CH$_2$)$_2$ | S |
| 2-937 | H | 4-MeO-Bz | H | H | 2-(ONO$_2$CH$_2$)-Pn$^c$ | (CH$_2$)$_2$ | S |
| 2-938 | H | Ph | H | H | 2-(ONO$_2$CH$_2$)-Pn$^c$ | (CH$_2$)$_2$ | S |
| 2-939 | H | 2-Then | H | H | 2-(ONO$_2$CH$_2$)-Pn$^c$ | (CH$_2$)$_2$ | S |
| 2-940 | H | 2-Fur | H | H | 2-(ONO$_2$CH$_2$)-Pn$^c$ | (CH$_2$)$_2$ | S |
| 2-941 | H | 3-Pyr | H | H | 2-(ONO$_2$CH$_2$)-Pn$^c$ | (CH$_2$)$_2$ | S |
| 2-942 | H | H | H | H | 3-(ONO$_2$CH$_2$)-Pn$^c$ | (CH$_2$)$_2$ | S |
| 2-943 | H | Me | H | H | 3-(ONO$_2$CH$_2$)-Pn$^c$ | (CH$_2$)$_2$ | S |
| 2-944 | H | Bz | H | H | 3-(ONO$_2$CH$_2$)-Pn$^c$ | (CH$_2$)$_2$ | S |
| 2-945 | H | 4-Me-Bz | H | H | 3-(ONO$_2$CH$_2$)-Pn$^c$ | (CH$_2$)$_2$ | S |
| 2-946 | H | 4-MeO-Bz | H | H | 3-(ONO$_2$CH$_2$)-Pn$^c$ | (CH$_2$)$_2$ | S |
| 2-947 | H | Ph | H | H | 3-(ONO$_2$CH$_2$)-Pn$^c$ | (CH$_2$)2 | S |
| 2-948 | H | 2-Then | H | H | 3-(ONO$_2$CH$_2$)-Pn$^c$ | (CH$_2$)$_2$ | S |
| 2-949 | H | 2-Fur | H | H | 3-(ONO$_2$CH$_2$)-Pn$^c$ | (CH$_2$)$_2$ | S |
| 2-950 | H | 3-Pyr | H | H | 3-(ONO$_2$CH$_2$)-Pn$^c$ | (CH$_2$)$_2$ | S |
| 2-951 | H | H | H | H | 2-[ONO$_2$(CH$_2$)$_2$]-Pn$^c$ | (CH$_2$)$_2$ | S |
| 2-952 | H | Me | H | H | 2-[ONO$_2$(CH$_2$)$_2$]-Pn$^c$ | (CH$_2$)$_2$ | S |
| 2-953 | H | Bz | H | H | 2-[ONO$_2$(CH$_2$)$_2$]-Pn$^c$ | (CH$_2$)$_2$ | S |
| 2-954 | H | H | H | H | 3-[ONO$_2$(CH$_2$)$_2$]-Pn$^c$ | (CH$_2$)$_2$ | S |
| 2-955 | H | Me | H | H | 3-[ONO$_2$(CH$_2$)$_2$]-Pn$^c$ | (CH$_2$)$_2$ | S |
| 2-956 | H | Bz | H | H | 3-[ONO$_2$(CH$_2$)$_2$]-Pn$^c$ | (CH$_2$)$_2$ | S |
| 2-957 | H | H | H | H | 2-[ONO$_2$(CH$_2$)$_3$]-Pn$^c$ | (CH$_2$)$_2$ | S |
| 2-958 | H | Me | H | H | 2-[ONO$_2$(CH$_2$)$_3$]-Pn$^c$ | (CH$_2$)$_2$ | S |
| 2-959 | H | Bz | H | H | 2-[ONO$_2$(CH$_2$)$_3$]-Pn$^c$ | (CH$_2$)$_2$ | S |
| 2-960 | H | H | H | H | 3-[ONO$_2$(CH$_2$)$_3$]-Pn$^c$ | (CH$_2$)$_2$ | S |
| 2-961 | H | Me | H | H | 3-[ONO$_2$(CH$_2$)$_3$]-Pn$^c$ | (CH$_2$)$_2$ | S |
| 2-962 | H | Bz | H | H | 3-[ONO$_2$(CH$_2$)$_3$]-Pn$^c$ | (CH$_2$)$_2$ | S |
| 2-963 | H | H | H | H | 2-[ONO$_2$(CH$_2$)$_4$]-Pn$^c$ | (CH$_2$)$_2$ | S |
| 2-964 | H | Me | H | H | 2-[ONO$_2$(CH$_2$)$_4$]-Pn$^c$ | (CH$_2$)$_2$ | S |
| 2-965 | H | Bz | H | H | 2-[ONO$_2$(CH$_2$)$_4$]-Pn$^c$ | (CH$_2$)$_2$ | S |
| 2-966 | H | H | H | H | 3-[ONO$_2$(CH$_2$)$_4$]-Pn$^c$ | (CH$_2$)$_2$ | S |
| 2-967 | H | Me | H | H | 3-[ONO$_2$(CH$_2$)$_4$]-Pn$^c$ | (CH$_2$)$_2$ | S |
| 2-968 | H | Bz | H | H | 3-[ONO$_2$(CH$_2$)$_4$]-Pn$^c$ | (CH$_2$)$_2$ | S |
| 2-969 | H | H | H | H | 2-(ONO$_2$CH$_2$)-Pn$^c$ | (CH$_2$)$_3$ | S |
| 2-970 | H | Me | H | H | 2-(ONO$_2$CH$_2$)-Pn$^c$ | (CH$_2$)$_3$ | S |
| 2-971 | H | Bz | H | H | 2-(ONO$_2$CH$_2$)-Pn$^c$ | (CH$_2$)$_3$ | S |
| 2-972 | H | H | H | H | 3-(ONO$_2$CH$_2$)-Pn$^c$ | (CH$_2$)$_3$ | S |
| 2-973 | H | Me | H | H | 3-(ONO$_2$CH$_2$)-Pn$^c$ | (CH$_2$)$_3$ | S |
| 2-974 | H | Bz | H | H | 3-(ONO$_2$CH$_2$)-Pn$^c$ | (CH$_2$)$_3$ | S |
| 2-975 | H | H | H | H | 2-[ONO$_2$(CH$_2$)$_2$]-Pn$^c$ | (CH$_2$)$_3$ | S |
| 2-976 | H | H | H | H | 3-[ONO$_2$(CH$_2$)$_2$]-Pn$^c$ | (CH$_2$)$_3$ | S |
| 2-977 | H | H | H | H | 2-[ONO$_2$(CH$_2$)$_3$]-Pn$^c$ | (CH$_2$)$_3$ | S |
| 2-978 | H | H | H | H | 3-[ONO$_2$(CH$_2$)$_3$]-Pn$^c$ | (CH$_2$)$_3$ | S |
| 2-979 | H | H | H | H | 2-[ONO$_2$(CH$_2$)$_4$]-Pn$^c$ | (CH$_2$)$_3$ | S |
| 2-980 | H | H | H | H | 3-[ONO$_2$(CH$_2$)$_4$]-Pn$^c$ | (CH$_2$)$_3$ | S |
| 2-981 | H | H | H | H | 2-(ONO$_2$CH$_2$)-Pn$^c$ | (CH$_2$)$_2$ | O |
| 2-982 | H | Me | H | H | 2-(ONO$_2$CH$_2$)-Pn$^c$ | (CH$_2$)$_2$ | O |
| 2-983 | H | Bz | H | H | 2-(ONO$_2$CH$_2$)-Pn$^c$ | (CH$_2$)$_2$ | O |
| 2-984 | H | 4-Me-Bz | H | H | 2-(ONO$_2$CH$_2$)-Pn$^c$ | (CH$_2$)$_2$ | O |
| 2-985 | H | 4-MeO-Bz | H | H | 2-(ONO$_2$CH$_2$)-Pn$^c$ | (CH$_2$)$_2$ | O |
| 2-986 | H | Ph | H | H | 2-(ONO$_2$CH$_2$)-Pn$^c$ | (CH$_2$)$_2$ | O |
| 2-987 | H | 2-Then | H | H | 2-(ONO$_2$CH$_2$)-Pn$^c$ | (CH$_2$)$_2$ | O |
| 2-988 | H | 2-Fur | H | H | 2-(ONO$_2$CH$_2$)-Pn$^c$ | (CH$_2$)$_2$ | O |
| 2-989 | H | 3-Pyr | H | H | 2-(ONO$_2$CH$_2$)-Pn$^c$ | (CH$_2$)$_2$ | O |
| 2-990 | H | H | H | H | 3-(ONO$_2$CH$_2$)-Pn$^c$ | (CH$_2$)$_2$ | O |
| 2-991 | H | Me | H | H | 3-(ONO$_2$CH$_2$)-Pn$^c$ | (CH$_2$)$_2$ | O |
| 2-992 | H | Bz | H | H | 3-(ONO$_2$CH$_2$)-Pn$^c$ | (CH$_2$)$_2$ | O |

TABLE 2-continued

| Compd. No. | R¹ | R² | R³ | R⁴ | R⁵ | A | X¹ |
|---|---|---|---|---|---|---|---|
| 2-993 | H | 4-Me-Bz | H | H | 3-(ONO$_2$CH$_2$)-Pn$^c$ | (CH$_2$)$_2$ | O |
| 2-994 | H | 4-MeO-Bz | H | H | 3-(ONO$_2$CH$_2$)-Pn$^c$ | (CH$_2$)$_2$ | O |
| 2-995 | H | Ph | H | H | 3-(ONO$_2$CH$_2$)-Pn$^c$ | (CH$_2$)$_2$ | O |
| 2-996 | H | 2-Then | H | H | 3-(ONO$_2$CH$_2$)-Pn$^c$ | (CH$_2$)$_2$ | O |
| 2-997 | H | 2-Fur | H | H | 3-(ONO$_2$CH$_2$) Pn$^c$ | (CH$_2$)$_2$ | O |
| 2-998 | H | 3-Pyr | H | H | 3-(ONO$_2$CH$_2$)-Pn$^c$ | (CH$_2$)$_2$ | O |
| 2-999 | H | H | H | H | 2-[ONO$_2$(CH$_2$)$_2$]-Pn$^c$ | (CH$_2$)$_2$ | O |
| 2-1000 | H | Me | H | H | 2-[ONO$_2$(CH$_2$)$_2$]-Pn$^c$ | (CH$_2$)$_2$ | O |
| 2-1001 | H | Bz | H | H | 2-[ONO$_2$(CH$_2$)$_2$]-Pn$^c$ | (CH$_2$)$_2$ | O |
| 2-1002 | H | H | H | H | 3-[ONO$_2$(CH$_2$)$_2$]-Pn$^c$ | (CH$_2$)$_2$ | O |
| 2-1003 | H | Me | H | H | 3-[ONO$_2$(CH$_2$)$_2$]-Pn$^c$ | (CH$_2$)$_2$ | O |
| 2-1004 | H | Bz | H | H | 3-[ONO$_2$(CH$_2$)$_2$]-Pn$^c$ | (CH$_2$)$_2$ | O |
| 2-1005 | H | H | H | H | 2-[ONO$_2$(CH$_2$)$_3$]-Pn$^c$ | (CH$_2$)$_2$ | O |
| 2-1006 | H | Me | H | H | 2-[ONO$_2$(CH$_2$)$_3$]-Pn$^c$ | (CH$_2$)$_2$ | O |
| 2-1007 | H | Bz | H | H | 2-[ONO$_2$(CH$_2$)$_3$]-Pn$^c$ | (CH$_2$)$_2$ | O |
| 2-1008 | H | H | H | H | 3-[ONO$_2$(CH$_2$)$_3$]-Pn$^c$ | (CH$_2$)$_2$ | O |
| 2-1009 | H | Me | H | H | 3-[ONO$_2$(CH$_2$)$_3$]-Pn$^c$ | (CH$_2$)$_2$ | O |
| 2-1010 | H | Bz | H | H | 3-[ONO$_2$(CH$_2$)$_3$]-Pn$^c$ | (CH$_2$)$_2$ | O |
| 2-1011 | H | H | H | H | 2-[ONO$_2$(CH$_2$)$_4$]-Pn$^c$ | (CH$_2$)$_2$ | O |
| 2-1012 | H | Me | H | H | 2-[ONO$_2$(CH$_2$)$_4$]-Pn$^c$ | (CH$_2$)$_2$ | O |
| 2-1013 | H | Bz | H | H | 2-[ONO$_2$(CH$_2$)$_4$]-Pn$^c$ | (CH$_2$)$_2$ | O |
| 2-1014 | H | H | H | H | 3-[ONO$_2$(CH$_2$)$_4$]-Pn$^c$ | (CH$_2$)$_2$ | O |
| 2-1015 | H | Me | H | H | 3-[ONO$_2$(CH$_2$)$_4$]-Pn$^c$ | (CH$_2$)$_2$ | O |
| 2-1016 | H | Bz | H | H | 3-[ONO$_2$(CH$_2$)$_4$]-Pn$^c$ | (CH$_2$)$_2$ | O |
| 2-1017 | H | H | H | H | 2-(ONO$_2$CH$_2$)-Pn$^c$ | (CH$_2$)$_3$ | O |
| 2-1018 | H | Me | H | H | 2-(ONO$_2$CH$_2$)-Pn$^c$ | (CH$_2$)$_3$ | O |
| 2-1019 | H | Bz | H | H | 2-(ONO$_2$CH$_2$)-Pn$^c$ | (CH$_2$)$_3$ | O |
| 2-1020 | H | H | H | H | 3-(ONO$_2$CH$_2$)-Pn$^c$ | (CH$_2$)$_3$ | O |
| 2-1021 | H | Me | H | H | 3-(ONO$_2$CH$_2$)-Pn$^c$ | (CH$_2$)$_3$ | O |
| 2-1022 | H | Bz | H | H | 3-(ONO$_2$CH$_2$)-Pn$^c$ | (CH$_2$)$_3$ | O |
| 2-1023 | H | H | H | H | 2-[ONO$_2$(CH$_2$)$_2$]-Pn$^c$ | (CH$_2$)$_3$ | O |
| 2-1024 | H | H | H | H | 3-[ONO$_2$(CH$_2$)$_2$]-Pn$^c$ | (CH$_2$)$_3$ | O |
| 2-1025 | H | H | H | H | 2-[ONO$_2$(CH$_2$)$_3$]-Pn$^c$ | (CH$_2$)$_3$ | O |
| 2-1026 | H | H | H | H | 3-[ONO$_2$(CH$_2$)$_3$]-Pn$^c$ | (CH$_2$)$_3$ | O |
| 2-1027 | H | H | H | H | 2-[ONO$_2$(CH$_2$)$_4$]-Pn$^c$ | (CH$_2$)$_3$ | O |
| 2-1028 | H | H | H | H | 3-[ONO$_2$(CH$_2$)$_4$]-Pn$^c$ | (CH$_2$)$_3$ | O |
| 2-1030 | H | H | H | H | 5-ONO$_2$-2-Pip | single bond | S |
| 2-1031 | H | H | H | H | 6-ONO$_2$-3-Pip | single bond | S |
| 2-1032 | H | H | H | H | 5-(ONO$_2$CH$_2$)-2-Pip | single bond | S |
| 2-1033 | H | H | H | H | 5-[ONO$_2$(CH$_2$)$_2$]-2-Pip | single bond | S |
| 2-1034 | H | H | H | H | 5-[ONO$_2$(CH$_2$)$_3$]-2-Pip | single bond | S |
| 2-1035 | H | H | H | H | 5-[ONO$_2$(CH$_2$)$_4$]-2-Pip | single bond | S |
| 2-1036 | H | H | H | H | 6-(ONO$_2$CH$_2$)-3-Pip | single bond | S |
| 2-1037 | H | H | H | H | 6-[ONO$_2$(CH$_2$)$_2$]-3-Pip | single bond | S |
| 2-1038 | H | H | H | H | 6-[ONO$_2$(CH$_2$)$_3$]-3-Pip | single bond | S |
| 2-1039 | H | H | H | H | 6-[ONO$_2$(CH$_2$)$_4$]-3-Pip | single bond | S |
| 2-1040 | H | H | H | H | 5-(ONO$_2$CH$_2$)-2-Pip | CH$_2$ | S |
| 2-1041 | H | Me | H | H | 5-(ONO$_2$CH$_2$)-2-Pip | CH$_2$ | S |
| 2-1042 | H | Ph | H | H | 5-(ONO$_2$CH$_2$)-2-Pip | CH$_2$ | S |
| 2-1043 | H | Bz | H | H | 5-(ONO$_2$CH$_2$)-2-Pip | CH$_2$ | S |
| 2-1044 | H | 4-Me-Bz | H | H | 5-(ONO$_2$CH$_2$)-2-Pip | CH$_2$ | S |
| 2-1045 | H | 4-MeO-Bz | H | H | 5-(ONO$_2$CH$_2$)-2-Pip | CH$_2$ | S |
| 2-1046 | H | H | H | H | 1-Me-5-(ONO$_2$CH$_2$)-2-Pip | CH$_2$ | S |
| 2-1047 | H | H | H | H | 5-[ONO$_2$(CH$_2$)$_2$]-2-Pip | CH$_2$ | S |
| 2-1048 | H | Me | H | H | 5-[ONO$_2$(CH$_2$)$_2$]-2-Pip | CH$_2$ | S |
| 2-1049 | H | Bz | H | H | 5-[ONO$_2$(CH$_2$)$_2$]-2-Pip | CH$_2$ | S |
| 2-1050 | H | H | H | H | 5-[ONO$_2$(CH$_2$)$_3$]-2-Pip | CH$_2$ | S |
| 2-1051 | H | Me | H | H | 5-[ONO$_2$(CH$_2$)$_3$]-2-Pip | CH$_2$ | S |
| 2-1052 | H | Bz | H | H | 5-[ONO$_2$(CH$_2$)$_3$]-2-Pip | CH$_2$ | S |
| 2-1053 | H | H | H | H | 5-[ONO$_2$(CH$_2$)$_4$]-2-Pip | CH$_2$ | S |
| 2-1054 | H | Me | H | H | 5-[ONO$_2$(CH$_2$)$_4$]-2-Pip | CH$_2$ | S |
| 2-1055 | H | Bz | H | H | 5-[ONO$_2$(CH$_2$)$_4$]-2-Pip | CH$_2$ | S |
| 2-1056 | H | H | H | H | 6-(ONO$_2$CH$_2$)-3-Pip | CH$_2$ | S |
| 2-1057 | H | Me | H | H | 6-(ONO$_2$CH$_2$)-3-Pip | CH$_2$ | S |
| 2-1058 | H | Ph | H | H | 6-(ONO$_2$CH$_2$)-3-Pip | CH$_2$ | S |
| 2-1059 | H | Bz | H | H | 6-(ONO$_2$CH$_2$)-3-Pip | CH$_2$ | S |
| 2-1060 | H | 4-Me-Bz | H | H | 6-(ONO$_2$CH$_2$)-3-Pip | CH$_2$ | S |
| 2-1061 | H | 4-MeO-Bz | H | H | 6-(ONO$_2$CH$_2$)-3-Pip | CH$_2$ | S |
| 2-1062 | H | H | H | H | 1-Me-6-(ONO$_2$CH$_2$)-3-Pip | CH$_2$ | S |
| 2-1063 | H | H | H | H | 6-[ONO$_2$(CH$_2$)$_2$]-3-Pip | CH$_2$ | S |
| 2-1064 | H | Me | H | H | 6-[ONO$_2$(CH$_2$)$_2$]-3-Pip | CH$_2$ | S |
| 2-1065 | H | Bz | H | H | 6-[ONO$_2$(CH$_2$)$_2$]-3-Pip | CH$_2$ | S |
| 2-1066 | H | H | H | H | 6-[ONO$_2$(CH$_2$)$_3$]-3-Pip | CH$_2$ | S |
| 2-1067 | H | Me | H | H | 6-[ONO$_2$(CH$_2$)$_3$]-3-Pip | CH$_2$ | S |
| 2-1068 | H | Bz | H | H | 6-[ONO$_2$(CH$_2$)$_3$]-3-Pip | CH$_2$ | S |
| 2-1069 | H | H | H | H | 6-[ONO$_2$(CH$_2$)$_4$]-3-Pip | CH$_2$ | S |

TABLE 2-continued

| Compd. No. | R¹ | R² | R³ | R⁴ | R⁵ | A | X¹ |
|---|---|---|---|---|---|---|---|
| 2-1070 | H | Me | H | H | 6-[ONO$_2$(CH$_2$)$_4$]-3-Pip | CH$_2$ | S |
| 2-1071 | H | Bz | H | H | 6-[ONO$_2$(CH$_2$)$_4$]-3-Pip | CH$_2$ | S |
| 2-1072 | H | H | H | H | 5-(ONO$_2$CH$_2$)-2-Pip | (CH$_2$)$_2$ | S |
| 2-1073 | H | Me | H | H | 5-(ONO$_2$CH$_2$)-2-Pip | (CH$_2$)$_2$ | S |
| 2-1074 | H | Bz | H | H | 5-(ONO$_2$CH$_2$)-2-Pip | (CH$_2$)$_2$ | S |
| 2-1075 | H | H | H | H | 1-Me-5-(ONO$_2$CH$_2$)-2-Pip | (CH$_2$)$_2$ | S |
| 2-1076 | H | H | H | H | 5-[ONO$_2$(CH$_2$)$_2$]-2-Pip | (CH$_2$)$_2$ | S |
| 2-1077 | H | H | H | H | 5-[ONO$_2$(CH$_2$)$_3$]-2-Pip | (CH$_2$)$_2$ | S |
| 2-1078 | H | H | H | H | 5-[ONO$_2$(CH$_2$)$_4$]-2-Pip | (CH$_2$)$_2$ | S |
| 2-1079 | H | H | H | H | 6-(ONO$_2$CH$_2$)-3-Pip | (CH$_2$)$_2$ | S |
| 2-1080 | H | Me | H | H | 6-(ONO$_2$CH$_2$)-3-Pip | (CH$_2$)$_2$ | S |
| 2-1081 | H | Bz | H | H | 6-(ONO$_2$CH$_2$)-3-Pip | (CH$_2$)$_2$ | S |
| 2-1082 | H | H | H | H | 1-Me-6-(ONO$_2$CH$_2$)-3-Pip | (CH$_2$)$_2$ | S |
| 2-1083 | H | H | H | H | 6-[ONO$_2$(CH$_2$)$_2$]-3-Pip | (CH$_2$)$_2$ | S |
| 2-1084 | H | H | H | H | 6-[ONO$_2$(CH$_2$)$_3$]-3-Pip | (CH$_2$)$_2$ | S |
| 2-1085 | H | H | H | H | 6-[ONO$_2$(CH$_2$)$_4$]-3-Pip | (CH$_2$)$_2$ | S |
| 2-1086 | H | H | H | H | 5-(ONO$_2$CH$_2$)-2-Pip | (CH$_2$)$_3$ | S |
| 2-1087 | H | H | H | H | 6-(ONO$_2$CH$_2$)-2-Pip | (CH$_2$)$_3$ | S |
| 2-1088 | H | H | H | H | 5-ONO$_2$-2-Pip | single bond | O |
| 2-1089 | H | H | H | H | 6-ONO$_2$-3-Pip | single bond | O |
| 2-1090 | H | H | H | H | 5-(ONO$_2$CH$_2$)-2-Pip | single bond | O |
| 2-1091 | H | H | H | H | 5-[ONO$_2$(CH$_2$)$_2$]-2-Pip | single bond | O |
| 2-1092 | H | H | H | H | 5-[ONO$_2$(CH$_2$)$_3$]-2-Pip | single bond | O |
| 2-1093 | H | H | H | H | 5-[ONO$_2$(CH$_2$)$_4$]-2-Pip | single bond | O |
| 2-1094 | H | H | H | H | 6-(ONO$_2$CH$_2$)-3-Pip | single bond | O |
| 2-1095 | H | H | H | H | 6-[ONO$_2$(CH$_2$)$_2$]-3-Pip | single bond | O |
| 2-1096 | H | H | H | H | 6-[ONO$_2$(CH$_2$)$_3$]-3-Pip | single bond | O |
| 2-1097 | H | H | H | H | 6-[ONO$_2$(CH$_2$)$_4$]-3-Pip | single bond | O |
| 2-1098 | H | H | H | H | 5-(ONO$_2$CH$_2$)-2-Pip | CH$_2$ | O |
| 2-1099 | H | Me | H | H | 5-(ONO$_2$CH$_2$)-2-Pip | CH$_2$ | O |
| 2-1100 | H | Ph | H | H | 5-(ONO$_2$CH$_2$)-2-Pip | CH$_2$ | O |
| 2-1101 | H | Bz | H | H | 5-(ONO$_2$CH$_2$)-2-Pip | CH$_2$ | O |
| 2-1102 | H | 4-Me-Bz | H | H | 5-(ONO$_2$CH$_2$)-2-Pip | CH$_2$ | O |
| 2-1103 | H | 4-MeO-Bz | H | H | 5-(ONO$_2$CH$_2$)-2-Pip | CH$_2$ | O |
| 2-1104 | H | H | H | H | 1-Me-5-(ONO$_2$CH$_2$)-2-Pip | CH$_2$ | O |
| 2-1105 | H | H | H | H | 5-[ONO$_2$(CH$_2$)$_2$]-2-Pip | CH$_2$ | O |
| 2-1106 | H | Me | H | H | 5-[ONO$_2$(CH$_2$)$_2$]-2-Pip | CH$_2$ | O |
| 2-1107 | H | Bz | H | H | 5-[ONO$_2$(CH$_2$)$_2$]-2-Pip | CH$_2$ | O |
| 2-1108 | H | H | H | H | 5-[ONO$_2$(CH$_2$)$_3$]-2-Pip | CH$_2$ | O |
| 2-1109 | H | Me | H | H | 5-[ONO$_2$(CH$_2$)$_3$]-2-Pip | CH$_2$ | O |
| 2-1110 | H | Bz | H | H | 5-[ONO$_2$(CH$_2$)$_3$]-2-Pip | CH$_2$ | O |
| 2-1111 | H | H | H | H | 5-[ONO$_2$(CH$_2$)$_4$]-2-Pip | CH$_2$ | O |
| 2-1112 | H | Me | H | H | 5-[ONO$_2$(CH$_2$)$_4$]-2-Pip | CH$_2$ | O |
| 2-1113 | H | Bz | H | H | 5-[ONO$_2$(CH$_2$)$_4$]-2-Pip | CH$_2$ | O |
| 2-1114 | H | H | H | H | 6-(ONO$_2$CH$_2$)-3-Pip | CH$_2$ | O |
| 2-1115 | H | Me | H | H | 6-(ONO$_2$CH$_2$)-3-Pip | CH$_2$ | O |
| 2-1116 | H | Ph | H | H | 6-(ONO$_2$CH$_2$)-3-Pip | CH$_2$ | O |
| 2-1117 | H | Bz | H | H | 6-(ONO$_2$CH$_2$)-3-Pip | CH$_2$ | O |
| 2-1118 | H | 4-Me-Bz | H | H | 6-(ONO$_2$CH$_2$)-3-Pip | CH$_2$ | O |
| 2-1119 | H | 4-MeO-Bz | H | H | 6-(ONO$_2$CH$_2$)-3-Pip | CH$_2$ | O |
| 2-1120 | H | H | H | H | 1-Me-6-(ONO$_2$CH$_2$)-3-Pip | CH$_2$ | O |
| 2-1121 | H | H | H | H | 6-[ONO$_2$(CH$_2$)$_2$]-3-Pip | CH$_2$ | O |
| 2-1122 | H | Me | H | H | 6-[ONO$_2$(CH$_2$)$_2$]-3-Pip | CH$_2$ | O |
| 2-1123 | H | Bz | H | H | 6-[ONO$_2$(CH$_2$)$_2$]-3-Pip | CH$_2$ | O |
| 2-1124 | H | H | H | H | 6-[ONO$_2$(CH$_2$)$_3$]-3-Pip | CH$_2$ | O |
| 2-1125 | H | Me | H | H | 6-[ONO$_2$(CH$_2$)$_3$]-3-Pip | CH$_2$ | O |
| 2-1126 | H | Bz | H | H | 6-[ONO$_2$(CH$_2$)$_3$]-3-Pip | CH$_2$ | O |
| 2-1127 | H | H | H | H | 6-[ONO$_2$(CH$_2$)$_4$]-3-Pip | CH$_2$ | O |
| 2-1128 | H | Me | H | H | 6-[ONO$_2$(CH$_2$)$_4$]-3-Pip | CH$_2$ | O |
| 2-1129 | H | Bz | H | H | 6-[ONO$_2$(CH$_2$)$_4$]-3-Pip | CH$_2$ | O |
| 2-1130 | H | H | H | H | 5-(ONO$_2$CH$_2$)-2-Pip | (CH$_2$)$_2$ | O |
| 2-1131 | H | Me | H | H | 5-(ONO$_2$CH$_2$)-2-Pip | (CH$_2$)$_2$ | O |
| 2-1132 | H | Bz | H | H | 5-(ONO$_2$CH$_2$)-2-Pip | (CH$_2$)$_2$ | O |
| 2-1133 | H | H | H | H | 1-Me-5-(ONO$_2$CH$_2$)-2-Pip | (CH$_2$)$_2$ | O |
| 2-1134 | H | H | H | H | 5-[ONO$_2$(CH$_2$)$_2$]-2-Pip | (CH$_2$)$_2$ | O |
| 2-1135 | H | H | H | H | 5-[ONO$_2$(CH$_2$)$_3$]-2-Pip | (CH$_2$)$_2$ | O |
| 2-1136 | H | H | H | H | 5-[ONO$_2$(CH$_2$)$_4$]-2-Pip | (CH$_2$)$_2$ | O |
| 2-1137 | H | H | H | H | 6-(ONO$_2$CH$_2$)-3-Pip | (CH$_2$)$_2$ | O |
| 2-1138 | H | Me | H | H | 6-(ONO$_2$CH$_2$)-3-Pip | (CH$_2$)$_2$ | O |
| 2-1139 | H | Bz | H | H | 6-(ONO$_2$CH$_2$)-3-Pip | (CH$_2$)$_2$ | O |
| 2-1140 | H | H | H | H | 1-Me-6-(ONO$_2$CH$_2$)-3-Pip | (CH$_2$)$_2$ | O |
| 2-1141 | H | H | H | H | 6-[ONO$_2$(CH$_2$)$_2$]-3-Pip | (CH$_2$)$_2$ | O |
| 2-1142 | H | H | H | H | 6-[ONO$_2$(CH$_2$)$_3$]-3-Pip | (CH$_2$)$_2$ | O |
| 2-1143 | H | H | H | H | 6-[ONO$_2$(CH$_2$)$_4$]-3-Pip | (CH$_2$)$_2$ | O |
| 2-1144 | H | H | H | H | 5-(ONO$_2$CH$_2$)-2-Pip | (CH$_2$)$_3$ | O |
| 2-1145 | H | H | H | H | 6-(ONO$_2$CH$_2$)-2-Pip | (CH$_2$)$_3$ | O |

TABLE 2-continued

| Compd. No. | R¹ | R² | R³ | R⁴ | R⁵ | A | X¹ |
|---|---|---|---|---|---|---|---|
| 2-1146 | H | H | H | H | 5-(ONO$_2$)-2-Pyrr | single bond | S |
| 2-1147 | H | H | H | H | 4-(ONO$_2$)-2-Pyrr | single bond | S |
| 2-1148 | H | H | H | H | 5-(ONO$_2$CH$_2$)-2-Pyrr | single bond | S |
| 2-1149 | H | H | H | H | 4-(ONO$_2$CH$_2$)-2-Pyrr | single bond | S |
| 2-1150 | H | H | H | H | 5-(ONO$_2$)-2-Pyrr | CH$_2$ | S |
| 2-1151 | H | H | H | H | 4-(ONO$_2$)-2-Prrr | CH$_2$ | S |
| 2-1152 | H | H | H | H | 5-(ONO$_2$CH$_2$)-2-Pyrr | CH$_2$ | S |
| 2-1153 | H | Me | H | H | 5-(ONO$_2$CH$_2$)-2-Pyrr | CH$_2$ | S |
| 2-1154 | H | Bz | H | H | 5-(ONO$_2$CH$_2$)-2-Pyrr | CH$_2$ | S |
| 2-1155 | H | H | H | H | 1-Me-5-(ONO$_2$CH$_2$)-2-Pyrr | CH$_2$ | S |
| 2-1156 | H | H | H | H | 4-(ONO$_2$CH$_2$)-2-Pyrr | CH$_2$ | S |
| 2-1157 | H | Me | H | H | 4-(ONO$_2$CH$_2$)-2-Pyrr | CH$_2$ | S |
| 2-1158 | H | Bz | H | H | 4-(ONO$_2$CH$_2$)-2-Pyrr | CH$_2$ | S |
| 2-1159 | H | H | H | H | 5-[ONO$_2$(CH$_2$)$_2$]-2-Pyrr | CH$_2$ | S |
| 2-1160 | H | H | H | H | 4-[ONO$_2$(CH$_2$)$_2$]-2-Pyrr | CH$_2$ | S |
| 2-1161 | H | H | H | H | 5-[ONO$_2$(CH$_2$)$_3$]-2-Pyrr | CH$_2$ | S |
| 2-1162 | H | H | H | H | 4-[ONO$_2$(CH$_2$)$_3$]-2-Pyrr | CH$_2$ | S |
| 2-1163 | H | H | H | H | 5-[ONO$_2$(CH$_2$)$_4$]-2-PyTr | CH$_2$ | S |
| 2-1164 | H | H | H | H | 4-[ONO$_2$(CH$_2$)$_4$]-2-Pyrr | CH$_2$ | S |
| 2-1165 | H | H | H | H | 5-(ONO$_2$CH$_2$)-2-Pyrr | (CH$_2$)$_2$ | S |
| 2-1166 | H | H | H | H | 4-(ONO$_2$CH$_2$)-2-Pyrr | (CH$_2$)$_2$ | S |
| 2-1167 | H | H | H | H | 5-(ONO$_2$)-2-Pyrr | single bond | O |
| 2-1168 | H | H | H | H | 4-(ONO$_2$)-2-Pyrr | single bond | O |
| 2-1169 | H | H | H | H | 5-(ONO$_2$CH$_2$)-2-Pyrr | single bond | O |
| 2-1170 | H | H | H | H | 4-(ONO$_2$CH$_2$)-2-Pyrr | single bond | O |
| 2-1171 | H | H | H | H | 5-(ONO$_2$)-2-Pyrr | CH$_2$ | O |
| 2-1172 | H | H | H | H | 4-(ONO$_2$)-2-Pyrr | CH$_2$ | O |
| 2-1173 | H | H | H | H | 5-(ONO$_2$CH$_2$)-2-Pyrr | CH$_2$ | O |
| 2-1174 | H | Ne | H | H | 5-(ONO$_2$CH$_2$)-2-Pyrr | CH$_2$ | O |
| 2-1175 | H | Bz | H | H | 5-(ONO$_2$-2)-2-Pyrr | CH$_2$ | O |
| 2-1176 | H | H | H | H | 1-Me-5-(ONO$_2$CH$_2$)-2-Pyrr | CH$_2$ | O |
| 2-1177 | H | H | H | H | 4-(ONO$_2$-2)-2-Pyrr | CH$_2$ | O |
| 2-1178 | H | Me | H | H | 4-(ONO$_2$-2)-2-Pyrr | CH$_2$ | O |
| 2-1179 | H | Bz | H | H | 4-(ONO$_2$CH$_2$)-2-Pyrr | CH$_2$ | O |
| 2-1180 | H | H | H | H | 5-[ONO$_2$(CH$_2$)$_2$]-2-Pyrr | CH$_2$ | O |
| 2-1181 | H | H | H | H | 4-[ONO$_2$(CH$_2$)$_2$]-2-Pyrr | CH$_2$ | O |
| 2-1182 | H | H | H | H | 5-[ONO$_2$(CH$_2$)$_3$]-2-Pyrr | CH$_2$ | O |
| 2-1183 | H | H | H | H | 4-[ONO$_2$(CH$_2$)$_3$]-2-Pyrr | CH$_2$ | O |
| 2-1184 | H | H | H | H | 5-[ONO$_2$(CH$_2$)$_4$]-2-Prrr | CH$_2$ | O |
| 2-1185 | H | H | H | H | 4-[ONO$_2$(CH$_2$)$_4$]-2-Pyrr | CH$_2$ | O |
| 2-1186 | H | H | H | H | 5-(ONO$_2$CH$_2$)-2-Pyrr | (CH$_2$)$_2$ | O |
| 2-1187 | H | H | H | H | 4-(ONO$_2$CH$_2$)-2-Pyrr | (CH$_2$)$_2$ | O |
| 2-1188 | H | H | H | H | 4-(ONO$_2$CH$_2$)-2-Aze | CH$_2$ | S |
| 2-1189 | H | H | H | H | 2-(ONO$_2$CH$_2$)-2-Azi | CH$_2$ | S |
| 2-1190 | H | H | H | H | 4-(ONO$_2$CH$_2$)-2-Aze | CH$_2$ | O |
| 2-1191 | H | H | H | H | 2-(ONO$_2$CH$_2$)-2-Azi | CH$_2$ | O |
| 2-1192 | H | H | H | H | 4-(ONO$_2$CH$_2$)-Hx$^c$ | CH(Me) | S |
| 2-1193 | H | Me | H | H | 4-(ONO$_2$CH$_2$)-Hx$^c$ | CH(Me) | S |
| 2-1194 | H | Bz | H | H | 4-(ONO$_2$CH$_2$)-Hx$^c$ | CH(Me) | S |
| 2-1195 | H | 4-Me-Bz | H | H | 4-(ONO$_2$CH$_2$)-Hx$^c$ | CH(Me) | S |
| 2-1196 | H | 4-MeO-Bz | H | H | 4-(ONO$_2$CH$_2$)-Hx$^c$ | CH(Me) | S |
| 2-1197 | H | H | H | H | 4-[ONO$_2$CH(Me)]-Hx$^c$ | single bond | S |
| 2-1198 | H | H | H | H | 4-[ONO$_2$(CH$_2$)$_2$]-Hx$^c$ | CH(Me) | S |
| 2-1199 | H | Me | H | H | 4-[ONO$_2$(CH$_2$)$_2$]-Hx$^c$ | CH(Me) | S |
| 2-1200 | H | Bz | H | H | 4-[ONO$_2$(CH$_2$)$_2$]-Hx$^c$ | CH(Me) | S |
| 2-1201 | H | H | H | H | 4-[ONO$_2$CH(Me)]-Hx$^c$ | CH$_2$ | S |
| 2-1202 | H | Me | H | H | 4-[ONO$_2$CH(Me)]-Hx$^c$ | CH$_2$ | S |
| 2-1203 | H | Bz | H | H | 4-[ONO$_2$CH(Me)]-Hx$^c$ | CH$_2$ | S |
| 2-1204 | H | 4-Me-Bz | H | H | 4-[ONO$_2$CH(Me)]-Hx$^c$ | CH$_2$ | S |
| 2-1205 | H | 4-MeO-Bz | H | H | 4-[ONO$_2$CH(Me)]-Hx$^c$ | CH$_2$ | S |
| 2-1206 | H | H | H | H | 4-[ONO$_2$CH(Me)]-Hx$^c$ | (CH$_2$)$_2$ | S |
| 2-1207 | H | Me | H | H | 4-[ONO$_2$CH(Me)]-Hx$^c$ | (CH$_2$)$_2$ | S |
| 2-1208 | H | Bz | H | H | 4-[ONO$_2$CH(Me)]-Hx$^c$ | (CH$_2$)$_2$ | S |
| 2-1209 | H | H | H | H | 4-[ONO$_2$CH$_2$CH(Me)]-Hx$^c$ | single bond | S |
| 2-1210 | H | H | H | H | 4-[ONO$_2$CH$_2$CH(Me)]-Hx$^c$ | CH$_2$ | S |
| 2-1211 | H | Me | H | H | 4-[ONO$_2$CH$_2$CH(Me)]-Hx$^c$ | CH$_2$ | S |
| 2-1212 | H | Bz | H | H | 4-[ONO$_2$CH$_2$CH(Me)]-Hx$^c$ | CH$_2$ | S |
| 2-1213 | H | 4-Me-Bz | H | H | 4-[ONO$_2$CH$_2$CH(Me)]-Hx$^c$ | CH$_2$ | S |
| 2-1214 | H | 4-MeO-Bz | H | H | 4-[ONO$_2$CH$_2$CH(Me)]-Hx$^c$ | CH$_2$ | S |
| 2-1215 | H | H | H | H | 4-[ONO$_2$CH$_2$CH(Me)]-Hx$^c$ | (CH$_2$)$_2$ | S |
| 2-1216 | H | Me | H | H | 4-[ONO$_2$CH$_2$CH(Me)]-Hx$^c$ | (CH$_2$)$_2$ | S |
| 2-1217 | H | Bz | H | H | 4-[ONO$_2$CH$_2$CH(Me)]-Hx$^c$ | (CH$_2$)$_2$ | S |
| 2-1218 | H | 4-Me-Bz | H | H | 4-ONO$_2$(CH$_2$)$_3$-Hx$^c$ | CH$_2$ | S |
| 2-1219 | H | 4-MeO-Bz | H | H | 4-ONO$_2$(CH$_2$)$_3$-Hx$^c$ | CH$_2$ | S |
| 2-1220 | H | H | H | H | 4-ONO$_2$(CH$_2$)$_3$-Hx$^c$ | CH(Me) | S |
| 2-1221 | H | Me | H | H | 4-ONO$_2$(CH$_2$)$_3$-Hx$^c$ | CH(Me) | S |

TABLE 2-continued

| Compd. No. | R¹ | R² | R³ | R⁴ | R⁵ | A | X¹ |
|---|---|---|---|---|---|---|---|
| 2-1222 | H | Bz | H | H | 4-ONO$_2$(CH$_2$)$_3$-Hx$^c$ | CH(Me) | S |
| 2-1223 | H | H | H | H | 4-ONO$_2$(CH$_2$)$_4$-Hx$^c$ | single bond | S |
| 2-1224 | H | H | H | H | 4-ONO$_2$(CH$_2$)$_4$-Hx$^c$ | CH$_2$ | S |
| 2-1225 | H | Me | H | H | 4-ONO$_2$(CH$_2$)$_4$-Hx$^c$ | CH$_2$ | S |
| 2-1226 | H | Bz | H | H | 4-ONO$_2$(CH$_2$)$_4$-Hx$^c$ | CH$_2$ | S |
| 2-1227 | H | 4-Me-Bz | H | H | 4-ONO$_2$(CH$_2$)$_4$-Hx$^c$ | CH$_2$ | S |
| 2-1228 | H | 4-MeO-Bz | H | H | 4-ONO$_2$(CH$_2$)$_4$-Hx$^c$ | CH$_2$ | S |
| 2-1229 | H | H | H | H | 4-ONO$_2$(CH$_2$)$_4$-Hx$^c$ | CH(Me) | S |
| 2-1230 | H | Me | H | H | 4-ONO$_2$(CH$_2$)$_4$-Hx$^c$ | CH(Me) | S |
| 2-1231 | H | Bz | H | H | 4-ONO$_2$(CH$_2$)$_4$-Hx$^c$ | CH(Me) | S |
| 2-1232 | H | H | H | H | 3-(ONO$_2$CH$_2$)-Hx$^c$ | CH(Me) | S |
| 2-1233 | H | Me | H | H | 3-(ONO$_2$CH$_2$)-Hx$^c$ | CH(Me) | S |
| 2-1234 | H | Bz | H | H | 3-(ONO$_2$CH$_2$)-Hx$^c$ | CH(Me) | S |
| 2-1235 | H | H | H | H | 3-[ONO$_2$(CH$_2$)$_2$]-Hx$^c$ | CH(Me) | S |
| 2-1236 | H | H | H | H | 3-[ONO$_2$CH(Me)]-Hx$^c$ | CH$_2$ | S |
| 2-1237 | H | Me | H | H | 3-[ONO$_2$CH(Me)]-Hx$^c$ | CH$_2$ | S |
| 2-1238 | H | Bz | H | H | 3-[ONO$_2$CH(Me)]-Hx$^c$ | CH$_2$ | S |
| 2-1239 | H | H | H | H | 3-[ONO$_2$CH(Me)]-Hx$^c$ | (CH$_2$)$_2$ | S |
| 2-1240 | H | H | H | H | 3-[ONO$_2$CH$_2$CH(Me)]-Hx$^c$ | CH$_2$ | S |
| 2-1241 | H | Me | H | H | 3-[ONO$_2$CH$_2$CH(Me)]-Hx$^c$ | CH$_2$ | S |
| 2-1242 | H | Bz | H | H | 3-[ONO$_2$CH$_2$CH(Me)]-Hx$^c$ | CH$_2$ | S |
| 2-1243 | H | H | H | H | 3-[ONO$_2$CH$_2$CH(Me)]-Hx$^c$ | (CH$_2$)$_2$ | S |
| 2-1244 | H | Me | H | H | 3-[ONO$_2$CH$_2$CH(Me)]-Hx$^c$ | (CH$_2$)$_2$ | S |
| 2-1245 | H | Bz | H | H | 3-[ONO$_2$CH$_2$CH(Me)]-Hx$^c$ | (CH$_2$)$_2$ | S |
| 2-1246 | H | H | H | H | 3-ONO$_2$(CH$_2$)$_3$-Hx$^c$ | CH(Me) | S |
| 2-1247 | H | H | H | H | 3-ONO$_2$(CH$_2$)$_4$-Hx$^c$ | CH$_2$ | S |
| 2-1248 | H | Me | H | H | 3-ONO$_2$(CH$_2$)$_4$-Hx$^c$ | CH$_2$ | S |
| 2-1249 | H | Bz | H | H | 3-ONO$_2$(CH$_2$)$_4$-Hx$^c$ | CH$_2$ | S |
| 2-1250 | H | H | H | H | 3-ONO$_2$(CH$_2$)$_4$-Hx$^c$ | CH(Me) | S |
| 2-1251 | H | H | H | H | 2-(ONO$_2$CH$_2$)-Hx$^c$ | CH(Me) | S |
| 2-1252 | H | Me | H | H | 2-(ONO$_2$CH$_2$)-Hx$^c$ | CH(Me) | S |
| 2-1253 | H | Bz | H | H | 2-(ONO$_2$CH$_2$)-Hx$^c$ | CH(Me) | S |
| 2-1254 | H | H | H | H | 2-[ONO$_2$(CH$_2$)$_2$]-Hx$^c$ | CH(Me) | S |
| 2-1255 | H | H | H | H | 2-[ONO$_2$CH(Me)]-Hx$^c$ | CH$_2$ | S |
| 2-1256 | H | Me | H | H | 2-[ONO$_2$CH(Me)]-Hx$^c$ | CH$_2$ | S |
| 2-1257 | H | Bz | H | H | 2-[ONO$_2$CH(Me)]-Hx$^c$ | CH$_2$ | S |
| 2-1258 | H | H | H | H | 2-[ONO$_2$CH(Me)]-Hx$^c$ | (CH$_2$)$_2$ | S |
| 2-1259 | H | H | H | H | 2-[ONO$_2$CH$_2$CH(Me)]-Hx$^c$ | CH$_2$ | S |
| 2-1260 | H | Me | H | H | 2-[ONO$_2$CH$_2$CH(Me)]-Hx$^c$ | CH$_2$ | S |
| 2-1261 | H | Bz | H | H | 2-[ONO$_2$CH$_2$CH(Me)]-Hx$^c$ | CH$_2$ | S |
| 2-1262 | H | H | H | H | 2-[ONO$_2$CH$_2$CH(Me)]-Hx$^c$ | (CH$_2$)$_2$ | S |
| 2-1263 | H | Me | H | H | 2-[ONO$_2$CH$_2$CH(Me)]-Hx$^c$ | (CH$_2$)$_2$ | S |
| 2-1264 | H | Bz | H | H | 2-[ONO$_2$CH$_2$CH(Me)]-Hx$^c$ | (CH$_2$)$_2$ | S |
| 2-1265 | H | H | H | H | 2-ONO$_2$(CH$_2$)$_3$-Hx$^c$ | CH(Me) | S |
| 2-1266 | H | H | H | H | 2-ONO$_2$(CH$_2$)$_4$-Hx$^c$ | CH$_2$ | S |
| 2-1267 | H | Me | H | H | 2-ONO$_2$(CH$_2$)$_4$-Hx$^c$ | CH$_2$ | S |
| 2-1268 | H | Bz | H | H | 2-ONO$_2$(CH$_2$)$_4$-Hx$^c$ | CH$_2$ | S |
| 2-1269 | H | H | H | H | 2-ONO$_2$(CH$_2$)$_4$-Hx$^c$ | CH(Me) | S |
| 2-1270 | H | H | H | H | 3-(ONO$_2$CH$_2$)-Pn$^c$ | CH(Me) | S |
| 2-1271 | H | H | H | H | 3-[ONO$_2$CH(Me)]-Pn$^c$ | CH$_2$ | S |
| 2-1272 | H | H | H | H | 3-[ONO$_2$CH(Me)]-Pn$^c$ | (CH$_2$)$_2$ | S |
| 2-1273 | H | H | H | H | 3-[ONO$_2$CH$_2$CH(Me)]-Pn$^c$ | CH$_2$ | S |
| 2-1274 | H | H | H | H | 3-[ONO$_2$CH$_2$CH(Me)]-Pn$^c$ | (CH$_2$)$_2$ | S |
| 2-1275 | H | H | H | H | 3-ONO$_2$(CH$_2$)$_3$-Pn$^c$ | CH(Me) | S |
| 2-1276 | H | H | H | H | 3-ONO$_2$(CH$_2$)$_4$-Pn$^c$ | CH$_2$ | S |
| 2-1277 | H | Me | H | H | 3-ONO$_2$(CH$_2$)$_4$-Pn$^c$ | CH$_2$ | S |
| 2-1278 | H | Bz | H | H | 3-ONO$_2$(CH$_2$)$_4$-Pn$^c$ | CH$_2$ | S |
| 2-1279 | H | H | H | H | 2-(ONO$_2$CH$_2$)-Pn$^c$ | CH(Me) | S |
| 2-1280 | H | H | H | H | 2-[ONO$_2$CH(Me)]-Pn$^c$ | CH$_2$ | S |
| 2-1281 | H | H | H | H | 2-[ONO$_2$CH(Me)]-Pn$^c$ | (CH$_2$)$_2$ | S |
| 2-1282 | H | H | H | H | 2-[ONO$_2$CH$_2$CH(Me)]-Pn$^c$ | CH$_2$ | S |
| 2-1283 | H | H | H | H | 2-[ONO$_2$CH$_2$CH(Me)]-Pn$^c$ | (CH$_2$)$_2$ | S |
| 2-1284 | H | H | H | H | 2-ONO$_2$(CH$_2$)$_3$-Pn$^c$ | CH(Me) | S |
| 2-1285 | H | H | H | H | 2-ONO$_2$(CH$_2$)$_4$-Pn$^c$ | CH$_2$ | S |
| 2-1286 | H | Me | H | H | 2-ONO$_2$(CH$_2$)$_4$-Pn$^c$ | CH$_2$ | S |
| 2-1287 | H | Bz | H | H | 2-ONO$_2$(CH$_2$)$_4$-Pn$^c$ | CH$_2$ | S |
| 2-1288 | H | H | H | H | 4-(ONO$_2$CH$_2$)-Hx$^c$ | CH(Me) | O |
| 2-1289 | H | Me | H | H | 4-(ONO$_2$CH$_2$)-Hx$^c$ | CH(Me) | O |
| 2-1290 | H | Bz | H | H | 4-(ONO$_2$CH$_2$)-Hx$^c$ | CH(Me) | O |
| 2-1291 | H | 4-Me-Bz | H | H | 4-(ONO$_2$CH$_2$)-Hx$^c$ | CH(Me) | O |
| 2-1292 | H | 4-MeO-Bz | H | H | 4-(ONO$_2$CH$_2$)-Hx$^c$ | CH(Me) | O |
| 2-1193 | H | H | H | H | 4-[ONO$_2$(CH$_2$)$_2$]-Hx$^c$ | CH(Me) | O |
| 2-1194 | H | Me | H | H | 4-[ONO$_2$(CH$_2$)$_2$]-Hx$^c$ | CH(Me) | O |
| 2-1195 | H | Bz | H | H | 4-[ONO$_2$(CH$_2$)$_2$]-Hx$^c$ | CH(Me) | O |
| 2-1296 | H | H | H | H | 4-[ONO$_2$CH(Me)]-Hx$^c$ | single bond | O |
| 2-1297 | H | H | H | H | 4-[ONO$_2$CH(Me)]-Hx$^c$ | CH$_2$ | O |

TABLE 2-continued

| Compd. No. | $R^1$ | $R^2$ | $R^3$ | $R^4$ | $R^5$ | A | $X^1$ |
|---|---|---|---|---|---|---|---|
| 2-1298 | H | Me | H | H | 4-[$ONO_2CH(Me)$]-$Hx^c$ | $CH_2$ | O |
| 2-1299 | H | Bz | H | H | 4-[$ONO_2CH(Me)$]-$Hx^c$ | $CH_2$ | O |
| 2-1300 | H | 4-Me-Bz | H | H | 4-[$ONO_2CH(Me)$]-$Hx^c$ | $CH_2$ | O |
| 2-1301 | H | 4-MeO-Bz | H | H | 4-[$ONO_2CH(Me)$]-$Hx^c$ | $CH_2$ | O |
| 2-1302 | H | H | H | H | 4-[$ONO_2CH(Me)$]-$Hx^c$ | $(CH_2)_2$ | O |
| 2-1303 | H | Me | H | H | 4-[$ONO_2CH(Me)$]-$Hx^c$ | $(CH_2)_2$ | O |
| 2-1304 | H | Bz | H | H | 4-[$ONO_2CH(Me)$]-$Hx^c$ | $(CH_2)_2$ | O |
| 2-1305 | H | H | H | H | 4-[$ONO_2CH_2CH(Me)$]-$Hx^c$ | single bond | O |
| 2-1306 | H | H | H | H | 4-[$ONO_2CH_2CH(Me)$]-$Hx^c$ | $CH_2$ | O |
| 2-1307 | H | Me | H | H | 4-[$ONO_2CH_2CH(Me)$]-$Hx^c$ | $CH_2$ | O |
| 2-1308 | H | Bz | H | H | 4-[$ONO_2CH_2CH(Me)$]-$Hx^c$ | $CH_2$ | O |
| 2-1309 | H | 4-Me-Bz | H | H | 4-[$ONO_2CH_2CH(Me)$]-$Hx^c$ | $CH_2$ | O |
| 2-1310 | H | 4-MeO-Bz | H | H | 4-[$ONO_2CH_2CH(Me)$]-$Hx^c$ | $CH_2$ | O |
| 2-1311 | H | H | H | H | 4-[$ONO_2CH_2CH(Me)$]-$Hx^c$ | $(CH_2)_2$ | O |
| 2-1312 | H | Me | H | H | 4-[$ONO_2CH_2CH(Me)$]-$Hx^c$ | $(CH_2)_2$ | O |
| 2-1313 | H | Bz | H | H | 4-[$ONO_2CH_2CH(Me)$]-$Hx^c$ | $(CH_2)_2$ | O |
| 2-1314 | H | 4-Me-Bz | H | H | 4-$ONO_2(CH_2)_3$-$Hx^c$ | $CH_2$ | O |
| 2-1315 | H | 4-MeO-Bz | H | H | 4-$ONO_2(CH_2)_3$-$Hx^c$ | $CH_2$ | O |
| 2-1316 | H | H | H | H | 4-$ONO_2(CH_2)_3$-$Hx^c$ | CH(Me) | O |
| 2-1317 | H | Me | H | H | 4-$ONO_2(CH_2)_3$-$Hx^c$ | CH(Me) | O |
| 2-1318 | H | Bz | H | H | 4-$ONO_2(CH_2)_3$-$Hx^c$ | CH(Me) | O |
| 2-1319 | H | H | H | H | 4-$ONO_2(CH_2)_4$-$Hx^c$ | single bond | O |
| 2-1320 | H | H | H | H | 4-$ONO_2(CH_2)_4$-$Hx^c$ | $CH_2$ | O |
| 2-1321 | H | Me | H | H | 4-$ONO_2(CH_2)_4$-$Hx^c$ | $CH_2$ | O |
| 2-1322 | H | Bz | H | H | 4-$ONO_2(CH_2)_4$-$Hx^c$ | $CH_2$ | O |
| 2-1323 | H | 4-Me-Bz | H | H | 4-$ONO_2(CH_2)_4$-$Hx^c$ | $CH_2$ | O |
| 2-1324 | H | 4-MeO-Bz | H | H | 4-$ONO_2(CH_2)_4$-$Hx^c$ | $CH_2$ | O |
| 2-1325 | H | H | H | H | 4-$ONO_2(CH_2)_4$-$Hx^c$ | CH(Me) | O |
| 2-1326 | H | Me | H | H | 4-$ONO_2(CH_2)_4$-$Hx^c$ | CH(Me) | O |
| 2-1327 | H | Bz | H | H | 4-$ONO_2(CH_2)_4$-$Hx^c$ | CH(Me) | O |
| 2-1328 | H | H | H | H | 3-($ONO_2CH_2$)-$Hx^c$ | CH(Me) | O |
| 2-1329 | H | Me | H | H | 3-($ONO_2CH_2$)-$Hx^c$ | CH(Me) | O |
| 2-1330 | H | Bz | H | H | 3-($ONO_2CH_2$)-$Hx^c$ | CH(Me) | O |
| 2-1331 | H | H | H | H | 3-[$ONO_2(CH_2)_2$]-$Hx^c$ | CH(Me) | O |
| 2-1332 | H | H | H | H | 3-[$ONO_2CH(Me)$]-$Hx^c$ | $CH_2$ | O |
| 2-1333 | H | Me | H | H | 3-[$ONO_2CH(Me)$]-$Hx^c$ | $CH_2$ | O |
| 2-1334 | H | Bz | H | H | 3-[$ONO_2CH(Me)$]-$Hx^c$ | $CH_2$ | O |
| 2-1335 | H | H | H | H | 3-[$ONO_2CH(Me)$]-$Hx^c$ | $(CH_2)_2$ | O |
| 2-1336 | H | H | H | H | 3-[$ONO_2CH_2CH(Me)$]-$Hx^c$ | $CH_2$ | O |
| 2-1337 | H | Me | H | H | 3-[$ONO_2CH_2CH(Me)$]-$Hx^c$ | $CH_2$ | O |
| 2-1338 | H | Bz | H | H | 3-[$ONO_2CH_2CH(Me)$]-$Hx^c$ | $CH_2$ | O |
| 2-1339 | H | H | H | H | 3-[$ONO_2CH_2CH(Me)$]-$Hx^c$ | $(CH_2)_2$ | O |
| 2-1340 | H | Me | H | H | 3-[$ONO_2CH_2CH(Me)$]-$Hx^c$ | $(CH_2)_2$ | O |
| 2-1341 | H | Bz | H | H | 3-[$ONO_2CH_2CH(Me)$]-$Hx^c$ | $(CH_2)_2$ | O |
| 2-1342 | H | H | H | H | 2-$ONO_2(CH_2)_3$-$Hx^c$ | CH(Me) | O |
| 2-1343 | H | H | H | H | 2-$ONO_2(CH_2)_4$-$Hx^c$ | $CH_2$ | O |
| 2-1344 | H | Me | H | H | 2-$ONO_2(CH_2)_4$-$Hx^c$ | $CH_2$ | O |
| 2-1345 | H | Bz | H | H | 2-$ONO_2(CH_2)_4$-$Hx^c$ | $CH_2$ | O |
| 2-1346 | H | H | H | H | 2-$ONO_2(CH_2)_4$-$Hx^c$ | CH(Me) | O |
| 2-1347 | H | H | H | H | 2-($ONO_2CH_2$)-$Hx^c$ | CH(Me) | O |
| 2-1348 | H | Me | H | H | 2-($ONO_2CH_2$)-$Hx^c$ | CH(Me) | O |
| 2-1349 | H | Bz | H | H | 2-($ONO_2CH_2$)-$Hx^c$ | CH(Me) | O |
| 2-1350 | H | H | H | H | 2-[$ONO_2(CH_2)_2$]-$Hx^c$ | CH(Me) | O |
| 2-1351 | H | H | H | H | 2-[$ONO_2CH(Me)$]-$Hx^c$ | $CH_2$ | O |
| 2-1352 | H | Me | H | H | 2-[$ONO_2CH(Me)$]-$Hx^c$ | $CH_2$ | O |
| 2-1353 | H | Bz | H | H | 2-[$ONO_2CH(Me)$]-$Hx^c$ | $CH_2$ | O |
| 2-1354 | H | H | H | H | 2-[$ONO_2CH(Me)$]-$Hx^c$ | $(CH_2)_2$ | O |
| 2-1355 | H | H | H | H | 2-[$ONO_2CH_2CH(Me)$]-$Hx^c$ | $CH_2$ | O |
| 2-1356 | H | Me | H | H | 2-[$ONO_2CH_2CH(Me)$]-$Hx^c$ | $CH_2$ | O |
| 2-1357 | H | Bz | H | H | 2-[$ONO_2CH_2CH(Me)$]-$Hx^c$ | $CH_2$ | O |
| 2-1358 | H | H | H | H | 2-[$ONO_2CH_2CH(Me)$]-$Hx^c$ | $(CH_2)_2$ | O |
| 2-1359 | H | Me | H | H | 2-[$ONO_2CH_2CH(Me)$]-$Hx^c$ | $(CH_2)_2$ | O |
| 2-1360 | H | Bz | H | H | 2-[$ONO_2CH_2CH(Me)$]-$Hx^c$ | $(CH_2)_2$ | O |
| 2-1361 | H | H | H | H | 2-$ONO_2(CH_2)_3$-$Hx^c$ | CH(Me) | O |
| 2-1362 | H | H | H | H | 2-$ONO_2(CH_2)_4$-$Hx^c$ | $CH_2$ | O |
| 2-1363 | H | Me | H | H | 2-$ONO_2(CH_2)_4$-$Hx^c$ | $CH_2$ | O |
| 2-1364 | H | Bz | H | H | 2-$ONO_2(CH_2)_4$-$Hx^c$ | $CH_2$ | O |
| 2-1365 | H | H | H | H | 2-$ONO_2(CH_2)_4$-$Hx^c$ | CH(Me) | O |
| 2-1366 | H | H | H | H | 3-($ONO_2CH_2$)-$Pn^c$ | CH(Me) | O |
| 2-1367 | H | H | H | H | 3-[$ONO_2CH(Me)$]-$Pn^c$ | $CH_2$ | O |
| 2-1368 | H | H | H | H | 3-[$ONO_2CH(Me)$]-$Pn^c$ | $(CH_2)2$ | O |
| 2-1369 | H | H | H | H | 3-[$ONO_2CH_2CH(Me)$]-$Pn^c$ | $CH_2$ | O |
| 2-1370 | H | H | H | H | 3-[$ONO_2CH_2CH(Me)$]-$Pn^c$ | $(CH_2)_2$ | O |
| 2-1371 | H | H | H | H | 3-$ONO_2(CH_2)_3$-$Pn^c$ | CH(Me) | O |
| 2-1372 | H | H | H | H | 3-$ONO_2(CH_2)_4$-$Pn^c$ | $CH_2$ | O |
| 2-1373 | H | Me | H | H | 3-$ONO_2(CH_2)_4$-$Pn^c$ | $CH_2$ | O |

TABLE 2-continued

| Compd. No. | R¹ | R² | R³ | R⁴ | R⁵ | A | X¹ |
|---|---|---|---|---|---|---|---|
| 2-1374 | H | Bz | H | H | 3-ONO₂(CH₂)₄-Pnᶜ | CH₂ | O |
| 2-1375 | H | H | H | H | 2-(ONO₂CH₂)-Pnᶜ | CH(Me) | O |
| 2-1376 | H | H | H | H | 2-[ONO₂CH(Me)]-Pnᶜ | CH₂ | O |
| 2-1377 | H | H | H | H | 2-[ONO₂CH(Me)]-Pnᶜ | (CH₂)₂ | O |
| 2-1378 | H | H | H | H | 2-[ONO₂CH₂CH(Me)]-Pnᶜ | CH₂ | O |
| 2-1379 | H | H | H | H | 2-[ONO₂CH₂CH(Me)]-Pnᶜ | (CH₂)₂ | O |
| 2-1380 | H | H | H | H | 2-ONO₂(CH₂)₃-Pnᶜ | CH(Me) | |
| 2-1381 | H | H | H | H | 2-ONO₂(CH₂)₄-Pnᶜ | CH₂ | O |
| 2-1382 | H | Me | H | H | 2-ONO₂(CH₂)₄-Pnᶜ | CH₂ | O |
| 2-1383 | H | Bz | H | H | 2-ONO₂(CH₂)₄-Pnᶜ | CH₂ | O |
| 2-1384 | H | H | H | H | 3-[ONO₂(CH₂)₂]-Pnᶜ | CH₂ | S |
| 2-1385 | H | Me | H | H | 3-[ONO₂(CH₂)₂]-Pnᶜ | CH₂ | S |
| 2-1386 | H | Bz | H | H | 3-[ONO₂(CH₂)₂]-Pnᶜ | CH₂ | S |
| 2-1387 | H | H | H | H | 2-[ONO₂(CH₂)₂]-Pnᶜ | CH₂ | S |
| 2-1388 | H | Me | H | H | 2-[ONO₂(CH₂)₂]-Pnᶜ | CH₂ | S |
| 2-1389 | H | Bz | H | H | 2-[ONO₂(CH₂)₂]-Pnᶜ | CH₂ | S |
| 2-1390 | H | H | H | H | 3-[ONO₂(CH₂)₂]-Pnᶜ | CH₂ | O |
| 2-1391 | H | Me | H | H | 3-[ONO₂(CH₂)₂]-Pnᶜ | CH₂ | O |
| 2-1392 | H | Bz | H | H | 3-[ONO₂(CH₂)₂]-Pnᶜ | CH₂ | O |
| 2-1393 | H | H | H | H | 2-[ONO₂(CH₂)₂]-Pnᶜ | CH₂ | O |
| 2-1394 | H | Me | H | H | 2-[ONO₂(CH₂)₂]-Pnᶜ | CH₂ | O |
| 2-1395 | H | Bz | H | H | 2-[ONO₂(CH₂)₂]-Pnᶜ | CH₂ | O |
| 2-1396 | H | H | H | H | 5-ONO₂-2-Pip | CH₂ | S |
| 2-1397 | H | Me | H | H | 5-ONO₂-2-Pip | CH₂ | S |
| 2-1398 | H | Bz | H | H | 5-ONO₂-2-Pip | CH₂ | S |
| 2-1399 | H | H | H | H | 6-ONO₂-3-Pip | CH₂ | S |
| 2-1400 | H | Me | H | H | 6-ONO₂-3-Pip | CH₂ | S |
| 2-1401 | H | Bz | H | H | 6-ONO₂-3-Pip | CH₂ | S |
| 2-1402 | H | H | H | H | 5-ONO₂-2-Pip | CH₂ | O |
| 2-1403 | H | Me | H | H | 5-ONO₂-2-Pip | CH₂ | O |
| 2-1404 | H | Bz | H | H | 5-ONO₂-2-Pip | CH₂ | O |
| 2-1405 | H | H | H | H | 6-ONO₂-3-Pip | CH₂ | O |
| 2-1406 | H | Me | H | H | 6-ONO₂-3-Pip | CH₂ | O |
| 2-1407 | H | Bz | H | H | 6-ONO₂-3-Pip | CH₂ | O |

In the above Tables, the abbreviations mean the following groups.

Aze . . . azetidinyl
Azi . . . aziridinyl
Bu . . . butyl
Buᶜ . . . cyclobutyl
Bz . . . benzyl
Et . . . ethyl
Fur . . . furyl
Hxᶜ . . . cyclohexyl
Me . . . methyl
Np . . . naphthyl
Ph . . . phenyl
Pip . . . piperidinyl
Pnᶜ . . . cyclopentyl
Prᶜ . . . cyclopropyl
Pyr . . . pyridyl
Pyrr . . . pyrrolidinyl
Then . . . thienyl
Thiz . . . thiazolyl In the above Tables, preferred compounds are:
Compound No. 1-1, 1-5, 1-6, 1-8, 1-9, 1-14, 1-17, 1-29, 1-30, 1-32, 1-36, 1-37, 1-39, 1-40, 1-45, 1-48, 1-59, 1-60, 1-61, 1-64, 1-65, 1-69, 1-70, 1-72, 1-78, 1-81, 1-92, 1-93, 1-94, 1-96, 1-97, 1-99, 1-101, 1-193, 1-105, 1-124, 1-128, 1-129, 1-130, 1-138, 1-169, 1-170, 1-178, 1-189, 1-190, 1-198, 1-207, 1-210, 1-213, 1-216, 1-219, 1-243, 1-245, 1-247, 1-249, 1-251, 1-282, 1-295, 1-309, 1-315, 1-346, 1-349, 1-351, 1-353, 1-355, 1-374, 1-388, 1-419, 1-439, 1-457, 1-460, 1-463, 1-466, 1-469, 1-493, 1-495, 1-497, 1-499, 1-501, 1-513, 1-525, 1-537, 1-549, 1-561, 1-573, 1-585, 1-597, 1-609, 1-621, 1-633, 1-645, 1-657, 1-669, 1-681, 1-693, 1-705, 1-717, 1-729, 1-741, 1-753, 1-765, 1-777, 1-789, 1-801, 1-813, 1-825, 1-837, 1-849, 1-861, 1-873, 1-885, 1-888, 1-891, 1-894, 1-897, 1-900, 1-903, 1-906, 1-909, 1-912, 1-915, 1-921, 1-924, 1-927, 1-930, 1-1224, 2-1, 2-32, 2-36, 2-45, 2-59, 2-60, 2-61, 2-65, 2-96, 2-99, 2-101, 2-105, 2-124, 2-138, 2-169, 2-189, 2-207, 2-210, 2-213, 2-216, 2-243, 2-245, 2-247, 2-249, 2-251, 2-282, 2-315, 2-346, 2-349, 2-351, 2-353, 2-355, 2-374, 2-388, 2-419, 2-439, 2-457, 2-460, 2-463, 2-466, 2-469, 2-493, 2-495, 2-497, 2-499, 2-501, 2-513, 2-525, 2-537, 2-549, 2-561, 2-!573, 2-585, 2-597, 2-609, 2-621, 2-633, 2-645, 2-657, 2-669, 2-681, 2-693, 2-705, 2-717, 2-729, 2-741, 2-753, 2-765, 2-777, 2-789, 2-801, 2-813, 2-825, 2-837, 2-849, 2-861, 2-873, 2-885, 2-888, 2-891, 2-894, 2-897, 2-900, 2-903, 2-906, 2-909, 2-912, 2-915 and 2-921.

More preferred compounds are:
Compound No. 1-1, 1-5, 1-8, 1-14, 1-29, 1-30, 1-32, 1-36, 1-39, 1-45, 1-48, 1-59, 1-60, 1-61, 1-64, 1-65, 1-69, 1-70, 1-72, 1-78, 1-81, 1-92, 1-93, 1-94, 1-96, 1-97, 1-99, 1-101, 1-103, 1-105, 1-124, 1-128, 1-129, 1-130, 1-138, 1-169, 1-170, 1-178, 1-189, 1-190, 1-198, 1-207, 1-210, 1-213, 1-216, 1-219, 1-243, 1-245, 1-247, 1-249, 1-2,51, 1-282, 1-295, 1-309, 1-315, 1-346, 1-349, 1-351, 1-353, 1-419, 1-439, 1-501, 1-513, 1-525, 1-573, 1-585, 1-621, 1-633, 1-681, 1-729, 1-753, 1-777, 1-900, 1-924, 1-1224, 2-1, 2-32, 2-36, 2-45, 2-59, 2-60, 2-61, 2-65, 2-99 and 2-169.

Particularly preferred compounds are:
Compound No. 1-32: N-(4-nitroxymethylcyclohexylmethyl)-2-oxothiazolidin-4-yl-carboxamide, Compound No. 1-36: N-(4-nitroxymethylcyclohexylmethyl)-5-methyl-2-oxothiazolidin-4-yl-carboxamide,
Compound No. 1-39: N-(4-nitroxymethylcyclohexylmethyl)-2-oxo-5-(2-thienyl)thiazolidin-4-yl-carboxamide,
Compound No. 1-45: N-(4-nitroxymethylcyclohexylmethyl)-5-(4-methoxyphenyl)-2-oxothiazolidin-4-yl-carboxamide,
Compound No. 1-59: N-(4-nitroxymethylcyclohexylmethyl)-5-benzyl-2-oxothiazolidin-4-yl-carboxamide,
Compound No. 1-60: N-(4-nitroxymethylcyclohexylmethyl)-5-(4-methylbenzyl)-2-oxothiazolidin-4-yl-carboxamide,
Compound No. 1-61: N-(4-nitroxymethylcyclohexylmethyl)-5-(4-methoxybenzyl)-2-oxothiazolidin-4-yl-carboxamide,
Compound No. 1-65: N-[2-(4-nitroxymethylcyclohexyl)ethyl]-2-oxothiazolidin-4-yl-carboxamide,
Compound No. 1-69: N-[2-(4-nitroxymethylcyclohexyl)ethyl]-5-methyl-2-oxothiazolidin-4-yl-carboxamide,
Compound No. 1-72: N-[2-(4-nitroxymethylcyclohexyl)ethyl]-2-oxo-5-(2-thienyl)thiazolidin-4-yl-carboxamide,
Compound No. 1-78: N-[2-(4-nitroxymethylcyclohexyl)ethyl]-5-(4-methoxyphenyl)-2-oxothiazolidin-4-yl-carboxamide,
Compound No. 1-92: N-[2-(4-nitroxymethylcyclohexyl)ethyl]-5-benzyl-2-oxothiazolidin-4-yl-carboxamide,
Compound No. 1-93: N-[2-(4-nitroxymethylcyclohexyl)ethyl]-5-(4-methylbenzyl)-2-oxothiazolidin-4-yl-carboxamide,
Compound No. 1-94: N-[2-(4-nitroxymethylcyclohexyl)ethyl]-5-(4-methoxybenzyl)-2-oxothiazolidin-4-yl-carboxamide,
Compound No. 1-169: N-[4-(2-nitroxyethyl)cyclohexylmethyl]-2-oxothiazolidin-4-yl-carboxamide,
Compound No. 1-207: N-[2-[4-(3-nitroxypropyl)cyclohexyl]ethyl]-2-oxothiazolidin-4-yl-carboxamide,
Compound No. 1-900: N-[4-(3-nitroxypropyl)cyclohexylmethyl]-2-oxothiazolidin-4-yl-carboxamide,
Compound No. 1-1224: N-[4-(4-nitroxybutyl)cyclohexylmethyl]-2-oxothiazolidin-4-yl-carboxamide,
Compound No. 2-32: N-(4-nitroxymethylcyclohexylmethyl)-2-oxothiazolidin-5-yl-carboxamide,
Compound No. 2-36: N-(4-nitroxymethylcyclohexylmethyl)-4-methyl-2-oxothiazolidin-5-yl-carboxamide,
Compound No. 2-45: N-(4-nitroxymethylcyclohexylmethyl)-4-(4-methoxyphenyl)-2-oxothiazolidin-5-yl-carboxamide,
Compound No. 2-59: N-(4-nitroxymethylcyclohexylmethyl)-4-benzyl-2-oxothiazolidin-5-yl-carboxamide,
Compound No. 2-60: N-(4-nitroxymethylcyclohexylmethyl)-4-(4-methylbenzyl)-2-oxothiazolidin-5-yl-carboxamide, and
Compound No. 2-61: N-(4-nitroxymethylcyclohexylmethyl)-4-(4-methoxybenzyl)-2-oxothiazolidin-5-yl-carboxamide.

The compound having the general formula (I) of the present invention is easily prepared according to the following Methods.

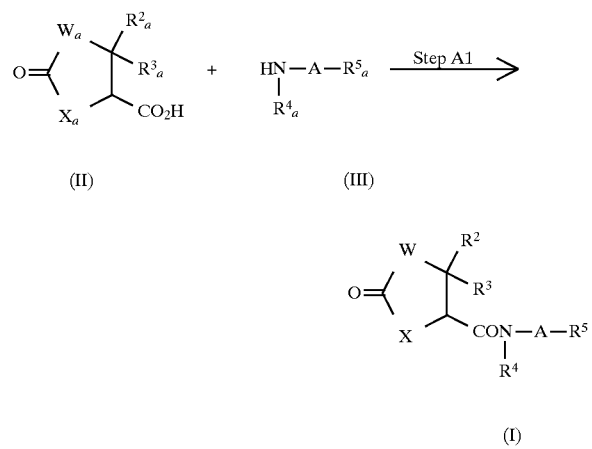

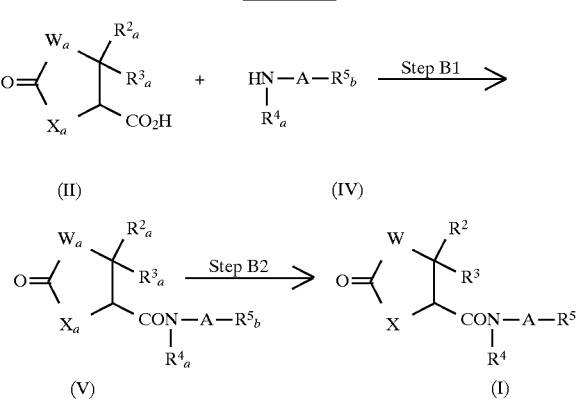

In the above formulae, W, X, $R^2$, $R^3$, $R^4$, $R^5$ and A have the same meanings as defined above, and $W_a$, $X_a$, $R^2_a$, $R^3_a$, $R^4_a$ and $R^5_a$ each represents the same meaning as W, X, $R^2$, $R^3$, $R^4$ and $R^5$, respectively except that the amino group or imino group (—NH—) in each group may optionally protected (preferably a protected amino group or imino group), and $R^5_b$ represents a substituted $C_3$–$C_8$ cycloalkyl group optionally containing a nitrogen atom [the substituent is essentially a group having the formula: —B—OH (wherein B has the same meaning as defined above) and desirably a $C_1$–$C_6$ alkyl group (an imino group of the group may be protected)].

A protective group of the amino group or the imino group is not particularly limited so long as it is usually used in the field of synthetic organic chemistry and includes, for example, a t-butyl group, a t-butoxycarbonyl group, a benzyl group which may be optionally substituted with $C_1$–$C_6$ alkyl, $C_1$–$C_6$ alkoxy or halogen such as benzyl, methylbenzyl, methoxybenzyl, fluorobenzyl and chlorobenzyl, a benzyloxycarbonyl group which may be optionally substituted with $C_1$–$C_6$ alkyl, $C_1$–$C_6$ alkoxy or halogen such as benzyloxycarbonyl, methylbenzyloxycarbonyl, methoxybenzyloxycarbonyl, fluorobenzyloxycarbonyl and chlorobenzyloxycarbonyl or a halogenoacetyl group such as chloroacetyl, bromoacetyl and iodoacetyl, preferably a t-butyl group, a t-butoxycarbonyl group, a p-methoxybenzyl group, a p-methoxybenzyloxycarbonyl group, a chloroacetyl group, a bromoacetyl group or an iodoacetyl group, more preferably a t-butoxycarbonyl group or a p-methoxybenzyloxycarbonyl group and particularly preferably a t-butoxycarbonyl group.

Method A is a method to prepare a compound (I).

Step A1 is a step to prepare a compound having the general formula (I) and is carried out by reacting a compound having the general formula (II) or a reactive derivative thereof (acid. halides, mixed acid anhydrides or active esters) with a compound having the general formula (III) or its acid addition salt (for example, mineral acid salts such as hydrochlorides, nitrates and sulfates) in an inert solvent and eliminating a protective group such as an amino group etc. of the resulting compound.

The reaction of the compound (II) with the compound (III) is carried out, for example, by the acid halide method, the mixed acid anhydride method, the active ester method or the condensation method.

The acid halide method is carried out by reacting the compound (II) with a halogenating agent (for example, thionyl chloride, oxalyl chloride, phosphorus pentachloride and the like) to prepare an acid halide and by reacting then the acid halide with the compound (III) or an acid addition salt thereof in an inert solvent in the presence or absence of a base.

The base employable here may include, for example, organic amines such as triethylamine, N-methylmorpholine, pyridine and 4-dimethylaminopyridine; alkali metal hydrogencarbonates such as sodium hydrogencarbonate and potassium hydrogencarbonate; and alkali metal carbonates such as sodium carbonate and potassium carbonate and preferably organic amines.

The inert solvent employable here is not particularly limited so long as it does not affect the reaction and may include, for example, hydrocarbons such as hexane, cyclohexane, benzene, toluene and xylene; halogenated hydrocarbons such as dichloromethane, 1,2-dichloroethane and carbon tetrachloride; ethers such as ether, tetrahydrofuran and dioxane; ketones such as acetone; amides such as N,N-dimethylformamide, N,N-dimethylacetamide, N-methyl-2-pyrrolidone and hexamethylphosphoramide; and sulfoxides such as dimethyl sulfoxide and preferably hydrocarbons, halogenated hydrocarbons, ethers or amides.

The reaction temperature varies depending on the starting compounds (II) and (III), the kind of solvent etc., and the reaction temperature for both the reaction of the halogenating agent with the compound (II) and the reaction of the acid halide with the compound (III) is usually at $-20°$ C. to $150°$ C. Preferably, the temperature for the former reaction is at $-10°$ C. to $50°$ C., and the temperature for the latter reaction is at $0°$ C. to $100°$ C. The reaction time varies depending on the reaction temperature etc. and the reaction time of both reactions is usually 15 minutes to 24 hours (preferably 30 minutes to 16 hours).

The mixed acid anhydride method is carried out by reacting a $C_1$–$C_6$ alkyl halogenocarbonate, a di-$C_1$–$C_6$ alkylcyanophosphoric acid or a di-$C_6$–$C_{10}$ arylphosphoryl azide with the compound (II) to prepare a mixed acid anhydride and by reacting then the mixed acid anhydride with the compound (III) or its acid addition salt.

The reaction for preparing the mixed acid anhydride is carried out by reacting a $C_1$–$C_6$ alkyl halogenocarbonate such as methyl chlorocarbonate, ethyl chlorocarbonate, isobutyl chlorocarbonate and hexyl chlorocarbonate (preferably ethyl chlorocarbonate or isobutyl chlorocarbonate), a di-$C_1$–$C_6$ alkylcyanophosphoric acid such as dimethylcyanophosphoric acid, diethylcyanophosphoric acid and dihexylcyanophosphoric acid (preferably diethylcyanophosphoric acid) or a di-$C_6$–$C_{10}$ arylphosphoryl azide such as diphenylphosphoryl azide, di(p-nitrophenyl)phosphoryl azide and dinaphthylphosphoryl azide (preferably diphenylphosphoryl azide) with the compound (II), preferably in an inert solvent in the presence of a base.

The base and the inert solvent employable here are similar to those employable in the acid halide method.

The reaction temperature varies depending on the starting compound (II), the kind of solvent, etc. and is usually $-20°$ C. to $50°$ C. (preferably $0°$ C. to $30°$ C.). The reaction time varies depending on the reaction temperature etc. and is usually 15 minutes to 24 hours (preferably 30 minutes to 16 hours).

The reaction of the mixed acid anhydride with the compound (III) or its acid addition salt is preferably carried out in an inert solvent in the presence or absence of a base. The base and the inert solvent employable here are similar to those employable in the acid halide method.

The reaction temperature varies depending on the starting compound (III), the kind of solvent, etc. and is usually $-20°$ C. to $100°$ C. (preferably $-100°$ C. to $50°$ C.). The reaction time varies depending on the reaction temperature etc. and is usually 15 minutes to 24 hours (preferably 30 minutes to 16 hours).

In the present method, in the case where dialkylcyanophosphoric acid or diarylphosphoryl azide is used, the compound (II) apd the compound (III) can be directly reacted in the presence of a base.

The active ester method is carried out by reacting the compound (II) with an active esterifying agent (for example, an N-hydroxy compound such as N-hydroxysuccinimide, N-hydroxybenzotriazole etc.) in the presence of a condensation agent (for example, dicyclohexylcarbodiimide and carbonyldiimidazole) to prepare an active ester and by reacting the active ester with the compound (III) or its acid addition salt.

The reaction for preparing the active ester is preferably carried out in an inert solvent, and the inert solvent employable here is similar to those employable in the acid halide method.

While the reaction temperature varies depending on the starting compounds (II) and (III), the kind of solvent, etc., in the active esterification reaction, it is usually $-20°$ C. to $50°$ C. (preferably $-10°$ C. to $30°$ C.), and in the reaction of the active ester compound with the compound (III), it is usually $-20°$ C. to $50°$ C. (preferably $-10°$ C. to $30°$ C.). The reaction time varies depending on the reaction temperature etc., and the reaction time of both reactions is usually 15 minutes to 24 hours (preferably 30 minutes to 16 hours).

The condensation method is carried out by reacting the compound (II) and the compound (III) or an acid addition salt thereof directly in the presence of a condensation agent (for example, dicyclohexylcarbodiimide, carbonyldiimidazole and 1-(N,N-dimethylaminopropyl)-3-ethylcarbodiimide hydrochloride). The present reaction is carried out in a similar manner to the reaction for preparing the active ester.

The protective group for the amino group or imino group is eliminated after completion of the above reaction by the method usually used in the field of synthetic organic chemistry.

In the case where the protective group is a t-butyl group, a t-butoxycarbonyl group, a methoxybenzyl group or a methoxybenzyloxycarbonyl group, it is eliminated by reacting the corresponding compound with an acid (for example, a mineral acid such as hydrochloric acid, sulfuric acid and nitric acid, an organic acid such as acetic acid, trifluoroacetic acid, methane sulfonic acid and p-toluene sulfonic acid, preferably hydrochloric acid) in an inert solvent (for example, an ether such as ether, tetrahydrofuran and dioxane, a halogenated hydrocarbon such as dichloromethane and 1,2-dichloroethane or an aromatic hydrocarbon such as benzene, toluene and xylene, preferably an ether) at 0° C. to 50° C. (preferably at about room temperature) for 30 minutes to 5 hours (preferably 1 hour to 2 hours).

Meanwhile, in the case where the protective group is a halogenoacetyl group, it is eliminated by reacting the corresponding compound with thiourea in an inert solvent (for example, an amide such as dimethylformamide and dimethylacetamide or a sulfoxide such as dimethyl sulfoxide, preferably an amide) at 0° C. to 50° C. (preferably at about room temperature) for 30 minutes to 5 hours (preferably 1 hour to 2 hours).

Moreover, in the case where the protective group is a benzyl group which may be optionally substituted or a benzyloxycarbonyl group which may be optionally substituted, it is eliminated by reacting the corresponding compound with hydrogen (preferably 1 to 3 atm.) in an inert solvent (for example, an ether such as ether, tetrahydrofuran and dioxane, an alcohol such as methanol and ethanol, preferably an alcohol) in the presence of a catalytic reduction catalyst (for example, palladium-carbon, platinum oxide) at 0° C. to 50° C. (preferably at about room temperature) for 30 minutes to 10 hours (preferably 1 hour to 5 hours).

After completion of the reaction, the desired compound in each reaction is collected from the reaction mixture by conventional procedures, for example, by collecting the precipitated crystal by filtration, after the insolubles are removed by filtration, if necessary; or by removing the insolubles by filtration, if necessary, neutralizing, if necessary, distilling off the solvent, adding water to the reaction mixture, extracting with a water-immiscible organic solvent such as ethyl acetate, drying the organic layer and then evaporating the extracting solvent. If necessary, the compound thus obtained can be further purified by conventional procedures, for example, recrystallization and column chromatography.

Method B is another method to prepare the compound (I).

Step B1 is a step to prepare a compound having the general formula (V) by reacting the compound (II) or a reactive derivative thereof (an acid halide, a mixed acid anhydride or an active ester) with a compound having the general formula (IV) or an acid addition salt thereof in an inert solvent. The present step is carried out, for example, by the acid halide method, the mixed acid anhydride method, the active ester method or the condensation method, and ig carried out in the similar manner to that in the former stage of Step A1 of Method A.

Step B2 is a step to prepare a compound having the general formula (I) and is carried out by reacting the compound having the general formula (V) with a nitrating agent in the absence of a solvent or in an inert solvent and eliminating the protective group such as an amino group etc. of the resulting compound.

The nitrating agent employable here may include, for example, fuming nitric acid, nitrocollidium tetrafluoroboron, thionylchloride nitric acid, thionylnitric acid and nitronium tetrafluoroboron and preferably fuming nitric acid, nitrocollidium tetrafluoroboron or thionylchloride nitric acid.

The inert solvent employable here is not particularly limited so long as it does not affect the reaction and may include, for example, hydrocarbons such as hexane, cyclohexane, benzene, toluene and xylene, halogenated hydrocarbons such as dichloromethane, 1,2-dichloroethane and carbon tetrachloride, ethers such as ether, tetrahydrofuran and dioxane, ketones such as acetone, nitrites such as acetonitrile, amides such as N,N-dimethylformamide, N,N-dimethylacetamide, N-methyl-2-pyrrolidone and hexamethylphosphoramide and sulfoxides such as dimethyl sulfoxide, preferably halogenated hydrocarbons, ethers, nitrites or amides and particularly preferably nitrites.

The reaction temperature varies depending on the starting compound (V), the kind of nitrating agent, etc. and is usually −20° C. to 50° C. (preferably about room temperature). The reaction time varies depending on the reaction temperature etc. and is usually 30 minutes to 24 hours (preferably 1 hour to 10 hours).

The protective group for the amino or imino group is eliminated after completion of the above reaction in the same manner as in the latter stage of Step A1 of Process A.

After completion of the reaction, the desired compound in each reaction is collected from the reaction mixture by conventional procedures. For example, the desired compound can be obtained by collecting the precipitated crystal by filtration; or by neutralizing, if necessary, distilling off the solvent, adding water to the reaction mixture, extracting with a water-immiscible organic solvent such as ethyl acetate, drying the organic layer and evaporating off the extracting solvent. If necessary, the compound thus obtained can be further purified by conventional procedures, for example, recrystallization and column chromatography.

The starting compound (II) is known or is easily prepared according to known methods [for example, Aust. J. Chem., 21, 1891 (1.968), J. Chem. Soc., 4614 (1958), NIHON YAKUGAKU ZASSHI (Japanese Journal of Pharmacy), 73, 949 (1953), Ciemische, Berichte, 91, 160 (1958), NIHON KAGAKU ZASSHI (Japanese Journal of Chemistry), 82, 1075 (1961) or Japanese Unexamined Patent Publication No. (KOKAI) Hei-5-213910].

The starting compounds (III) and (IV) are known or are easily prepared according to known methods [for example, J. Chem. Soc. Perkin. Trans., 1, 1770 (1979), Tetrahedron Lett., 4285 (1970), Heterocycles, 34, 739 (1992), Chem. Abst. 66, 62144w (1967) and the like].

The starting compounds (III) and (IV) are also prepared according to the following processes.

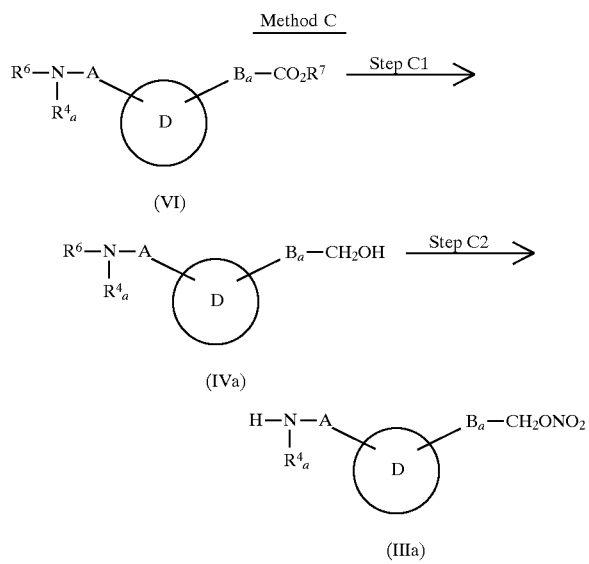

-continued
Method D
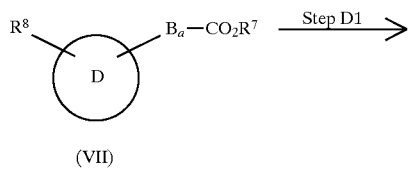
(VII)
Step D1 →
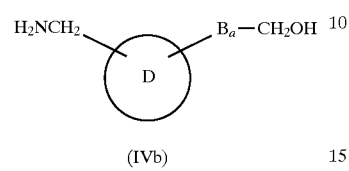
(IVb)
Method E
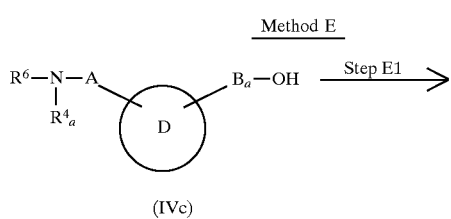
(IVc)
Step E1 →
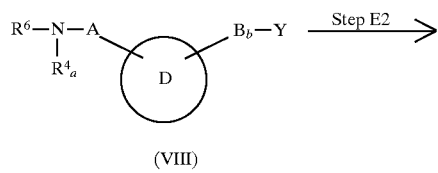
(VIII)
Step E2 →
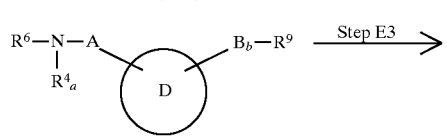
(IX)
Step E3 →
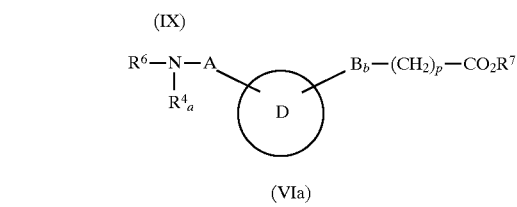
(VIa)
Method F
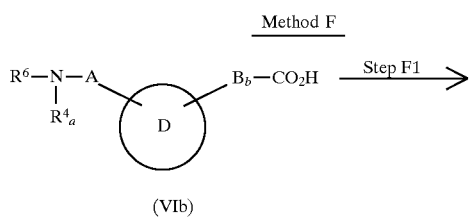
(VIb)
Step F1 →
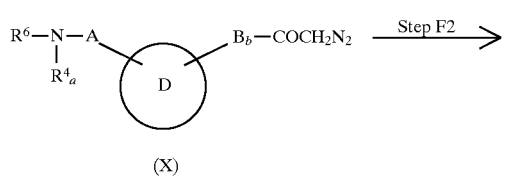
(X)
Step F2 →
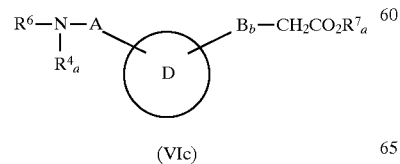
(VIc)
-continued
Method G
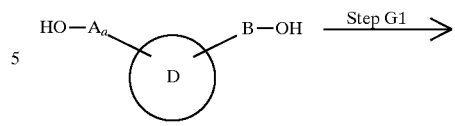
(XI)
Step G1 →
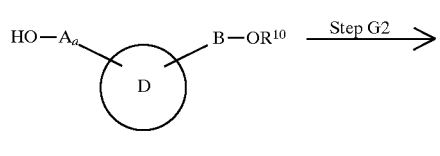
(XII)
Step G2 →
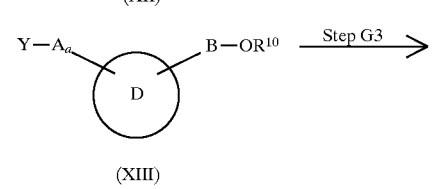
(XIII)
Step G3 →
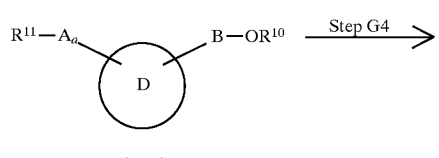
(XIV)
Step G4 →
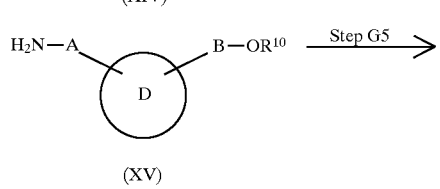
(XV)
Step G5 →
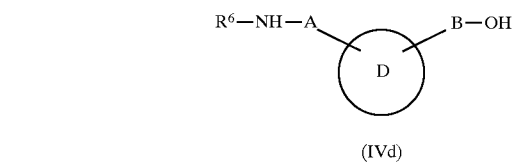
(IVd)
Method H
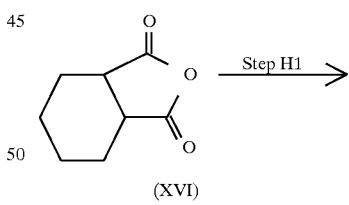
(XVI)
Step H1 →
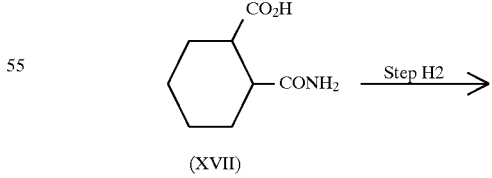
(XVII)
Step H2 →
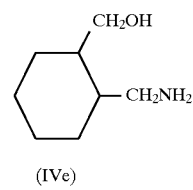
(IVe)

Method I

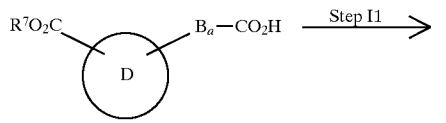

(XVIII)

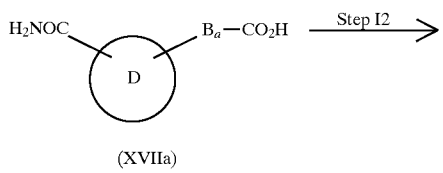

(XVIIa)

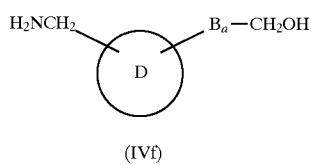

(IVf)

Method J

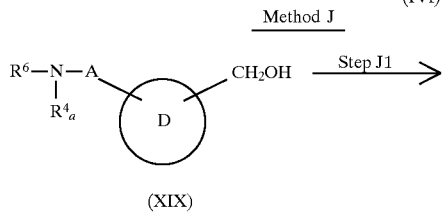

(XIX)

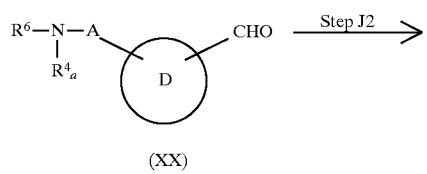

(XX)

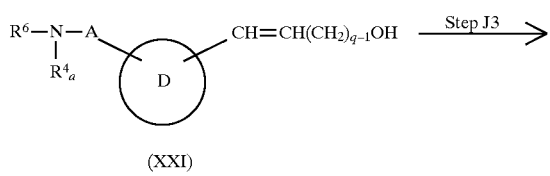

(XXI)

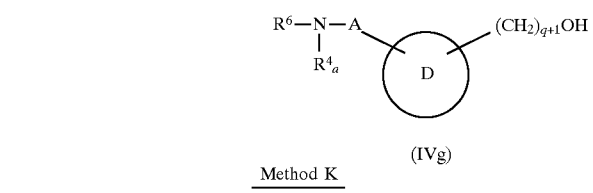

(IVg)

Method K

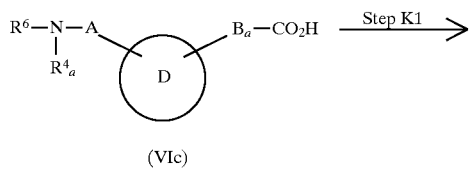

(VIc)

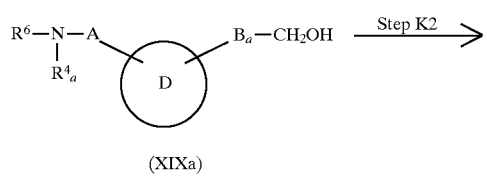

(XIXa)

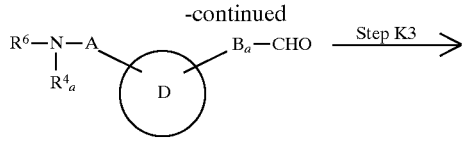

(XXa)

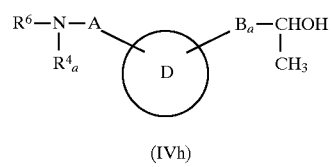

(IVh)

In the above formulae, $R^4a$, A and B have the same meanings as defined above; $R^6$ represents a hydrogen atom or an amino protective group; $R^7$ represents a hydrogen atom, a $C_1$–$C_6$ alkyl group or a $C_1$–$C_6$ alkanoyl group (for example, a formyl, acetyl, propionyl, butyryl, isobutyryl, valeryl, isovaleryl or hexanoyl group, preferably an acetyl, propionyl, butyryl or isobutyryl group and particularly preferably an isobutyryl group); $R^7a$ represents a hydrogen atom or a $C_1$–$C_6$ alkyl group; $R^8$ represents a carbamoyl group or a cyano group; $R^9$ represents a cyano group or a group having the formula: —$CH(CO_2R^7a)_2$ (wherein $R^7a$ has the same meaning as defined above); $R^{10}$ represents a hydroxy-protective group (for example, a 5- or 6-membered cyclic ether group such as 2-tetrahydrofuryl, 2-tetrahydropyranyl, 4-methoxy-2-tetrahydropyranyl and 2-tetrahydrothiopyranyl, a tri-$C_1$–$C_4$ alkylsilyl group such as trimethylsilyl, triethylsilyl and t-butyldimethylsilyl, a benzyl group which may be optionally substituted with $C_1$–$C_6$ alkyl, $C_1$–$C_6$ alkoxy or halogen such as benzyl, methylbenzyl, methoxybenzyl, fluorobenzyl and chlorobenzyl, a benzyloxycarbonyl group which may optionally be substituted with $C_1$–$C_6$ alkyl, $C_1$–$C_6$ alkoxy or halogen such as benzyloxycarbonyl, methylbenzyloxycarbonyl, methoxybenzyloxycarbonyl, fluorobenzyloxycarbonyl and chlorobenzyloxycarbonyl and preferably a 2-tetrahydropyranyl, t-butyldimethylsilyl or p-methoxybenzyloxycarbonyl group); $R^{11}$ represents a cyano group or an azide group; Aa represents a single bond or a $C_1$–$C_5$ alkylene group; Ba represents a single bond or a $C_1$–$C_5$ alkylene group; Bb represents a single bond or a $C_1$–$C_4$ alkylene group; the group having the formula:

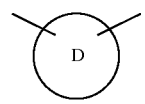

represents a $C_3$–$C_8$ cycloalkylene group containing optionally a nitrogen atom which may be optionally protected and being optionally substituted by a $C_1$–$C_6$ alkyl group; Y represents a halogen atom (preferably a chlorine atom or a bromine atom), a $C_1$–$C_6$ alkylsulfonyloxy group (preferably a methanesulfonyloxy group or an ethanesulfonyloxy group) or an arylsulfonyloxy group (preferably a benzenesulfonyloxy group or a toluenesulfonyloxy group); p represents 0 or 1; and q represents 2 or 3.

Method C is a method to prepare a compound of formula (IIIa) which corresponds to a compound of formula (III) in which $R^5a$ is a substituted $C_3$–$C_8$ cycloalkyl group containing optionally a nitrogen atom which may optionally be protected (the substituent is essentially a group having the formula: —Ba—$CH_2ONO_2$ (wherein Ba has the same meaning as defined above) and desirably a $C_1$–$C_6$ alkyl group).

Step C1 is a step to prepare a compound having the general formula (IVa) and is carried out by reacting an aminocarboxylic acid having the general formula (VI) with a reducing agent (preferably a boron hydride compound such as sodium borohydride and sodium borocyanohydride and an aluminum hydride compound such as lithium aluminum hydride) in an inert solvent (preferably an ether such as ether and tetrahydrofuran) at 0° C. to 50° C. (preferably at about room temperature) for 30 minutes to 10 hours (preferably 1 hour to 5 hours). Meanwhile, an amino group, etc. in a compound (IV) where $R^6$ is a hydrogen atom can be also protected by reacting the compound with t-butyl chloride, t-butoxycarbonyl chloride, t-butoxycarbonyl bromide, benzyl chloride which may optionally be substituted with $C_1$–$C_6$ alkyl, $C_1$–$C_6$ alkoxy or halogen, benzyloxycarbonyl chloride which may optionally be substituted with $C_1$–$C_6$ alkyl, $C_1$–$C_6$ alkoxy or halogen, halides such as chloroacetyl chloride, bromoacetyl bromide and iodoacetyl chloride or dicarbonate such as di-t-butyl dicarbonate, dibenzyl dicarbonate and di($C_1$–$C_6$ alkyl, $C_1$–$C_6$ alkoxy or halogenobenzyl) dicarbonate in an inert solvent (preferably ethers such as ether and tetrahydrofuran or alcohols such as methanol and ethanol) in the presence or absence of a base (preferably amines such as triethylamine and pyridine) at 0° C. to 50° C. (preferably at about room temperature) for 30 minutes to 10 hours (preferably 1 hour to 5 hours).

Step C2 is a step to prepare the compound (IIIa) and is carried out by nitrating the compound (IVa) and if necessary, by eliminating the protective group such as for an amino group etc. The present step is carried out in a similar manner to Step B2 of the above Method B. Meanwhile, in the reaction for eliminating the protective group such as for an amino group etc., the protective group can also be selectively eliminated by selecting reaction conditions depending on the kind of the protective group.

Method D is another method to prepare a compound (IVb) which corresponds to a compound (IVa) in which a group having the formula: $R^6$—N($R^4$a)—A— (wherein $R^4$a, $R^6$ and A have the same meanings as defined above) is an aminomethyl group.

Step D1 is a step to prepare a compound having the general formula (IVb) and is carried out by reacting the compound having the general formula (VII) with a reducing agent (for example, preferably a boron hydride compound such as sodium borohydride and sodium borocyanohydride or an aluminum hydride compound such as lithium aluminum hydride) in an inert solvent (preferably an ether such as ether and tetrahydrofuran) at 0° C. to 150° C. (preferably at 30° C. to 100° C.) for 15 minutes to 10 hours (preferably 30 minutes to 5 hours). Meanwhile, the compound (IVb) can be prepared by catalytic reduction of Step A1 of the above Method A.

Method E is a method to prepare a compound (VIa) which corresponds to the compound (VI) in which the group having the formula: —Ba—$CO_2R^7$ (wherein $R^7$ and Ba have the same meanings as defined above) is a group having the formula: —Bb—$(CH_2)_p CO_2R^7$ (wherein $R^7$, Bb and p have the same meanings as defined above).

Step E1 is a step to prepare a compound having the general formula (VIII) and is carried out by reacting the compound of formula (IVc) with halides such as thionyl chloride, phosphorous trichloride, phosphorous tribromochloride, phosphorous oxychloride, methanesulfonyl chloride, ethanesulfonyl chloride, benzenesulfonyl chloride, benzenesulfonyl bromide and p-toluenesulfonyl chloride or sulfonic anhydrides such as methanesulfonic anhydride, ethanesulfonic anhydride, benzenesulfonic anhydride and p-toluenesulfonic anhydride in an inert solvent (preferably ethers such as ether and tetrahydrofuran or halogenated hydrocarbons such as methylene chloride and chloroform) in the presence or absence of a base (preferably amines such as triethylamine and pyridine) at 0° C. to 50° C. (preferably at about room temperature) for 30 minutes to 10 hours (preferably 1 hour to 5 hours). Meanwhile, the corresponding halide can be also prepared by reacting the obtained sulfonyloxy compound with an alkali metal halide such as sodium bromide and sodium iodide in an inert solvent (preferably ketones such as acetone or amides such as dimethylformamide and dimethylacetamide) at 0° C. to 50° C. (preferably at about room temperature) for 30 minutes to 20 hours (preferably 1 hour to 10 hours).

Step E2 is a step to prepare a compound having the general formula (IX) and is carried out by reacting a compound (VIII) with an alkali metal cyanide such as lithium cyanide, sodium cyanide and potassium cyanide or a malonic acid derivative having the formula: $M^{+-}CH(CO_2R^7a)_2$ (wherein $R^7a$ has the same meaning as defined above and M represents an alkali metal atom) in an inert solvent (preferably ethers such as ether and tetrahydrofuran or amides such as dimethylformamide and dimethylacetamide) at 0° C. to 50° C. (preferably at about room temperature) for 30 minutes to 10 hours (preferably 1 hour to 5 hours).

Meanwhile, the present step is also carried out preferably in the presence of sodium iodide.

Step E3 is a step to prepare the compound (VIa) and a compound which corresponds to the compound (VIa) in which $R^7$ is a hydrogen atom and p is 0 is prepared by reacting a compound which corresponds to the compound (IX) in which $R^9$ is a cyano group with an acid (preferably a mineral acid such as hydrochloric acid, nitric acid and sulfuric acid) in an aqueous solution at 0° C. to 150° C. (preferably 30° C. to 120° C.) for 30 minutes to 10 hours (preferably 1 hour to 5 hours). Meanwhile, a compound which corresponds to the compound (VIa) in which $R^7$ is a hydrogen atom and p is 1 is prepared, if desired, by reacting a compound which corresponds to the compound (IX) in which $R^9$ is a group having the formula —$CH(CO_2R^7a)_2$ (wherein $R^7a$ has the same meaning as defined above) with a base (preferably alkali metal hydroxides such as lithium hydroxide, sodium hydroxide and potassium hydroxide) in an inert solvent (preferably aqueous ethers such as aqueous ether and aqueous tetrahydrofuran or aqueous alcohols such as aqueous methanol and aqueous ethanol) at 0° C. to 50° C. (preferably at about room temperature) for 30 minutes to 10 hours (preferably 1 hour to 5 hours) to hydrolize, and then by heating in an inert solvent (preferably aromatic hydrocarbons such as benzene, toluene and xylene) at 50° C. to 200° C. (preferably 100° C. to 150° C.) for 30 minutes to 10 hours (preferably 1 hour to 5 hours).

Moreover, the corresponding ester can be prepared, if desired, by reacting the thus obtained carboxylic acid compound with a diazo $C_1$–$C_6$ alkyl such as diazomethane, dizaoethane and diazohexane in an inert solvent (preferably ethers such as ether and tetrahydrofuran) at 0° C. to 50° C. (preferably at about room temperature) for 5 minutes to 2 hours (preferably 10 minutes to 1 hour) or by reacting the thus obtained carboxylic acid compound with a $C_1$–$C_6$ alcohol such as methanol, ethanol and hexanol in a similar manner to that of Step A1 of the above Method A. The corresponding acyl compound can be obtained by reacting the carboxylic acid compound with a $C_1$–$C_6$ alkyl halogenocarbonate in the similar manner to in the preparation process of the mixed acid anhydride in Step A1 of the above Method A.

Method F is another method to prepare a compound (VIc) which corresponds to the compound (VIa) in which p is 1.

Step F1 is a step to prepare a compound having the formula (X) and is carried out by reacting the starting compound with a $C_1$–$C_6$ alkyl halogenocarbonate such as methyl chlorocarbonate, ethyl chlorocarbonate, isobutyl chlorocarbonate and hexyl chlorocarbonate in an inert solvent (preferably ethers such as ether and tetrahydrofuran and halogenated hydrocarbons such as methylene chloride and chloroform) in the presence or absence of a base (preferably amines such as triethylamine, pyridine and N-methylmorpholine) at −50° C. to 50° C. (preferably −20° C. to 0° C.) for 30 minutes to 10 hours (preferably 1 hour to 5 hours) and by then reacting the resulting product with diazomethane in an inert solvent (preferably ethers such as ether and tetrahydrofuran and halogenated hydrocarbons such as methylene chloride and chloroform) at −50° C. to 50° C. (preferably −20° C. to 0° C.) for 30 minutes to 10 hours (preferably 1 hour to 5 hours).

Step F2 is a step to prepare a compound (VIc) and is carried out by reacting the compound (X) with excess amount of water or $C_1$–$C_6$ alcohol serving also as an inert solvent in the presence of a silver compound such as a silver carboxylate such as silver acetate and silver benzoate, a silver sulfonate such as silver methanesulfonate, silver benzenesulfonate and silver p-toluenesulfonate, silver powders and a silver oxide (preferably silver benzoate or silver oxide) in the presence or absence of organic amines (for example, triethylamine and pyridine) at 0° C. to 50° C. (preferably at about room temperature) for 30 minutes to 10 hours (preferably 1 hour to 5 hours). A compound which corresponds to the compound (VIc) in which $R^7a$ is a hydrogen atom is prepared by reacting the compound (X) with water and a compound which corresponds to the compound (VIc) in which $R^7a$ is a $C_1$–$C_6$ alkyl group is prepared by reacting the compound (X) with $C_1$–$C_6$ alcohol. The thus obtained carboxylic acid can be esterified or acylated in a similar manner to that of Step E3 of the above Method E.

Method G is a method to prepare the compound (IVd) which corresponds to the compound (IVa) in which $R^4a$ is a hydrogen atom.

Step G1 is a step to prepare a compound having the general formula (XII) and is carried out by protecting a hydroxyl group of a compound having the general formula (XI). The reaction for protecting a hydroxyl group varies depending on the kind of protective group and is carried out by a reaction well known in the field of synthetic organic chemistry.

In the case where the protective group is a 5- or 6-membered cyclic ether group, a hydroxyl group can be protected by reacting the corresponding compound with an unsaturated ether such as dihydrofuran, dihydropyran, 4-methoxydihydropyran and dihydrothiopyran in an inert solvent (preferably ethers such as ether and tetrahydrofuran and halogenated hydrocarbons such as methylene chloride and chloroform) in the presence of an acid (for example, a mineral acid such as hydrochloric acid, sulfuric acid and nitric acid or organic acids such as acetic acid, trifluoroacetic acid, methanesulfonic acid and p-toluenesulfonic acid, preferably hydrochloric acid) at 0° C. to 50° C. (preferably at about room temperature) for 30 minutes to 5 hours (preferably 1 hour to 2 hours).

In the case where the protective group is a tri-$C_1$–$C_4$ alkylsilyl group, an optionally substituted benzyl group or an optionally substituted benzyloxycarbonyl group, the protection of the hydroxyl group is carried out by reacting the corresponding compound with a halide such as trimethylsilyl chloride, triethylsilyl chloride, t-butyldimethylsilyl chloride, t-butyldimethylsilyl bromide, benzyl chloride, benzyl bromide, methylbenzyl chloride, methoxybenzyl chloride, fluorobenzyl chloride, chlorobenzyl chloride, benzyloxycarbonyl chloride, methylbenzyloxycarbonyl chloride, methoxybenzyloxycarbonyl chloride, fluorobenzyloxycarbonyl chloride and chlorobenzyloxycarbonyl chloride in an inert solvent (preferably ethers such as ether and tetrahydrofuran, halogenated hydrocarbons such as methylene chloride and chloroform, amides such as dimethylformamide and dimethylacetamide or sulfoxides such as dimethyl sulfoxide) in the presence of a base (preferably alkali metal hydrides such as lithium hydride, sodium hydride and potassium hydride or amines such as triethylamine, pyridine and N-methylmorpholine) at 0° C. to 50° C. (preferably at about room temperature) for 30 minutes to 24 hours (preferably 1 hour to 20 hours).

Step G2 is a step to prepare a compound having the general formula (XIII) and is carried out by halogenating or sulfonating the compound (XII). The present step is carried out in the similar manner to in Step E1 of the above Method E.

Step G3 is a step to prepare a compound having the general formula (XIV) and is carried out by reacting the compound (XIII) with alkali metal cyanides such as lithium cyanide, sodium cyanide and potassium cyanide or alkali metal azides such as lithium azide, sodium azide and potassium azide in an inert solvent (preferably ethers such as ether and tetrahydrofuran, amides such as dimethylformamide and dimethylacetamide or sulfoxides such as dimethyl sulfoxide) at 0° C. to 200° C. (preferably 50° C. to 150° C.) for 15 minutes to 20 hours (preferably 30 minutes to 10 hours).

Step G4 is a step to prepare a compound having the general formula (XV) and is carried out by reducing the compound (XIV). The present step is carried out in a similar manner to that of Step D1 of the above Method D.

Step G5 is a step to prepare the compound (IVd) and is carried out by eliminating the hydroxy-protective group from the compound (XV) and if desired, by protecting an amino group.

The hydroxy-protective group is eliminated by a process usually used in the field of synthetic organic chemistry.

In the case where the protective group is a 5- or 6-membered cyclic ether group, a methoxybenzyl group or a methoxybenzyloxycarbonyl group, the protecting group is eliminated by reacting the corresponding compound with an acid. The present reaction is carried out in a similar manner to the elimination reaction in which the protective group for a group such as an amino group etc. is a t-butyl group in Step A1 of the above Method A.

In the case where the protective group is a tri-substituted silyl group, the protecting group is eliminated by reacting the corresponding compound with a compound which produces a fluoride anion such as tetrabutylammonium fluoride in an inert solvent (preferably ethers such as tetrahydrofuran and dioxane) at −10° C. to 50° C. (preferably 0° C. to 30° C.) for 2 hours to 24 hours (preferably 10 hours to 18 hours).

In the case where the protective group is an optionally substituted benzyl group or an optionally substituted benzyloxycarbonyl group, the protecting group is eliminated by subjecting the corresponding compound to catalytic reduction. The present reaction is carried out in a similar manner to the elimination reaction in which the amino-protective group is an optionally substituted benzyl group in Step A1 of the above Method A.

The reaction for protecting an amino group is carried out in a similar manner to that of Step C1 of the above Method C.

Method H is a method to prepare a compound having the general formula (IVe) included in the compound (IVa).

Step H1 is a step to prepare a compound having the general formula (XVII) and is carried out by reacting a compound having the general formula (XVI) with conc. ammonia at 0° C. to 50° C. (preferably at about room temperature) for 30 minutes to 20 hours (preferably 1 hour to 10 hours).

Step H2 is a step to prepare the compound (IVe) and is carried out by reducing the compound (XVII). The present step is carried out in a similar manner to Step D1 of the above Method D.

Method I is a method to prepare a compound having the general formula (IVf) included in the compound (IVa).

Step I1 is a step to prepare a compound having the general formula (XVIIa) and is carried out by reacting a compound having the general formula (XVIII) with conc. ammonia in a similar manner to Step H1 of the above Method H.

Step I2 is a step to prepare the compound (IVf) and is carried out by reducing the compound (XVIIa). The present step is carried out in a similar manner to Step D1 of the above Method D.

Method J is a method to prepare a compound having the general formula (IVg) included in the compound (IVa).

Step J1 is a step to prepare the compound having the general formula (XX) and is carried out by reacting a compound having the general formula (XIX) with an oxidizing agent (for example, chromic acid-pyridine, dimethyl sulfoxide-oxalyl chloride, dimethyl sulfoxide-chlorine gas, dimethyl sulfoxide-trifluoroacetic anhydride and succineimidodimethylsulfonium chloride, preferably dimethyl sulfoxide-oxalyl chloride) in an inert solvent (preferably halogenated hydrocarbons such as dichloromethane and chloroform, amides such as dimethylformamide and dimethylacetamide and sulfoxides such as dimethyl sulfoxide) at 0° C. to 50° C. (preferably at about room temperature) for 15 minutes to 20 hours (preferably 30 minutes to 10 hours).

Step J2 is a step to prepare a compound having the general formula (XXI) and is carried out by reacting the compound (XX) with a compound having the formula: $(R^{12})_3P^+(CH_2)_qOH\ Ya^-$ (wherein q has the same meaning as defined above, $R^{12}$ represents a $C_6$–$C_{10}$ aryl group and Ya represents a halogen atom) in an inert solvent (preferably ethers such as ether and tetrahydrofuran) in the presence of a base (preferably strong basic amines such as 1,5-diazabicyclo[4.3.0]non-5-ene and 1,8-diazabicyclo[5.4.0]undec-7-enene and alkyl lithium such as butyl lithium) at –20° C. to 150° C. (preferably 0° C. to 100° C.) for 1 hour to 10 days (preferably 5 hours to 7 days).

Step J3 is a step to prepare the compound (IVg) and is carried out by subjecting the compound (XXI) to catalytic reduction in a similar manner to that of Step A1 of the above Method A.

Method K is a method to prepare a compound having the general formula (Ivh) included in the compound (IVa).

Step K1 is a step to prepare a compound having the general formula (XIXa) and is carried out by reducing a compound having the general formula (VIc). The present step is carried out in a similar manner to Step D1 of the above Method D.

Step K2 is a step to prepare the compound (XXa) and is carried out by oxidizing the compound (XIXa). The present step is carried out in a similar manner to Step J1 of Method J.

Step K3 is to prepare the compound (Ivh) and is carried out by reacting the compound (XXa) with Grignard reagent such as methylmagnesium chloride and methylmagnesium bromide in an inert solvent (preferably ethers such as ether and tetrahydrofuran) at –20° C. to 50° C. (preferably 0° C. to 30° C.) for 10 minutes to 5 hours (preferably 15 minutes to 2 hours).

After completion of the reaction, the desired compound in each reaction is collected from the reaction mixture by conventional procedures. For example, the desired compound can be obtained by collecting the precipitated crystal by filtration; or by removing insolubles, if necessary, if the reaction mixture contains insolubles, neutralizing the reaction solution, if necessary, if the reaction solution is acidic or alkaline, extracting with a water-immiscible organic solvent such as ethyl acetate, drying the organic layer and evaporating the extracting solvent. If necessary, the desired compound can be further purified by conventional procedures, for example, recrystallization and column chromatography.

The starting compounds (VI), (VII), (XI), (XVI) and (XVIII) are known or easily prepared by the known procedures (for example, Chem. Abst. 64, 3379f (1966), Chemische, Berichte, 67, 1783 (1934), Chemische, Berichte, 71, 759 (1938), J. Am. Chem. Soc., 62, 2891 (1940), J. Am. Chem. Soc., 82, 3257 (1960), J. Am. Chem. Soc., 88, 3522 (1966), Tetrahedron, 21, 2725 (1965), Tetrahedron, 48, 9753 (1992), etc.)

The starting compound (III) can easily be prepared by reacting the compound (IV) in a similar manner to that of Step B2 of Method B.

EFFECT OF THE INVENTION

The compound having the general formula (I) or a pharmacologically acceptable salt thereof of the present invention exhibits a potent collateral vessel dilating effect without causing adverse side effects such as headache, dizziness, tachycardia or detrimental effects on the digestive system, liver, bone etc., and it does not undergo the first-pass effect. Therefore, it is useful as a therapeutic agent and a preventing agent (preferably a therapeutic agent) for angina pectoris.

INDUSTRIAL APPLICABILITY

In the case where the compound (I) of the present invention and a pharmacologically acceptable salt thereof are used as a therapeutic agent or a preventing agent for angina pectoris, the compound or its mixture with a suitable pharmacologically acceptable excipient or diluent can be administered orally or parenterally either in the form of a tablet, a capsule, a granule, a powder, a syrup or an injection preparation.

These preparations are prepared by known methods using additives such as excipients (for example, sugar derivatives such as lactose, sucrose, glucose, mannitol and sorbitol; starch derivatives such as corn starch, mashed potato starch, α-starch, dextrine and carboxymethyl starch; cellulose derivatives such as crystalline cellulose, low hydroxypropyl-substituted cellulose, hydroxypropylmethyl cellulose, carboxymethyl cellulose, carboxymethyl cellulose calcium and internally bridged carboxymethyl cellulose sodium; gum arabic; dextran; Pullulan; silicate derivatives such as light silicic acid anhydride, synthetic aluminium silicate and magnesium meta-silicic acid aluminate; phosphate derivatives such as calcium phosphate; carbonate derivatives such as calcium carbonate; and sulfate derivatives such as calcium sulfate), binders (for example, the above excipients; gelatin; polyvinylpyrrolidone; and Macrogol); disintegrating agents (for example, the above excipients; chemically modified starch-cellulose derivatives such as Crosscarmelose sodium, sodium carboxymethyl starch and bridged polyvinylpyrrolidone), lubricants (for example, talc; stearic acid; and metal stearates such as calcium stearate and magnesium stearate; colloidal silica; waxes such as beeswax and spermaceti; boric acid; glycol; carboxylic acis such as fumaric acid and adipic acid; sodium carboxylate such as sodium benzoate; sulfates such as sodium sulfate; leucine; lauryl sulfates such as sodium laurylsulfate and magnesium laurylsulfate; silicic acids such as silicic acid anhydride and silicic acid hydrate; and starch derivatives in the above excipients), stabilizers (for example, p-hydroxybenzoates such as methylparaben and propylparaben; alcohols such as chlorobutanol, benzyl alcohol and phenylethyl alcohol; benzalkonium chloride; phenols such as phenol and cresol; thimerosal; acetic anhydride; and sorbic acid); corrigents (for example, sweeteners, sour agents and perfumes conventionally used), diluents and solvents for injection agents (for example, water, ethanol and glycerin). While the dose varies depending on the condition and age of the patient to be treated, it is desirably administered 1 to 6 times daily depending on the condition: in the case of oral administration, the lower limit is 1 mg each time (preferably 5 mg) and the upper limit is 1000 mg (preferably 300 mg) for an adult; and in the case of intravenous administration, the lower limit is 0.1 mg each time (preferably 0.5 mg) and the upper limit is 100 mg (preferably 50 mg) for an adult.

BEST MODE FOR PRACTICING THE INVENTION

The present invention will be described below more specifically by way of Examples, Reference examples, Test examples and Preparation examples, but the invention is not limited thereto.

EXAMPLE 1

N-[Trans-4-nitroxymethylcyclohexylmethyl]-(4R)-2-oxothiazolidin-4-yl-carboxamide (Exemplary Compound No. 1-32)

In 7 ml of dry benzene was suspended 0.35 g of (4R)-2-oxo-4-thiazolidinecarboxylic acid, and 0.42 ml of oxalyl chloride and a few drops of dimethylformamide were added thereto at room temperature and stirred at room temperature for 2 hours. The solvent was distilled off under reduced pressure to obtain the acid chloride as a pale yellow oil.

Meanwhile, 0.51 g of trans-4-nitroxymethylcyclohexylmethylamine hydrochloride was suspended in 10 ml of dry dichloromethane, and 0.95 ml of triethylamine and 5 ml of a solution of the acid chloride in dry dichloromethane were added dropwise thereto with stirring under ice-cooling and stirred at the same temperature for 1 hour. The solvent was distilled off under reduced pressure. The residue was subjected to silica gel column chromatography employing ethyl acetate as an eluting solvent to separate and purify and crystallized from ether to obtain 0.30 g of the desired compound as a colorless crystalline solid.

m.p.: 117°–119° C. (decomp.); NMR spectrum (CDCl$_3$+d$_6$-DMSO) δ ppm: 0.90–1.15(4H,m), 1.40–1.60(1H,m), 1.60–1.95(5H,m), 3.14(2H,m), 3.60–3.78(2H,m), 4.20–4.38(3H,m), 7.10(1H,bs), 7.67(1H,bs)

EXAMPLE 2

N-[Cis-4-nitroxymethylcyclohexylmethyl]-(4R)-2-oxothiazolidin-4-yl-carboxamide (Exemplary Compound No. 1-32)

In 8 ml of dry tetrahydrofuran was suspended 0.40 g of (4R)-2-oxo-4-thiazolidinecarboxylic acid and 0.73 g of cis-4-nitroxymethylcyclohexylmethylamine hydrochloride, and 1.14 ml of triethylamine and 0.70 ml of diphenylphosphoric azide were added thereto with stirring under ice-cooling, and the resulting mixture was stirred at room temperature for 4 hours. The solvent was distilled off under reduced pressure and the residue was purified by silica gel column chromatography (eluting solvent: cyclohexane/ethyl acetate=2/1). The thus obtained yellow oil was treated with ether to obtain 0.69 g of a pale yellow crystalline solid. The pale yellow crystalline solid was dissqlved in acetone, ethyl acetate was added thereto, acetone was distilled off under reduced pressure, and the residue was allowed to stand at room temperature to obtain 0.44 g of the desired compound as a colorless columnar crystalline solid.

m.p.: 94°–96° C. (decomp.); NMR spectrum (CDCl$_3$+d$_6$-DMSO) δ ppm: 1.30–1.65(8H,m), 1.65–1.83(1H,m), 1.87–2.05(1H,m), 3.13–3.35(2H,m), 3.60–3.76(2H,m), 4.23–4.33(1H,m), 4.38(2H,J=7 Hz), 7.05–7.20(1H,bm), 7.69(1H,s)

EXAMPLE 3

N-[Trans-4-(2-nitroxyethyl)cyclohexylmethl]-(4R)-2-oxothiazolidin-4-yl-carboxamide (Exemplary Compound No. 1-169)

In 20 ml of anhydrous tetrahydrofuran was suspended 191 mg of (4R)-2-oxo-4-thiazolidinecarboxylic acid and 294 mg of trans-4-(2-nitroxyethyl)cyclohexylmethylamine hydrochloride, and 0.54 ml of triethylamine and 0.28 ml of diphenylphosphoric azide were added thereto with stirring under ice-cooling, and the resulting mixture was stirred at room temperature for 4 hours. The solvent was distilled off under reduced pressure, and the residue was purified by silica gel column chromatography (eluting solvent: cyclohexane/ethyl acetate=1/3) and recrystallizated from dichloromethane-diisopropyl ether to obtain 200 mg of the desired compound as a colorless crystalline solid.

m.p.: 78°–80° C.; NMR spectrum (CDCl$_3$) δ ppm: 0.82–1.08(4H,m), 1.25–1.90(8H,m), 3.05–3.23(2H,m), 3.66 (1H,dd,J=4.6 Hz,J=11.2 Hz), 3.84(1H,dd,J=8.6 Hz,J=11.2 Hz), 4.32–4.40(1H,m), 4.51(2H,t, J=6.6 Hz), 6.50–6.70(2H, m)

EXAMPLE 4

N-[Trans-4-(3-nitroxypropyl)cyclohexylmethl]-(4R)-2-oxothiazolidin-4-yl-carboxamide (Exemplary Compound No. 1-900)

898 mg of the desired compound were obtained as a colorless crystalline solid using similar procedures to those in Example 3 by using 908 mg of (4R)-2-oxo-4-thiazolidinecarboxylic acid and 1.30 g of trans-4-(3-nitroxypropyl)cyclohexylmethylamine hydrochloride.

m.p.: 110°–112° C.; NMR spectrum (CDCl$_3$) δ ppm: 0.80–1.08(4H,m), 1.10–1.90(10H,m), 3.05–3.25(2H,m), 3.63(1H,dd,J=4.5 Hz,J=11 Hz), 3.81(1H,dd,J=8.6 Hz,J=11 Hz), 4.30–4.40(1H,m), 4.43(2H,t,J=6.7 Hz), 6.45–6.70(2H, m)

EXAMPLE 5

N-[Trans-4-(1-nitroxyethyl)cyclohexylmethyl]-(4R)-2-oxothiazolidin-4-yl-carboxamide (Exemplary Compound No. 1-1201)

305 mg of the desired compound were obtained as a colorless crystalline solid using similar procedures to those in Example 3 by using 311 mg of (4R)-2-oxo-4-thiazolidinecarboxylic acid and 421 mg of trans-4-(1-nitroxyethyl)cyclohexylmethylamine hydrochloride.

m.p.: 85°–87° C. (decomp.); NMR spectrum (CDCl$_3$) δ ppm: 0.85–1.25(5H,m), 1.32(3H,d,J=5.9 Hz), 1.40–1.67 (2H,m), 1.70–1.97(4H,m), 3.10–3.28(2H,m), 3.62(1H,dd, J=4 Hz,J=11 Hz), 3.82(1H,dd,J=8.6 Hz,J=11 Hz), 4.32–4.40 (1H,m), 4.86–5.00(1H,m), 6.26(1H,s), 6.48(1H,bs)

EXAMPLE 6

N-[Trans-1-(4-nitroxymethylcyclohexyl)ethyl]-(4R)-2-oxothiazolidin-4-yl-carboxamide (Exemplary Compound No. 1-1192)

The desired compound, two isomers (based on an asymmetric carbon atom to which the methyl group is bonded), i.e. 110 mg of isomer A and 85 mg of isomer B were obtained as a colorless crystalline solid, respectively using similar procedures to those in Example 3 by using 300 mg of (4R)-2-oxo-4-thiazolidinecarboxylic acid and 400 mg of trans-1-(4-nitroxymethylcyclohexyl)ethylamine hydrochloride.

Isomer A

Thin layer chromatography: Rf=0.27 (developing solvent: cyclohexane/ethyl acetate=1/2); m.p.: 147°–150° C. (decomp.); NMR spectrum (CDCl$_3$) δ ppm: 0.92–1.20(4H, m), 1.13(3H,d,J=6.6 Hz), 1.30–1.95(6H,m), 3.63(1H,dd,J= 4.6 Hz,J=11 Hz), 3.80(1H,dd,J=8.6 Hz,J=11 Hz), 3.89(1H, dd,J=6.6 Hz,J=16 Hz), 4.27(2H,d,J=6.6 Hz), 4.30–4.42(1H, m), 6.23(1H,d,J=8.6 Hz), 6.54(1H,s)

Isomer B

Thin layer chromatography: Rf=0.14 (developing solvent: cyclohexane/ethyl acetate=1/2)

m.p.: 131°–133° C. (decomp.); NMR spectrum (CDCl$_3$) δ ppm: 0.92–1.20(4H,m), 1.14(3H,d,J=6.6 Hz), 1.25–1.96 (6H,m), 3.60(1H,dd,J=4 Hz,J=11 Hz), 3.84(1H,dd,J=8.6 Hz,J=11 Hz), 3.87–4.00(1H,m), 4.33(2H,d,J=6.6 Hz), 4.30–4.40(1H,m), 6.06 (1H,s), 6.24(1H,d,J=8.6 Hz)

EXAMPLE 7

N-[Trans-4-(1-methyl-2-nitroxyethyl)cyclohexylmethyl]-(4R)-2-oxothiazolidin-4-yl-carboxamide (Exemplary Compound No. 1-1210)

91 mg of the desired-compound were obtained as a colorless oil using similar procedures to those in Example 3 by using 76.9 mg of (4R)-2-oxo-4-thiazolidinecarboxylic acid and 110 mg of trans-4-(1-methyl-2-nitroxyethyl)cyclohexylmethylamine hydrochloride.

NMR spectrum (d$_6$-DMSO) δ ppm: 0.78–1.45(6H,m), 0.89(3H,d,J=6.9 Hz), 2.94(2H,t,J=6.2 Hz), 3.25–3.40(1H, m), 3.65(1H,dd,J=8.5 Hz,J=11 Hz), 4.22–4.40(2H,m), 4.45–4.57(1H,m), 8.00(1H,t,J=5.6 Hz), 8.25(1H,s)

EXAMPLE 8

N-[Trans-2-(4-nitroxymethylcyclohexyl)ethyl]-(4R)-2-oxothiazolidin-4-yl-carboxamide (Exemplary Compound No. 1-65)

221 mg of the desired compound were obtained as a colorless crystalline solid using similar procedures to those in Example 3 by using 152 mg of (4R)-2-oxo-4-thiazolidinecarboxylic acid and 205 mg of trans-2-(4-nitroxymethylcyclohexyl)ethylamine hydrochloride.

m.p.: 82°–84° C.; NMR spectrum (CDCl$_3$) δ ppm: 0.85–1.55(7H,m), 1.62–1.90(5H,m), 3.20–3.43(2H,m), 3.64 (1H,d,d,J=4.6 Hz,J=11 Hz), 3.79(1H,dd,J=8.6 Hz,J=11 Hz), 4.27(2H,d,J=6.4 Hz), 4.30–4.40(1H,m), 6.71(1H,t,J=5.3 Hz), 7.05(1H,s)

EXAMPLE 9

N-[Trans-2-[4-(3-nitroxypropyl)cyclohexyl]ethyl]-(4R)-2-oxothiazolidin-4-yl-carboxamide (Exemplary Compound No. 1-207)

83 mg of the desired compound were obtained as a colorless crystalline solid using similar procedures to those in Example 3 by using 98.6 mg of (4R)-2-oxo-4-thiazolidinecarboxylic acid and 149 mg of trans-2-[4-(3-nitroxypropyl)cyclohexyl)ethylamine hydrochloride to obtain.

m.p.: 101°–103° C. (decomp.); NMR spectrum (d$_6$-DMSO) δ ppm: 0.75–0.98(4H,m), 1.10–1.38(6H,m), 1.60–1.80(6H,m), 3.05–3.17(2H,m), 3.20–3.38(1H,m), 3.64 (1H,dd,J=8.3 Hz,J=11 Hz), 4.17–4.28(1H,m), 4.49(2H,t,J= 6.6 Hz), 7.99(1H,t,J=5.4 Hz), 8.25(1H,s)

EXAMPLE 10

N-(3-Nitroxymethylcyclohexyl)-(4R)-2-oxothiazolidin-4-yl-carboxamide (Exemplary Compound No. 1-669)

The desired compound, two isomers, i.e. 301 mg of isomer A and 231 mg of isomer B were obtained as a colorless crystalline solid, respectively using similar procedures to those in Example 3 by using 1.05 g of (4R)-2-oxo-4-thiazolidinecarboxylic acid and 1.67 g of 3-nitroxymethylcyclohexylamine hydrochloride.

Isomer A

Thin layer chromatography: Rf=0.52 (developing solvent: ethyl acetate); m.p.: 173°–177° C. (decomp.); NMR spectrum (CDCl$_3$+d$_6$-DMSO) δ ppm: 0.90–1.50(4H,m), 1.72–2.10(5H,m), 3.60–3.90(3H,m), 4.22–4.40(3H,rm), 6.97(1H,d,J=7.9 Hz), 7.59(1H,s)

Isomer B

Thin layer chromatography: Rf=0.43 (developing solvent: ethyl acetate); m.p.: 141°–143° C (decomp.); NMR spectrum (CDCl$_3$+d$_6$-DMSO) δ ppm: 0.88–1.52(4H,m), 1.70–2.25(5H,m), 3.60–3.90(3H,m), 4.22–4.35(3H,m), 6.92 (1H,d,J=7.6 Hz), 7.50(1H,s)

EXAMPLE 11

N-(4-Nitroxymethylcyclohexyl)-(4R)-2-oxothiazolidin-4-yl-carboxamide (Exemplary Compound No. 1-1)

602 mg of the desired compound were obtained as a colorless crystalline solid using similar procedures to those in Example 3 by using 486 mg of (4R)-2-oxo-4-thiazolidinecarboxylic acid and 837 mg of 4-nitroxymethylcyclohexylamine hydrochloride.

m.p.: 124°–126° C. (decomp.); NMR spectrum (CDCl$_3$+ d$_6$-DMSO) δ ppm: 1.15–2.00(9H,m), 3.60–3.77(2H,m), 3.98–4.13(1H,m), 4.25–4.35(1H,m), 4.37(2H,d,J=6.7 Hz), 6.86(1H, d,J=6.9 Hz), 7.73(1H,s)

EXAMPLE 12

N-(Trans-2-nitroxymethylcyclohexylmethyl)-(4R)-2-oxothiazolidin-4-yl-carboxamide (Exemplary Compound No. 1-633)

319 mg of the desired compound were obtained as a colorless crystalline solid using similar procedures to those in Example 3 by using 397 mg of (4R)-2-oxo-4-thiazolidinecarboxylic acid and 541 mg of trans-2-nitroxymethylcyclohexylmethylamine hydrochloride.

m.p.: 108°–111° C. (decomp.); NMR spectrum (CDCl$_3$) δ ppm: 1.00–1.35(4H,m), 1.40–1.90(6H,m), 3.22–3.50(2H, m), 3.63(1H,dd,J=5.3 Hz,J=10.6 Hz), 3.81(1H,dd,J=8.6 Hz,J=10.6 Hz), 4.32–4.60(3H,m), 6.68(1H,bs), 6.76(1H,s)

EXAMPLE 13

N-(Cis-2-nitroxymethylcyclohexylmethyl)-(4R)-2-oxothiazolidin-4-yl-carboxamide (Exemplary Compound No. 1-633)

61 mg of the desired compound were obtained as a colorless crystalline solid using similar procedures to those in Example 3 by using 480 mg of (4R)-2-oxo-4-thiazolidinecarboxylic acid and 570 mg of cis-2-nitroxymethylcyclohexylmethylamine hydrochloride.

m.p.: 74°–77° C. (decomp.); NMR spectrum (CDCl$_3$) δ ppm: 0.80–1.70(8H,m), 1.88–2.06(1H,m), 2.06–2.22(1H, m), 3.13–3.50(2H,m), 3.60–3.70(1H,m), 3.75–3.90(1H,m), 4.30–4.62(3H,m), 6.75(1H,s), 6.84(1H,s)

EXAMPLE 14

N-(3-Nitroxymethylcyclohexylmethyl)-(4R)-2-oxothiazolidin-4-yl-carboxamide (Exemplary Compound No. 1-681)

850 mg of the desired compound were obtained as a yellow oil using similar procedures to those in Example 3 by using 490 mg of (4R)-2-oxo-4-thiazolidinecarboxylic acid and 890 mg of 3-nitroxymethylcyclohexylmethylamine hydrochloride.

NMR spectrum (CDCl$_3$+d$_6$-DMSO) δ ppm: 0.60–1.10 (2H,m), 1.20–1.93(7.5H,m), 2.05–2.20(0.5H,m), 3.06–3.40 (2H,m), 3.60–3.72(1H,m), 3.75–3.87(1H,m), 4.20–4.45(3H, m), 6.70–7.05(2H,m)

EXAMPLE 15

N-(2-Nitroxymethylcyclopentyl)-(4R)-2-oxothiazolidin-4-yl-carboxamide (Exemplary Compound No. 1-525)

The desired compound, two isomers, i.e. 153 mg of isomer A and 88 mg of isomer B were obtained as a colorless crystalline solid, respectively using similar procedures to those in Example 3 by using 294 mg of (4R)-2-oxo-4-thiazolidinecarboxylic acid and 471 mg of 2-nitroxymethylcyclopentylamine hydrochloride obtained in Reference example 79.

Isomer A

Thin layer chromatography: Rf=0.57 (developing solvent: ethyl acetate); m.p.: 109°–111° C.; NMR spectrum (CDCl$_3$+d$_6$-DMSO) δ ppm: 1.40–2.10(6H,m), 2.40–2.58(1H,m), 3.69(2H,d,J=7.3 Hz), 4.23–4.60(4H,m), 7.04(1H,d,J=7.9 Hz), 7.82(1H,s)

Isomer B

Thin layer chromatography: Rf=0.49 (developing solvent: ethyl acetate); m.p.: 103°–105° C.; NMR spectrum (CDCl$_3$+d$_6$-DMSO) δ ppm: 1.40–2.10(6H,m), 2.40–2.57(1H,m), 3.70(2H,d,J=6.6 Hz), 4.20–4.35(2H,m), 4.25–4.58(2H,m), 7.05(1H,d,J=7.9 Hz), 7.67(1H,s)

EXAMPLE 16

N-(2-Nitroxymethylcyclopentyl)-(4R)-2-oxothiazolidin-4-yl-carboxamide (Exemplary Compound No. 1-525)

The desired compound, two isomers, i.e. 148 mg of isomer A and 209 mg of isomer B were obtained as a colorless crystalline solid, respectively using similar procedures to those in Example 3 by using 444 mg of (4R)-2-oxo-4-thiazolidinecarboxylic acid and 532 mg of 2-nitroxymethylcyclopentylamine hydrochloride obtained in Reference example 81.

Isomer A

Thin layer chromatography: Rf=0.27 (developing solvent: cyclohexane/ethyl acetate=1/2); m.p.: 96°–98° C.; NMR spectrum (CDCl$_3$+d$_6$-DMSO) δ ppm: 1.20–2.25(7H,m), 3.58–3.76(2H,m), 3.95–4.17(1H,m), 4.23–4.35(1H,m), 4.42 (1H,dd,J=7.3 Hz,J=10.6 Hz), 4.55(1H,dd,J=6 Hz,J=10.6 Hz), 7.22(1H,d,J=7.4 Hz), 7.54(1H,s)

Isomer B

Thin layer chromatography: Rf=0.18 (developing solvent: cyclohexane/ethyl acetate=1/2); m.p.: 118°–120° C.; NMR spectrum (CDCl$_3$+d$_6$-DMSO) δ ppm: 1.36–2.25(7H,m), 3.68(2H,d, J=6.2 Hz), 3.97–4.15(1H,m), 4.23–4.35(1H,m), 4.42(1H,dd,J=7.2 Hz,J=10.5 Hz), 4.55(1H,dd,J=5.9 Hz,J= 10.5 Hz), 7.23(1H,d,J=7.5 Hz), 7.53(1H,s)

EXAMPLE 17

N-[4-(4-Nitroxybutyl)cyclohexylmethyl]-(4R)-2-oxothiazolidin-4-yl-carboxamide (Exemplary Compound No. 1-1224)

44 mg of the desired compound were obtained as a colorless crystalline solid using similar procedures to those in Example 3 by using 32.4 mg of (4R)-2-oxo-4-thiazolidinecarboxylic acid and 49 mg of 4-(4-nitroxybutyl) cyclohexylmethylamine hydrochloride.

m.p.: 90°–93° C. (decomp.); NMR spectrum (CDCl$_3$) δ ppm: 0.80–1.05(4H,m), 1.05–2.05(12H,m), 3.06–3.30(2H, m), 3.62(1H,dd,J=4.5 Hz,J=11.3 Hz), 3.82(1H,dd,J=8.6 Hz,J=11.3 Hz), 4.30–4.40(1H,m), 4.45(2H,t,J=6.6 Hz), 6.33–6.60(2H,m), 6.86(1H,d,J=6.9 Hz), 7.73(1H,s)

EXAMPLE 18

N-(5-Nitroxymethyl-2-piperidinylmethyl)-(4R)-2-oxothiazolidin-4-yl-carboxamide hydrochloride (Exemplary Compound No. 1-1040)

In 40 ml of dry tetrahydrofuran and 20 ml of dry dimethylformamide were suspended 224 mg of (4R)-2-oxo-4-thiazolidinecarboxylic acid and 350 mg of 5-nitroxymethyl-2-piperidylmethylamine dihydrochloride, and 0.94 ml of triethylamine and 0.188 ml of diethyl cyanophosphate were added thereto with stirring under ice-cooling, and the resulting mixture was stirred at room temperature for 5 hours. To the reaction mixture were added 0.463 ml of di-t-butyl dicarbonate and a catalytic amount of 4-dimethylaminopyridine, and the resulting mixture was stirred at room temperature for 1 hour. Further, 2.0 ml of di-t-butyl dicarbonate was added thereto and the mixture was stirred at 30° C. for 1.5 hours. The insolubles were filtered and the solvent was distilled off under reduced pressure. The residue was purified by using silica gel column chromatography (eluting solvent: cyclohexane/ethyl acetate=2/3–1/6) and the fraction having an Rf of 0.14 by thin layer chromatography (developing solvent: cyclohexane/ethyl acetate=1/2) was collected by separation. The thus obtained foam was dissolved in 5.0 ml of 4N hydrochloric acid-dioxane and the mixture was stirred at room temperature for 30 minutes. To the mixture was added 20 ml of ether, and the crystal was collected by filtration to obtain 40 mg of the desired compound as a pale yellow crystalline solid.

m.p.: 95°–99° C. (decomp.); NMR spectrum (CDCl$_3$) δ ppm: 1.20–1.50(2H,m), 1.75–1.95(2H,m), 2.10–2.30(1H, m), 2.65–3.20(2H,m), 3.40–3.50(1H,m), 3.60–3.70(1H,m), 4.28–4.38(1H,m), 4.40–4.55(2H,m), 8.30(1H,s), 8.40(1H, bs)

REFERENCE EXAMPLE 1

Trans-4-N-t-butoxycarbonylaminomethylcyclohexylcarboxylic acid

In 50 ml of water was dissolved 5.0 g of trans-4-aminomethylcyclohexylcarboxylic acid, and 6.6 ml of triethylamine was added thereto. Then, a solution of 11.2 ml of di-tert-butyldicarbonate in dioxane (20 ml) was added to the mixture, and the resulting mixture was stirred at room temperature for 3 hours. The dioxane was distilled off under reduced pressure and an aqueous citric acid solution was added to the resulting aqueous solution to adjust pH to 4.0. The mixture was extracted with ethyl acetate, and the extracts were washed with a saturated aqueous sodium chloride solution and dried over anhydrous magnesium sulfate. The solvent was distilled off to obtain a colorless crystalline solid. Isopropyl ether was added to the crystalline solid, and the crystalline solid was collected by filtration and dried to obtain 7.0 g of the desired compound as a colorless crystalline solid.

m.p.: 126°–128° C.; NMR spectrum (CDCl$_3$) δ ppm: 0.85–1.05(2H,m), 1.30–1.60(9H,m), 1.75–1.92(2H,m), 1.95–2.12(2H,m), 2.18–2.35(1H,m), 2.85–3.05(2H,m), 4.60 (1H,bs)

REFERENCE EXAMPLE 2

Trans-4-N-t-butoxycarbonylaminomethyl-1-hydroxymethylcyclohexane

In anhydrous tetrahydrofuran (60 ml) was dissolved 5.0 g of the compound of Reference example 1, and 1M solution of 22.0 ml of lithium aluminum hydride in tetrahydrofuran was added dropwise thereto with stirring under ice-cooling and the mixture was stirred at room temperature for 2 hours. An excess amount of sodium sulfate decahydrate was added to the reaction mixture, the insolubles were filtered off, and the filtrate was subjected to distillation under reduced pressure. The residue was dissolved in dichloromethane and dried over anhydrous magnesium sulfate, and the solvent was distilled off. The thus obtained residue was purified by silica gel column chromatography employing cyclohexane-ethyl acetate (2:1) as an eluting solvent to obtain 1.4 g of the desired compound as a colorless crystalline solid.

m.p.: 88°–89° C.; NMR spectrum (CDCl$_3$) δ ppm: 0.85–1.05(4H,m), 1.25–1.52(11H,m), 1.75–1.90(4H,m), 2.98(2H,t,J=6.4 Hz), 3.45(2H,d,J=6.2 Hz), 4.61(1H,bs)

REFERENCE EXAMPLE 3

Trans-4-N-t-butoxycarbonylaminomethyl-1-nitroxymethyl-cyclohexane

To 24 ml of anhydrous acetonitrile were added 1.3 g of nitronium tetrafluoroborate and 1.19 g of 2,4,6-collidine with stirring under ice-cooling, and the mixture was stirred at the same temperature for 0.5 hour. To the reaction mixture was added 1.2 g of the compound of Reference example 2, and the resulting mixture was stirred at room temperature for 70 minutes. The solvent was distilled off under reduced pressure, ethyl acetate was added to the residue, and the insolubles were filtered off. The residue obtained by distillation of the solvent under reduced pressure was purified by silica gel column chromatography employing cyclohexane-ethyl acetate (9:1) as an eluting solvent to obtain 1.09 g of the desired compound as a pale yellow crystalline solid.

m.p.: 65°–67° C.; NMR spectrum (CDCl$_3$) δ ppm: 0.85–1.13(4H,m), 1.44(10H,s), 1.60–1.95(5H,m), 2.98(2H, t,J=6.4 Hz), 4.27(2H,d,J=6.4 Hz), 4.59(1H,bs)

REFERENCE EXAMPLE 4

Trans-4-nitroxymethylcyclohexylmethylamine hydrochloride 1.1 g of the compound of Reference example 3 was dissolved in 15 ml of 4N hydrochloric acid/dioxane solution and stirred at room temperature for 1 hour. The precipitated crystalline solid was collected by filtration and washed successively with dioxane and ether. Further, the crystal was washed with ethanol and ether and dried to obtain 0.25 g of the desired compound as a colorless crystalline solid.

m.p.: 166°–168° C. (decomp.); NMR spectrum (d$_6$-DMSO) δ ppm: 0.85–1.10(4H,m), 1.45–1.90(6H,m), 2.62 (2H,d,J=6.8 Hz), 4.37(2H,d,J=6.5 Hz), 8.06(3H,bs)

REFERENCE EXAMPLE 5

Dimethyl cis-1,4-cyclohexanedicarboxylate

In 30 ml of methanol was dissolved 3.0 g of cis-1,4-cyclohexanedicarboxylic acid, and 33.0 ml of a trimethylsilyldiazomethane solution (2M hexane solution) was added thereto. The mixture was stirred at room temperature for 1 hour and allowed to stand at room temperature overnight. The solvent was distilled off under reduced pressure. The residue was dissolved in ethyl acetate and the resulting solution was washed successively with an aqueous sodium bicarbonate solution and an aqueous sodium chloride solution, and dried over anhydrous magnesium sulfate. The solvent was distilled off under reduced pressure to obtain 3.46 g of the desired compound as a yellow oil.

NMR spectrum (CDCl$_3$) δ ppm: 1.60–1.98(8H,m), 2.40–2.55(2H,m), 3.68(6H,m)

REFERENCE EXAMPLE 6

Monomethyl cis-1,4-cyclohexanedicarboxylate

In 35 ml of methanol was dissolved 3.46 g of dimethyl cis-1,4-cyclohexanedicarboxylate, and 17.3 ml of 1N aqueous sodium hydroxide solution was added thereto, and the resulting mixture was stirred at room temperature for 1.5 hours. The solvent was distilled off under reduced pressure and the obtained aqueous solution was washed with ethyl acetate. The pH of the mixture was adjusted to 1 with diluted hydrochloric acid under ice-cooling and the mixture was extracted with ethyl acetate. The extracts were washed with an aqueous sodium chloride solution and dried over anhydrous magnesium sulfate. The solvent was distilled off under reduced pressure to obtain a colorless crystalline solid. Isopropyl ether was added to the crystalline solid and the crystalline solid was collected by filtration to obtain 1.76 g of the desired compound as a pale yellow crystalline solid.

m.p.: 91°–93° C.; NMR spectrum (CDCl$_3$+d$_6$-DMSO) δ ppm: 1.60–2.00(8H,m), 2.42–2.52(2H,m), 3.67(3H,s)

REFERENCE EXAMPLE 7

Cis-4-carbamoylcyclohexanecarboxylic acid

In 55 ml of conc. aqueous ammonia was dissolved 5.29 g of monomethyl cis-1,4-cyclohexanecarboxylate, and the mixture was allowed to stand at room temperature for 6 days. The pH of the mixture was adjusted to 1 with conc. hydrochloric acid under ice-cooling and the precipitated crystalline solid was collected by filtration and washed with water to obtain a brown crystalline solid. The crystalline solid was recrystallized from ethyl acetate to obtain 2.96 g of the desired compound as a pale yellow columnar crystalline solid.

m.p.: 209°–211° C.; NMR spectrum ($d_6$-DMSO) δ ppm: 1.30–1.80(6H,m), 1.80–1.96(2H,m), 2.05–2.22(1H,m), 2.30–2.40(1H,m), 6.67(1H,s), 7.17(1H,s), 12.09(1H,s)

REFERENCE EXAMPLE 8

Cis-4-N-t-butoxycarbonylaminomethyl-1-hydroxymethylcyclohexane

In 35 ml of tetrahydrofuran was suspended 3.40 g of cis-4-carbamoylcyclohexanecarboxylic acid, and 50.0 ml of 1M lithium aluminum hydride in tetrahydrofuran were added thereto with stirring under ice-cooling. The mixture was stirred at room temperature for 0.5 hour and heated under reflux with stirring for 1 hour. To the resulting mixture was added 13.0 g of sodium sulfate decahydrate with stirring under ice-cooling to decompose excess lithium aluminum hydride. The insolubles were separated by filtration using Celite and the solvent was distilled off under reduced pressure. The residue was dissolved in dichloromethane and dried over anhydrous magnesium sulfate, and the solvent was distillated off under reduced pressure to obtain a colorless oil. The oil was dissolved in 30 ml of methanol, 3.0 ml of di-t-butyl dicarbonate was added thereto and the mixture was stirred at room temperature for 0.5 hour. The solvent was distilled off under reduced pressure and the thus obtained residue was purified by silica gel column chromatography (eluting solvent: cyclohexane/ethyl acetate=2/1) to obtain a colorless crystalline solid. Isopropyl ether was added to the crystalline solid and a crystalline solid was collected by filtration to obtain 1.69 g of the desired compound as a colorless crystalline solid.

m.p.: 93°–95° C.; NMR spectrum (CDCl$_3$) δ ppm: 1.28–1.75(20H,m), 3.07(2H,t,J=6.6 Hz), 3.53(2H,d,J=4.6 Hz), 4.56(1H,bs)

REFERENCE EXAMPLE 9

Cis-N-t-butoxycarbonyl-4-nitroxymethylcyclohexylmethylamine 1.40 g of the desired compound was obtained as a pale yellow crystalline solid using similar procedures to those in REFERENCE EXAMPLE 3 by using 1.60 g of cis-4-N-t-butoxycarbonylaminomethyl-1-hydroxymethylcyclohexane and 1.05 g of nitronium tetrafluoroborate.

m.p.: 64°–66° C.; NMR spectrum (CDCl$_3$) δ ppm: 1.25–1.75(18H,m), 1.88–2.02(1H,m), 3.08(2H,t,J=6.6 Hz), 4.36(2H,d,J=7.3 Hz), 4.54(1H,bs)

REFERENCE EXAMPLE 10

Cis-4-nitroxymethylcyclohexylmethylamine hydrochloride 0.94 g of the desired compound was obtained as a colorless crystalline solid using similar procedures to those in Reference example 4 by using 1.40 g of cis-N-t-butoxycarbonyl-4-nitroxymethylcyclohexylmethylamine and 14.0 ml of 4N hydrochloric acid-dioxane.

m.p.: 181°–182° C. (decomp.); NMR spectrum (CDCl$_3$) δ ppm: 1.25–1.75(18H,m), 1.88–2.02(1H,m), 3.08(2H,t,J=6.6 Hz), 4.36(2H,d,J=7.3 Hz), 4.54(1H,bs)

REFERENCE EXAMPLE 11

Trans-N-t-butoxycarbonyl-4-(2-diazoacetyl)cyclohexylmethylamine

In 60 ml of dry tetrahydrofuran was dissolved 3.00 g of trans-4-N-t-butoxycarbonylaminomethylcyclohexanecarboxylic acid, and 1.28 ml of N-methylmorpholine and 1.51 ml of isobutyl chloroformate were added thereto at −20° C., and the resulting mixture was stirred at −20° C. for 2 hours. The precipitated hydrochloric acid salt of N-methylmorpholine was separated by filtration and the filtrate was added to 200 ml of a solution of diazomethane in ether obtained from 7.0 g of N-nitrosomethylurea at −20° C. The reaction mixture was stirred at −20° C. for 2 hours and further stirred at room temperature overnight. The solvent was distilled off under reduced pressure and the residue was purified by silica gel column chromatography (eluting solvent: dichloromethane/ethyl acetate=8/1) to obtain a pale yellow crystalline solid. The crystalline solid was recrystallized from isopropyl ether to obtain 948 mg of the desired compound as a pale yellow crystalline solid.

m.p.: 106°–107° C.; NMR spectrum (CDCl$_3$) δ ppm: 0.85–1.07(2H,m), 1.30–1.55(12H,m), 1.78–1.96(4H,m), 2.05–2.37(1H,m), 2.98(2H,t,J=7.4 Hz), 4.59(1H,bs), 5.26(1H,s)

REFERENCE EXAMPLE 12

Methyl trans-4-N-t-butoxycarbonylaminomethylcyclohexylacetate

In 30 ml of methanol was dissolved 923 mg of trans-N-t-butoxycarbonyl-4-(2-diazoacetyl)cyclohexylmethylamine, and 5.0 ml of a solution of 128 mg of silver acetate in triethylamine were added dropwise thereto at room temperature, and the resulting mixture was stirred at room temperature for 1 hour and 25 minutes. To the reaction mixture was added 10 ml of a saturated aqueous sodium chloride solution, and the resulting mixture was stirred at room temperature for 5 minutes and filtered by using Celite. The filtrate was distilled off under reduced pressure and the residue was dissolved in ethyl acetate. The resulting solution was washed successively with an aqueous sodium bicarbonate solution and an aqueous sodium chloride solution, and dried over anhydrous magnesium sulfate. The solvent was distilled off under reduced pressure and the residue was purified by silica gel column chromatography (eluting solvent: cyclohexane/ethyl acetate=4/1) to obtain a colorless crystalline solid. The crystalline solid was. recrystallized from isopropyl ether to obtain 796 mg of the desired compound as a colorless needle-shaped crystalline solid.

m.p.: 53°–55° C.; NMR spectrum (CDCl$_3$) δ ppm: 0.85–1.12(4H,m), 1.25–1.58(1H,m), 1.44(9H,s), 1.63–1.88(5H,m), 2.20(2H,d,J=6.7 Hz), 2.96(2H,t,J=6.4 Hz), 3.66(3H,s), 4.65(1H,bs)

REFERENCE EXAMPLE 13

Trans-N-t-butoxycarbonyl-4-(2-hydroxyethyl)cyclohexylmethylamine

In 10 ml of ethanol and 7.0 ml of tetrahydrofuran were dissolved 796 mg of methyl trans-4-N-t- butoxycarbonylaminomethylcyclohexylacetate, and 1.55 g of anhydrous calcium chloride was added thereto with stirring under ice-cooling. The resulting mixture was stirred under ice-cooling for 1 hour and 530 mg of sodium borohydride was added thereto, and the mixture was stirred at the same temperature for 30 minutes, at room temperature for 1 hour and 25 minutes, and further at 40°–45° C. for 4 hours. To the reaction mixture was added 5.0 ml of acetone, and the mixture was stirred for 1 hour and-filtered using Celite. The filtrate was distilled off under reduced pressure and the residue was purified by silica gel column chromatography (eluting solvent: cyclohexane/ethyl acetate=3/1) to obtain a colorless crystalline solid. The crystalline solid was recrystallized from hexane to obtain 619 mg of the desired compound as a colorless crystalline solid.

m.p.: 78°–80° C.; NMR spectrum (CDCl$_3$) δ ppm: 0.83–1.05(4H,m), 1.25–1.55(4H,m), 1.44(9H,s), 1.65–1.88 (4H,m), 2.59(1H,s), 2.95(2H,t,J=6.3 Hz), 3.66(2H,t,J=6.7 Hz), 4.84(1H,bs)

REFERENCE EXAMPLE 14

Trans-N-t-butoxycarbonyl-4-(2-nitroxyethyl) cyclohexylmethylamine 437 mg of the desired compound were obtained as a colorless needle-shaped crystalline solid using similar procedures to those in Reference example 3 by using 574 mg of trans-N-t-butoxycarbonyl-4-(2-hydroxyethyl) cyclohexylmethylamine and 418 mg of nitronium tetrafluoroborate.

m.p.: 60°–61° C.; NMR spectrum (CDC$_3$) δ ppm: 0.82–1.05(4H,m), 1.25–1.50(2H,m), 1.44(9H,s), 1.62(2H,q, J=6.6 Hz,J=13.2 Hz), 1.70–1.88(2H,m), 2.90–3.00(2H,m), 4.49(2H,t,J=7.6 Hz), 4.65–4.85(1H,bs)

REFERENCE EXAMPLE 15

Trans-4-(2-nitroxyethyl)cyclohexylmethylamine hydrochloride 298 mg of the desired compound were obtained as a pale yellow crystalline solid using similar procedures to those in Reference example 4 by using 437 mg of trans-N-t-butoxycarbonyl-4-(2-nitroxy)ethylcyclohexylmethylamine and 2.0 ml of 4N hydrochloric acid-dioxane.

m.p.: 175°–176° C. (decomp.); NMR spectrum (CDCl$_3$+ d$_6$-DMSO) δ ppm: 0.85–1.12(4H,m), 1.20–2.02(8H,m), 2.65–2.88(2H,m), 4.49(2H,t,J=6.7 Hz), 8.20–8.60(3H,bs)

REFERENCE EXAMPLE 16

Trans-N-t-butoxycarbonyl-4-methanesulfonyloxymethylcyclohexylmethylamine

In 500 ml of dry dichloromethane was dissolved 10.0 g of trans-4-N-t-butoxycarbonylaminomethyl-1-hydroxymethylcyclohexane, and 14.3 ml of triethylamine and 14.3 g of methanesulfonic acid anhydride were added thereto with stirring under ice-cooling, and the resulting mixture was stirred at the same temperature for 50 minutes. The solvent was distilled off under reduced pressure and the residue was dissolved in ethyl acetate. The resulting solution was washed successively with an aqueous citric acid solution, an aqueous sodium chloride solution, an aqueous sodium bicarbonate solution and an aqueous sodium chloride solution, and dried over anhydrous magnesium sulfate. The solvent was distilled off under reduced pressure to obtain a colorless crystalline solid. Isopropyl ether was added to the crystalline solid and the crystalline solid was collected by filtration to obtain 13.24 g of the desired compound as a colorless crystalline solid.

m.p.: 105°–107° C.; NMR spectrum (CDCl$_3$) δ ppm: 0.83–1.13(4H,m), 1.30–1.53(1H,m), 1.44(9H,s), 1.60–1.94 (5H,m), 2.88–3.10(2H,m), 3.00(3H,s), 4.03(2H,d,J=6.6 Hz), 4.59(1H,bs)

REFERENCE EXAMPLE 17

Trans-N-t-butoxycarbonyl-4-iodomethylcyclohexylmethylamine

In 130 ml of anhydrous acetone was dissolved 13.24.g of trans-N-t-butoxycarbonyl-4-methanesulfonyloxymethylcyclohexylmethylamine, and 12.32 g of sodium iodide was added thereto, and the resulting mixture was heated under reflux for 3 hours and 45 minutes. The solvent was distilled off under reduced pressure and the residue was dissolved in ethyl acetate. The resulting solution was washed successively with an aqueous sodium thiosulfate solution and an aqueous sodium chloride solution, and dried over anhydrous magnesium sulfate. The solvent was distilled off under reduced pressure and the residue was purified by silica gel column chromatography (eluting solvent: cyclohexane/ethyl acetate=4/1) to obtain a pale yellow crystalline solid. The crystalline solid was recrystallized from hexane to obtain 13.67 g of the desired compound as a colorless crystalline solid.

m.p.: 81°–83° C.; NMR spectrum (CDCl$_3$) δ ppm: 0.83–1.10(4H,m), 1.25–1.52(2H,m), 1.44(9H,s), 1.67–2.02 (4H,m), 2.98(2H,t,J=6.4 Hz), 3.10(2H,d,J=6.4 Hz), 4.59(1H, bs)

REFERENCE EXAMPLE 18

Diethyl trans-4-N-t-butoxycarbonylaminomethylcyclohexylmethylmalonate

In 10 ml of anhydrous dimethylformamide was dissolved 0.856 ml of diethyl malonate, and 123.5 mg of sodium hydride were added thereto with stirring under ice-cooling, and the mixture was stirred at the same temperature for 30 minutes. To the reaction mixture was added 1.0 g of trans-N-t-butoxycarbonyl-4-iodomethylcyclohexylmethylamine, and the mixture was heated with stirring at the internal temperature of 70° C. for 1 hour and 30 minutes. After the mixture was allowed to stand, an excess amount of an aqueous ammonium chloride solution was added thereto, and the solvent was distilled off under reduced pressure. The residue was dissolved in ethyl acetate and the resulting solution was washed with an aqueous sodium chloride solution and dried over anhydrous magnesium sulfate. The solvent was distilled off under reduced pressure. The residue was purified by silica gel column chromatography (eluting solvent: cyclohexane/ethyl acetate=4/1) to obtain 946 mg of the desired compound as a colorless oil.

NMR spectrum (CDCl$_3$) δ ppm: 0.78–1.08(4H,m), 1.10–1.60(8H,m), 1.44(9H,s), 1.65–1.90(6H,m), 2.95(2H,t, J=6.3 Hz), 3.44(1H,t,J=7.8 Hz), 4.10–4.35(4H,m), 4.59(1H, bs)

REFERENCE EXAMPLE 19

Trans-3-(4-N-t-butoxycarbonylaminomethylcyclohexyl)propionic acid

In 110 ml of methanol was dissolved 11.64 g of diethyl t r a n s - 4 - N - t - butoxycarbonylaminomethylcyclohexylmethylmalonate, and 80.0 ml of 10% aqueous sodium hydroxide solution was added thereto with stirring at room temperature, and the mixture was stirred at the same temperature for 2 hours and 10 minutes. Methanol was distilled off under reduced pressure and an aqueous citric acid solution was added thereto with stirring under ice-cooling to adjust the pH of the mixture to 4, and extracted with ethyl acetate. The extracts were washed successively with water and an aqueous sodium chloride solution and dried over anhydrous magnesium sulfate, and the solvent was distilled off under reduced pressure. The obtained crystal was suspended in 180 ml of xylene and heated under reflux for 1.5 hours. The solvent was distilled off under reduced pressure, a mixed solution of hexane and a small amount of isopropyl ether was added to the obtained crystalline solid, and the crystalline solid was collected by filtration to obtain 6.88 g of the desired compound as a colorless crystalline solid.

m.p.: 90°–92° C.; NMR spectrum (CDCl$_3$) δ ppm: 0.82–1.05(4H,m), 1.13–2.00(8H,m), 1.44(9H,s), 2.36(2H,t, J=7.6 Hz), 2.96(2H,t,J=6.3 Hz), 4.60(1H,bs)

REFERENCE EXAMPLE 20

Trans-3-(4-N-t-butoxycarbonylaminomethylcyclohexyl)propanol

In 10 ml of dry tetrahydrofuran was dissolved 1.0 g of trans-3-(4-N-t-butoxycarbonylaminomethylcyclohexyl) propionic acid, and 0.54 ml of triethylamine and 0.15 ml of isobutyl chloroformate were added thereto with stirring under ice-cooling, and the mixture was stirred at the same temperature for 30 minutes. The insolubles were separated by filtration using Celite and the filtrate was added dropwise to 5 ml of an aqueous solution of 0.40 g of sodium borohydride with stirring under ice-cooling, and the mixture was stirred at the same temperature for 1 hour. To the reaction mixture was added 10 ml of acetone, and the resulting mixture was stirred at room temperature for 10 minutes. The solvent was distilled off under reduced pressure. Water and ethyl acetate were added to the residue, and the ethyl acetate layer was separated, washed with an aqueous sodium chloride and dried over anhydrous. magnesium sulfate. The solvent was distilled off under reduced pressure to obtain a colorless crystalline solid. The crystalline solid was recrystallized from a mixed solution of hexane and a small amount of isopropyl ether to obtain 763 mg of the desired compound as a colorless crystalline solid.

m.p.: 76°–80° C.; NMR spectrum (CDCl$_3$) δ ppm: 0.80–1.05(4H,m), 1.05–1.90(10H,m), 1.44(9H,s), 2.96(2H, t,J=6.3 Hz), 3.63(2H,t,J=6.5 Hz), 4.59(1H,bs)

REFERENCE EXAMPLE 21

Trans-N-t-butoxycarbonyl-4-(3-nitroxypropyl) cyclohexylmethylamine 2.20 g of the desired compound were obtained as a colorless needle-shaped crystalline solid using similar procedures to those in Reference example 3 by using 4.0 g of trans-3-(4-N-tbutoxycarbonylaminomethylcyclohexyl) propanol and 2.87 g of nitronium tetrafluoroborate.

m.p.: 94°–95° C.; NMR spectrum (CDCl$_3$) δ ppm: 0.78–1.02(4H,m), 1.07–1.55(4H,m), 1.44(9H,s), 1.65–1.88 (6H,m), 2.97(2H,t,J=6.4 Hz), 4.43(2H,d,J=6.8 Hz), 4.58 (1H,bs)

REFERENCE EXAMPLE 22

Trans-4-(3-nitroxypropyl)cyclohexylmethylamine hydrochloride 1.57 g of the desired compound were obtained as a colorless crystalline solid using similar procedures to those in Reference example 4 by using 2.19 g of trans-N-t-butoxycarbonyl-4-(3-nitroxypropyl) cyclohexylmethylamine and 20.0 ml of 4N hydrochloric acid-dioxane.

m.p.: 174°–180° C. (decomp.); NMR spectrum (d$_6$-DMSO) δ ppm: 0.75–1.02(4H,m), 1.05–1.30(3H,m), 1.35–1.87(7H,m), 2.62(2H,d,J=6.5 Hz), 4.50(2H,t,J=6.6 Hz), 7.85–8.20(3H,bs)

REFERENCE EXAMPLE 23

Trans-4-benzyloxymethyl-1-hydroxymethylcyclohexane

In 10 ml of tetrahydrofuran was suspended 1.51 g of sodium hydride (55% content), and a solution of 5.0 g of trans-1,4-dihydroxymethylcyclohexane dissolved in 20 ml of tetrahydrofuran was added dropwise thereto with stirring under ice-cooling, and the reaction mixture was stirred at room temperature for 50 minutes. To the reaction mixture was added 3.79 ml of benzyl bromide with stirring under ice-cooling and the mixture was stirred under ice-cooling for 1 hour and further at room temperature overnight. The insolubles were separated by filtration and the filtrate was concentrated under reduced pressure. The residue was dissolved in ethyl acetate, and the solution was washed successively with an aqueous sodium chloride solution, 10% aqueous hydrochloric acid solution, an aqueous sodium chloride solution and an aqueous sodium bicarbonate solution and dried over anhydrous magnesium sulfate. The solvent was distilled off under reduced pressure. The residue was purified by silica gel column chromatography (eluting solvent: cyclohexane/ethyl acetate=20/1–5/1) to obtain 1.75 g of the desired compound as a colorless oil.

NMR spectrum (CDCl$_3$) δ ppm: 0.85–1.08(4H,m), 1.18–1.30(1H,m), 1.35–1.68(2H,m), 1.72–1.95(4H,m), 3.29 (2H,d,J=6.6 Hz), 3.46(2H,t,J=5.3 Hz), 4.50(2H,s), 7.20–740 (5H,m)

REFERENCE EXAMPLE 24

Trans-4-benzyloxymethylcyclohexylaldehyde

A solution of 60 ml of anhydrous dichloromethane and 1.33 ml of dimethyl sulfoxide were cooled in a dry ice-acetone bath and 1.30 ml of oxalyl chloride was added dropwise thereto, and the mixture was stirred at the same temperature for 10 minutes. A solution of 1.75 g of trans-4-benzyloxymethyl-1-hydroxymethylcyclohexane dissolved in 10 ml of anhydrous dichloromethane was added dropwise thereto, and the resulting mixture was stirred at the same temperature for 3 hours and 45 minutes. To the reaction mixture was added 5.2 ml of triethylamine at the same temperature, and the dry ice-acetone bath was removed, and the temperature of the mixture was returned gradually to 0° C. and excess amount of an aqueous ammonium chloride solution was added thereto. To the reaction mixture were added 200 ml of ethyl acetate, and the resulting mixture was washed successively with an aqueous sodium chloride solution, 10% aqueous hydrochloric acid solution, an aqueous sodium bicarbonate solution and an aqueous sodium chloride solution. The mixture was dried over anhydrous magnesium sulfate and the solvent was distilled off under reduced pressure. The residue was purified by silica gel column chromatography (eluting solvent: cyclohexane/ethyl acetate=40/1–20/1) to obtain 1.47 g of the desired compound as a colorless oil.

NMR spectrum (CDCl$_3$) δ ppm: 0.95–1.14(2H,m), 1.20–1.39(2H,m), 1.50–1.70(1H,m), 1.90–2.08(4H,m), 2.10–2.25(1H,m), 3.30(2H,d,J=5.9 Hz),4.50(2H,s), 7.20–7.40(5H,m), 9.62(1H,d,J=1.3 Hz)

REFERENCE EXAMPLE 25

Trans-4-benzyloxymethyl-1-(1-hydroxyethyl) cyclohexane

In 50 ml of tetrahydrofuran was dissolved 1.27 g of trans-4-benzyloxymethylcyclohexylaldehyde, and 6.7 ml of methyl magnesium bromide (0.9M tetrahydrofuran solution) were added dropwise thereto, while the mixture was cooled in a dry ice-acetone bath, and the mixture was stirred at the same temperature for 30 minutes. To the reaction mixture was added 11.0 ml of 10% aqueous acetic acid solution, and further 200 ml of ethyl acetate was added thereto. The mixture was washed successively with an aqueous sodium chloride solution, 10% aqueous hydrochloric acid solution, an aqueous sodium chloride solution, an aqueous sodium bicarbonate solution and an aqueous sodium chloride solution and dried over anhydrous magnesium sulfate. The solvent was distilled off under reduced pressure. The residue was purified by silica gel column chromatography (eluting solvent: cyclohexane/ethyl acetate=5/1–4/1) to obtain 807 mg of the desired compound as a colorless oil.

NMR spectrum (CDCl$_3$) δ ppm: 0.90–1.15(4H,m), 1.20 (3H,d,J=5.9 Hz), 1.20–2.05(7H,m), 3.32(2H,d,J=6.6 Hz), 3.52–3.68(1H,m), 4.54(2H,s), 7.25–7.48(5H,m)

REFERENCE EXAMPLE 26

Trans-4-benzyloxymethyl-1-(1-t-butyldimethylsilyloxyethyl)cyclohexane

In 50 ml of dry dimethyl sulfoxide were dissolved 2.0 g of trans-4-benzyloxymethyl-1-(1-hydroxyethyl) cyclohexane, and 2.24 ml of triethylamine and 1.88 g of t-butyldimethylsilyl chloride were added thereto with stirring at room temperature, and the mixture was stirred at room temperature for 2 hours and 50 minutes. To the reaction mixture were added 200 ml of ethyl acetate, and the mixture was washed successively with an aqueous citric acid solution, an aqueous sodium chloride solution, an aqueous sodium bicarbonate solution and an aqueous sodium chloride solution. The mixture was dried over anhydrous magnesium sulfate and the solvent was distilled off under reduced pressure. The residue was purified by silica gel column chromatography (eluting solvent: cyclohexane/ethyl acetate=50/1) to obtain 2.76 g of the desired compound as a colorless oil.

NMR spectrum (CDCl$_3$) δ ppm: 0.02(3H,s), 0.03(3H,s), 0.80–1.30(4H,m), 0.88 (9H,s), 1.08(3H,d,J=6.6 Hz), 1.45–1.90(6H,m), 3.27(2H,d,J=6.6 Hz), 3.45–3.60(1H,m), 4.50(2H,s), 7.20–7.40(5H,m)

REFERENCE EXAMPLE 27

Trans-4-hydroxymethyl-1-(1-t-butyldimethylsilyloxyethyl)cyclohexane

In 50 ml of dry ethanol was dissolved 2.7 g of trans-4-benzyloxymethyl-1-(1-t-butyldimethylsilyloxyethyl) cyclohexane, and 2.0 g of 10% palladium-carbon was added thereto, and the resulting mixture was heated under reflux for 9 hours and 50 minutes while stirring under a hydrogen stream. Further, 2.0 g of 10% palladium-carbon was added to the reaction mixture and the resulting mixture was heated under reflux for 4 hours and 15 minutes while stirring under a hydrogen stream. After completion of the reaction, palladium-carbon was separated by filtration and the solvent was distilled off under reduced pressure to obtain 1.85 g of the desired compound as a colorless oil.

NMR spectrum (CDCl$_3$) δ ppm: 0.03(3H,s), 0.04(3H,s), 0.70–1.95 (1H,m), 0.88 (9H,s), 1.09(1.5H,d,J=6 Hz), 1.13 (1.5H,d,J=6 Hz), 3.45(2H,d,J=6 Hz), 3.50–3.62(1H,m)

REFERENCE EXAMPLE 28

Trans-4-(1-t-butyldimethylsilyloxyethyl) cyclohexylmethylmethanesulfonate

In 50 ml of dry dichloromethane were dissolved 1.85 g of trans-4-hydroxymethyl-1-(1-t-butyldimethylsilyloxyethyl) cyclohexane and 1.89 ml of triethylamine, and 1.77 g of methanesulfonic acid anhydride was added thereto with stirring under ice-cooling, and the mixture was stirred at the same temperature for 35 minutes. To the reaction mixture were added 200 ml of ethyl acetate, and the resulting mixture was washed successively with an aqueous sodium chloride solution, an aqueous citric acid solution, an aqueous sodium chloride solution, an aqueous sodium bicarbonate solution and an aqueous sodium chloride solution. The mixture was dried over anhydrous magnesium sulfate and the solvent was distilled off under reduced pressure. The residue was purified by silica gel column chromatography (eluting solvent: cyclohexane/ethyl acetate=5/1) to obtain 2.01 g of the desired compound as a colorless oil.

NMR spectrum (CDCl$_3$) δ ppm: 0.02(3H,s), 0.03(3H,s), 0.88(9H,s), 0.94–1.30(5H,m), 1.08(3H,d,J=6.6 Hz), 1.50–1.95(5H,m), 2.99(3H,s), 3.50–3.62(1H,m), 4.03(2H,d, J=6.6 Hz)

REFERENCE EXAMPLE 29

Trans-4-azidomethyl-1-(1-t-butyldimethylsilyloxyethyl)cyclohexane

In 50 ml of dry dimethylformamide was suspended 2.0 g of trans-4-(1-t-butyldimethylsilyloxyethyl) cyclohexylmethylmethanesulfonate and 1.85 g of sodium azide, and the resulting mixture was stirred at 110° C. for 45 minutes. To the reaction mixture were added 200 ml of ethyl acetate, and the mixture was washed three times with an aqueous sodium chloride solution and dried over anhydrous magnesium sulfate, and the solvent was distilled off under reduced pressure to obtain 1.7 g of the desired compound as a pale yellow oil. This oil was used for the subsequentareaction without purification.

NMR spectrum (CDCl$_3$) δ ppm: 0.02(3H,s), 0.03(3H,s), 0.88(9H,s), 0.90–1.28(5H,m), 1.08(3H,d,J=6.6 Hz), 1.40–1.94(5H,m), 3.12(2H,d,J=6.6 Hz), 3.48–3.62(1H,m)

REFERENCE EXAMPLE 30

Trans-N-t-butoxycarbonyl-4-(1-t-butyldimethylsilyloxyethyl)cyclohexylmethylamine In 50 ml of ethanol were dissolved 1.7 g of trans-4-azidomethyl-1-(1-t-butyldimethylsilyloxyethyl) cyclohexane, 2.57 ml of di-t-butyl dicarbonate and a catalytic amount of 4-dimethylaminopyridine, and 1.0 g of 10% palladium-carbon was added thereto, and the mixture was stirred under a hydrogen stream at room temperature for 1 hour. After completion of the reaction, the palladium-carbon was separated by filtration and the solvent was distilled off under reduced pressure. The residue was purified by silica gel column chromatography (eluting solvent: cyclohexane/ethyl acetate=50/1–10/1) to obtain 1.31 g of the desired compound as a colorless crystalline solid.

m.p.: 67°–70° C.; NMR spectrum (CDCl$_3$) δ ppm: 0.02 (3H,s), 0.03(3H,s), 0.80–1.92(10H,m), 0.88(9H,s), 1.07(3H, d,J=5.9 Hz), 1.44(9H,s), 2.95(2H,t,J=6 Hz), 3.45–3.60(1H, m), 4.56(1H,bs)

REFERENCE EXAMPLE 31

Trans-N-t-butoxycarbonyl-4-(1-hydroxyethyl) cyclohexylmethylamine

In 20 ml of dry tetrahydrofuran was dissolved 1.3 g of trans-N-t-butoxycarbonyl-4-(1-t-butyldimethylsilyloxyethyl)cyclohexylmethylamine, and 5.25 ml of tetrabutylammonium fluoride (1.0M tetrahydrofuran solution) were added dropwise thereto with stirring under ice-cooling, and the mixture was stirred at room temperature for 55 minutes. Then, 5.0 ml of tetrabutylammonium fluoride (1.0M tetrahydrofuran solution) were added dropwise thereto and the mixture was stirred at room temperature overnight and further at 50° C. for 9 hours. To the reaction mixture were added 200 ml of ethyl acetate, and the mixture was washed successively with an aqueous citric acid solution, an aqueous sodium chloride solution, an aqueous sodium bicarbonate solution and an aqueous sodium chloride solution. The mixture was dried over anhydrous magnesium sulfate and the solvent was distilled off under reduced pressure. The residue was purified by silica gel column chromatography (eluting solvent: cyclohexane/ethyl acetate=2/1) to obtain 701 mg of the desired compound as a colorless crystalline solid. Further, 38 mg of the desired compound was obtained from the mother liquid.

m.p.: 75°–76° C.; NMR spectrum (CDCl$_3$) δ ppm: 0.80–1.97(11H,m), 1.16(3H,d,J=6.6 Hz), 1.44(9H,s), 2.97 (2H,t,J=6.6 Hz), 3.48–3.62(1H,m), 4.57(1H,bs)

REFERENCE EXAMPLE 32

Trans-N-t-butoxycarbonyl-4-(1-nitroxyethyl) cyclohexylmethylamine 533 mg of the desired compound were obtained as a colorless oil using similar procedures to those in Reference example 3 by using 739 mg of trans-N-t-butoxycarbonyl-4-(1-hydroxyethyl)cyclohexylmethylamine and 561 mg of nitronium tetrafluoroborate.

NMR spectrum (CDCl$_3$) δ ppm: 0.84–1.97(10H,m), 1.31 (3H,d,J=5.9 Hz), 1.44(9H,s), 2.97(2H,t,J=6 Hz), 4.56(1H, bs), 4.85–4.98(1H,m)

REFERENCE EXAMPLE 33

Trans-4-(1-nitroxyethyl)cyclohexylmethylamine hydrochloride 427 mg of the desired compound were obtained as a colorless crystalline solid using similar procedures to those in Reference example 4 by using 533 mg of trans-N-t-butoxycarbonyl-4-(1-nitroxyethyl)cyclohexylmethylamine and 10.0 ml of 4N-hydrochloric acid-dioxane.

m.p.: 160°–163° C. (decomp.); NMR spectrum (d$_6$-DMSO) δ ppm: 0.80–1.20(4H,m), 1.28(3H,d,J=6.6 Hz), 1.42–1.90(6H,m), 2.63(2H,d,J=7.3 Hz), 4.92–5.08(1H,m), 7.80–8.20(3H,bs)

REFERENCE EXAMPLE 34

Trans-4-benzyloxymethyl-1-(1-methanesulfonyloxyethyl)cyclohexane

In 50 ml of anhydrous dichloromethane were dissolved 1.50 g of trans-4-benzyloxymethyl-1-(1-hydroxyethyl) cyclohexane and 1.68 ml of triethylamine, and 1.58 g of methanesulfonic acid anhydride was added thereto with stirring under ice-cooling, and the mixture was stirred at room temperature for 1 hour and 25 minutes. The solvent was distilled off under reduced pressure and 150 ml of ethyl acetate was added to the residue. The mixture was washed successively with an aqueous sodium chloride solution, 10% aqueous hydrochloric acid solution, an aqueous sodium chloride solution, an aqueous sodium bicarbonate solution and an aqueous sodium chloride solution and dried over anhydrous magnesium sulfate, and the solvent was distilled off under reduced pressure. The residue was purified by silica gel column chromatography employing dichloromethane as an eluent to obtain 1.71 g of the desired compound as a pale yellow oil.

NMR spectrum (CDCl$_3$) δ ppm: 0.85–1.20(4H,m), 1.39 (3H,d,J=5.9 Hz), 1.45–1.95(6H,m), 2.99(3H,s), 3.28(2H,d, J=6.6 Hz), 4.49(2H,s), 4.55–4.68(1H,m), 7.20–7.40(5H,m)

REFERENCE EXAMPLE 35

Trans-4-benzyloxymethyl-1-(1-azidoethyl) cyclohexane

In 50 ml of dry dimethylformamide were suspended 1.70 g of trans-4-benzyloxymethyl-1-(1-methanesulfonyloxyethyl)cyclohexane and 1.69 g of sodium azide, and the mixture was stirred at 110° C. for 30 minutes. To the reaction mixture were added 200 ml of ethyl acetate, and the mixture was washed three times with an aqueous sodium chloride solution and dried over anhydrous magnesium sulfate. The solvent was distilled off under reduced pressure to obtain 1.48 g of the desired compound as a pale yellow oil. This compound was used for the subsequent reaction without purification.

NMR spectrum (CDCl$_3$) δ ppm: 0.85–1.16(4H,m), 1.20–1.96(6H,m), 1.24(3H,d,J=6.6 Hz), 3.20–3.33(3H,m), 4.49(2H,s), 7.20–7.40(5H,m)

REFERENCE EXAMPLE 36

Trans-4-(1-N-t-butoxycarbonylaminoethyl)-1-hydroxymethylcyclohexane

In 50 ml of dry ethanol were dissolved 1.48 g of trans-4-benzyloxymethyl-1-(1-azidoethyl)cyclohexane, 1.20 ml of di-t-butyl dicarbonate and a catalytic amount of 4-dimethylaminopyridine, and 1.0 g of 10% palladium-carbon was added thereto, and the resulting mixture was stirred under hydrogen of 1 atm. at room temperature for 1 hour, at 50° C. for 40 minutes and further with heating under reflux for 1 hour. Then, 1.0 g of 10% palladium-carbon was added thereto and the resulting mixture was heated under reflux under hydrogen of 1 atm. for 1 hour and 20 minutes. Further, 2.0 g of 10% palladium-carbon was added thereto and the mixture was heated under reflux under hydrogen of 1 atm. for 3 hours. Moreover, 5 drops of 10% aqueous hydrochloric acid solution was added thereto and the mixture was heated under reflux at 1 atm. of hydrogen for 4 hours and 45 minutes. After completion of the reaction, palladium-carbon was separated by filtration and the solvent was distilled off under reduced pressure. The residue was dissolved in a mixed solution of 10 ml of methanol and 10 ml of dichloromethane, and 0.72 ml of triethylamine, 1.20 ml of di-t-butyl dicarbonate and a catalytic amount of 4-dimethylaminopyridine were added thereto, and the mixture was stirred at room temperature for 1 hour. To the reaction mixture were added 150 ml of ethyl acetate, and the mixture was washed successively with an aqueous citric acid solution, an aqueous sodium chloride solution, an aqueous sodium bicarbonate solution and an aqueous sodium chloride solution and dried over anhydrous magnesium sulfate. The solvent was distilled off under reduced pressure. The residue was purified by silica gel column chromatography employing cyclohexane-ethyl acetate (5:2–2:1) as an eluting solvent to obtain 617 mg of the desired compound as a colorless crystalline solid.

m.p.: 93.5°–95° C.; NMR spectrum (CDCl$_3$) δ ppm: 0.83–1.92(11H,m), 1.08(3H,d,J=6.6 Hz), 1.44(9H,s), 3.40–3.62(3H,m), 4.28–4.45(1H,m)

REFERENCE EXAMPLE 37

N-t-Butoxycarbonyl-1-(trans-4-nitroxymethylcyclohexyl)ethylamine 57 mg of the desired compound were obtained as a colorless crystalline solid using similar procedures to those in Reference example 3 by using 860 mg of trans-4-(1-t-butoxycarbonylaminoethyl)-1-hydroxymethylcyclohexane and 555 mg of nitronium tetrafluoroborate.

m.p.: 45°–47° C.; NMR spectrum (CDCl$_3$) δ ppm: 0.92–1.92(10H,m), 1.08(3H,d,J=7.3 Hz), 1.44(9H,s), 3.40–3.60(1H,m), 4.25–4.40(1H,m), 4.26(2H,d,J=6.6 Hz)

REFERENCE EXAMPLE 38

1-(Trans-4-nitroxymethylcyclohexyl)ethylamine hydrochloride 502 mg of the desired compound were obtained as a pale yellow crystalline solid using similar procedures to those in Reference example 4 by using 660 mg of N-t-butoxycarbonyl-1-(trans-4-nitroxymethylcyclohexyl) ethylamine and 10.0 ml of 4N hydrochloric acid-dioxane.

m.p.: 168°–169° C. (decomp.); NMR spectrum (d$_6$-DMSO) δ ppm: 0.90–1.10(4H,m), 1.13(3H,d,J=6.6 Hz), 1.35–1.88(6H,m), 2.92–3.10(1H,m), 4.37(2H,d,J=6.6 Hz), 7.75–8.00(3H,bs)

REFERENCE EXAMPLE 39

Trans-4-N-t-butoxycarbonylaminomethylcyclohexylacetonitrile

In 50 ml of dry dimethylformamide were suspended 5.86 g of trans-N-t-butoxycarbonyl-4-methanesulfonyloxymethylcyclohexylmethylamine, 3.28 g of sodium iodide and 1.07 g of sodium cyanide, and the mixture was heated with stirring at 110° C. for 40 minutes. The reaction mixture was poured into 100 ml of ice-water and the mixture was extracted with 150 ml of ethyl acetate. The extracts were washed successively with an aqueous sodium chloride solution, an aqueous citric acid solution, an aqueous sodium chloride solution, an aqueous sodium thiosulfate solution, an aqueous sodium chloride solution, an aqueous sodium bicarbonate solution and an aqueous sodium chloride solution and dried over anhydrous magnesium sulfate. The solvent was distilled off under reduced pressure and the residue was purified by silica gel column chromatography employing cyclohexane-ethyl acetate (10:1–5:1) as an eluting solvent to obtain 3.87 g of the desired compound as a colorless crystalline solid.

m.p.: 78°–79° C.; NMR spectrum (CDCl$_3$) δ ppm: 0.85–1.28(4H,m), 1.30–2.00(6H,m), 1.48(9H,s), 2.30(2H,d, J=6.6 Hz), 3.02(2H,t,J=6.3 Hz), 4.52–4.70(1H,m)

REFERENCE EXAMPLE 40

Trans-4-N-t-butoxycarbonylaminomethylcyclohexyl acetic acid

In a mixed solution of 20 ml of conc. hydrochloric acid and 10 ml of conc. sulfuric acid was suspended 1.02 g of trans-4-N-t-butoxycarbonylaminomethylcyclohexylacetonitrile, and the resulting mixture was heated under reflux for 1 hour and 25 minutes. The reaction mixture was poured into 150 ml of ice-water and neutralized with an excess amount of sodium bicarbonate. Further, 200 ml of dioxane and 5.0 ml of di-t-butyl dicarbonate were added thereto and the resulting mixture was stirred at room temperature overnight. The mixture was acidified with an aqueous citric acid solution, concentrated to about 100 ml under reduced pressure, and extracted three times with 300 ml of ethyl acetate. The extracts were washed with an aqueous sodium chloride solution and dried over anhydrous magnesium sulfate, and the solvent was distilled off under reduced pressure to obtain 0.98 g of the desired compound as a colorless crystalline solid.

m.p.: 123°–124° C.; NMR spectrum (CDCl$_3$) δ ppm: 0.85–1.10(4H,m), 1.30–1.90(6H,m), 1.44(9H,s), 2.23(2H,d, J=7.0 Hz), 2.97(2H,t,J=6.3 Hz), 4.50–4.66 (1H,m)

REFERENCE EXAMPLE 41

Methyl 2-(trans-4-N-t-butoxycarbonylaminomethylcyclohexyl)propionate

In 20 ml of dry tetrahydrofuran was dissolved 0.49 ml of diisopropylamine, and 2.19 ml of a butyl lithium solution (1.6M tetrahydrofuran solution) was added dropwise thereto under cooling in a dry ice-acetone bath. The dry ice-acetone bath was removed and the mixture was stirred until the temperature of the mixture became 0° C. To the reaction mixture was again added dropwise a solution obtained by dissolving 500 mg of methyl trans-4-t-butoxycarbonylaminomethylcyclohexylacetate in 5 ml of dry tetrahydrofuran under cooling in a dry ice-acetone bath. The resulting mixture was stirred for 1 hour and 30 minutes and then 0.26 ml of iodomethyl was added thereto, and further the mixture was stirred at the same temperature for 2 hours and 15 minutes. The temperature (–73° C.) of the reaction mixture was elevated to –40° C. in 2 hours and an excess amount of aqueous ammonium chloride solution was added thereto. The reaction mixture was extracted with 150 ml of ethyl acetate, and the extracts were washed successively with an aqueous sodium chloride solution, an aqueous citric acid solution, an aqueous sodium chloride solution, an aqueous sodium thiosulfate solution, an aqueous sodium chloride solution, an aqueous sodium bicarbonate solution and an aqueous sodium chloride solution and dried over anhydrous magnesium sulfate. The solvent was distilled off under reduced pressure and the residue was purified by silica gel column chromatography employing cyclohexane-ethyl acetate (10:1–6:1) as an eluting solvent to obtain 250 mg of the desired compound as a colorless oil.

NMR spectrum (CDCl$_3$) δ ppm: 0.80–1.10(4H,m), 1.11 (3H,d,J=6.9 Hz), 1.25–1.85(6H,m), 1.44(9H,s), 2.16–2.34 (1H,m), 2.96(2H,t,J=6.3 Hz), 3.66 (3H,s), 4.57(1H,bs)

REFERENCE EXAMPLE 42

Trans-4-N-t-butoxycarbonylaminomethyl-1-(2-hydroxy-1-methylethyl)cyclohexane

In 5 ml of dry tetrahydrofuran were dissolved 95 mg of methyl 2-(trans-4-N-t- butoxycarbonylaminomethylcyclohexyl)propionate, and 0.32 ml of lithium aluminum hydride solution (1.0M tetrahydrofuran solution) was added dropwise thereto under cooling in a dry ice-acetone bath, and the resulting mixture was stirred for 30 minutes. To the reaction mixture were added 10 ml of an aqueous ammonium chloride solution, and the mixture was extracted with 50 ml of ethyl acetate. The extracts were washed successively with an aqueous sodium chloride solution, an aqueous citric acid solution, an aqueous sodium chloride solution, an aqueous sodium bicarbonate solution and an aqueous sodium chloride solution and dried over anhydrous magnesium sulfate. The solvent was distilled off under reduced pressure and the residue was purified by silica gel column chromatography employing cyclohexane-ethyl acetate (4:1) as an eluting solvent to obtain 80 mg of the desired compound as a colorless oil.

NMR spectrum ($CDCl_3$) δ ppm: 0.80–1.83(12H,m), 0.89 (3H,d,J=7.1 Hz), 1.44(9H,s), 2.95(2H,t,J=6.4 Hz), 3.47(1H, dd,J=6.7 Hz,J=10.5 Hz), 3.61(1H,dd,J=5.9 Hz,J=10.5 Hz), 4.47–4.65(1H,m)

REFERENCE EXAMPLE 43

Trans-4-N-t-butoxycarbonylaminomethyl-1-(1-methyl-2-nitroxyethyl)cyclohexane 150 mg of the desired compound were obtained as a colorless crystalline solid using similar procedures to those in Reference example 3 by using 210 mg of trans-4-N-t-butoxycarbonylaminomethyl-1-(2-hydroxy-1-methylethyl)-cyclohexane and 151 mg of nitrgnium tetrafluoroborate.

m.p.: 55°–57° C.; NMR spectrum ($CDCl_3$) δ ppm: 0.84–1.86(11H,m), 0.96(3H,d,J=6.9 Hz), 1.44(9H,s), 2.96 (2H,t,J=6.3 Hz), 4.27(1H,dd,J=7.2 Hz,J=10.4 Hz), 4.44(1H, dd,J=5.8 Hz,J=10.4 Hz), 4.50–4.64(1H,m)

REFERENCE EXAMPLE 44

Trans-4-(1-methyl-2-nitroxyethyl)cyclohexylmethylamine hydrochloride 111 mg of the desired compound were obtained as a pale yellow crystalline solid using similar procedures to those in Reference example 4 by using 150 mg of trans-4-N-t-butoxy-carbonylaminomethyl-1-(1-methyl-2-nitroxyethyl)cyclohexane and 10.0 ml of 4N hydrochloric acid-dioxane.

m.p.: 114°–116° C. (decomp.); NMR spectrum ($d_6$-DMSO) δ ppm: 0.80–1.85(11H,m), 0.90(3H,d,J=6.8 Hz), 2.57–2.70(2H,m), 4.36(1H,dd,J=6.9 Hz,J=10.3 Hz), 4.52 (1H,dd,J=5.8 Hz,J=10.5 Hz), 7.60–7.90(3H,bs)

REFERENCE EXAMPLE 45

Trans-4-t-butyldimethylsilyloxymethyl-1-hydroxymethycyclohexane

In 250 ml of dry dimethylformamide were dissolved 10.0 g of trans-1,4-dihydroxymethylcyclohexane and 14.5 ml of triethylamine, and a solution of 10.24 g of t-butyldimethylsilyl chloride dissolved in 50 ml of dry dimethylformamide was added dropwise thereto with stirring under ice-cooling, and the resulting mixture was stirred under ice-cooling for 1 hour. To the reaction mixture were added 200 ml of ethyl acetate, the precipitated triethylamine hydrochloride was removed by filtration, and the filtrate was concentrated under reduced pressure. The residue was purified by silica gel column chromatography employing cyclohexane-ethyl acetate (2:1) as an eluting solvent to obtain 11.9 g of the desired compound as a colorless oil.

NMR spectrum ($CDCl_3$) δ ppm: 0.03(6H,s), 0.85–1.04 (4H,m), 0.89(9H,s), 1.25–1.90(7H,m), 3.35–3.50(4H,m)

REFERENCE EXAMPLE 46

Trans-4-methanesulfonyloxymethyl-1-t-butyldimethylsilyloxymethylcyclohexane

In 200 ml of dry dichloromethane were dissolved 11.9 g of trans-4-t-butyldimethylsilyloxymethyl-1-hydroxymethylcyclohexane, and 9.63 ml of triethylamine and 9.98 g of methanesulfonic acid anhydride were added thereto with stirring under ice-cooling, and the resulting mixture was stirred at room temperature for 30 minutes. To the reaction mixture were added 200 ml of ethyl acetate, and the mixture was washed with an aqueous sodium bicarbonate solution and an aqueous sodium chloride solution and dried over anhydrous magnesium sulfate, and the solvent was distilled off under reduced pressure. The residue was purified by silica gel column chromatography employing cyclohexane-ethyl acetate (8:1–5:1) as an eluting solvent to obtain 12.2 g of the desired compound as a colorless oil.

NMR spectrum ($CDCl_3$) δ ppm: 0.03(6H,s), 0.82–1.14 (4H,m), 0.89 (9H,s), 1.35–1.92(6H,m), 3.00(3H,s), 3.41(2H, d,J=6.6 Hz), 4.04 (1H,d,J=6.6 Hz)

REFERENCE EXAMPLE 47

Trans-4-t-butyldimethylsilyloxymethylcyclohexylacetonitrile

In 100 ml of dry dimethylformamide were suspended 11.0 g of trans-4-methanesulfonyloxymethyl-1-t-butyldimethylsilyloxymethylcyclohexane, 5.87 g of sodium iodide and 1.92 g of sodium cyanide, and the mixture was stirred at 50° C. for 1 hour and 45 minutes and further at 110° C. for 45 minutes. The reaction mixture was poured into 100 ml of ice-water and the mixture was extracted with 300 ml of ether. The extracts were washed with an aqueous citric acid solution, an aqueous sodium chloride solution, an aqueous sodium bicarbonate solution and an aqueous sodium chloride solution and dried over anhydrous magnesium sulfate, and the solvent was distilled off under reduced pressure. The residue was purified by silica gel column chromatography employing cyclohexane-ethyl acetate (20:1–5:1) as an eluting solvent to obtain 7.41 g of the desired compound as a colorless oil.

NMR spectrum ($CDCl_3$) δ ppm: 0.03(6H,s), 0.82–1.20 (4H,m), 0.89(9H,s), 1.34–1.95(6H,m), 2.25(2H,d,J=6.6 Hz), 3.41 (1H,d,J=5.9 Hz)

REFERENCE EXAMPLE 48

N-t-Butoxycarbonyl-2-(trans-4-t-butyldimethylsilyloxymethylcyclohexyl)ethylamine In 20 ml of dry tetrahydrofuran was dissolved 1.0 g of trans-4-t-butyldimethylsilyloxymethylcyclohexylacetonitrile, and 3.74 ml of lithium aluminum hydride solution (1.0M tetrahydrofuran solution) were added dropwise thereto under cooling in a dry ice-acetone bath, and the mixture was stirred for 1 hour and further at 0° C. for 25 minutes. Then, 3.74 ml of 1N aqueous hydrochloric acid solution were added thereto and the mixture was stirred for 20 minutes. To the reaction mixture were added 2.06 ml of di-t-butyl dicarbonate, and the mixture was stirred at room temperature for 2 hours and 15 minutes. To the reaction mixture were added 150 ml of ethyl acetate, and the mixture was washed with an aqueous citric acid solution, an aqueous sodium chloride solution, an aqueous sodium bicarbonate solution and an aqueous sodium chloride solution and dried over anhydrous magnesium sulfate, and the solvent was distilled off under reduced pressure. The residue was purified by silica gel column chromatography employing cyclohexane-ethyl acetate (40:1–20:1) as an eluting solvent to obtain 1.05 g of the desired compound as a colorless oil.

NMR spectrum (CDCl$_3$) δ ppm: 0.03(6H,s), 0.80–1.05 (4H,m), 0.89(9H,s), 1.10–1.90(8H,m), 1.44(9H,s), 3.05–3.22(2H,m), 3.39(1H,d,J=6.3 Hz), 4.35–4.55(1H,m)

REFERENCE EXAMPLE 49

Trans-4-(2-t-butoxycarbonylaminoethyl)-1-hydroxymethylcyclohexane

In 10 ml of dry tetrahydrofuran was dissolved 1.05 g of N-t-butoxycarbonyl-2-(trans-4-t-butyldimethylsilyloxymethylcyclohexyl)ethylamine, and 8.48 ml of tetrabutylammonium fluoride (1.0M tetrahydrofuran solution) were added dropwise thereto with stirring under ice-cooling, and the resulting mixture was stirred at room temperature overnight. To the reaction mixture were added 150 ml of ethyl acetate, and the mixture was washed with an aqueous sodium bicarbonate solution and an aqueous sodium chloride solution and dried over anhydrous magnesium sulfate, and the solvent was distilled off under reduced pressure. The residue was purified by silica gel column chromatography employing cyclohexane-ethyl acetate (2:1) as an eluting solvent to obtain 471 mg of the desired compound as a colorless crystalline solid.

m.p.: 75°–76° C.; NMR spectrum (CDCl$_3$) δ ppm: 0.85–1.90(13H,m), 1.44(9H,s), 3.05–3.28(2H,m), 3.40–3.58 (2H,m), 4.30–4.60(1H,m)

REFERENCE EXAMPLE 50

N-t-Butoxycarbonyl-2-(trans-4-nitroxymethylcyclohexyl)ethylamine 340 mg of the desired compound were obtained as a pale yellow crystalline solid using similar procedures to those in Reference example 3 by using 470 mg of trans-4-(2-t-butoxycarbonylaminoethyl)-1-hydroxymethylcyclohexane and 357 mg of nitronium tetrafluoroborate.

NMR spectrum (CDCl$_3$) δ ppm: 0.85–1.14(4H,m), 1.20–1.90(8H,m), 1.44(9H,s), 3.05–3.20(2H,m), 4.26(2H,d, J=6.5 Hz), 4.35–4.55(1H,m)

REFERENCE EXAMPLE 51

2-(Trans-4-nitroxymethylcyclohexyl)ethylamine hydrochloride 206 mg of the desired compound were obtained as a pale yellow crystalline solid using similar procedures to those in Reference example 4 by using 340 mg of N-t-butoxycarbonyl-2-(trans-4-nitroxymethylcyclohexyl)ethylamine and 5.0 ml of 4N hydrochloric acid-dioxane.

m.p.: 162–165 (decomp.); NMR spectrum (d$_6$-DMSO) δ ppm: 0.80–1.12(4H,m), 1.15–1.53(3H,m), 1.55–1.80(5H, m), 2.70–2.88(2H,m), 4.36(2H, d,J=6.1 Hz), 7.70–8.10(3H, bs)

REFERENCE EXAMPLE 52

N-t-Butoxycarbonyl-2-(trans-4-methanesulfonyloxymethylcyclohexyl)ethylamine

In 50 ml of dry dichloromethane was dissolved 1.0 g of trans-4-(2-t-butoxycarbonylaminoethyl)-1-hydroxymethylcyclohexane, and 0.81 ml of triethylamine and 829 mg of methanesulfonic acid anhydride were added thereto with stirring under ice-cooling, and the mixture was stirred at room temperature for 40 minutes. Then, the solvent was distilled off under reduced pressure and 150 ml of ethyl acetate was added to the residue. The mixture was washed successively with an aqueous sodium chloride solution, an aqueous sodium bicarbonate solution and an aqueous sodium chloride solution and dried over anhydrous magnesium sulfate, and the solvent was distilled off under reduced pressure. Isopropyl ether was added to the resulting crystalline solid and a crystalline solid was collected by filtration to obtain 1.13 g of the desired compound as a colorless crystalline solid.

m.p.: 83°–84° C.; NMR spectrum (CDCl$_3$) δ ppm: 0.85–1.14(4H,m), 1.16–1.90(8H,m), 1.44(9H,s), 3.00(3H,s), 3.05–3.10(2H,m), 4.03(2H,d,J=6.3 Hz), 4.35–4.55 (1H,m)

REFERENCE EXAMPLE 53

Diethyl trans-4-(2-N-t-butoxycarbonylaminoethyl) cyclohexylmethylmalonate

In 50 ml of dry dimethylformamide was dissolved 1.02 ml of diethyl malonate, and 147 mg of sodium hydride (55% content) was added thereto with stirring under ice-cooling, and the mixture was stirred for 30 minutes. To the reaction mixture was added 1.13 g of N-t-butoxycarbonyl-2-(trans-4-methanesulfonyloxymethylcyclohexyl)ethylamine, and the mixture was heated with stirring at 110° C. for 40 minutes. Further, 505 mg of sodium iodide was added thereto and the mixture was heated with stirring at 110° C. for 1 hour and 5 minutes. To the reaction mixture were added 200 ml of ethyl acetate, and the mixture was washed successively with an aqueous sodium chloride solution, an aqueous sodium thiosulfate solution and an aqueous sodium chloride solution and dried over anhydrous magnesium sulfate, and the solvent was distilled off under reduced pressure. The residue was purified by silica gel column chromatography employing cyclohexane-ethyl acetate (10:1–5:1) as an eluting solvent to obtain 895 mg of the desired compound as a colorless oil.

NMR spectrum (CDCl$_3$) δ ppm: 0.80–1.02(4H,m), 1.10–1.85(14H,m), 1.44(9H,s), 3.05–3.20(2H,m), 3.43(1H, t,J=7.6 Hz), 4.10–4.28(6H,m), 4.35–4.55(1H,m)

REFERENCE EXAMPLE 54

Trans-4-(2-N-t-butoxycarbonylaminoethyl) cyclohexylmethylmalonic acid

In 10 ml of ethanol were dissolved 890 mg of diethyl trans-4-(2-N-t-butoxycarbonylaminoethyl) cyclohexylmethylmalonate, and 10 ml of 2.5N sodium hydroxide was added thereto with stirring under ice-cooling, and the mixture was stirred at room temperature for 3.5 hours. The reaction mixture was poured into 50 ml of ice-water, acidified with citric acid and extracted with 200 ml of ethyl acetate. The extracts were washed with an aqueous sodium chloride solution and dried over anhydrous magnesium sulfate, and the solvent was distilled off under reduced pressure. Isopropyl ether was added to the resulting crystalline solid and a crystalline solid was collected by filtration to obtain 563 mg of the desired compound as a colorless crystalline solid.

m.p.: 152°–153° C. (decomp.); NMR spectrum (d$_6$-DMSO) δ ppm: 0.72–0.95(4H,m), 1.05–1.82(10H,m), 1.37 (9H,s), 2.82–2.98(2H,m), 3.20–3.35(1H,m), 6.65–6.80(1H, m)

REFERENCE EXAMPLE 55

3-[Trans-4-(2-N-t-butoxycarbonylaminoethyl) cyclohexyl]proionic acid 620 mg of trans-4-(2-N-t-butoxycarbonylaminoethyl) cyclohexylmethylmalonic acid and 10 ml of xylene were heated under reflux for 1 hour and 40 minutes. The solvent was distilled off under reduced pressure and hexane was added to the residue, and the resulting crystalline solid was collected by filtration to obtain 453 mg of the desired compound as a colorless crystalline solid.

m.p.: 107°–113° C.; NMR spectrum (CDCl$_3$) δ ppm: 0.68–0.95(4H,m), 1.10–1.80(10H,m), 1.37(9H,s), 2.19(2H, t,J=7.5 Hz), 2.85–3.00(2H,m), 6.65–6.78(1H,m)

REFERENCE EXAMPLE 56

Trans-4-(2-N-t-butoxycarbonylaminoethyl)-1-(3-hydroxypropyl)cyclohexane

In 10 ml of dry tetrahydrofuran were dissolved 450 mg of 3-[trans-4-(2-N-t-butoxycarbonylaminoethyl)cyclohexyl] propionic acid, and 0.42 ml of triethylamine and 0.22 ml of isobutyl chloroformate were added thereto with stirring under ice-cooling, and the mixture was stirred at room temperature for 3 hours. The insolubles were filtered using Celite and the filtrate was added dropwise to 10 ml of an aqueous solution of 171 mg of sodium borohydride with stirring under ice-cooling. The mixture was stirred under ice-cooling for 20 minutes and further at room temperature for 1 hour and 40 minutes. An excess amount of aqueous ammonium chloride solution was added thereto and the mixture was extracted with 200 ml of ethyl acetate. The extracts were washed successively with an aqueous sodium chloride solution, an aqueous sodium bicarbonate solution and an aqueous sodium chloride solution and dried over anhydrous magnesium sulfate, and the solvent was distilled off under reduced pressure. The residue was purified by silica gel column chromatography employing cyclohexane-ethyl acetate (3:1) as an eluting solvent. Hexane was added to the resulting crystalline solid and a crystalline solid was collected by filtration to obtain 284 mg of the desired compound as a colorless crystalline solid.

m.p.: 62°–64° C.; NMR spectrum (CDCl$_3$) δ ppm: 0.78–1.05(4H,m), 1.05–1.85(13H,m), 1.44(9H,s), 3.05–3.25 (2H,m), 3.55–3.70(2H,m), 4.30–4.60(1H,m)

REFERENCE EXAMPLE 57

Trans-N-t-butoxycarbonyl-2-[4-(3-nitroxypropyl) cyclohexyl]ethylamine 195 mg of the desired compound were obtained as a pale yellow crystalline solid using similar procedures to those in REFERENCE EXAMPLE 3 by using 270 mg of trans-4-(2-N-t-butoxycarbonylaminoethyl)-1-(3-hydroxypropyl)cyclohexane and 185 mg of nitronium tetrafluoroborate.

m.p.: 48°–49° C.; NMR spectrum (CDCl$_3$) δ ppm: 0.80–1.02(4H,m), 1.10–1.82(12H,m), 1.44(9H,s), 3.05–3.20 (2H,m), 4.42(2H,t,J=6.7 Hz)

REFERENCE EXAMPLE 58

2-[Trans-4-(3-nitroxypropyl)cyclohexyl]ethylamine hydrochloride 149 mg of the desired compound were obtained as a colorless crystalline solid using similar procedures to those in Reference example 4 by using 195 mg of trans-N-t-butoxycarbonyl-2-[4-(3-nitroxypropyl)cyclohexyl] ethylamine and 10.0 ml of 4N hydrochloric acid-dioxane.

m.p.: 165°–167° C. (decomp.); NMR spectrum (d$_6$-DMSO) δ ppm: 0.75–1.00(4H,m), 1.05–1.80(12H,m),2.78 (2H,t,J=7.7 Hz), 4.50(2H,t,J=6.6 Hz), 7.65–7.95(3H,bs)

REFERENCE EXAMPLE 59

N-t-butoxycarbonyl-3-nitroxymethylcyclohexylamine 2.65 g of the desired compound were obtained as a colorless crystalline solid using similar procedures to those in Reference example 3 by using 3.0 g of N-t-butoxycarbonyl-3-hydroxymethylcyclohexylamine and 3.48 g of nitronium tetrafluoroborate.

m.p.: 68°–70° C.; NMR spectrum (CDCl$_3$) δ ppm: 0.78–1.50(4H,m), 1.44(9H,s), 1.70–2.18(5H,m), 3.35–3.58 (1H,m), 4.29(2H,d,J=5.9 Hz), 4.30–5.50(1H,m)

REFERENCE EXAMPLE 60

3-Nitroxymethylcyclohexylamine hydrochloride 1.90 g of the desired compound were obtained as a colorless crystalline solid using similar procedures to those in Reference example 4 by using 2.65 g of N-t-butoxycarbonyl-3-nitroxymethylcyclohexylamine and 27.0 ml of 4N hydrochloric acid-dioxane.

m.p.: 168°–169° C. (decomp.); NMR spectrum (d$_6$-DMSO) δ ppm: 0.85–1.40(4H,m), 1.60–2.05(5H,m), 2.90–3.05(1H,m), 4.35–4.50(2H,m), 8.00–8.40(3H,bs)

REFERENCE EXAMPLE 61

N-t-butoxycarbonyl-4-nitroxymethylcyclohexylamine 2.34 g of the desired compound were obtained as a colorless crystalline solid using similar procedures to those in Reference example 3 by using 3.0 g of N-t-butoxycarbonyl-4-hydroxymethylcyclohexylamine and 3.48 g of nitronium tetrafluoroborate.

m.p.: 83°–84° C.; NMR spectrum (CDCl$_3$) δ ppm: 1.05–2.10(9H,m), 1.45(9H,s), 3.65–3.85(1H,m), 4.26(0.3H, d,J=6.6 Hz), 4.33(1.7H,d,J=6.6 Hz), 4.45–4.70(1H, m)

REFERENCE EXAMPLE 62

4-Nitroxymethylcyclohexylamine hydrochloride 1.34 g of the desired compound was obtained as a colorless crystalline solid using similar procedures to those in Reference example 4 by using 2.32 g of N-t-butoxycarbonyl-4-nitroxymethylcyclohexylamine and 23.0 ml of 4N hydrochloric acid-dioxane.

m.p.: 155°–157° C. (decomp.); NMR spectrum (d$_6$-DMSO) δ ppm: 1.10–2.05(9H,m), 2.85–2.97(0.14H,m), 3.13–3.25(0.86H,m), 4.36(0.28H,d,J=6.5 Hz), 4.44(1.72H, d,J=6.5 Hz), 8.00–8.40(3H,bs)

REFERENCE EXAMPLE 63

Trans-2-carbamoylcyclohexanecarboxylic acid

To 40 ml of aqueous conc. ammonia were added 10.0 g of trans-1,2-cyclohexanedicarboxylic acid anhydride with stirring at room temperature, and the mixture was stirred at room temperature for 4 hours and 15 minutes. The pH of the reaction mixture was adjusted to 1 with conc. hydrochloric acid with stirring under ice-cooling and the precipitated crystalline solid was collected by filtration and washed with water. The crystalline solid was recrystallized from ethanol to obtain 6.93 g of the desired compound as a colorless crystalline solid.

m.p.: 183°–186° C.; NMR spectrum ($d_6$-DMSO) δ ppm: 1.10–1.35(4H,m), 1.60–2.05(4H,m), 2.20–2.45(2H,m), 6.65 (1H,s), 7.22(1H,s), 11.88(1H,s)

REFERENCE EXAMPLE 64

Trans-N-t-butoxycarbonyl-2-hydroxymethylcyclohexylmethylamine

In 40 ml of dry tetrahydrofuran were suspended 4.0 g of trans-2-carbamoylcyclohexanecarboxylic acid, and 54.0 ml of lithium aluminium hydride-tetrahydrofuran solution (1.0M solution) were added dropwise thereto with stirring under ice-cooling, and the resulting mixture was stirred at room temperature for 55 minutes and heated under reflux for 1 hour. To the reaction mixture were added 13.0 g of sodium sulfate decahydrate with stirring under ice-cooling, and the mixture was stirred for 1 hour and 15 minutes. The reaction mixture was filtered using Celite and washed with ethanol, and the filtrate was concentrated to about 100 ml under reduced pressure. To the concentrate were added 6.4 ml of di-t-butyl dicarbonate with stirring at room temperature, and the mixture was stirred at room temperature for 30 minutes. The reaction mixture was concentrated under reduced pressure and the residue was purified by silica gel column chromatography employing cyclohexane-ethyl acetate (2:1) as an eluting solvent to obtain 1.47 g of the desired compound as a pale pink oil.

NMR spectrum ($d_6$-DMSO) δ ppm: 0.90–1.90(10H,m), 1.44(9H,s), 2.90–3.08(1H,m), 3.22–3.40(1H,m), 3.43–3.80 (3H,m), 5.10–5.30 (1H,m)

REFERENCE EXAMPLE 65

Trans-N-t-butoxycarbonyl-2-nitroxymethylcyclohexylmethylamine 885 mg of the desired compound were obtained as a yellow oil using similar procedures to those in Reference example 3 by using 893 mg of trans-N-t-butoxycarbonyl-2-hydroxymethyl-cyclohexylmethylamine and 723 mg of nitronium tetrafluoroborate.

NMR spectrum ($CDCl_3$) δ ppm: 0.90–1.90(10H,m), 1.44 (9H,s), 2.95–3.16(1H,m), 3.16–3.37(1H,m), 4.40(1H,dd,J=5.9 Hz,J=10.6 Hz), 4.44–4.70(2H,m)

REFERENCE EXAMPLE 66

Trans-2-nitroxymethylcyclohexylmethylamine hydrochloride 600 mg of the desired compound were obtained as a colorless crystalline solid using similar procedures to those in Reference example 4 by using 885 mg of trans-N-t-butoxycarbonyl-2-nitroxymethylcyclohexylmethylamine and 5.0 ml of 4N hydrochloric acid-dioxane.

m.p.: 144°–146° C. (decomp.); NMR spectrum ($CDCl_3$) δ ppm: 1.12–1.45(4H,m), 1.65–2.10(6H,m), 2.85–3.05(1H, m), 3.13–3.30(1H,m), 4.53(2H,d,J=3.3 Hz), 8.10–8.60(3H, bs)

REFERENCE EXAMPLE 67

Cis-2-carbamoylcyclohexanecarboxylic acid 2.07 g of the desired compound were obtained as a colorless crystalline solid using similar procedures to those in Reference example 63 by using 20 ml of aqueous conc. ammonia and 2.50 g of cis-1,2-cyclohexanedicarboxylic acid anhydride.

m.p.: 156°–158° C.; NMR spectrum ($CDCl_3$) δ ppm: 1.30–2.25(8H,m), 2.60–2.75(1H,m), 2.85–2.96(1H,m), 5.82–6.05(1H,bs), 6.10–6.28(1H,bs)

REFERENCE EXAMPLE 68

Cis-N-t-butoxycarbonyl-2-hydroxymethylcyclohexylmethylamine 0.73 g of the desired compound was obtained as a pale pink oil using similar procedures to those in Reference example 64 by using 2.0 g of cis-2-carbamoylcyclohexanecarboxyiic acid, 29.0 ml of lithium aluminum hydride-tetrahydrofuran solution (1.0M solution) and 3.2 ml of di-t-butyl dicarbonate.

NMR spectrum ($CDCl_3$) δ ppm: 1.20–1.95(10H,m), 1.44 (9H,s), 2.30–2.55(1H,bs), 2.90–3.08(1H,m), 3.10–3.25(1H, m), 3.50–3.80(2H,m), 4.80–5.00(1H,bs)

REFERENCE EXAMPLE 69

Cis-N-t-butoxycarbonyl-2-nitroxymethylcyclohexylmethylamine 1.79 g of the desired compound were obtained as a yellow oil using similar procedures to those in Reference example 3 by using 2.49 g of cis-N-t-butoxycarbonyl-2-hydroxymethylcyclohexylmethylamine and 2.0 g of nitronium tetrafluoroborate.

NMR spectrum ($CDCl_3$) δ ppm: 1.20–2.20(10H,m), 1.44 (9H,s), 3.00–3.20(2H,m), 4.35–4.65(3H,m)

REFERENCE EXAMPLE 70

Cis-2-nitroxymethylcyclohexylmethylamine hydrochloride 1.15 g of the desired compound was obtained as a colorless crystalline solid using in similar procedures to those in Reference example 4 by using 1.79 g of cis-N-t-butoxycarbonyl-2-nitroxymethylcyclohexylmethylamine and 10.0 ml of 4N hydrochloric acid-dioxane.

m.p.: 158°–160° C. (decomp.); NMR spectrum ($CDCl_3$) δ ppm: 1.30–2.30(10H,m), 2.90–3.10(2H,m), 4.35–4.60(2H, m), 8.00–8.50(3H,bs)

REFERENCE EXAMPLE 71

Dimethyl 1,3-cyclohexanedicarboxylate

To a diazomethane-ether solution prepared accoding to Arndt's method (Arndt; Org. Synth. Collect Vol. II, 165) from 40.0 g of N-methylnitrosourea were added 11.0 g of 1,3-cyclohexanedicarboxylic acid, and the mixture was stirred at room temperature for 30 minutes. After completion of the reaction, the solvent was distilled off under reduced pressure and the residue was dissolved in ethyl acetate and washed with an aqueous sodium bicarbonate solution and an aqueous sodium chloride solution. After the residue was dried over anhydrous magnesium sulfate, the solvent was distilled off under reduced pressure to obtain 8.33 g of the desired compound as a pale yellow oil.

NMR spectrum ($CDCl_3$) δ ppm: 1.20–2.40(9.3H,m), 2.62–2.75(0.7H,m), 3.67(6H,m)

REFERENCE EXAMPLE 72

Monomethyl 1,3-cyclohexanedicarboxylate

In 85 ml of methanol were dissolved 8.33 g of dimethyl 1,3-cyclohexanedicarboxylate, and 41.6 ml of 1N aqueous sodium hydroxide solution was added thereto, and the resulting mixture was stirred at room temperature for 4 hours. The solvent was distilled off under reduced pressure and the aqueous solution was washed with ethyl acetate. The pH was adjusted to 1 with diluted hydrochloric acid under ice-cooling and extracted with ethyl acetate. The extracts were washed with an aqueous sodium chloride solution and dried over anhydrous magnesium sulfate, and the solvent was distilled off under reduced pressure to obtain 6.7 g of the desired compound as a colorless oil.

NMR spectrum (CDCl$_3$) δ ppm: 1.20–2.45(9.3H,m), 2.65–2.80(0.7H,m), 3.68(3H,s)

REFERENCE EXAMPLE 73

3-Carbamoylcyclohexanecarboxylic acid

In 70 ml of aqueous conc. ammonia were dissolved 6.7 g of monomethyl 1,3-cyclohexanedicarboxylate, and the resulting mixture was allowed to stand at room temperature for 17 days. The pH of the mixture was adjusted to 1 with conc. hydrochloric acid under ice-cooling and the mixture was extracted with ethyl acetate. The extracts were washed with an aqueous sodium chloride solution and dried over anhydrous magnesium sulfate, and the solvent was distilled off under reduced pressure to obtain 2.64 g of the desired compound as a colorless crystalline solid. m.p.: 102°–128° C.; NMR spectrum (d$_6$-DMSO) δ ppm: 1.00–2.70(10H,m), 6.69(1H,s), 7.20(1H,s)

REFERENCE EXAMPLE 74

3-N-t-Butoxycarbonylaminomethyl-1-hydroxymethylcyclohexane 1.52 g of the desired compound were obtained as a colorless oil using similar procedures to those in Reference example 8 by using 3.60 g of 3-carbamoylcyclohexanecarboxylic acid, 53.0 ml of 1M lithium aluminum hydride in tetrahydrofuran solution and 4.8 ml of di-t-butyldicarbonate.

NMR spectrum (CDCl$_3$) δ ppm: 0.50–1.95(10H,m), 1.44 (9H,s), 2.88–3.20(2H,m), 3.40–3.60(3H,m), 4.60(1H,bs)

REFERENCE EXAMPLE 75

N-t-Butoxycarbonyl-3-nitroxymethylcyclohexylmethylamine 1.22 g of the desired compound was obtained as a pale yellow oil using similar procedures to those in Reference example 3 by using 1.50 g of 3-N-t-butoxycarbonylaminomethyl-1-hydroxymethylcyclohexane and 1.15 g of nitronium tetrafluoroborate.

NMR spectrum (CDCl$_3$) δ ppm: 0.60–1.90(10H,m), 1.44 (9H,s), 2.90–3.13(2H,m), 4.27(1.5H,d,J=5.9 Hz), 4.35 (0.5H,d,J=6.6 Hz), 4.58(1H,bs)

REFERENCE EXAMPLE 76

3-Nitroxymethylcyclohexylmethylamine hydrochloride 0.40 g of the desired compound was obtained as a colorless crystalline solid using similar procedures to those in Reference example 4 by using 1.22 g of N-t-butoxycarbonyl-3-nitroxymethylcyclohexylamine and 13.0 ml of 4N hydrochloric acid-dioxane.

m.p.: 109°–111° C. (decomp.); NMR spectrum (d$_6$-DMSO) δ ppm: 0.60–2.15(10H,m), 2.55–2.80(2H,m), 4.26–4.45(2H,m), 7.80–8.30(3H,bs)

REFERENCE EXAMPLE 77

N-t-Butoxycarbonyl-2-hydroxymethylcyclopentylamine

In 60 ml of methanol were dissolved 3.18 g of 2-hydroxymethylcyclopentylamine, and 9.72 ml of di-t-butyl dicarbonate were added thereto, and the resulting mixture was stirred at room temperature for 1.5 hour and further allowed to stand at room temperature overnight. The solvent was distilled off under reduced pressure and the residue was purified by silica gel column chromatography employing cyclohexane-ethyl acetate (4:1) as an eluting solvent to obtain 0.88 g of the desired compound, isomer A (a compound which has a low polarity) as a colorless crystalline solid and 0.43 g of the desired compound, isomer B (a compound which has a high polarity) as a colorless crystalline solid.

Isomer A

Thin layer chromatography: Rf=0.47 (developing solvent: cyclohexane/ethyl acetate=2/1); m.p.: 107°–108° C.; NMR spectrum (CDCl$_3$) δ ppm: 1.00–1.75(6H,m), 1.46(9H,s), 1.90–2.20(2H,m), 3.32–3.48(1H,m), 3.59(2H,dd,J=4.0 Hz,J=11.9 Hz), 4.05–4.20(1H,m), 4.49(1H,d,J=7.9 Hz)

Isomer B

Thin layer chromatography: Rf=0.38 (developing solvent:cyclohexane/ethyl acetate=2/1); m.p.: 65°–67° C.; NMR spectrum (CDCl$_3$) δ ppm: 1.20–1.5(3H,m), 1.45(9H, s), 1.53–2.10(5H,m), 3.40–3.77(3H,m), 4.55–4.75(1H,bs)

REFERENCE EXAMPLE 78

N-t-Butoxycarbonyl-2-nitroxymethylcyclopentylamine 0.94 g of the desired compound was obtained as a yellow oil using similar procedures to those in Reference example 3 by using 1.43 g of isomer A obtained in Reference example 77 and 1.76 g of nitronium tetrafluoroborate.

NMR spectrum (CDCl$_3$) δ ppm: 1.30–2.10(6H,m), 1.45 (9H,s),2.20–2.48(1H,m), 4.00–4.20(1H,m), 4.32(2H,dd,J= 6.6 Hz,J=10.6 Hz), 4.30–4.50(1H,m), 4.61(2H,d,dJ=5.9 Hz,J=10.6 Hz)

REFERENCE EXAMPLE 79

2-Nitroxymethylcyclopentylamine hydrochloride 0.53 g of the desired compound was obtained as a colorless crystalline solid using similar procedures to those in Reference example 4 by using 0.94 g of the compound obtained in Reference example 78 and 9.5 ml of 4N hydrochloric acid-dioxane.

m.p.: 133°–135° C. (decomp.); NMR spectrum (CDCl$_3$) δ ppm: 1.50–1.85(5H,m), 1.90–2.02(1H,m), 2.35–2.45(1H, m), 3.50–3.60(1H,m), 4.57(2H,d,J=7.8 Hz), 8.10–8.40(1H, bs)

REFERENCE EXAMPLE 80

N-t-Butoxycarbonyl-2-nitroxymethylcyclopentylamine 1.08 g of the desired compound was obtained as a yellow oil using similar procedures to those in Reference example 3 by using 1.16 g of isomer B obtained in Reference example 77 and 1.43 g of nitronium tetrafluoroborate.

NMR spectrum (CDCl$_3$) δ ppm: 1.30–1.80(4H,m), 1.45 (9H,s), 1.88–2.15(3H,m), 3.60–3.80(1H,m), 4.38(2H,dd,J= 7.3 Hz,J=10.6 Hz), 4.40–4.55(1H,m), 4.63(2H,d,dJ=5.0 Hz,J=10.6 Hz)

REFERENCE EXAMPLE 81

2-Nitroxymethylcyclopentylamine hydrochloride 0.64 g of the desired compound was obtained as a colorless crystalline solid using similar procedures to those in Reference example 4 by using 1.08 g of the compound obtained in Reference example 80 and 11.0 ml of 4N hydrochloric acid-dioxane.

m.p.: 128°–132° C (decomp.); NMR spectrum (CDCl$_3$) δ ppm: 1.35–2.05(6H,m), 2.28–2.40(1H,m), 3.25–3.45(1H, m), 4.53(1H,dd,J=6.9 Hz,J=10.3 Hz), 4.69(1H,dd,J=5.9 Hz,J=10.3 Hz), 8.15–8.50(1H,bs)

REFERENCE EXAMPLE 82

Trans-4-N-t-butoxycarbonylaminomethylcyclohexylaldehyde

To a solution of 150 ml of dry dichloromethane and 3.64 ml of dimethyl sulfoxide were added dropwise 3.58 ml of oxalyl chloride under cooling in a dry ice-acetone bath, and the resulting mixture was stirred at the same temperature for 45 minutes. To the reaction mixture were added dropwise a solution of 5.0 g of trans-4-N-t-butoxycarbonylaminomethyl-1-hydroxymethylcyclohexane dissolved in 25 ml of dry dichloromethane, and the mixture was stirred at the same temperature for 1 hour. Further, 14.3 ml of triethylamine was added thereto and the mixture was stirred at the same temperature for 2 hours. The dry ice-acetone bath was removed and the temperature of the reaction mixture was slowly returned to 0° C., and 50 ml of aqueous ammonium chloride solution were added thereto. To the reaction mixture were added 200 ml of ethyl acetate, and the mixture was washed with an aqueous sodium chloride solution, 10% aqueous hydrochloric acid solution, an aqueous sodium chloride solution, an aqueous sodium bicarbonate solution and an aqueous sodium chloride solution and dried over anhydrous magnesium sulfate, and the solvent was distilled off under reduced pressure. The residue was purified by silica gel column chromatography employing cyclohexane-ethyl acetate (5:1–2:1) as an eluting solvent to obtain 4.29 g of the desired compound as a colorless crystalline solid.

m.p.: 64°–66° C.; NMR spectrum (CDCl$_3$) δ ppm: 0.90–1.10(2H,m), 1.16–1.55(3H,m), 1.45(9H,s), 1.80–2.10 (4H,m), 2.10–2.25(1H,m), 3.00(2H,t,J=6.4 Hz), 4.50–4.70 (1H,bs), 9.62(1H,d,J=1.2 Hz)

REFERENCE EXAMPLE 83

4-(4-N-t-Butoxycarbonylaminomethylcyclohexyl)-3-buten-1-ol

In 20 ml of dry dioxane were suspended 500 mg of trans-4-N-t-butoxycarbonylaminomethylcyclohexylaldehyde and 995 mg of (3-hydroxypropyl)triphenylphosphonium bromide, and 0.37 ml of 1,8-diazabicyclo[5.4.0]undec-7-ene was added thereto, and the mixture was heated under reflux for 2 days. Then, 20 ml of dry acetonitrile were added to the reaction mixture and the mixture was heated under reflux for 3 days. Further, 995 mg of (3-hydroxypropyl) triphenylphosphonium bromide and 0.37 ml of 1,8-diazabicyclo[5.4.0]undec-7-ene were added thereto and the mixture was heated under reflux for 2 days. Moreover, 995 mg of (3-hydroxypropyl)triphenylphosphonium bromide and 0.37 ml of 1,8-diazabicyclo[5.4.0]undec-7-ene were added thereto and the mixture was heated under reflux for 5 days. The solvent was distilled off under reduced pressure and the residue was purified by silica gel column chromatography employing cyclohexane-ethyl acetate (4:1) as an eluting solvent to obtain 252 mg of the desired compound as a yellow oil.

NMR spectrum (CDCl$_3$) δ ppm: 0.85–2.60(13H,m), 1.44 (9H,s), 2.97(1.2H,t,J=6.4 Hz), 3.06(0.8H,t,J=6.4 Hz), 3.56–3.70(1.2H,m), 4.00–4.10(0.8H,m), 4.47–4.77(1H,m), 5.20–5.50(2H,m)

REFERENCE EXAMPLE 84

4-(4-N-t-Butoxycarbonylaminomethylcyclohexyl) butan-1-ol

To 20 ml of ethanol were added 313 mg of 4-(4-N-t-butoxycarbonylaminomethylcyclohexyl)-$^3$-buten-1-ol and 100 mg of 10% palladium-carbon, and the mixture was stirred under hydrogen of 1 atm. at 60° C. for 4 hours. The insolubles were filtered using Celite and the solvent in the filtrate was distilled off under reduced pressure. The residue was purified by silica gel column chromatography employing cyclohexane-ethyl acetate (4:1) as an eluting solvent to obtain 212 mg of the desired compound as a colorless oil.

NMR spectrum (CDCl$_3$) δ ppm: 0.75–2.00(17H,m), 1.44 (9H,s), 2.96(1.4H,t,J=6.4 Hz), 3.05(0.7H,t,J=6.4 Hz), 3.64 (2H,t,J=6.6 Hz), 4.50–4.70(1H,m)

REFERENCE EXAMPLE 85

N-t-Butoxycarbonyl-4-(4-nitroxybutyl) cyclohexylmethylamine 95.9 mg of the desired compound were obtained as a yellow oil using similar procedures to those in Reference example 3 by using 212 mg of 4-(4-N-t-butoxycarbonylaminomethylcyclohexyl)butan-1-ol and 145 mg of nitronium tetrafluoroborate.

NMR spectrum (CDCl$_3$) δ ppm: 0.75–1.00(4H,m), 1.05–2.00(12H,m), 1.44(9H,s), 2.96(1.5H,t,J=6.4 Hz), 3.06 (0.5H,t,J=6.5 Hz), 4.44(2H,t,J=6.6 Hz), 4.46–4.65(1H,m)

REFERENCE EXAMPLE 86

4-(4-Nitroxybutyl)cyclohexylmethylamine hydrochloride 53.1 mg of the desired compound were obtained as a colorless crystalline solid using similar procedures to those in Reference example 4 by using 95.9 mg of N-t-butoxycarbonyl-4-(4-nitroxybutyl)cyclohexylmethylamine and 2.0 ml of 4N hydrochloric acid-dioxane.

NMR spectrum (CDCl$_3$) δ ppm: 0.70–2.05(16H,m), 2.70–3.00(2H,m), 4.57(2H,t,J=6.6 Hz), 8.15–8.50(3H,bs)

REFERENCE EXAMPLE 87

1-Benzyl-2-N-t-butoxycarbonylaminomethyl-5-hydroxymethylpiperidine

In 100 ml of dry tetrahydrofuran were dissolved 3.06 g of ethyl 1-benzyl-2-cyano-5-piperidinecarboxylate, and 56.2 ml of 1M lithium aluminum hydride in tetrahydrofuran solution were added dropwise thereto under ice-cooling, and the mixture was stirred at room temperature for 20 minutes and further heated under reflux for 1.5 hours. The reaction mixture was added dropwise to 300 ml of ice-water and the insolubles were filtered using Celite. To the filtrate were added 3.1 ml of di-t-butyl dicarbonate and a catalytic amount of 4-dimethylaminopyridine, and the mixture was stirred at room temperature for 1 hour and 55 minutes. Acetic acid was added to the reaction mixture to adjust the pH of the mixture to 7 and further 3.1 ml of di-t-butyl dicarbonate and a catalytic amount of 4-dimethylaminopyridine were added thereto, and the mixture was stirred at room temperature for 2.5 hours. Moreover, 3.1 ml of di-t-butyl dicarbonate and a catalytic amount of 4-dimethylaminopyridine were added thereto and the mixture was stirred at room temperature for 50 minutes. Tetrahydrofuran was distilled off under reduced pressure and the residue was extracted with ethyl acetate, and the solvent was distilled off under reduced pressure. The residue was purified by silica gel column chromatography (eluting solvent: cyclohexane/ethyl acetate=3/4–1/4) to obtain 1.64 g of isomer A (a compound which has a low polarity) and 0.84 g of isomer B (a compound which has a high polarity) as a yellow oil and as a pale red oil, respectively.

Isomer A

Thin layer chromatography: Rf=0.56 (developing solvent: dichloromethane/methanol=9/1); NMR spectrum (CDCl$_3$) δ ppm: 1.44(9H,s), 1.50–2.00(5H,m), 2.36–2.75(3H,m), 3.25–3.40(2H,m), 3.41(1H,d,J=13.4 Hz), 3.59(2H,Abq,J=13 Hz), 3.99(1H,d,J=13.4 Hz), 4.80(1H,bs), 7.20–7.40(5H,m)

Isomer B

Thin layer chromatography: Rf=0.48 (developing solvent: dichloromethane/methanol=9/1); NMR spectrum (CDCl$_3$) δ ppm: 1.45(9H,s), 1.50–1.85(5H m), 2.25–2.40(1H,m), 2.94 (1H,d,J=9.3 Hz), 3.16(1H,d,J=13.6 Hz), 3.20–3.65(5H,m), 4.03(1H,d,J=13.6 Hz), 5.01(1H,bs), 7.18–7.38(5H,m)

REFERENCE EXAMPLE 88

1-t-Butoxycarbonyl-2-N-t-butoxycarbonylaminomethyl-5-hydroxymethylpiperidine

In 20 ml of ethanol was dissolved 0.84 g of the compound (isomer B) in Reference example 87, and 200 mg of 10% palladium-carbon was added thereto and the mixture was stirred under a hydrogen stream at room temperature for 3 hours and 40 minutes. Further, 200 mg of 10% palladium-carbon were added to the mixture and stirred at room temperature under hydrogen stream for 11 hours. To the reaction mixture was added 0.69 ml of di-t-butyl dicarbonate and the mixture was allowed to stand at room temperature for 8 days. The reaction mixture was filtered and the filtrate was distilled off under reduced pressure. Theresidue was purified by silica gel column chromatography (eluting solvent: cyclohexane/ethyl acetate=2/3–1/2) to obtain 658 mg of the desired compound as a colorless foam.

NMR spectrum (CDCl$_3$) δ ppm: 1.43(9H,s), 1.48(9H,s), 1.55–1.95(5H,m), 2.90–3.22(2H,m), 3.35–3.65(3H,m), 3.98 (1H,d,J=14.6 Hz), 4.13–4.26(1H,m), 4.75(1H,bs)

REFERENCE EXAMPLE 89

1-t-Butoxycarbonyl-2-N-t-butoxycarbonylaminomethyl-5-nitroxymethylpiperidine 523 mg of the desired compound were obtained as a yellow foam using similar procedures to those in Reference example 3 by using 658 mg of 1-t-butoxycarbonyl-2-N-t-butoxycarbonylaminomethyl-5-hydroxymethylpiperidine and 373 mg of nitronium tetrafluoroborate.

NMR spectrum (CDCl$_3$) δ ppm: 1.42(9H,m), 1.45(9H,m), 1.65–1.95(4H,m), 2.05–2.18(1Hm), 3.05–3.16(2H,m), 3.48–3.63(1H,m), 3.95(1H,d,J=14.2 Hz), 4.20–4.40(2H,m), 4.54(1H,dd,J=8.6 Hz,J=10.8 Hz), 4.78(1H,bs)

REFERENCE EXAMPLE 90

5-Nitroxymethyl-2-piperidylmethylamine dihydrochloride 351 mg of the desired compound were obtained as a colorless foam using similar procedures to those in Reference example 4 by using 523 mg of 1-t-butoxycarbonyl-2-N-t-butoxycarbonylaminomethyl-5-nitroxymethylpiperidine and 20 ml of 4N hydrochloric acid-dioxane.

NMR spectrum (d$_6$-DMSO) δ ppm: 1.20–1.45(1H,m), 1.58–2.05(4H,m), 2.20–2.40(1H,m), 2.65–2.90(1H,m), 2.95–3.50(4H,m), 4.48(2H,d,J=5.8 Hz)

TEST EXAMPLE 1

Collateral Vessel Dilating Action by Intravenous Administration

Beagle dogs (male) weighing 9 to 13 kg were anesthetized by intravenous injection of pentobarbital at a dose of 30 mg/kg and the experiment was carried out under artificial respiration. In order to measure the pressure of the left carotid artery, a polyethylene cannula (Atom intravenous catheter 2F) was inserted retrograde into one of the branch vessels of the left thyroidal artery. The left carotid artery upstream from this pressure measurement site was occluded for 1 minute with an arterial clamp, and the pressure immediately before occlusion (P) and the decrease in peripheral pressure (ΔP) were measured. Thereafter, the test sample was administered through another polyethylene cannula inserted into the femoral vein. The left carotid artery was occluded for 1 minute after 5, 15, 30, 45 and 60 minutes, and pressure immediately before occlusion (P$_t$) and the decrease in peripheral pressure (ΔP$_t$) each time were measured. The collateral vessel dilating effect (Collateral Index= CI) of the test sample was calculated by the following formula:

$$CI=100-(\Delta P_t/P_t) \times 100/(\Delta P/P)$$

As a result of this test, the compounds of Examples 1, 4, 8 and 9 exhibited an excellent action, the CI$_{60}$ (average CI value from 0 minute to 60 minutes) at a dose of 0.1 mg/kg being more than 15.

TEST EXAMPLE 2

Collateral Vessel Dilating Action by Intraportal Administation

While test specimens were prepared according to the method described above, the animal was laparotomized along the abdominal median line, and a branch .of the mesenteric vein was exposed and incised so as to administer the test sample into the portal vein. A polyethylene cannula (Atom intravenous catheter 2F) was inserted antegrade into the vein to reside in the portal vein, and then the test sample was administered through it. In order to test the first-pass effect of the test sample, it was first administered intravenously (femoral vein) and its collateral vessel dilating action of the sample for 60 minutes was measured. After 2 or 3 hours, the same test sample was then administered into the portal vein and its collateral vessel dilating action for 60 minutes was measured, and those actions were compared with each other.

As a result of this test, the compound of Example 1 exhibited an excellent action.

PREPARATION EXAMPLE 1

| Capsule | |
| --- | --- |
| Compound of Example 1 | 20.0 mg |
| Lactose | 158.7 |
| Corn starch | 70.0 |
| Magnesium stearate | 1.3 |
| | 250 mg |

The thus formulated powder is mixed and passes through a sieve of 60 mesh, and then the powder is encapsulated in No.3 gelatin capsule of 250 mg to prepare a capsule.

PREPARATION EXAMPLE 2

| Tablet | |
| --- | --- |
| Compound of Example 1 | 20.0 mg |
| Lactose | 154.0 |
| Corn starch | 25.0 |
| Magnesium stearate | 1.0 |
| | 200 mg |

The thus formulated powder is mixed and a 200 mg-tablet is made by means of a tablet making machine.

If necessary, sugar coating can be applied to the tablet.

We claim:

1. A thiazolidinone compound having the general formula:

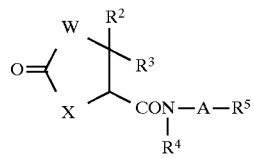

(I)

wherein:

W represents a sulfur atom or an oxygen atom, and X represents a group having the formula —N(R$^1$)—; or X represents a sulfur atom or an oxygen atom, and W represents a group having the formula —N(R$^1$)—;

R$^1$ represents a hydrogen atom, an alkyl group having from 1 to 6 carbon atoms or an alkyl group having from 1 to 4 carbon atoms substituted by an aryl group as defined below;

R$^2$ and R$^3$ may be the same or different and each represents a hydrogen atom, an alkyl group having from 1 to 6 carbon atoms, an alkyl group having from 1 to 4 carbon atoms substituted by an aryl group as defined below, an aryl group as defined below, or a 5- or 6-membered aromatic heterocyclic group containing 1 to 3 hetero groups selected from the group consisting of nitrogen atoms, oxygen atoms and sulfur atoms, said aromatic heterocyclic group being unsubstituted or being substituted by a substituent selected from the group consisting of alkyl groups having from 1 to 6 carbon atoms, halogen atoms, amino groups and mono- and di-alkylamino groups wherein the or each alkyl group has from 1 to 6 carbon atoms;

R$^4$ represents a hydrogen atom, an alkyl group having from 1 to 6 carbon atoms or an alkyl group having from 1 to 4 carbon atoms substituted by an aryl group as defined below;

R$^5$ represents a cycloalkyl group having from 3 to 8 carbon atoms, said group optionally containing a ring nitrogen atom, said group being substituted by a group having the formula —B—ONO$_2$ and said group further optionally being substituted by an alkyl group having from 1 to 6 carbon atoms, wherein B represents a single bond or an alkylene group having from 1 to 6 carbon atoms;

A represents a single bond or an alkylene group having from 1 to 6 carbon atoms; and said aryl group represents an aryl group having from 6 to 10 carbon atoms which may optionally be substituted by a substituent selected from the group consisting of alkyl groups having from 1 to 6 carbon atoms, alkoxy groups having from 1 to 6 carbon atoms, halogen atoms, amino groups, mono- and di- alkylamino groups wherein the or each alkyl group has from 1 to 6 carbon atoms, and nitro groups;

and pharmacologically acceptable salts thereof.

2. The thiazolidinone compound or a pharmacologically acceptable salt thereof according to claim 1, wherein W represents a sulfur atom or an oxygen atom and X represents a group having the formula —NR$^1$—; or X represents a sulfur atom and W represents a group having the formula —NR$^1$—.

3. The thiazolidinone compound or a pharmacologically acceptable salt thereof according to claim 1, wherein W represents a sulfur atom or an oxygen atom and X represents a group having the formula —NR$^1$—.

4. The thiazolidinone compound or a pharmacologically acceptable salt thereof according to claim 1, wherein W represents a sulfur atom and X represents a group having the formula —NR$^1$—.

5. The thiazolidinone compound or a pharmacologically acceptable salt thereof according to claim 1, wherein R$^1$ represents a hydrogen atom, an alkyl group having from 1 to 4 carbon atoms, a benzyl group or a phenethyl group.

6. The thiazolidinone compound or a pharmacologically acceptable salt thereof according to claim 1, wherein R$^1$ represents a hydrogen atom, a methyl group or a benzyl group.

7. The thiazolidinone compound or a pharmacologically acceptable salt thereof according to claim 1, wherein R$^1$ represents a hydrogen atom.

8. The thiazolidinone compound or a pharmacologically acceptable salt thereof according to claim 1, wherein R$^2$ and R$^3$ may be the same or different and each represents:

a hydrogen atom;

an alkyl group having from 1 to 4 carbon atoms;

an alkyl group having from 1 to 4 carbon atoms substituted by a phenyl group which may be unsubstituted or substituted by a substituent selected from the group consisting of alkyl groups having from 1 to 4 carbon atoms, alkoxy groups having from 1 to 4 carbon atoms, hydroxy groups, halogen atoms and nitro groups;

a naphthylmethyl group;

a phenyl group which may be unsubstituted or substituted by a substitutent selected from the group consisting of alkyl groups having from 1 to 4 carbon atoms, alkoxy groups having from 1 to 4 carbon atoms, hydroxy groups, halogen atoms and nitro groups;

a naphthyl group, or a furyl, thienyl, pyridyl, oxazolyl, thiazolyl, isoxazolyl or isothiazolyl group which may be optionally substituted by a substituent selected from the group consisting of alkyl groups having 1 or 2 carbon atoms, fluorine atom and chlorine atoms.

9. The thiazolidinone compound or a pharmacologically acceptable salt thereof according to claim 1, wherein $R^2$ and $R^3$ may be the same or different and each represents:

a hydrogen atom;

a methyl group;

an ethyl group;

a benzyl group which may be optionally substituted by a substituent selected from the group consisting of methyl groups, methoxy groups, hydroxy groups, fluorine atoms and chlorine atoms;

a phenethyl group which may be optionally substituted by a substituent selected from the group consisting of methyl groups, methoxy groups, hydroxy groups, fluorine atoms and chlorine atoms;

a phenyl group which may be optionally substituted by a substituent selected from the group consisting of methyl groups, methoxy groups, hydroxy groups, fluorine atoms and chlorine atoms;

a furyl group;

a thienyl group; or a pyridyl group.

10. The thiazolidinone compound or a pharmacologically acceptable salt thereof according to claim 1, wherein:

$R^2$ represents a hydrogen atom, a methyl group, an ethyl group, a benzyl group which may be optionally substituted by a substituent selected from the group consisting of methyl groups, methoxy groups and hydroxyl groups, a phenyl group which may be optionally substituted by a methyl group or a methoxy group, or a thienyl group; and $R^3$ represents a hydrogen atom; or $R^2$ and $R^3$ each represent a methyl group.

11. The thiazolidinone compound or a pharmacologically acceptable salt thereof according to claim 1, wherein:

$R^2$ represents a hydrogen atom, a methyl group, a benzyl group which may be optionally substituted by a methyl group or a methoxy group, or a phenyl group; and $R^3$ represents a hydrogen atom; or $R^2$ and $R^3$ each represent a methyl group.

12. The thiazolidinone compound or a pharmacologically acceptable salt thereof according to claim 1, wherein $R^2$ represents a hydrogen atom, a methyl group or a benzyl group, and $R^3$ represents a hydrogen atom.

13. The thiazolidinone compound or a pharmacologically acceptable salt thereof according to claim 1, wherein $R^2$ represents a hydrogen atom and $R^3$ represents a hydrogen atom.

14. The thiazolidinone compound or a pharmacologically acceptable salt thereof according to claim 1, wherein $R^4$ represents a hydrogen atom, an alkyl group having from 1 to 4 carbon atoms, a benzyl group or a phenethyl group.

15. The thiazolidinonelcompound or a pharmacologically acceptable salt thereof according to claim 1, wherein $R^4$ represents a hydrogen atom, a methyl group or a benzyl group.

16. The thiazolidinone compound or a pharmacologically acceptable salt thereof according to claim 1, wherein $R^4$ represents a hydrogen atom.

17. The thiazolidinone compound or a pharmacologically acceptable salt thereof according to claim 1, wherein $R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO$_2$ and further being optionally substituted by a methyl group, wherein B represents a single bond, a methylene group, an ethylene group, a trimethylene group or a tetramethylene group.

18. The thiazolidinone compound or a pharmacologically acceptable salt thereof according to claim 1, wherein $R^5$ represents a cyclopropyl group, cyclopentyl group or cyclohexyl group, said groups being substituted by a group having the formula —B—ONO$_2$ wherein B represents a methylene group, an ethylene group, a trimethylene group or a tetramethylene group.

19. The thiazolidinone compound or a pharmacologically acceptable salt thereof according to claim 1, wherein $R^5$ represents a cyclopentyl group or a cyclohexyl group, said groups being substituted by a group having the formula —B—ONO$_2$ wherein B represents a methylene group, an ethylene group, a trimethylene group or a tetramethylene group.

20. The thiazolidinone compound or a pharmacologically acceptable salt thereof according to claim 1, wherein $R^5$ represents a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyclohexyl group, a 3-, 4-, 5- or 6-nitroxymethylpiperidin-2-yl group or a 3-, 4-, 5- or 6-nitroxymethyl-1-methylpiperidin-2-yl group.

21. The thiazolidinone compound or a pharmacologically acceptable salt thereof according to claim 1, wherein $R^5$ represents a 2- or 3-nitroxymethylcyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group or a 2-, 3- or 4-(4-nitroxybutyl)cyclohexyl group.

22. The thiazolidinone compound or a pharmacologically acceptable salt thereof according to claim 1, wherein $R^5$ represents a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl)cyclohexyl group.

23. The thiazolidinone compound or a pharmacologically acceptable salt thereof according to claim 1, wherein $R^5$ represents a 3- or 4-nitroxymethylcyclohexyl group, a 4-(2-nitroxyethyl)cyclohexyl group, a 4-(3-nitroxypropyl)cyclohexyl group or a 4-(4-nitroxybutyl)cyclohexyl group.

24. The thiazolidinone compound or a pharmacologically acceptable salt thereof according to claim 1, wherein $R^5$ represents a 4-nitroxymethylcyclohexyl group.

25. The thiazolidinone compound or a pharmacologically acceptable salt thereof according to claim 1, wherein A represents a single bond or an alkylene group having 1 or 2 carbon atoms.

26. The thiazolidinone compound or a pharmacologically acceptable salt thereof according to claim 1, wherein A represents a methylene group or an ethylene group.

27. The thiazolidinone compound or a pharmacologically acceptable salt thereof according to claim 1, wherein A represents a methylene group.

28. The thiazolidinone compound or a pharmacologically acceptable salt thereof according to claim 1, wherein:

W represents a sulfur atom or an oxygen atom, and X represents a group having the formula —NR$^1$—; or X represents a sulfur atom, and W represents a group having the formula —NR$^1$—;

$R^1$ represents a hydrogen atom, an alkyl group having from 1 to 4 carbon atoms, a benzyl group or a phenethyl group;

$R^2$ and $R^3$ may be the same or different and each represents a hydrogen atom, an alkyl group having from 1 to 4 carbon atoms, an alkyl group having from 1 to 4 carbon atoms substituted by a phenyl group which may be unsubstituted or substituted by a substituent selected from the group consisting of alkyl groups having from 1 to 4 carbon atoms, alkoxy groups having from 1 to 4 carbon atoms, hydroxy groups, halogen atoms and nitro groups, a naphthylmethyl group, a phenyl group which may be unsubstituted or substituted by a substitutent selected from the group consisting of alkyl groups having from 1 to 4 carbon atoms, alkoxy groups having from 1 to 4 carbon atoms, hydroxy groups, halogen atoms and nitro groups, a naphthyl group, or a furyl, thienyl, pyridyl, oxazolyl, thiazolyl, isoxazolyl or isothiazolyl group which may be optionally substituted by a substituent selected from the group consisting of alkyl groups having 1 or 2 carbon atoms, fluorine atom and chlorine atoms, $R^4$ represents a hydrogen atom, an alkyl group having from 1 to 4 carbon atoms, a benzyl group or a phenethyl group;

$R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO$_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

29. The thiazolidinone compound or a pharmacologically acceptable salt thereof according to claim 1, wherein:

W represents a sulfur atom or an oxygen atom, and X represents a group having the formula —NR$^1$—;

$R^1$ represents a hydrogen atom, a methyl group or a benzyl group;

$R^2$ and $R^3$ may be the same or different and each represents a hydrogen atom, a methyl group, an ethyl group, a benzyl group which may be optionally substituted by a substituent selected from the group consisting of methyl groups, methoxy groups, hydroxy groups, fluorine atoms and chlorine atoms, a phenethyl group which may be optionally substituted by a substituent selected from the group consisting of methyl groups, methoxy groups, hydroxy groups, fluorine atoms and chlorine atoms, a phenyl group which may be optionally substituted by a substituent selected from the group consisting of methyl groups, methoxy groups, hydroxy groups, fluorine atoms and and chlorine atoms, a furyl group, a thienyl group, or a pyridyl group;

$R^4$ represents a hydrogen atom, a methyl group or a benzyl group;

$R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO$_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

30. The thiazolidinone compound or a pharmacologically acceptable salt thereof according to claim 1, wherein:

W represents a sulfur atom, and X represents a group having the formula —NR—;

$R^1$ represents a hydrogen atom, a methyl group or a benzyl group;

$R^2$ and $R^3$ may be the same or different and each represents a hydrogen atom, a methyl group, an ethyl group, a benzyl group which may be optionally substituted by a substituent selected from the group consisting of methyl groups, methoxy groups, hydroxy groups, fluorine atoms and chlorine atoms, a phenethyl group which may be optionally substituted by a substituent selected from the group consisting of methyl groups, methoxy groups, hydroxy groups, fluorine atoms and and chlorine atoms, a phenyl group which may be optionally substituted by a substituent selected from the group consisting of methyl groups, methoxy groups, hydroxy groups, fluorine atoms and and chlorine atoms, a furyl group, a thienyl group, or a pyridyl group;

$R^4$ represents a hydrogen atom, a methyl group or a benzyl group;

$R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO$_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

31. The thiazolidinone compound or a pharmacologically acceptable salt thereof according to claim 1, wherein:

W represents a sulfur atom, and X represents a group having the formula —NR$^1$—;

$R^1$ represents a hydrogen atom, a methyl group or a benzyl group;

$R^2$ represents a hydrogen atom, a methyl group, an ethyl group, a benzyl group which may be optionally substituted by a substituent selected from the group consisting of methyl groups, methoxy groups and hydroxyl groups, a phenyl group which may be optionally substituted by a methyl group or a methoxy group, or a thienyl group; and $R^3$ represents a hydrogen atom; or $R^2$ and $R^3$ each represent a methyl group;

$R^4$ represents a hydrogen atom, a methyl group or a benzyl group;

$R^5$ represents a cyclopropyl group, cyclopentyl group or cyclohexyl group, said groups being substituted by a group having the formula —B—$ONO_2$ wherein B represents a methylene group, an ethylene group, a trimethylene group or a tetramethylene group; and A represents a single bond or an alkylene group having 1 or 2 carbon atoms.

32. The thiazolidinone compound or a pharmacologically acceptable salt thereof according to claim 1, wherein:

W represents a sulfur atom, and X represents a group having the formula —$NR^1$—;

$R^1$ represents a hydrogen atom, a methyl group or a benzyl group;

$R^2$ represents a hydrogen atom, a methyl group, a benzyl group which may be optionally substituted by a methyl group or a methoxy group, or a phenyl group, and $R^3$ represents a hydrogen atom; or $R^2$ and $R^3$ each represent a methyl group;

$R^4$ represents a hydrogen atom, a methyl group or a benzyl group;

$R^5$ represents a cyclopentyl group or a cyclohexyl group, said groups being substituted by a group having the formula —B—$ONO_2$ wherein B represents a methylene group, an ethylene group, a trimethylene group or a tetramethylene group; and A represents a single bond or an alkylene group having 1 or 2 carbon atoms.

33. The thiazolidinone compound or a pharmacologically acceptable salt thereof according to claim 1, wherein:

W represents a sulfur atom, and X represents a group having the formula —$NR^1$—;

$R^1$ represents a hydrogen atom, a methyl group or a benzyl group;

$R^2$ represents a hydrogen atom, a methyl group or a benzyl group;

$R^3$ represents a hydrogen atom;

$R^4$ represents a hydrogen atom, a methyl group or a benzyl group;

$R^5$ represents a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)-cyclohexyl group, a 3-, 4-, 5- or 6-nitroxymethylpiperidin-2-yl group or a 3-, 4-, 5- or 6-nitroxymethyl-1-methylpiperidin-2-yl group; and A represents a single bond or an alkylene group having 1 or 2 carbon atoms.

34. The thiazolidinone compound or a pharmacologically acceptable salt thereof according to claim 1, wherein;

W represents a sulfur atom, and X represents a group having the formula —$NR^1$—;

$R^1$ represents a hydrogen atom;

$R^2$ represents a hydrogen atom, a methyl group or a benzyl group;

$R^3$ represents a hydrogen atom;

$R^4$ represents a hydrogen atom;

$R^5$ represents a 2- or 3-nitroxymethylcyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group or a 2-, 3- or 4-(4-nitroxybutyl)cyclohexyl group; and A represents a methylene group or an ethylene group.

35. The thiazolidinone compound or a pharmacologically acceptable salt thereof according to claim 1, wherein:

W represents a sulfur atom, and X represents a group having the formula —$NR^1$—;

$R^1$ represents a hydrogen atom;

$R^2$ represents a hydrogen atom, a methyl group or a benzyl group;

$R^3$ represents a hydrogen atom;

$R^4$ represents a hydrogen atom;

$R^5$ represents a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl)cyclohexyl group; and A represents a methylene group or an ethylene group.

36. The thiazolidinone compound or a pharmacologically acceptable salt thereof according to claim 1, wherein:

W represents a sulfur atom, and X is a group having the formula —$NR^1$—;

$R^1$ represents a hydrogen atom, $R^2$ represents a hydrogen atom;

$R^3$ represents a hydrogen atom;

$R^4$ represents a hydrogen atom;

$R^5$ represents a 3- or 4-nitroxymethylcyclohexyl group, a 4-(2-nitroxyethyl)cyclohexyl group, a 4-(3-nitroxypropyl)cyclohexyl group or a 4-(4-nitroxybutyl) cyclohexyl group; and A is a methylene group.

37. The thiazolidinone compound or a pharmacologically acceptable salt thereof according to claim 1, wherein:

W represents a sulfur atom, and X represents a group having the formula —$NR^1$—;

$R^1$ represents a hydrogen atom;

$R^2$ represents a hydrogen atom;

$R^3$ represents a hydrogen atom;

$R^4$ represents a hydrogen atom;

$R^5$ represents a 4-nitroxymethylcyclohexyl group; and

A represents a methylene group.

38. The thiazolidinone compound according to claim 1, selected from the group consisting of:

N-(4-Nitroxymethylcyclohexylmethyl)-2-oxothiazolidin-4-yl-carboxamide,

N-(4-nitroxymethylcyclohexylmethyl)-5-methyl-2-oxothiazolidin-4-yl-carboxamide,

N-(4-nitroxymethylcyclohexylmethyl)-2-oxo-5-(2-thienyl)thiazolidin-4-yl-carboxamide, N-(4-nitroxymethylcyclohexylmethyl)-5-(4-methoxyphenyl)-2-oxothiazolidin-4-yl-carboxamide, N-(4-nitroxymethylcyclohexylmethyl)-5-benzyl-2-oxothiazolidin-4-yl-carboxamide, N-(4-nitroxymethylcyclohexylmethyl)-5-(4-methylbenzyl)-2-oxothiazolidin-4-yl-carboxamide, N-(4-nitroxymethylcyclohexylmethyl)-5-(4-methoxybenzyl)-2-oxothiazolidin-4-yl-carboxamide, N-[2-(4-nitroxymethylcyclohexyl)ethyl]-2-oxothiazolidin-4-yl-carboxamide, N-[2-(4-nitroxymethylcyclohexyl)ethyl]-5-methyl-2-oxothiazolidin-4-yl-carboxamide, N-[2-(4-nitroxymethylcyclohexyl)ethyl]-2-oxo-5-(2-thienyl)thiazolidin-4-yl-carboxamide, N-[2-(4-nitroxymethylcyclohexyl)ethyl]-5-(4-methoxyphenyl)-2-oxothiazolidin-4-yl-carboxamide, N-[2-(4-nitroxymethylcyclohexyl)ethyl]-5-benzyl-2-oxothiazolidin-4-yl-carboxamide, N-[2-(4-nitroxymethylcyclohexyl)ethyl]-5-(4-methylbenzyl)-2-oxothiazolidin-4-yl-carboxamide, N-[2-(4-nitroxymethylcyclohexyl)ethyl]-5-(4-methoxybenzyl)-2-oxothiazolidin-4-yl-carboxamide, N-[4-(2-nitroxyethyl)cyclohexylmethyl]-2-oxothiazolidin-4-yl-carboxamide, N-[2-[4-(3-nitroxypropyl)cyclohexyl]ethyl]-2-oxothiazolidin-4-yl-carboxamide, N-[4-(3-nitroxypropyl)cyclohexylmethyl]-2-oxothiazolidin-4-yl-carboxamide, N-[4-(4-nitroxybutyl)cyclohexylmethyl]-2-oxothiazolidin-4-yl-carboxamide, N-(4-nitroxymethylcyclohexylmethyl)-2-oxothiazolidin-5-yl-carboxamide, N-(4-nitroxymethylcyclohexylmethyl)-4-methyl-2-oxothiazolidin-5-yl-carboxamide, N-(4-nitroxymethylcyclohexylmethyl)-4-(4-methoxyphenyl)-2-oxothiazolidin-5-yl-carboxamide, N-(4-nitroxymethylcyclohexylmethyl)-4-benzyl-2-oxothiazolidin-5-yl-carboxamide, N-(4-nitroxymethylcyclohexylmethyl)-4-(4-methylbenzyl)-2-oxothiazolidin-5-yl-carboxamide, and N-(4-nitroxymethylcyclohexylmethyl)-4-(4-methoxybenzyl)-2-oxothiazolidin-5-yl-carboxamide, or a pharmacologically acceptable salt thereof.

39. A pharmaceutical composition for the treatment or prophylaxis of angina pectoris comprising an effective amount of an active compound in admixture with a pharmacologically acceptable carrier or diluent, wherein said active compound is selected from the group consisting of thiazolidinone compounds having the general formula:

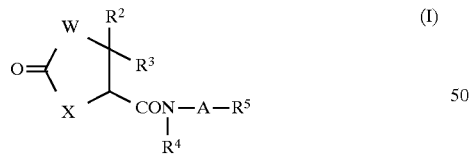

wherein:

W represents a sulfur atom or an oxygen atom, and X represents a group having the formula —N($R^1$)—; or X represents a sulfur atom or an oxygen atom, and W represents a group having the formula —N($R^1$)—;

$R^1$ represents a hydrogen atom, an alkyl group having from 1 to 6 carbon atoms or an alkyl group having from 1 to 4 carbon atoms substituted by an aryl group as defined below;

$R^2$ and $R^3$ may be the same or different and each represents a hydrogen atom, an alkyl group having from 1 to 6 carbon atoms, an alkyl group having from 1 to 4 carbon atoms substituted by an aryl group as defined below, an aryl group as defined below, or a 5- or 6-membered aromatic heterocyclic group containing 1 to 3 hetero groups selected from the group consisting of nitrogen atoms, oxygen atoms and sulfur atoms, said aromatic heterocyclic group being unsubstituted or being substituted by a substituent selected from the group consisting of alkyl groups having from 1 to 6 carbon atoms, halogen atoms, amino groups and mono- and di-alkylamino groups wherein the or each alkyl group has from 1 to 6 carbon atoms;

$R^4$ represents a hydrogen atom, an alkyl group having from 1 to 6 carbon atoms or an alkyl group having from 1 to 4 carbon atoms substituted by an aryl group as defined below;

$R^5$ represents a cycloalkyl group having from 3 to 8 carbon atoms, said group optionally containing a ring nitrogen atom, said group being substituted by a group having the formula —B—$ONO_2$ and said group further optionally being substituted by an alkyl group having from 1 to 6 carbon atoms, wherein B represents a single bond or an alkylene group having from 1 to 6 carbon atoms;

A represents a single bond or an alkylene group having from 1 to 6 carbon atoms; and said aryl group represents an aryl group having from 6 to 10 carbon atoms which may optionally be substituted by a substituent selected from the group consisting of alkyl groups having from 1 to 6 carbon atoms, alkoxy groups having from 1 to 6 carbon atoms, halogen atoms, amino groups, mono- and di- alkylamino groups wherein the or each alkyl group has from 1 to 6 carbon atoms, and nitro groups;

and pharmacologically acceptable salts thereof.

40. The pharmaceutical composition according to claim 39, wherein:

W represents a sulfur atom or an oxygen atom, and X represents a group having the formula —$NR^1$—; or X represents a sulfur atom, and W represents a group having the formula —$NR^1$—;

$R^1$ represents a hydrogen atom, an alkyl group having from 1 to 4 carbon atoms, a benzyl group or a phenethyl group;

$R^2$ and $R^3$ may be the same or different and each represents a hydrogen atom, an alkyl group having from 1 to 4 carbon atoms, an alkyl group having from 1 to 4 carbon atoms substituted by a phenyl group which may be unsubstituted or substituted by a substituent selected from the group consisting of alkyl groups having from 1 to 4 carbon atoms, alkoxy groups having from 1 to 4 carbon atoms, hydroxy groups, halogen atoms and nitro groups, a naphthylmethyl group, a phenyl group which may be unsubstituted or substituted by a substitutent selected from the group consisting of alkyl groups having from 1 to 4 carbon atoms, alkoxy groups having from 1 to 4 carbon atoms, hydroxy groups, halogen atoms and nitro groups, a naphthyl group, or a furyl, thienyl, pyridyl, oxazolyl, thiazolyl, isoxazolyl or isothiazolyl group which may be optionally substituted by a substituent selected from the group consisting of alkyl groups having 1 or 2 carbon atoms, fluorine atoms and chlorine atoms;

$R^4$ represents a hydrogen atom, an alkyl group having from 1 to 4 carbon atoms, a benzyl group or a phenethyl group;

R⁵ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO₂ and further being optionally substituted by a methyl group, wherein B represents a single bond, a methylene group, an ethylene group, a trimethylene group or a tetramethylene group; and A represents a single bond or an alkylene group having 1 or 2 carbon atoms.

41. The pharmaceutical composition according to claim 39, wherein:

W represents a sulfur atom or an oxygen atom, and X represents a group having the formula —NR¹—;

R¹ represents a hydrogen atom, a methyl group or a benzyl group;

R² and R³ may be the same or different and each represents
- a hydrogen atom,
- a methyl group,
- an ethyl group,
- a benzyl group which may be optionally substituted by a substituent selected from the group consisting of methyl groups, methoxy groups, hydroxy groups, fluorine atoms and chlorine atoms,
- a phenethyl group which may be optionally substituted by a substituent selected from the group consisting of methyl groups, methoxy groups, hydroxy groups, fluorine atoms and chlorine atoms,
- a phenyl group which may be optionally substituted by a substituent selected from the group consisting of methyl groups, methoxy groups, hydroxy groups, fluorine atoms and chlorine atoms,
- a furyl group,
- a thienyl group, or
- a pyridyl group;

R⁴ represents a hydrogen atom, a methyl group or a benzyl group;

R⁵ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO₂ and further being optionally substituted by a methyl group, wherein B represents a single bond, a methylene group, an ethylene group, a trimethylene group or a tetramethylene group; and A represents a single bond or an alkylene group having 1 or 2 carbon atoms.

42. The pharmaceutical composition according to claim 39, wherein:

W represents a sulfur atom, and X represents a group having the formula —NR¹—;

R¹ represents a hydrogen atom, a methyl group or a benzyl group;

R² and R³ may be the same or different and each represents
- a hydrogen atom,
- a methyl group,
- an ethyl group,
- a benzyl group which may be optionally substituted by a substituent selected from the group consisting of methyl groups, methoxy groups, hydroxy groups, fluorine atoms and chlorine atoms,
- a phenethyl group which may be optionally substituted by a substituent selected from the group consisting of methyl groups, methoxy groups, hydroxy groups, fluorine atoms and chlorine atoms,
- a phenyl group which may be optionally substituted by a substituent selected from the group consisting of methyl groups, methoxy groups, hydroxy groups, fluorine atoms and chlorine atoms,
- a furyl group,
- a thienyl group, or
- a pyridyl group;

R⁴ represents a hydrogen atom, a methyl group or a benzyl group;

R⁵ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO₂ and further being optionally substituted by a methyl group, wherein B represents a single bond, a methylene group, an ethylene group, a trimethylene group or a tetramethylene group; and A represents a single bond or an alkylene group having 1 or 2 carbon atoms.

43. The pharmaceutical composition according to claim 39, wherein:

W represents a sulfur atom, and X represents a group having the formula —NR¹—;

R¹ represents a hydrogen atom, a methyl group or a benzyl group;

R² represents a hydrogen atom, a methyl group, an ethyl group, a benzyl group which may be optionally substituted by a substituent selected from the group consisting of methyl groups, methoxy groups and hydroxyl groups, a phenyl group which may be optionally substituted by a methyl group or a methoxy group, or a thienyl group; and R³ represents a hydrogen atom; or R² and R³ each represent a methyl group;

R⁴ represents a hydrogen atom, a methyl group or a benzyl group;

R⁵ represents a cyclopropyl group, cyclopentyl group or cyclohexyl group, said groups being substituted by a group having the formula —B—ONO₂ wherein B represents a methylene group, an ethylene group, a trimethylene group or a tetramethylene group; and A represents a single bond or an alkylene group having 1 or 2 carbon atoms.

44. The pharmaceutical composition according to claim 39, wherein:

W represents a sulfur atom, and X represents a group having the formula —NR¹—;

R¹ represents a hydrogen atom, a methyl group or a benzyl group;

R² represents a hydrogen atom, a methyl group, a benzyl group which may be optionally substituted by a methyl group or a methoxy group, or a phenyl group, and R³ represents a hydrogen atom; or R² and R³ each represent a methyl group;

R⁴ represents a hydrogen atom, a methyl group or a benzyl group;

R⁵ represents a cyclopentyl group or a cyclohexyl group, said groups being substituted by a group having the formula —B—ONO₂ wherein B represents a methylene group, an ethylene group, a trimethylene group or a tetramethylene group; and A represents a single bond or an alkylene group having 1 or 2 carbon atoms.

45. The pharmaceutical composition according to claim 39, wherein:

W represents a sulfur atom, and X represents a group having the formula —NR$^1$—;

R$^1$ represents a hydrogen atom, a methyl group or a benzyl group;

R$^2$ represents a hydrogen atom, a methyl group or a benzyl group;

R$^3$ represents a hydrogen atom;

R$^4$ represents a hydrogen atom, a methyl group or a benzyl group;

R$^5$ represents a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyclohexyl group, a 3-, 4-, 5- or 6-nitroxymethylpiperidin-2-yl group or a 3-, 4-, 5- or 6-nitroxymethyl-1-methylpiperidin-2-yl group; and A represents a single bond or an alkylene group having 1 or 2 carbon atoms.

46. The pharmaceutical composition according to claim 39, wherein:

W represents a sulfur atom, and X represents a group having the formula —NR$^1$—;

R$^1$ represents a hydrogen atom;

R$^2$ represents a hydrogen atom, a methyl group or a benzyl group;

R$^3$ represents a hydrogen atom;

R$^4$ represents a hydrogen atom;

R$^5$ represents a 2- or 3-nitroxymethylcyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group or a 2-, 3- or 4-(4-nitroxybutyl)cyclohexyl group; and A represents a methylene group or an ethylene group.

47. The pharmaceutical composition according to claim 39, wherein:

W represents a sulfur atom, and X represents a group having the formula —NR$^1$—;

R$^1$ represents a hydrogen atom;

R$^2$ represents a hydrogen atom, a methyl group or a benzyl group;

R$^3$ represents a hydrogen atom;

R$^4$ represents a hydrogen atom;

R$^5$ represents a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl)cyclohexyl group; and A represents a methylene group or an ethylene group.

48. The pharmaceutical composition according to claim 39, wherein:

W represents a sulfur atom, and X is a group having the formula —NR$^1$—;

R$^1$ represents a hydrogen atom;

R$^2$ represents a hydrogen atom;

R$^3$ represents a hydrogen atom;

R$^4$ represents a hydrogen atom;

R$^5$ represents a 3- or 4-nitroxymethylcyclohexyl group, a 4-(2-nitroxyethyl)cyclohexyl group, a 4-(3-nitroxypropyl)cyclohexyl group or a 4-(4-nitroxybutyl) cyclohexyl group; and A is a methylene group.

49. The pharmaceutical composition according to claim 39, wherein:

W represents a sulfur atom, and X represents a group having the formula —NR$^1$—;

R$^1$ represents a hydrogen atom;

R$^2$ represents a hydrogen atom;

R$^3$ represents a hydrogen atom;

R$^4$ represents a hydrogen atom;

R$^5$ represents a 4-nitroxymethylcyclohexyl group; and

A represents a methylene group.

50. The pharmaceutical composition according to claim 39, wherein said active compound is selected from the group consisting of:

N-(4-Nitroxymethylcyclohexylmethyl)-2-oxothiazolidin-4-yl-carboxamide,

N-(4-nitroxymethylcyclohexylmethyl)-5-methyl-2-oxothiazolidin-4-yl-carboxamide,

N-(4-nitroxymethylcyclohexylmethyl)-2-oxo-5-(2-thienyl)thiazolidin-4-yl-carboxamide, N-(4-nitroxymethylcyclohexylmethyl)-5-(4-methoxyphenyl)-2-oxothiazolidin-4-yl-carboxamide, N-(4-nitroxymethylcyclohexylmethyl)-5-benzyl-2-oxothiazolidin-4-yl-carboxamide, N-(4-nitroxymethylcyclohexylmethyl)-5-(4-methylbenzyl)-2-oxothiazolidin-4-yl-carboxamide, N-(4-nitroxymethylcyclohexylmethyl)-5-(4-methoxybenzyl)-2-oxothiazolidin-4-yl-carboxamide, N-[2-(4-nitroxymethylcyclohexyl)ethyl]-2-oxothiazolidin-4-yl-carboxamide, N-[2-(4-nitroxymethylcyclohexyl)ethyl]-5-methyl-2-oxothiazolidin-4-yl-carboxamide, N-[2-(4-nitroxymethylcyclohexyl)ethyl]-2-oxo-5-(2-thienyl)thiazolidin-4-yl-carboxamide, N-[2-(4-nitroxymethylcyclohexyl)ethyl]-5-(4-methoxyphenyl)-2-oxothiazolidin-4-yl-carboxamide, N-[2-(4-nitroxymethylcyclohexyl)ethyl]-5-benzyl-2-oxothiazolidin-4-yl-carboxamide, N-[2-(4-nitroxymethylcyclohexyl)ethyl]-5-(4-methylbenzyl)-2-oxothiazolidin-4-yl-carboxamide, N-[2-(4-nitroxymethylcyclohexyl)ethyl]-5-(4-methoxybenzyl)-2-oxothiazolidin-4-yl-carboxamide, N-[4-(2-nitroxyethyl)cyclohexylmethyl]-2-oxothiazolidin-4-yl-carboxamide, N-[2-[4-(3-nitroxypropyl)cyclohexyl]ethyl]-2-oxothiazolidin-4-yl-carboxamide, N-[4-(3-nitroxypropyl)cyclohexylmethyl]-2-oxothiazolidin-4-yl-carboxamide, N-[4-(4-nitroxybutyl)cyclohexylmethyl]-2-oxothiazolidin-4-yl-carboxamide, N-(4-nitroxymethylcyclohexylmethyl)-2-oxothiazolidin-5-yl-carboxamide, N-(4-nitroxymethylcyclohexylmethyl)-4-methyl-2-oxothiazolidin-5-yl-carboxamide, N-(4-nitroxymethylcyclohexylmethyl)-4-(4-methoxyphenyl)-2-oxothiazolidin-5-yl-carboxamide, N-(4-nitroxymethylcyclohexylmethyl)-4-benzyl-2-oxothiazolidin-5-yl-carboxamide, N-(4-nitroxymethylcyclohexylmethyl)-4-(4-methylbenzyl)-2-oxothiazolidin-5-yl-carboxamide, and N-(4-nitroxymethylcyclohexylmethyl)-4-(4-methoxybenzyl)-2-oxothiazolidin-5-yl-carboxamide;

and pharmacologically acceptable salts thereof.

51. A method for the treatment or prophylaxis of angina pectoris comprising administering to a patient an effective amount of an active compound in admixture with a pharmacologically acceptable carrier or diluent, wherein said active compound is selected from the group consisting of thiazolidinone compounds having the general formula:

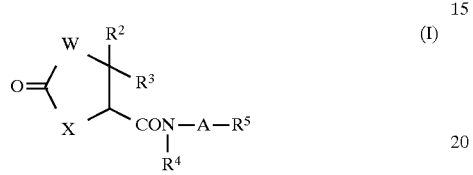

wherein:

W represents a sulfur atom or an oxygen atom, and X represents a group having the formula —N($R^1$)—; or X represents a sulfur atom or an oxygen atom, and W represents a group having the formula —N($R^1$)—;

$R^1$ represents a hydrogen atom, an alkyl group having from 1 to 6 carbon atoms or an alkyl group having from 1 to 4 carbon atoms substituted by an aryl group as defined below;

$R^2$ and $R^3$ may be the same or different and each represents a hydrogen atom, an alkyl group having from 1 to 6 carbon atoms, an alkyl group having from 1 to 4 carbon atoms substituted by an aryl group as defined below, an aryl group as defined below, or a 5- or 6-membered aromatic heterocyclic group containing 1 to 3 hetero groups selected from the group consisting of nitrogen atoms, oxygen atoms and sulfur atoms, said aromatic heterocyclic group being unsubstituted or being substituted by a substituent selected from the group consisting of alkyl groups having from 1 to 6 carbon atoms, halogen atoms, amino groups and mono- and di-alkylamino groups wherein the or each alkyl group has from 1 to 6 carbon atoms;

$R^4$ represents a hydrogen atom, an alkyl group having from 1 to 6 carbon atoms or an alkyl group having from 1 to 4 carbon atoms substituted by an aryl group as defined below;

$R^5$ represents a cycloalkyl group having from 3 to 8 carbon atoms, said group optionally containing a ring nitrogen atom, said group being substituted by a group having the formula —B—$ONO_2$ and said group further optionally being substituted by an alkyl group having from 1 to 6 carbon atoms, wherein B represents a single bond or an alkylene group having from 1 to 6 carbon atoms;

A represents a single bond or an alkylene group having from 1 to 6 carbon atoms; and said aryl group represents an aryl group having from 6 to 10 carbon atoms which may optionally be substituted by a substituent selected from the group consisting of alkyl groups having from 1 to 6 carbon atoms, alkoxy groups having from 1 to 6 carbon atoms, halogen atoms, amino groups, mono- and di- alkylamino groups wherein the or each alkyl group has from 1 to 6 carbon atoms, and nitro groups;

and pharmacologically acceptable salts thereof.

52. The method according to claim 51, wherein:

W represents a sulfur atom or an oxygen atom, and X represents a group having the formula —$NR^1$—; or X represents a sulfur atom, and W represents a group having the formula —$NR^1$—;

$R^1$ represents a hydrogen atom, an alkyl group having from 1 to 4 carbon atoms, a benzyl group or a phenethyl group;

$R^2$ and $R^3$ may be the same or different and each represents a hydrogen atom, an alkyl group having from 1 to 4 carbon atoms, an alkyl group having from 1 to 4 carbon atoms substituted by a phenyl group which may be unsubstituted or substituted by a substituent selected from the group consisting of alkyl groups having from 1 to 4 carbon atoms, alkoxy groups having from 1 to 4 carbon atoms, hydroxy groups, halogen atoms and nitro groups, a naphthylmethyl group, a phenyl group which may be unsubstituted or substituted by a substitutent selected from the group consisting of alkyl groups having from 1 to 4 carbon atoms, alkoxy groups having from 1 to 4 carbon atoms, hydroxy groups, halogen atoms and nitro groups, a naphthyl group, or a furyl, thienyl, pyridyl, oxazolyl, thiazolyl, isoxazolyl or isothiazolyl group which may be optionally substituted by a substituent selected from the group consisting of alkyl groups having 1 or 2 carbon atoms, fluorine atoms and chlorine atoms;

$R^4$ represents a hydrogen atom, an alkyl group having from 1 to 4 carbon atoms, a benzyl group or a phenethyl group;

$R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—$ONO_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

53. The method according to claim 51, wherein:

W represents a sulfur atom or an oxygen atom, and X represents a group having the formula —$NR^1$—;

$R^1$ represents a hydrogen atom, a methyl group or a benzyl group;

$R^2$ and $R^3$ may be the same or different and each represents a hydrogen atom, a methyl group, an ethyl group, a benzyl group which may be optionally substituted by a substituent selected from the group consisting of methyl groups, methoxy groups, hydroxy groups, fluorine atoms and chlorine atoms, a phenethyl group which may be optionally substituted by a substituent selected from the group consisting of methyl groups, methoxy groups, hydroxy groups, fluorine atoms and chlorine atoms, a phenyl group which may be optionally substituted by a substituent selected from the group consisting of methyl groups, methoxy groups, hydroxy groups, fluorine atoms and chlorine atoms,
a furyl group,
a thienyl group, or
a pyridyl group;

$R^4$ represents a hydrogen atom, a methyl group or a benzyl group;

$R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—$ONO_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

54. The method according to claim 51, wherein:

W represents a sulfur atom, and X represents a group having the formula —$NR^1$—;

$R^1$ represents a hydrogen atom, a methyl group or a benzyl group;

$R^2$ and $R^3$ may be the same or different and each represents
a hydrogen atom,
a methyl group,
an ethyl group,
a benzyl group which may be optionally substituted by a substituent selected from the group consisting of methyl groups, methoxy groups, hydroxy groups, fluorine atoms and chlorine atoms,
a phenethyl group which may be optionally substituted by a substituent selected from the group consisting of methyl groups, methoxy groups, hydroxy groups, fluorine atoms and chlorine atoms,
a phenyl group which may be optionally substituted by a substituent selected from the group consisting of methyl groups, methoxy groups, hydroxy groups, fluorine atoms and chlorine atoms,
a furyl group,
a thienyl group, or
a pyridyl group;

$R^4$ represents a hydrogen atom, a methyl group or a benzyl group;

$R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—$ONO_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

55. The method according to claim 51, wherein:

W represents a sulfur atom, and X represents a group having the formula —$NR^1$—;

$R^1$ represents a hydrogen atom, a methyl group or a benzyl group;

$R^2$ represents a hydrogen atom, a methyl group, an ethyl group, a benzyl group which may be optionally substituted by a substituent selected from the group consisting of methyl groups, methoxy groups and hydroxyl groups, a phenyl group which may be optionally substituted by a methyl group or a methoxy group, or a thienyl group; and $R^3$ represents a hydrogen atom; or $R^2$ and $R^3$ each represent a methyl group;

$R^4$ represents a hydrogen atom, a methyl group or a benzyl group;

$R^5$ represents a cyclopropyl group, cyclopentyl group or cyclohexyl group, said groups being substituted by a group having the formula —B—$ONO_2$ wherein B represents a methylene group, an ethylene group, a trimethylene group or a tetramethylene group; and A represents a single bond or an alkylene group having 1 or 2 carbon atoms.

56. The method according to claim 51, wherein:

W represents a sulfur atom, and X represents a group having the formula —$NR^1$—;

$R^1$ represents a hydrogen atom, a methyl group or a benzyl group;

$R^2$ represents a hydrogen atom, a methyl group, a benzyl group which may be optionally substituted by a methyl group or a methoxy group, or a phenyl group, and $R^3$ represents a hydrogen atom; or $R^2$ and $R^3$ each represent a methyl group;

$R^4$ represents a hydrogen atom, a methyl group or a benzyl group;

$R^5$ represents a cyclopentyl group or a cyclohexyl group, said groups being substituted by a group having the formula —B—$ONO_2$ wherein B represents a methylene group, an ethylene group, a trimethylene group or a tetramethylene group; and A represents a single bond or an alkylene group having 1 or 2 carbon atoms.

57. The method according to claim 51, wherein:

W represents a sulfur atom, and X represents a group having the formula —$NR^1$—;

$R^1$ represents a hydrogen atom, a methyl group or a benzyl group;

$R^2$ represents a hydrogen atom, a methyl group or a benzyl group;

$R^3$ represents a hydrogen atom;

$R^4$ represents a hydrogen atom, a methyl group or a benzyl group;

$R^5$ represents a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyetliyl)cyclohexyl group, a 2-, 3- or 4-(3-nitroxypropyl)cyclohexyl group, a 2-, 3- or 4-(4-nitroxybutyl)cyclohexyl group, a 3-, 4-, 5- or 6-nitroxymethylpiperidin-2-yl group or a 3-, 4-, 5- or 6-nitroxymethyl-1-methylpiperidin-2-yl group; and A represents a single bond or an alkylene group having 1 or 2 carbon atoms.

58. The method according to claim 51, wherein:

W represents a sulfur atom, and X represents a group having the formula —$NR^1$—;

$R^1$ represents a hydrogen atom;

$R^2$ represents a hydrogen atom, a methyl group or a benzyl group;

$R^3$ represents a hydrogen atom;

$R^4$ represents a hydrogen atom;

$R^5$ represents a 2- or 3-nitroxymethylcyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group or a 2-, 3- or 4-(4-nitroxybutyl)cyclohexyl group; and A represents a methylene group or an ethylene group.

59. The method according to claim 51, wherein:

W represents a sulfur atom, and X represents a group having the formula —NR¹—;

R¹ represents a hydrogen atom;

R² represents a hydrogen atom, a methyl group or a benzyl group;

R³ represents a hydrogen atom;

R⁴ represents a hydrogen atom;

R⁵ represents a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl)cyclohexyl group, and A represents a methylene group or an ethylene group.

60. The method according to claim 51, wherein:

W represents a sulfur atom, and X is a group having the formula —NR¹—;

R¹ represents a hydrogen atom;

R² represents a hydrogen atom;

R³ represents a hydrogen atom;

R⁴ represents a hydrogen atom;

R⁵ represents a 3- or 4-nitroxymethylcyclohexyl group, a 4-(2-nitroxyethyl)cyclohexyl group, a 4-(3-nitroxypropyl)cyclohexyl group or a 4-(4-nitroxybutyl)cyclohexyl group; and A is a methylene group.

61. The method according to claim 51, wherein:

W represents a sulfur atom, and X represents a group having the formula —NR¹—;

R¹ represents a hydrogen atom;

R² represents a hydrogen atom;

R³ represents a hydrogen atom;

R⁴ represents a hydrogen atom;

R⁵ represents a 4-nitroxymethylcyclohexyl group; and

A represents a methylene group.

62. The method according to claim 51, wherein said active compound is selected from the group consisting of:

N-(4-Nitroxymethylcyclohexylmethyl)-2-oxothiazolidin-4-yl-carboxamide,

N-(4-nitroxymethylcyclohexylmethyl)-5-methyl-2-oxothiazolidin-4-yl-carboxamide,

N-(4-nitroxymethylcyclohexylmethyl)-2-oxo-5-(2-thienyl)thiazolidin-4-yl-carboxamide, N-(4-nitroxymethylcyclohexylmethyl)-5-(4-methoxyphenyl)-2-oxothiazolidin-4-yl-carboxamide, N-(4-nitroxymethylcyclohexylmethyl)-5-benzyl-2-oxothiazolidin-4-yl-carboxamide, N-(4-nitroxymethylcyclohexylmethyl)-5-(4-methylbenzyl)-2-oxothiazolidin-4-yl-carboxamide, N-(4-nitroxymethylcyclohexylmethyl)-5-(4-methoxybenzyl)-2-oxothiazolidin-4-yl-carboxamide, N-[2-(4-nitroxymethylcyclohexyl)ethyl]-2-oxothiazolidin-4-yl-carboxamide, N-[2-(4-nitroxymethylcyclohexyl)ethyl]-5-methyl-2-oxothiazolidin-4-yl-carboxamide, N-[2-(4-nitroxymethylcyclohexyl)ethyl]-2-oxo-5-(2-thienyl)thiazolidin-4-yl-carboxamide, N-[2-(4-nitroxymethylcyclohexyl)ethyl]-5-(4-methoxyphenyl)-2-oxothiazolidin-4-yl-carboxamide, N-[2-(4-nitroxymethylcyclohexyl)ethyl]-5-benzyl-2-oxothiazolidin-4-yl-carboxamide, N-[2-(4-nitroxymethylcyclohexyl)ethyl]-5-(4-methylbenzyl)-2-oxothiazolidin-4-yl-carboxamide, N-[2-(4-nitroxymethylcyclohexyl)ethyl]-5-(4-methoxybenzyl)-2-oxothiazolidin-4-yl-carboxamide, N-[4-(2-nitroxyethyl)cyclohexylmethyl]-2-oxothiazolidin-4-yl-carboxamide, N-[2-[4-(3-nitroxypropyl)cyclohexyl]ethyl]-2-oxothiazolidin-4-yl-carboxamide, N-[4-(3-nitroxypropyl)cyclohexylmethyl]-2-oxothiazolidin-4-yl-carboxamide, N-[4-(4-nitroxybutyl)cyclohexylmethyl]-2-oxothiazolidin-4-yl-carboxamide, N-(4-nitroxymethylcyclohexylmethyl)-2-oxothiazolidin-5-yl-carboxamide, N-(4-nitroxymethylcyclohexylmethyl)-4-methyl-2-oxothiazolidin-5-yl-carboxamide, N-(4-nitroxymethylcyclohexylmethyl)-4-(4-methoxyphenyl)-2-oxothiazolidin-5-yl-carboxamide, N-(4-nitroxymethylcyclohexylmethyl)-4-benzyl-2-oxothiazolidin-5-yl-carboxamide, N-(4-nitroxymethylcyclohexylmethyl)-4-(4-methylbenzyl)-2-oxothiazolidin-5-yl-carboxamide, and N-(4-nitroxymethylcyclohexylmethyl)-4-(4-methoxybenzyl)-2-oxothiazolidin-5-yl-carboxamide;

and pharmacologically acceptable salts thereof.

63. A process for preparing a thiazolidinone compound having the general formula:

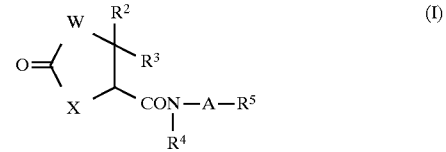

wherein:

W represents a sulfur atom or an oxygen atom, and X represents a group having the formula —N(R¹)—; or X represents a sulfur atom or an oxygen atom, and W represents a group having the formula —N(R¹)—;

R¹ represents a hydrogen atom, an alkyl group having from 1 to 6 carbon atoms or an alkyl group having from 1 to 4 carbon atoms substituted by an aryl group as defined below;

R² and R³ may be the same or different and each represents a hydrogen atom, an alkyl group having from 1 to 6 carbon atoms, an alkyl group having from 1 to 4 carbon atoms substituted by an aryl group as defined below, an aryl group as defined below, or a 5- or 6-membered aromatic heterocyclic group containing 1 to 3 hetero groups selected from the group consisting of nitrogen atoms, oxygen atoms and sulfur atoms, said aromatic heterocyclic group being unsubstituted or being substituted by a substituent selected from the group consisting of alkyl groups having from 1 to 6 carbon atoms, halogen atoms, amino groups and mono- and di- alkylamino groups wherein the or each alkyl group has from 1 to 6 carbon atoms;

R[4] represents a hydrogen atom, an alkyl group having from 1 to 6 carbon atoms or an alkyl group having from 1 to 4 carbon atoms substituted by an aryl group as defined below;

R[5] represents a cycloalkyl group having from 3 to 8 carbon atoms, said group optionally containing a ring nitrogen atom, said group being substituted by a group having the formula —B—ONO$_2$ and said group further optionally being substituted by an alkyl group having from 1 to 6 carbon atoms, wherein B represents a single bond or an alkylene group having from 1 to 6 carbon atoms;

A represents a single bond or an alkylene group having from 1 to 6 carbon atoms; and said aryl group represents an aryl group having from 6 to 10 carbon atoms which may optionally be substituted by a substituent selected from the group consisting of alkyl groups having from 1 to 6 carbon atoms, alkoxy groups having from 1 to 6 carbon atoms, halogen atoms, amino groups, mono- and di- alkylamino groups wherein the or each alkyl group has from 1 to 6 carbon atoms, and nitro groups;

or a pharmacologically acceptable salt thereof, which comprises reacting a compound having the following general formula or a reactive derivative thereof:

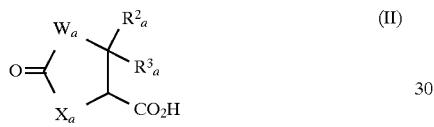

(II)

wherein Wa, Xa, R$^2$a and R$^3$a have the same meanings as W, X, R$^2$ and R$^3$, as defined above, respectively except that an amino group or an imino group (—NH—) in any of said groups may be optionally protected, with a compound having the general formula, or an acid addition salt thereof:

(III)

wherein A has the same meaning as defined above, and R$^4$a and R$^5$a have the same meanings as R$^4$ and R$^5$, as defined above, respectively except that an amino group or an imino group (—NH—) in either of said groups may be optionally protected; and if desired, eliminating a protective group such as an amino protecting group from the compound thus obtained.

64. The process according to claim 63, wherein the reagents and reaction conditions are chosen to prepare a thiazolidinone compound or a pharmacologically acceptable salt thereof wherein:

W represents a sulfur atom or an oxygen atom, and X represents a group having the formula —NR$^1$—; or X represents a sulfur atom, and W represents a group having the formula —NR$^1$—;

R[1] represents a hydrogen atom, an alkyl group having from 1 to 4 carbon atoms, a benzyl group or a phenethyl group;

R[2] and R[3] may be the same or different and each represents
a hydrogen atom,
an alkyl group having from 1 to 4 carbon atoms,
an alkyl group having from 1 to 4 carbon atoms substituted by a phenyl group which may be unsubstituted or substituted by a substituent selected from the group consisting of alkyl groups having from 1 to 4 carbon atoms, alkoxy groups having from 1 to 4 carbon atoms, hydroxy groups, halogen atoms and nitro groups,
a naphthylmethyl group,
a phenyl group which may be unsubstituted or substituted by a substitutent selected from the group consisting of alkyl groups having from 1 to 4 carbon atoms, alkoxy groups having from 1 to 4 carbon atoms, hydroxy groups, halogen atoms and nitro groups,
a naphthyl group, or
a furyl, thienyl, pyridyl, oxazolyl, thiazolyl, isoxazolyl or isothiazolyl group which may be optionally substituted by a substituent selected from the group consisting of alkyl groups having 1 or 2 carbon atoms, fluorine atom and chlorine atoms;

R[4] represents a hydrogen atom, an alkyl group having from 1 to 4 carbon atoms, a benzyl group or a phenethyl group;

R[5] represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO$_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

65. The process according to claim 63, wherein the reagents and reaction conditions are chosen to prepare a thiazolidinone compound or a pharmacologically acceptable salt thereof wherein:

W represents a sulfur atom or an oxygen atom, and X represents a group having the formula —NR$^1$—;

R[1] represents a hydrogen atom, a methyl group or a benzyl group;

R[2] and R[3] may be the same or different and each represents
a hydrogen atom,
a methyl group,
an ethyl group,
a benzyl group which may be optionally substituted by a substituent selected from the group consisting of methyl groups, methoxy groups, hydroxy groups, fluorine atoms and chlorine atoms,
a phenethyl group which may be optionally substituted by a substituent selected from the group consisting of methyl groups, methoxy groups, hydroxy groups, fluorine atoms and chlorine atoms,
a phenyl group which may be optionally substituted by a substituent selected from the group consisting of methyl groups, methoxy groups, hydroxy groups, fluorine atoms and chlorine atoms,
a furyl group,
a thienyl group, or
a pyridyl group;

R[4] represents a hydrogen atom, a methyl group or a benzyl group;

R[5] represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—ONO$_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

66. The process according to claim 63, wherein the reagents and reaction conditions are chosen to prepare a thiazolidinone compound or a pharmacologically acceptable salt thereof wherein:

W represents a sulfur atom, and X represents a group having the formula —$NR^1$—;

$R^1$ represents a hydrogen atom, a methyl group or a benzyl group;

$R^2$ and $R^3$ may be the same or different and each represents
  a hydrogen atom,
  a methyl group,
  an ethyl group,
  a benzyl group which may be optionally substituted by a substituent selected from the group consisting of methyl groups, methoxy groups, hydroxy groups, fluorine atoms and chlorine atoms,
  a phenethyl group which may be optionally substituted by a substituent selected from the group consisting of methyl groups, methoxy groups, hydroxy groups, fluorine atoms and chlorine atoms,
  a phenyl group which may be optionally substituted by a substituent selected from the group consisting of methyl groups, methoxy groups, hydroxy groups, fluorine atoms and chlorine atoms,
  a furyl group,
  a thienyl group, or
  a pyridyl group;

$R^4$ represents a hydrogen atom, a methyl group or a benzyl group;

$R^5$ represents a cycloalkyl group having from 3 to 6 carbon atoms, a pyrrolidinyl group or a piperidinyl group, said cycloalkyl group, pyrrolidinyl group or piperidinyl group being substituted by a group having the formula —B—$ONO_2$ and further being optionally substituted by a methyl group, wherein B represents a single bond, a methylene group, an ethylene group, a trimethylene group or a tetramethylene group; and A represents a single bond or an alkylene group having 1 or 2 carbon atoms.

67. The process according to claim 63, wherein the reagents and reaction conditions are chosen to prepare a thiazolidinone compound or a pharmacologically acceptable salt thereof wherein:

W represents a sulfur atom, and X represents a group having the formula —$NR^1$—;

$R^1$ represents a hydrogen atom, a methyl group or a benzyl group;

$R^2$ represents a hydrogen atom, a methyl group, an ethyl group, a benzyl group which may be optionally substituted by a substituent selected from the group consisting of methyl groups, methoxy groups and hydroxyl groups, a phenyl group which may be optionally substituted by a methyl group or a methoxy group, or a thienyl group; and $R^3$ represents a hydrogen atom; or $R^2$ and $R^3$ each represent a methyl group;

$R^4$ represents a hydrogen atom, a methyl group or a benzyl group;

$R^5$ represents a cyclopropyl group, cyclopentyl group or cyclohexyl group, said groups being substituted by a group having the formula —B—$ONO_2$ wherein B represents a methylene group, an ethylene group, a trimethylene group or a tetramethylene group; and A represents a single bond or an alkylene group having 1 or 2 carbon atoms.

68. The process according to claim 63, wherein the reagents and reaction conditions are chosen to prepare a thiazolidinone compound or a pharmacologically acceptable salt thereof wherein:

W represents a sulfur atom, and X represents a group having the formula —$NR^1$—;

$R^1$ represents a hydrogen atom, a methyl group or a benzyl group;

$R^2$ represents a hydrogen atom, a methyl group, a benzyl group which may be optionally substituted by a methyl group or a methoxy group, or a phenyl group, and $R^3$ represents a hydrogen atom; or $R^2$ and $R^3$ each represent a methyl group;

$R^4$ represents a hydrogen atom, a methyl group or a benzyl group;

$R^5$ represents a cyclopentyl group or a cyclohexyl group, said groups being substituted by a group having the formula —B—$ONO_2$ wherein B represents a methylene group, an ethylene group, a trimethylene group or a tetramethylene group; and A represents a single bond or an alkylene group having 1 or 2 carbon atoms.

69. The process according to claim 63, wherein the reagents and reaction conditions are chosen to prepare a thiazolidinone compound or a pharmacologically acceptable salt thereof wherein:

W represents a sulfur atom, and X represents a group having the formula —$NR^1$—;

$R^1$ represents a hydrogen atom, a methyl group or a benzyl group;

$R^2$ represents a hydrogen atom, a methyl group or a benzyl group;

$R^3$ represents a hydrogen atom;

$R^4$ represents a hydrogen atom, a methyl group or a benzyl group;

$R^5$ represents a 2- or 3-nitroxymethylcyclopentyl group, a 2- or 3-(2-nitroxyethyl)cyclopentyl group, a 2- or 3-(3-nitroxypropyl)cyclopentyl group, a 2- or 3-(4-nitroxybutyl)cyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group, a 2-, 3- or 4-(4-nitroxybutyl)cyclohexyl group, a 3-, 4-, 5- or 6-nitroxymethylpiperidin-2-yl group or a 3-, 4-, 5- or 6-nitroxymethyl-1-methylpiperidin-2-yl group; and A represents a single bond or an alkylene group having 1 or 2 carbon atoms.

70. The process according to claim 63, wherein the reagents and reaction conditions are chosen to prepare a thiazolidinone compound or a pharmacologically acceptable salt thereof wherein:

W represents a sulfur atom, and X represents a group having the formula —$NR^1$—;

$R^1$ represents a hydrogen atom;

$R^2$ represents a hydrogen atom, a methyl group or a benzyl group;

$R^3$ represents a hydrogen atom,

159

R⁴ represents a hydrogen atom;

R⁵ represents a 2- or 3-nitroxymethylcyclopentyl group, a 2-, 3- or 4-nitroxycyclohexyl group, a 2-, 3- or 4-nitroxymethylcyclohexyl group, a 2-, 3- or 4-(2-nitroxyethyl)cyclohexyl group, a 2-, 3- or 4-(3-nitroxypropyl)cyclohexyl group or a 2-, 3- or 4-(4-nitroxybutyl)cyclohexyl group; and A represents a methylene group or an ethylene group.

71. The process according to claim 63, wherein the reagents and reaction conditions are chosen to prepare a thiazolidinone compound or a pharmacologically acceptable salt thereof wherein:

W represents a sulfur atom, and X represents a group having the formula —NR¹—;

R¹ represents a hydrogen atom;

R² represents a hydrogen atom, a methyl group or a benzyl group;

R³ represents a hydrogen atom;

R⁴ represents a hydrogen atom;

R⁵ represents a 3-nitroxymethylcyclopentyl group, a 4-nitroxycyclohexyl group, a 2-, 3- or 4-nitroxymethylcyclohexyl group, a 3- or 4-(2-nitroxyethyl)cyclohexyl group, a 3- or 4-(3-nitroxypropyl)cyclohexyl group or a 3- or 4-(4-nitroxybutyl)cyclohexyl group; and A represents a methylene group or an ethylene group.

72. The process according to claim 63, wherein the reagents and reaction conditions are chosen to prepare a thiazolidinone compound or a pharmacologically acceptable salt thereof wherein:

W represents a sulfur atom, and X is a group having the formula —NR¹—;

R¹ represents a hydrogen atom;

R² represents a hydrogen atom;

R³ represents a hydrogen atom;

R⁴ represents a hydrogen atom;

R⁵ represents a 3- or 4-nitroxymethylcyclohexyl group, a 4-(2-nitroxyethyl)cyclohexyl group, a 4-(3-nitroxypropyl)cyclohexyl group or a 4-(4-nitroxybutyl)cyclohexyl group; and A is a methylene group.

73. The process according to claim 63, wherein the reagents and reaction conditions are chosen to prepare a thiazolidinone compound or a pharmacologically acceptable salt thereof wherein:

W represents a sulfur atom, and X represents a group having the formula —NR¹—;

R¹ represents a hydrogen atom;

R² represents a hydrogen atom;

R³ represents a hydrogen atom;

R⁴ represents a hydrogen atom;

R⁵ represents a 4-nitroxymethylcyclohexyl group; and

A represents a methylene group.

160

74. The process according to claim 63, wherein the reagents and reaction conditions are chosen to prepare a thiazolidinone compound selected from the group consisting of:

N-(4-Nitroxymethylcyclohexylmethyl)-2-oxothiazolidin-4-yl-carboxamide,

N-(4-nitroxymethylcyclohexylmethyl)-5-methyl-2-oxothiazolidin-4-yl-carboxamide,

N-(4-nitroxymethylcyclohexylmethyl)-2-oxo-5-(2-thienyl)thiazolidin-4-yl-carboxamide, N-(4-nitroxymethylcyclohexylmethyl)-5-(4-methoxyphenyl)-2-oxothiazolidin-4-yl-carboxamide, N-(4-nitroxymethyicyclohexyimethyl)-5-benzyl-2-oxothiazolidin-4-yl-carboxamide, N-(4-nitroxymethylcyclohexylmethyl)-5-(4-methylbenzyl)-2-oxothiazolidin-4-yl-carboxamide, N-(4-nitroxymethylcyclohexylmethyl)-5-(4-methoxybenzyl)-2-oxothiazolidin-4-yl-carboxamide, N-[2-(4-nitroxymethylcyclohexyl)ethyl]-2-oxothiazolidin-4-yl-carboxamide, N-[2-(4-nitroxymethylcyclohexyl)ethyl]-5-methyl-2-oxothiazolidin-4-yl-carboxamide, N-[2-(4-nitroxymethylcyclohexyl)ethyl]-26oxo-5-(2-thienyl)thiazolidin-4-yl-carboxamide, N-[2-(4-nitroxymethylcyclohexyl)ethyl]-5-(4-methoxyphenyl)-2-oxothiazolidin-4-yl-carboxamide, N-[2-(4-nitroxymethylcyclohexyl)ethyl]-5-benzyl-2-oxothiazolidin-4-yl-carboxamide, N-[2-(4-nitroxymethylcyclohexyl)ethyl]-5-(4-methylbenzyl)-2-oxothiazolidin-4-yl-carboxamide, N-[2-(4-nitroxymethylcyclohexyl)ethyl]-5-(4-methoxybenzyl)-2-oxothiazolidin-4-yl-carboxamide, N-[4-(2-nitroxyethyl)cyclohexylmethyl]-2-oxothiazolidin-4-yl-carboxamide, N-[2-[4-(3-nitroxypropyl)cyclohexyl]ethyl]-2-oxothiazolidin-4-yl-carboxamide, N-[4-(3-nitroxypropyl)cyclohexylmethyl]-2-oxothiazolidin-4-yl-carboxamide, N-[4-(4-nitroxybutyl)cyclohexylmethyl]-2-oxothiazolidin-4-yl-carboxamide, N-(4-nitroxymethylcyclohexylmethyl)-2-oxothiazolidin-5-yl-carboxamide, N-(4-nitroxymethylcyclohexylmethyl)-4-methyl-2-oxothiazolidin-5-yl-carboxamide, N-(4-nitroxymethylcyclohexylmethyl)-4-(4-methoxyphenyl)-2-oxothiazolidin-5-yl-carboxamide, N-(4-nitroxymethylcyclohexylmethyl)-4-benzyl-2-oxothiazolidin-5-yl-carboxamide, N-(4-nitroxymethylcyclohexylmethyl)-4-(4-methylbenzyl)-2-oxothiazolidin-5-yl-carboxamide, and N-(4-nitroxymethylcyclohexylmethyl)-4-(4-methoxybenzyl)-2-oxothiazolidin-5-yl-carboxamide;

or a pharmacologically acceptable salt thereof.

* * * * *

UNITED STATES PATENT AND TRADEMARK OFFICE
CERTIFICATE OF CORRECTION

PATENT NO.    : 5,843,973
DATED         : December 1, 1998
INVENTOR(S)   : Ishihara et al It is certified that error appears in the above-identified patent and that said Letters Patent is hereby corrected as shown below:

Title Page, right column, in the ABSTRACT, third line from the bottom: after "alkylene" delete "," and insert --. The compound--.

Column 137, line 56 (Claim 15): delete "thiazolidinonelcompound" and insert --thiazolidinone compound--.

Column 140, line 19 (Claim 30): delete "-NR-" and insert -- -NR$^1$- --.

Signed and Sealed this

Seventeenth Day of April, 2001

Attest:

NICHOLAS P. GODICI

Attesting Officer    Acting Director of the United States Patent and Trademark Office